US007582641B2

(12) United States Patent
Charifson et al.

(10) Patent No.: US 7,582,641 B2
(45) Date of Patent: *Sep. 1, 2009

(54) GYRASE INHIBITORS AND USES THEREOF

(75) Inventors: Paul S. Charifson, Framingham, MA (US); David D. Deininger, Arlington, MA (US); Anne-Laure Grillot, Cambridge, MA (US); Yusheng Liao, Lexington, MA (US); Steven M. Ronkin, Watertown, MA (US); Dean Stamos, Framingham, MA (US); Emanuele Perola, Cambridge, MA (US); Tiansheng Wang, Concord, MA (US); Arnaud LeTiran, Lexington, MA (US); Joseph Drumm, Westborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 418 days.

This patent is subject to a terminal disclaimer.

(21) Appl. No.: 10/986,569

(22) Filed: Nov. 11, 2004

(65) Prior Publication Data

US 2005/0256136 A1    Nov. 17, 2005

Related U.S. Application Data

(63) Continuation-in-part of application No. 10/971,573, filed on Oct. 21, 2004, and a continuation-in-part of application No. PCT/US2004/034919, filed on Oct. 21, 2004, said application No. 10/971,573 is a continuation-in-part of application No. 10/901,928, filed on Jul. 29, 2004, said application No. PCT/US2004/034919 is a continuation-in-part of application No. 10/901,928.

(51) Int. Cl.
*A61K 31/506* (2006.01)
*C07D 239/26* (2006.01)

(52) U.S. Cl. .................. 514/256; 544/296; 544/333

(58) Field of Classification Search .............. 546/200; 514/256; 544/296, 333

See application file for complete search history.

(56) References Cited

U.S. PATENT DOCUMENTS

| 4,174,400 | A | 11/1979 | Mrozik |
| 4,512,998 | A | 4/1985 | Nafissi-Varchei |
| 5,529,998 | A | 6/1996 | Habich et al. |
| 5,643,935 | A | 7/1997 | Dykstra et al. |
| 6,632,809 | B2 | 10/2003 | Grillot et al. |
| 2004/0043989 | A1 | 3/2004 | Grillot et al. |
| 2005/0038247 | A1 | 2/2005 | Charifson et al. |
| 2006/0025424 | A1 | 2/2006 | Charifson et al. |

FOREIGN PATENT DOCUMENTS

| EP | 0 433 648 | | 6/1991 |
| EP | 0738726 | A1 | 10/1996 |
| EP | 1 055 668 | A1 | 11/2000 |
| WO | 99/35155 | | 7/1999 |
| WO | 00/49015 | | 8/2000 |
| WO | 00/71522 | | 11/2000 |
| WO | 02/060879 | | 8/2002 |
| WO | 03/105846 | | 12/2003 |
| WO | 2005/012292 | A1 | 3/2004 |
| WO | 2007056330 | | 5/2007 |

OTHER PUBLICATIONS

Tanitame et. al. "Design, synthesis and structure-activity relationship studies of novel indazole analogues as DNA gyrase inhibitors with Gram-positive antibacterial activity" Bioorganic & Medicinal Chemistry Letters 2004, 14, 2857-2862.*
Guven et. al. "Synthesis and Antimicrobial Activity of Some novel Furyl and Benzimidazole Substituted Benzyl Ethers" Journal of Heterocyclic Chemistry 2007, 44, 731.*
, He et. al. "Synthesis and biological evaluation of novel benzimidazoles as potential antibacterial agents." Bioorganic & Medicinal Chemistry Letters 2004, 14, 1217-1220.*
Charles W. Stratton, MD "In Vitro Susceptibility Testing Versus in Vivo Effectiveness" The Medical Clinics of North America 2006, 90, 1077-1088.*
Skopenko, V.V., et al., "Organotin Carbamoyldicyanomethanide, nitrosocarbamoylcyanomethanide, and carbamoylcyanides," retrieved from STN Database accession No. 101:230674, XP002254350 abstract and Dopovidi Akademii Nauk Ukrains'Koi RSR, Seriya B: Geologichni, Khimichni Ta Biologichni Nauki, 7:44-46 (1984).
Hubschwerlen et al., "Pyrimido[1,6-a]benzimidazoles: A New Class of DNA Gyrase Inhibitors" J. Med. Chem, vol. 35, No. 8, pp. 1385-1392, 1992.
Sun et al., "Synthesis and Evaluation of Terbenzimidazoles as Topoisomerase I Inhibitors" J. Med. Chem., vol. 38, No. 18, pp. 3638-3644, 1995.
Kus et al., "Synthesis and Antimicrobial Activities of 5-fluoro-1,2,6-trisubstituted Benzimidazole Carboxamide and Acetamide Derivatives" Arch. Pharm. Pharm. Med. Chem., vol. 334, No. 11, pp. 361-365, 2001.
Singh S.K. et al., "Studies in antiparasitic agents: Part 13- Synthesis of 4-aryl-2 substitutedamino-thiazoles as potential anthelminitics," Indian J. Chem., 28B (9): 786-789 (1989).
Nicolaus B.J.R., "Symbiotic Approach to Drug Design," Decision Making in Drug Research, pp. 173-186 (1983).

* cited by examiner

*Primary Examiner*—Rita J Desai
*Assistant Examiner*—David K O'Dell
(74) *Attorney, Agent, or Firm*—Michael C. Badia

(57) ABSTRACT

The present invention relates to methods of treating, preventing, or lessening the severity of resistant bacterial infections in mammals, utilizing compounds of formula I or formula VII or pharmaceutically salts thereof. The present invention also relates to methods of using compounds of formula I or formula VII in combination with one or more additional antibacterial agents and/or one or more additional therapeutic agents that increase the susceptibility of bacterial organisms to antibiotics.

28 Claims, No Drawings

GYRASE INHIBITORS AND USES THEREOF

CROSS REFERENCE TO RELATED APPLICATIONS

This application, as a continuation-in-part patent application claims the benefit, under 35 U.S.C. §120, of U.S. patent application Ser. No. 10/971,573, filed Oct. 21, 2004, entitled "Gyrase Inhibitors and Uses Thereof" and of International patent application number PCT/US04/34919, filed Oct. 21, 2004 entitled "Gyrase Inhibitors and Uses Thereof", both of which claim the benefit, under 35 U.S.C. §120, of U.S. continuation-in-part patent application Ser. No. 10/901,928 filed Jul. 29, 2004, entitled "Gyrase Inhibitors and Uses Thereof", which claims the benefit, under 35 U.S.C. §120, of U.S. patent application Ser. No. 10/767,638, filed Jan. 29, 2004, which claims the benefit, under 35 U.S.C. §119, of U.S. provisional patent application No. 60/443,917, filed Jan. 31, 2003, entitled "Gyrase Inhibitors and Uses Thereof", and each of the above applications are hereby incorporated by reference.

FIELD OF THE INVENTION

This invention is in the field of medicinal chemistry and relates to compounds, and pharmaceutical compositions thereof, that inhibit bacterial gyrase and Topo IV. The compounds are useful as inhibitors of bacterial gyrase and Topo IV activity. The present invention also relates to methods of using the compounds of this invention for treating resistant bacterial infections in patients. The present invention also relates to treating resistant bacterial infections in patients using compounds of the present invention in combination with one or more additional antibacterial agents and/or one or more additional therapeutic agents that increase the susceptibility of bacterial organisms to antibiotics.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis*, and *Enterococcus*. The appearance of vancomycin resistant *enterococcus* was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., *Current Opinion in Anti-infective Investigational Drugs*, 1999, 1, 1; Levy, "The Challenge of Antibiotic Resistance", *Scientific American*, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in *The Medical Reporter*, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", *FDA Consumer* magazine, September, 1995).

As a result of the need to combat drug-resistant bacteria and the increasing failure of the available drugs, there has been a resurgent interest in discovering new antibiotics. One attractive strategy for developing new antibiotics is to inhibit DNA gyrase, a bacterial enzyme necessary for DNA replication, and therefore, necessary for bacterial cell growth and division. Gyrase activity is also associated with events in DNA transcription, repair and recombination.

Gyrase is one of the topoisomerases, a group of enzymes which catalyze the interconversion of topological isomers of DNA (see generally, Kornberg and Baker, *DNA Replication*, 2d Ed., Chapter 12, 1992, W.H. Freeman and Co.; Drlica, *Molecular Microbiology*, 1992, 6, 425; Drlica and Zhao, *Microbiology and Molecular Biology Reviews*, 1997, 61, 377). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase would be selective for this enzyme and be relatively inactive against the eukaryotic type II topoisomerases.

The widely used quinolone antibiotics inhibit bacterial DNA gyrase. Examples of the quinolones include the early compounds such as nalidixic acid and oxolinic acid, as well as the later, more potent fluoroquinolones such as norfloxacin, ciprofloxacin, and trovafloxacin. These compounds bind to GyrA and stabilize the cleaved complex, thus inhibiting overall gyrase function, leading to cell death. However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, *Trends in Microbiology*, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, *Mol. Microbiol.*, 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, *Trends in Microbiology*, 1997, 5, 102). It would be desirable to have a new, effective GyrB inhibitor that overcomes these drawbacks. Such an inhibitor would be an attractive antibiotic candidate, without a history of resistance problems that plague other classes of antibiotics.

Replication fork movement along circular DNA can generate topological changes both ahead of the replication complex as well as behind in the already replicated regions (Champoux, J. J., *Annu. Rev. Biochem.*, 2001, 70, 369-413). While DNA gyrase can introduce negative supercoils to compensate for the topological stresses ahead of the replication fork, some overwinding can diffuse back into the already replicated region of DNA resulting in precatenanes. If not removed, the presence of the precatenanes can result in interlinked (catenated) daughter molecules at the end of replication. TopoIV is responsible for separating the catenated daughter plasmids as well as removal of precatenanes formed during replication ultimately allowing for segragation of the daughter molecules into daughter cells. Topo IV is composed of two ParC and 2 parE subunits as a $C_2E_2$ tetramer (where the C and E monomers are homologous to the A and B monomers of gyrase, respectively) that requires ATP hydrolysis (at the N-terminus of the E subunit) to reset the enzyme to re-enter the catalytic cycle. Topo IV is highly conserved among bacteria and is essential for bacterial replication (Drlica and Zhao, *Microbiol. Mol. Biol. Rev.*, 1997, 61, 377).

While little attention has been paid to inhibitors that target ParE of TopoIV, the action of the newer quinolones on the ParC region has been widely studied (Hooper, D. C., *Clin. Infect. Dis.*, 2000, 31(Suppl 2): S24-28). It has been demonstrated that moxifloxacin and gatifloxacin have more balanced activities against Gyrase and TopoIV resulting in expanded Gram positive coverage as well as lower levels of resistance caused primary-target mutation. In those cases, susceptibility is limited by the sensitivity of the second target to the antibacterial agent. Thus, agents that can effectively inhibit multiple essential targets can result in an expanded spectrum of potencies, improved antibacterial potencies, improved potency against single target mutants, and/or lower spontaneous rates of resistance.

As bacterial resistance to antibiotics has become an important public health problem, there is a continuing need to develop newer and more potent antibiotics. More particularly, there is a need for antibiotics that represent a new class of compounds not previously used to treat bacterial infection. Such compounds would be particularly useful in treating nosocomial infections in hospitals where the formation and transmission of resistant bacteria are becoming increasingly prevalent.

SUMMARY OF THE INVENTION

It has now been found that compounds of this invention are useful in methods of treating, preventing, or lessening the severity of a bacterial infection in a patient, wherein the bacterial infection is characterized by the presence of one or more of the following: Methicillin resistant Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound of formula I:

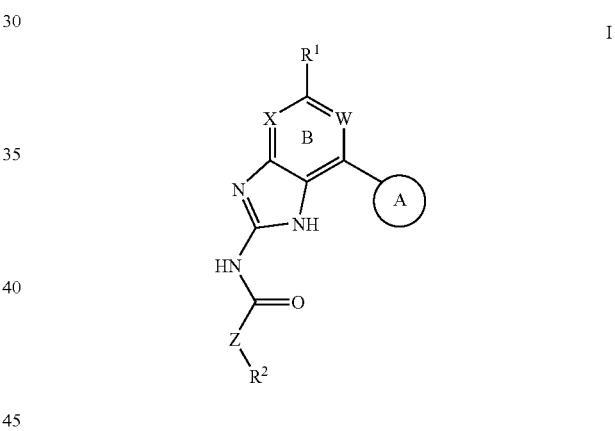

or a pharmaceutically acceptable salt thereof, wherein:

W, X, Z, $R^1$, ring A, and $R^2$ are as defined below.

The compounds of this invention are also useful in methods of treating, preventing, or lessening the severity of a bacterial infection in a patient, wherein the bacterial infection is characterized by the presence of one or more of the following: Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound of formula VII:

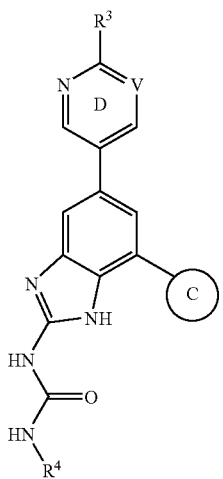

or a pharmaceutically acceptable salt thereof, wherein:

V, $R^3$, $R^4$ and Ring C are as defined below.

The present invention also relates to methods for treating resistant bacterial infections in patients. The present invention also relates to treating resistant bacterial infections in patients using compounds of the present invention in combination with one or more additional antibacterial agents and/or one or more additional therapeutic agents that increase the susceptibility of bacterial organisms to antibiotics.

DESCRIPTION OF THE INVENTION

The present invention provides methods of treating, preventing, or lessening the severity of a bacterial infection in a patient, wherein the bacterial infection is characterized by the presence of one or more of the following: Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound of formula I:

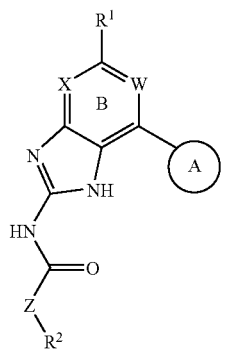

or a pharmaceutically acceptable salt thereof, wherein:
W is selected from nitrogen, CH, or CF;
X is selected from CH or CF;
Z is O or NH;
$R^1$ is phenyl or a 5-6 membered heteroaryl ring having 1-3 heteroatoms independently selected from oxygen, nitrogen, or sulfur, wherein:
  $R^1$ is substituted with 0-3 groups independently selected from —(T)$_y$—Ar, R', oxo, C(O)R', CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R';
y is 0 or 1;
T is a straight or branched $C_{1-4}$ alkylidene chain, wherein one methylene unit of T is optionally replaced by —O—, —NH—, or —S—;
each R' is independently selected from hydrogen, $C_{1-4}$ aliphatic, or a 5-6 membered saturated, unsaturated, or aryl ring having 0-3 heteroatoms independently selected from nitrogen, oxygen, or sulfur, wherein:
  R' is substituted with 0-3 groups independently selected from halogen, oxo, R°, N(R°)$_2$, OR°, CO$_2$R°, NR°(O)R°, C(O)N(R°)$_2$, SO$_2$R°, SO$_2$N(R°)$_2$, or NR°SO$_2$R°, wherein:
    each R° is independently selected from hydrogen, $C_{1-4}$ aliphatic, or a 5-6 membered saturated, unsaturated, or aryl ring having 0-3 heteroatoms independently selected from nitrogen, oxygen, or sulfur, and wherein:
    two substituents on adjacent positions of $R^1$ may be taken together to form a 5-7 membered saturated, partially unsaturated, or aryl ring having 0-3 heteroatoms independently selected from nitrogen, oxygen, or sulfur;
Ar is a 3-8 membered saturated, unsaturated, or aryl ring, a 3-7 membered heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur, wherein:
  Ar is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', C(O)R', SO$_2$N(R')$_2$, or NR'SO$_2$R';
$R^2$ is selected from hydrogen or a $C_{1-3}$ aliphatic group; and
Ring A is a 5-6 membered heteroaryl ring having 1-4 heteroatoms independently selected from nitrogen, oxygen, or sulfur, provided that said ring has a hydrogen-bond acceptor in the position adjacent to the point of attachment to Ring B, wherein:
  Ring A is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R', and wherein:
two substituents on adjacent positions of Ring A may be taken together to form a 5-7 membered saturated, partially unsaturated, or aryl ring having 0-3 heteroatoms independently selected from nitrogen, oxygen, or sulfur.

The present invention also provides methods of treating, preventing, or lessening the severity of a bacterial infection in a patient, wherein the bacterial infection is characterized by the presence of one or more of the following: Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound of formula VII:
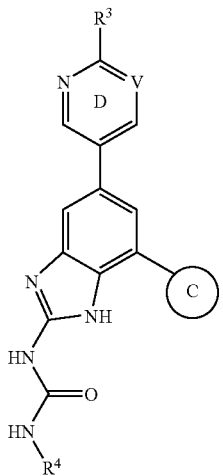
VII or a pharmaceutically acceptable salt thereof, wherein:

V is selected from nitrogen, CH, or CF;

$R^3$ is hydrogen or $C_{1-4}$ aliphatic, wherein:

when $R^3$ is $C_{1-4}$ aliphatic, $R^3$ is substituted with 0-3 groups independently selected from OH, $R^5$, or $OR^5$;

wherein:

$R^5$ is $C_{1-3}$ aliphatic, wherein:

two $R^5$ aliphatic groups may be optionally taken together with the carbon to which they are bound to form a $C_{3-4}$ cycloalkyl ring;

provided that if $R^3$ is hydrogen, then V is not nitrogen or CH;

$R^4$ is a $C_{1-3}$ aliphatic group; and

Ring C is a 6-membered heteroaryl ring having 1-2 nitrogens, wherein:

Ring C is substituted with 1-3 groups selected from $R^6$; wherein:

each $R^6$ is independently selected from $OR^7$ or halogen; and $R^7$ is $C_{1-4}$ aliphatic; or Ring C is an unsubstituted 2-pyrimidine ring.

The present invention relates to a compound of formula I:

I or a pharmaceutically acceptable salt thereof, wherein:

W is selected from nitrogen, CH, or CF;

X is selected from CH or CF;

Z is O or NH;

$R^1$ is phenyl or a 5-6 membered heteroaryl ring having 1-3 heteroatoms independently selected from oxygen, nitrogen, or sulfur, wherein:

$R^1$ is substituted with 0-3 groups independently selected from $—(T)_y—Ar$, R', oxo, C(O)R', $CO_2R'$, OR', $N(R')_2$, SR', $NO_2$, halogen, CN, $C(O)N(R')_2$, NR'C(O)R', $SO_2R'$, $SO_2N(R')_2$, or $NR'SO_2R'$;

y is 0 or 1;

T is a straight or branched $C_{1-4}$ alkylidene chain, wherein one methylene unit of T is optionally replaced by —O—, —NH—, or —S—;

each R' is independently selected from hydrogen, $C_{1-4}$ aliphatic, or a 5-6 membered saturated, unsaturated, or aryl ring having 0-3 heteroatoms independently selected from nitrogen, oxygen, or sulfur, wherein:

R' is substituted with 0-3 groups independently selected from halogen, oxo, $R^o$, $N(R^o)_2$, $OR^o$, $CO_2R^o$, $NR^oC(O)R^o$, $C(O)N(R^o)_2$, $SO_2R^o$, $SO_2N(R^o)_2$, or $NR^oSO_2R^o$, wherein:

each $R^o$ is independently selected from hydrogen, $C_{1-4}$ aliphatic, or a 5-6 membered saturated, unsaturated, or aryl ring having 0-3 heteroatoms independently selected from nitrogen, oxygen, or sulfur, and wherein:

two substituents on adjacent positions of $R^1$ may be taken together to form a 5-7 membered saturated, partially unsaturated, or aryl ring having 0-3 heteroatoms independently selected from nitrogen, oxygen, or sulfur;

Ar is a 3-8 membered saturated, unsaturated, or aryl ring, a 3-7 membered heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur, wherein:

Ar is substituted with 0-3 groups independently selected from R', oxo, $CO_2R'$, OR', $N(R')_2$, SR', $NO_2$, halogen, CN, $C(O)N(R')_2$, NR'C(O)R', $SO_2R'$, C(O)R', $SO_2N(R')_2$, or $NR'SO_2R'$;

$R^2$ is selected from hydrogen or a $C_{1-3}$ aliphatic group; and

Ring A is a 5-6 membered heteroaryl ring having 1-4 heteroatoms independently selected from nitrogen, oxygen, or sulfur, provided that said ring has a hydrogen-bond acceptor in the position adjacent to the point of attachment to Ring B, wherein:

Ring A is substituted with 0-3 groups independently selected from R', oxo, $CO_2R'$, OR', $N(R')_2$, SR', $NO_2$, halogen, CN, $C(O)N(R')_2$, NR'C(O)R', $SO_2R'$, $SO_2N(R')_2$, or $NR'SO_2R'$, and wherein:

two substituents on adjacent positions of Ring A may be taken together to form a 5-7 membered saturated, partially unsaturated, or aryl ring having 0-3 heteroatoms independently selected from nitrogen, oxygen, or sulfur.

The present invention also relates to a compound of formula VII:

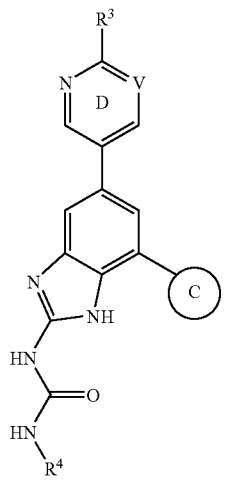

or a pharmaceutically acceptable salt thereof, wherein:
V is selected from nitrogen, CH, or CF;
$R^3$ is hydrogen or $C_{1-4}$ aliphatic, wherein:
  when $R^3$ is $C_{1-4}$ aliphatic, $R^3$ is substituted with 0-3 groups independently selected from OH, $R^5$, or $OR^5$;
    wherein:
      $R^5$ is $C_{1-3}$ aliphatic, wherein:
        two $R^5$ aliphatic groups may be optionally taken together with the carbon to which they are bound to form a $C_{3-4}$ cycloalkyl ring;
  provided that if $R^3$ is hydrogen, then V is not nitrogen or CH;
$R^4$ is a $C_{1-3}$ aliphatic group; and
Ring C is a 6-membered heteroaryl ring having 1-2 nitrogens, wherein:
  Ring C is substituted with 1-3 groups selected from $R^6$;
  wherein:
    each $R^6$ is independently selected from $OR^7$ or halogen; and
    $R^7$ is $C_{1-4}$ aliphatic; or
  Ring C is an unsubstituted 2-pyrimidine ring.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group", as used herein, means a straight-chain or branched $C_1$-$C_8$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "unsaturated", as used herein, means that a moiety has one or more units of unsaturation, and includes aryl rings.

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "hydrogen bond acceptor", as used herein, means an atom capable of accepting a hydrogen bond. A typical hydrogen bond acceptor is a sulfur, oxygen, or nitrogen atom, especially a nitrogen that is $sp^2$-hybridized, an ether oxygen, or a thioether sulfur. A preferred hydrogen bond acceptor is a nitrogen that is $sp^2$-hybridized.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

Examples of suitable Ring A moieties are set forth in Table 1 below.

TABLE 1

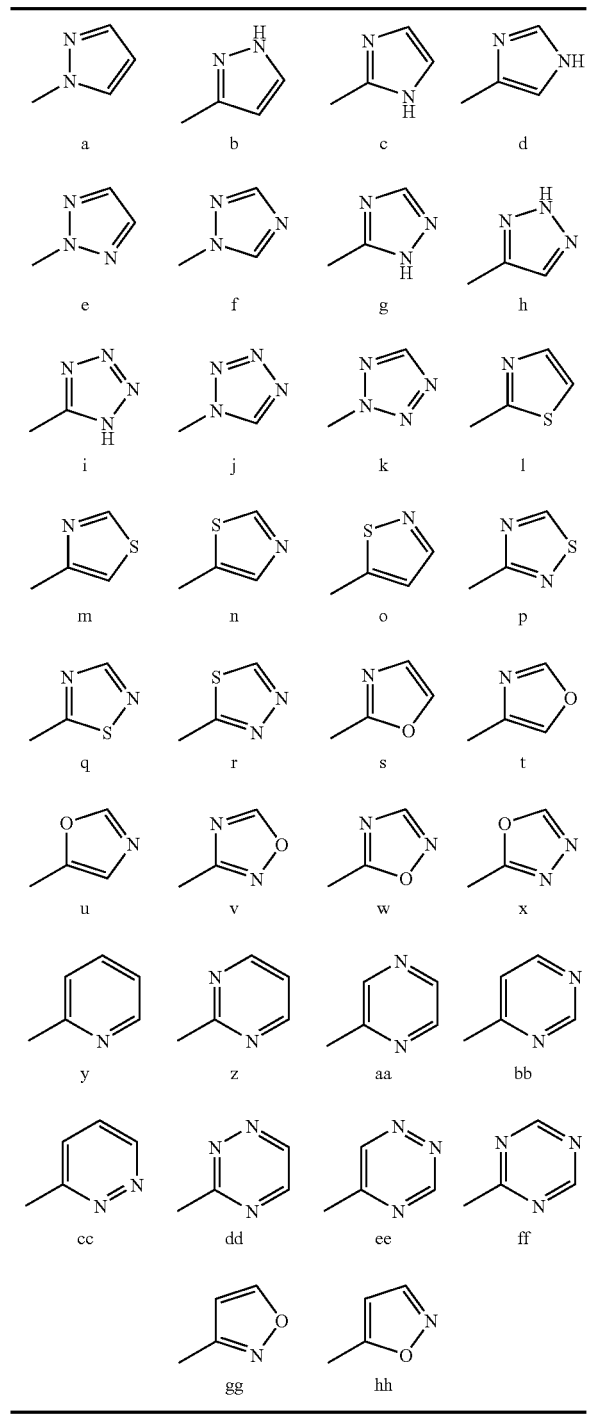

wherein each Ring A is optionally substituted as defined above.

According to one embodiment, Ring A of formula I is a 5-membered heteroaryl ring having 1-4 heteroatoms independently selected from nitrogen, oxygen, or sulfur, provided that said ring has a hydrogen-bond acceptor in the position adjacent to the point of attachment to Ring B, wherein said Ring A is optionally substituted as defined herein supra.

According to another embodiment, Ring A of formula I is a 6-membered heteroaryl ring having 1-3 nitrogens, provided that said ring has a nitrogen atom in the position adjacent to the point of attachment to Ring B, wherein said Ring A is optionally substituted as defined herein supra.

In certain embodiments, Ring A moieties of formula I are selected from rings a, b, c, d, e, f, g, h, i, j, k, l, m, p, q, r, s, t, v, w, x, y, z, aa, bb, cc, dd, and ee, wherein each Ring A is optionally substituted as defined above.

In other embodiments, the Ring A moieties of formula I are selected from rings a, f, l, s, w, y, and z, wherein each Ring A is optionally substituted as defined above.

When Ring A of formula I is a bicyclic heteroaryl ring, preferred bicyclic Ring A moieties include benzothiazole, benzimidazole, benzoxazole, and quinoline.

According to one embodiment, substituents on Ring A of formula I, if present, are selected from oxo, N(R')$_2$, C(O)N(R')$_2$, CO$_2$R', halogen, N(R')SO$_2$R', C(O)R', OR', or R'. According to another embodiment, R' substituents on Ring A of formula I include methyl, ethyl, propyl, piperazinyl, piperidinyl, or morpholinyl, wherein said R' groups are optionally substituted with R°, N(R°)$_2$ or OR°.

According to one embodiment, the R$^1$ group of formula I is optionally substituted phenyl.

According to another embodiment, the R$^1$ group of formula I is an optionally substituted 5-membered heteroaryl ring having 1-3 heteroatoms independently selected from nitrogen, oxygen, or sulfur.

According to another embodiment, the R$^1$ group of formula I is an optionally substituted 5-membered heteroaryl ring having 1-3 nitrogens.

Yet another embodiment of the present invention relates to a compound of formula I wherein R$^1$ is an optionally substituted 6-membered heteroaryl ring having 1-2 nitrogens.

In certain embodiments, the R$^1$ group of formula I is selected from an optionally substituted phenyl or 5-6 membered heteroaryl ring having 1-2 nitrogens. In other embodiments, the R$^1$ group of formula I is selected from an optionally substituted pyrid-2-yl, pyrid-3-yl, pyrid-4-yl, pyridone, pyrimidin-2-yl, pyrimidin-4-yl, pyrimidin-5-yl, pyrimidin-6-yl, imidazol-1-yl, imidazol-2-yl, imidazol-4-yl, or imidazol-5-yl ring. According to yet another embodiment, the R$^1$ group of formula I is an optionally substituted ring selected from pyrid-3-yl, pyrid-4-yl, pyridone, pyrimidin-5-yl, or imidazol-1-yl.

In certain embodiments, substituents on the R$^1$ group of formula I, when present, are selected from halogen, oxo, —(T)$_y$—Ar, R', CO$_2$R', OR', N(R')$_2$, SR', C(O)N(R')$_2$, NR'C(O)R', SO$_2$R', SO$_2$N(R')$_2$, or NR'SO$_2$R'. According to other embodiments, substituents on the R$^1$ group of formula I, when present, are selected from oxo, fluoro, chloro, N(CH$_3$)$_2$, NHCH$_2$CH$_3$, NH-cyclopropyl, NH$_2$, NHC(O)CH$_3$, C(O)NHcyclopropyl, methyl, ethyl, t-butyl, isobutyl, cyclopropyl, isopropyl, CH$_2$phenyl, CH$_2$pyridin-3-yl, OH, OCH$_3$, OCH$_2$CH$_3$, OCH$_2$phenyl, OCH$_2$pyridin-3-yl, CH$_2$piperidinyl, CH$_2$cyclopropyl, or CH$_2$CH$_2$OCH$_3$.

According to another embodiment, substituents on the R¹ group of formula I, when present, include an optionally substituted $C_{1-3}$ alkyl group.

According to another embodiment, substituents on the R¹ group of formula I, when present, include a $C_{1-3}$ alkyl group optionally substituted with an OH group.

According to another embodiment, substituents on the R¹ group of formula I, when present, include a $C_{1-3}$ alkyl group substituted with an OH group.

According to another embodiment, substituents on the $C_{1-3}$ alkyl group, when present, include methyl, gem-dimethyl, ethyl, propyl, isopropyl, cyclopropyl, or cyclobutyl, and an OH group.

According to one embodiment, R¹ is substituted with —(T)$_y$—Ar wherein T is a straight or branched $C_{1-3}$ alkylidene chain wherein one methylene unit of T is optionally replaced by —O—, —NH—, or —S—. According to another embodiment, T is a straight or branched $C_{1-3}$ alkylidene chain wherein one methylene unit of T is replaced by —O—, —NH—, or —S—. Yet another embodiment of the present invention relates to a compound of formula I wherein R¹ is substituted with —(T)$_y$—Ar and Ar is an optionally substituted 5-6 membered saturated ring having 1-2 heteroatoms independently selected from oxygen, nitrogen, or sulfur. According to another embodiment, the Ar group of formula I is an optionally substituted 5-membered heteroaryl ring having 1-3 heteroatoms independently selected from nitrogen, oxygen, or sulfur. According to yet another embodiment, the Ar group of formula I is an optionally substituted 6-membered heteroaryl ring having 1-3 nitrogens. Yet another embodiment relates to a compound of formula I wherein Ar is optionally substituted phenyl.

When the R¹ group of formula I is substituted with —(T)$_y$—Ar, examples of substituents on Ar include halogen, OR', R', CO$_2$R', SO$_2$R', oxo, and C(O)R'.

According to one embodiment, when two substituents on adjacent positions of R¹ of formula I are taken together to form an optionally substituted ring fused to R¹, rings formed thereby include 5-6 membered saturated, partially unsaturated, or aryl rings having 0-2 heteroatoms independently selected from nitrogen, oxygen, or sulfur. According to another embodiment, said ring fused to R¹ is selected from a 5-membered saturated ring having two oxygens or a 6-membered saturated ring having two oxygens. Examples of substituents on said ring fused to R¹ include halogen, such as fluorine.

One embodiment of the present invention relates to a compound of formula I wherein R² is selected from methyl, ethyl, isopropyl, or cyclopropyl. According to another embodiment, R² is methyl or ethyl. According to yet another embodiment, R² of formula I is ethyl.

According to one embodiment, the present invention relates to a compound of formula I wherein Z is NH.

According to another embodiment, the present invention relates to a compound of formula I wherein Z is O.

Compounds of the present invention fall within the genus of compounds described in PCT/US 01/48855. However, applicants have discovered that the presence of the Ring A moiety, as defined above, imparts surprising and unexpectedly increased gyrase inhibitory, TopoIV activity, and antimicrobial potency.

According to one embodiment, the present invention relates to a compound of formula II:

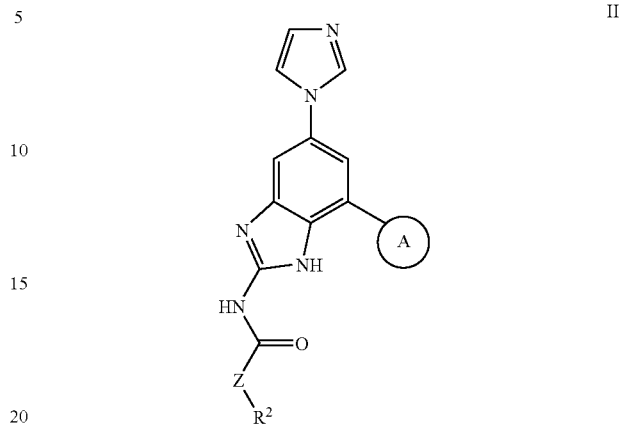

or a pharmaceutically acceptable salt thereof, wherein Z, R² and Ring A are as defined above and the imidazole ring depicted is optionally substituted in the 4-position with C(O)N(R')$_2$ and/or substituted in the 2-position with R'.

According to one embodiment, the imidazole ring of formula II is optionally substituted with a $C_{1-3}$ alkyl group.

According to another embodiment, the imidazole ring of formula II is substituted with a $C_{1-3}$ alkyl group that is optionally substituted with an OH group.

According to another embodiment, the imidazole ring of formula II is substituted with a $C_{1-3}$ alkyl group that is substituted with an OH group.

According to another embodiment, the imidazole ring of formula II is substituted with a methyl, gem-dimethyl, ethyl, propyl, isopropyl, cyclopropyl, or cyclobutyl, and an OH group.

According to another embodiment, the present invention relates to a compound of formula II-a:

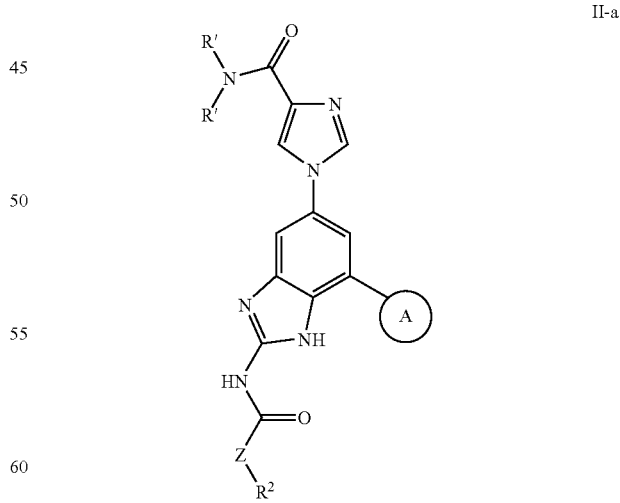

or a pharmaceutically acceptable salt thereof, wherein Z, R², R', and Ring A are as defined above.

Other embodiments describing R² and Ring A groups of formula II-a are those described for formula I above.

Other embodiments describing R' groups of formula II-a are selected from hydrogen or $C_{1-4}$ aliphatic.

According to one embodiment, the present invention relates to a compound of formula II or II-a wherein Z is NH.

According to another embodiment, the present invention relates to a compound of formula II or II-a wherein Z is O.

According to another embodiment, the present invention relates to a compound of formula III:

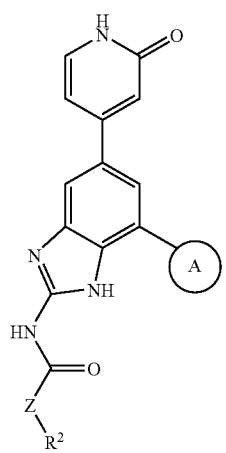

III or a pharmaceutically acceptable salt thereof, wherein Z, $R^2$ and Ring A are as defined above, and the pyridone ring depicted is substituted with 0-2 groups independently selected from —$(CH_2)_y$—Ar, halogen, oxo, R', $CO_2R'$, OR', $N(R')_2$, SR', $C(O)N(R')_2$, $NR'C(O)R'$, $SO_2R'$, $SO_2N(R')_2$, or $NR'SO_2R'$.

Other embodiments describing $R^2$ and Ring A groups of formula III are those described for formula I above.

Other embodiments describing substituents on the pyridone ring of formula III are those described above as preferred substituents on $R^1$ of formula I.

According to another embodiment, the pyridone ring of formula III is optionally substituted with a $C_{1-3}$ alkyl group.

According to another embodiment, the pyridone ring of formula III is substituted with a $C_{1-3}$ alkyl group that is optionally substituted with an OH group.

According to another embodiment, the pyridone ring of formula III is substituted with a $C_{1-3}$ alkyl group that is substituted with an OH group.

According to another embodiment, the pyridone ring of formula III is substituted with a methyl, gem-dimethyl, ethyl, propyl, isopropyl, cyclopropyl, or cyclobutyl, and an OH group.

According to one embodiment, the present invention relates to a compound of formula III wherein Z is NH.

According to another embodiment, the present invention relates to a compound of formula III wherein Z is O.

According to another embodiment, the present invention relates to a compound of formula III-a:

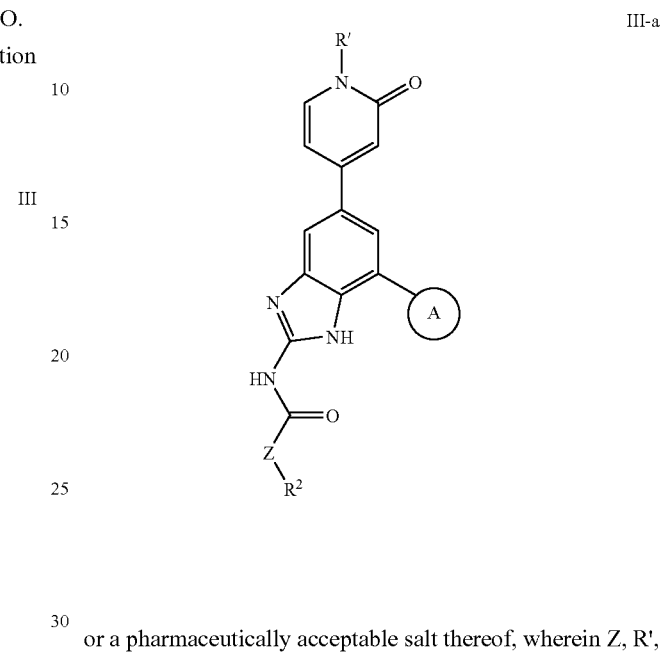

III-a or a pharmaceutically acceptable salt thereof, wherein Z, R', $R^2$ and Ring A are as defined above.

Other embodiments describing $R^2$ groups of formula III-a are those described for $R^2$ groups of formula I above.

Other embodiments describing Ring A groups of formula III-a are those described for Ring A groups of formula I above.

In certain embodiments, the R' substituents on the pyridone ring of formula III-a are selected from hydrogen or $C_{1-4}$ aliphatic wherein R' is optionally substituted with phenyl or pyridyl. In other embodiments, the R' substituents on the pyridone ring of formula III-a are selected from methyl, ethyl, t-butyl, isobutyl, cyclopropyl, isopropyl, $CH_2$phenyl, $CH_2$pyridin-3-yl, $CH_2$piperidinyl, $CH_2$cyclopropyl, or $CH_2CH_2OCH_3$.

According to another embodiment, the pyridone ring of formula III-a is optionally substituted with a $C_{1-3}$ alkyl group.

According to another embodiment, the pyridone ring of formula III-a is substituted with a $C_{1-3}$ alkyl group that is optionally substituted with an OH group.

According to another embodiment, the pyridone ring of formula III-a is substituted with a $C_{1-3}$ alkyl group that is substituted with an OH group.

According to another embodiment, the pyridone ring of formula III-a is substituted with a methyl, ethyl, propyl, isopropyl, cyclopropyl, or cyclobutyl, and an OH group.

According to one embodiment, the present invention relates to a compound of formula III-a wherein Z is NH.

According to another embodiment, the present invention relates to a compound of formula III-a wherein Z is O.

Yet another embodiment of the present invention relates to a compound of formula IV:

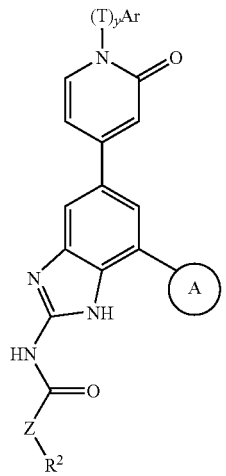

IV or a pharmaceutically acceptable salt thereof, wherein y, Z, T, Ar, $R^2$ and Ring A are as defined above.

According to one embodiment, the pyridone ring of formula IV is optionally substituted with a $C_{1-3}$ alkyl group.

According to another embodiment, the pyridone ring of formula IV is substituted with a $C_{1-3}$ alkyl group that is optionally substituted with an OH group.

According to another embodiment, the pyridone ring of formula IV is substituted with a $C_{1-3}$ alkyl group that is substituted with an OH group.

According to another embodiment, the pyridone ring of formula IV is substituted with a methyl, gem-dimethyl, ethyl, propyl, isopropyl, cyclopropyl, or cyclobutyl, and an OH group.

Other embodiments describing Ring A and $R^2$ groups of formula IV are those set forth for those Ring A and $R^2$ groups of formula I, supra.

According to one embodiment, the Ar group of formula IV is an optionally substituted 5-6 membered saturated ring having 1-2 heteroatoms independently selected from oxygen, nitrogen, or sulfur.

According to another embodiment, the Ar group of formula IV is an optionally substituted 5-membered heteroaryl ring having 1-3 heteroatoms independently selected from nitrogen, oxygen, or sulfur.

According to another embodiment, the Ar group of formula IV is an optionally substituted 6-membered heteroaryl ring having 1-3 nitrogens.

Yet another embodiment relates to a compound of formula IV wherein Ar is optionally substituted phenyl.

According to one embodiment, the present invention relates to a compound of formula IV wherein Z is NH.

Examples of substituents on the Ar group of formula IV include halogen, OR', R', $CO_2R'$, $SO_2R'$, oxo, and C(O)R'.

According to another embodiment, the present invention relates to a compound of formula IV wherein Z is O.

Yet another embodiment of the present invention relates to a compound of formula V:

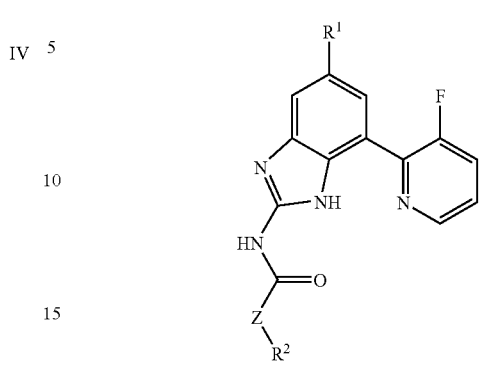

V or a pharmaceutically acceptable salt thereof, wherein y, Z, $R^2$ and $R^1$ are as defined above.

Other embodiments describing $R^1$ and $R^2$ groups of formula V are those set forth for those $R^1$ and $R^2$ groups of formula I, supra.

According to one embodiment, the present invention relates to a compound of formula V wherein Z is NH.

Examples of substituents on the Ar group of formula V include halogen, OR', R', $CO_2R'$, $SO_2R'$, oxo, and C(O)R'.

According to another embodiment, the Ar group of formula V is optionally substituted with a $C_{1-3}$ alkyl group.

According to another embodiment, the Ar group of formula V is substituted with a $C_{1-3}$ alkyl group that is optionally substituted with an OH group.

According to another embodiment, the Ar group of formula V is substituted with a $C_{1-3}$ alkyl group that is substituted with an OH group.

According to another embodiment, the Ar group of formula V is substituted with a methyl, gem-dimethyl, ethyl, propyl, isopropyl, cyclopropyl, or cyclobutyl, and an OH group.

According to another embodiment, the present invention relates to a compound of formula V wherein Z is O.

According to another embodiment of the present invention relates to a compound of formula VI:

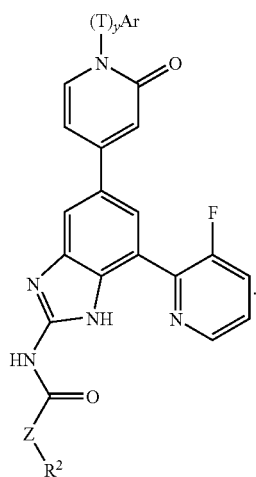

VI or a pharmaceutically acceptable salt thereof, wherein y, Z, T, Ar, and $R^2$ are as defined above.

Other embodiments describing the R² group of formula VI are those set forth for the R² group of formula I, supra.

According to one embodiment, the Ar group of formula VI is an optionally substituted 5-6 membered saturated ring having 1-2 heteroatoms independently selected from oxygen, nitrogen, or sulfur.

According to another embodiment, the Ar group of formula VI is an optionally substituted 5-membered heteroaryl ring having 1-3 heteroatoms independently selected from nitrogen, oxygen, or sulfur.

According to another embodiment, the Ar group of formula VI is an optionally substituted 6-membered heteroaryl ring having 1-3 nitrogens.

Yet another embodiment relates to a compound of formula VI wherein Ar is optionally substituted phenyl.

According to another embodiment, the pyridone ring of formula VI is optionally substituted with a $C_{1-3}$ alkyl group.

According to another embodiment, the pyridone ring of formula VI is substituted with a $C_{1-3}$ alkyl group that is optionally substituted with an OH group.

According to another embodiment, the pyridone ring of formula VI is substituted with a $C_{1-3}$ alkyl group that is substituted with an OH group.

According to another embodiment, the pyridone ring of formula VI is substituted with a methyl, gem-dimethyl, ethyl, propyl, isopropyl, cyclopropyl, or cyclobutyl, and an OH group.

According to one embodiment, the present invention relates to a compound of formula VI wherein Z is NH.

Examples of substituents on the Ar group of formula VI include halogen, OR', R', CO₂R', SO₂R', oxo, and C(O)R'.

According to another embodiment, the present invention relates to a compound of formula VI wherein Z is O.

According to another embodiment, the present invention relates to a compound of formula VII:

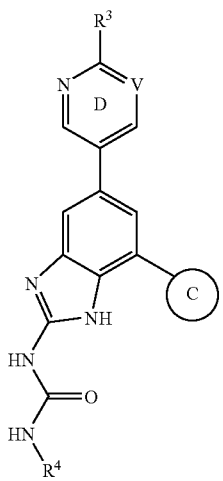

VII or a pharmaceutically acceptable salt thereof, wherein:
V is selected from nitrogen, CH, or CF;
R³ is hydrogen or $C_{1-4}$ aliphatic, wherein:
  when R³ is $C_{1-4}$ aliphatic, R³ is substituted with 0-3 groups independently selected from OH, R⁵, or OR;
  wherein:
    R⁵ is $C_{1-3}$ aliphatic, wherein:
      two R⁵ aliphatic groups may be optionally taken together with the carbon to which they are bound to form a $C_{3-4}$ cycloalkyl ring;
  provided that if R³ is hydrogen, then V is not nitrogen or CH;
R⁴ is a $C_{1-3}$ aliphatic group; and
Ring C is a 6-membered heteroaryl ring having 1-2 nitrogens, wherein:
  Ring C is substituted with 1-3 groups selected from R⁶;
  wherein:
    each R⁶ is independently selected from OR⁷ or halogen; and
    R⁷ is $C_{1-4}$ aliphatic; or
  Ring C is an unsubstituted 2-pyrimidine ring.

According to another embodiment, the present invention relates to a compound of formula VII:

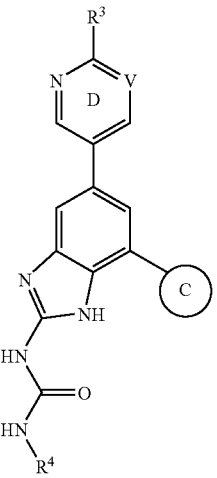

VII or a pharmaceutically acceptable salt thereof, wherein:
V is selected from nitrogen or CH;
R³ is $C_{1-4}$ aliphatic, wherein:
  when R³ is $C_{1-4}$ aliphatic, R³ is substituted with 0-3 groups independently selected from OH, R⁵, or OR⁵;
  wherein:
    R⁵ is $C_{1-3}$ aliphatic, wherein:
      two R⁵ aliphatic groups may be optionally taken together with the carbon to which they are bound to form a $C_{3-4}$ cycloalkyl ring;
R⁴ is a $C_{1-3}$ aliphatic group; and
Ring C is a 6-membered heteroaryl ring having 1-2 nitrogens, wherein:
  Ring C is substituted with 1-3 groups selected from R⁶;
  wherein:
    each R⁶ is independently selected from OR⁷ or halogen; and
    R⁷ is $C_{1-4}$ aliphatic.

According to another embodiment of compounds of formula VII, Ring C is a 2-pyridyl ring substituted with one occurrence of R⁶.

According to another embodiment of compounds of formula VII, Ring C is

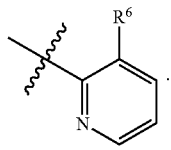

According to another embodiment of compounds of formula VII, $R^6$ is selected from halogen or $OR^7$.
According to another embodiment of compounds of formula VII, $R^7$ is methyl.
According to another embodiment of compounds of formula VII, $R^6$ is fluoro.
According to another embodiment of compounds of formula VII, the

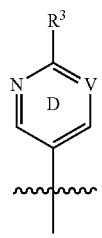

radical is:

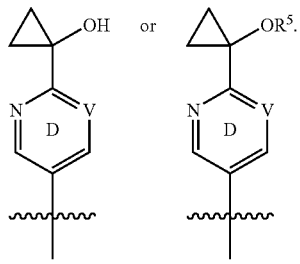

According to another embodiment of compounds of formula VII, $R^3$ is an optionally substituted $C_{1-3}$ alkyl group.
According to another embodiment of compounds of formula VII, $R^3$ is a $C_{1-3}$ alkyl group optionally substituted with an OH group.
According to another embodiment of compounds of formula VII, $R^3$ is a $C_{1-3}$ alkyl group substituted with an OH group
According to another embodiment of compounds of formula VII, V is nitrogen and $R^3$ is substituted with two groups independently selected from $R^5$ and OH.
According to another embodiment of compounds of formula VII, V is CH and $R^3$ is substituted with two groups independently selected from $R^5$ and OH.
According to another embodiment of compounds of formula VII, $R^3$ is substituted with one $R^5$ group and one OH group.
According to another embodiment of compounds of formula VII, $R^3$ is a $C_{1-3}$ alkyl group substituted with methyl, gem-dimethyl, ethyl, propyl, isopropyl, cyclopropyl, or cyclobutyl, and an OH group.

According to another embodiment, the present invention relates to a compound of formula VIIA, VIIB or VIIC:

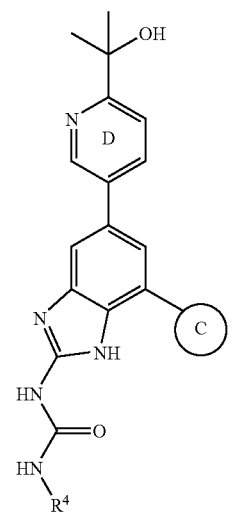

VIIA

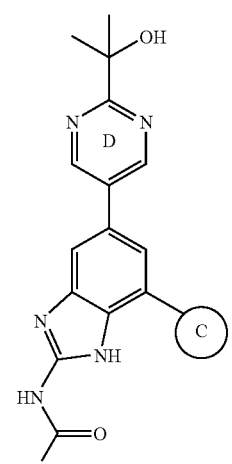

VIIB

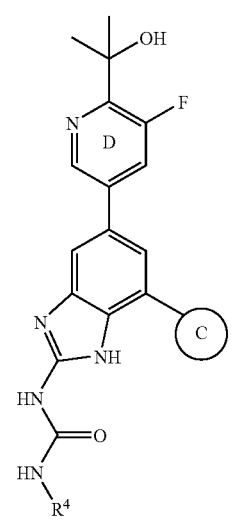

VIIC or a pharmaceutically acceptable salt thereof, wherein:
$R^4$ is a $C_{1-3}$ aliphatic group; and Ring C is a 6-membered heteroaryl ring having 1-2 nitrogens, wherein:
Ring C is substituted with 1-3 groups selected from $R^6$; wherein:
each $R^6$ is independently selected from $OR^7$ or halogen;
$R^7$ is $C_{1-4}$ aliphatic; or
Ring C is an unsubstituted 2-pyrimidine ring.

According to another embodiment, the present invention relates to a compound of formula VIID, VIIE, VIIF or VIIG:

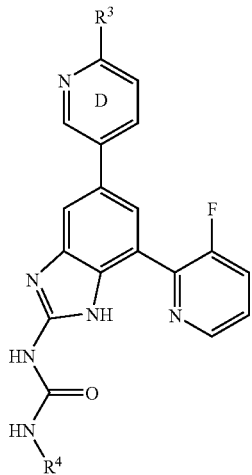

VIID

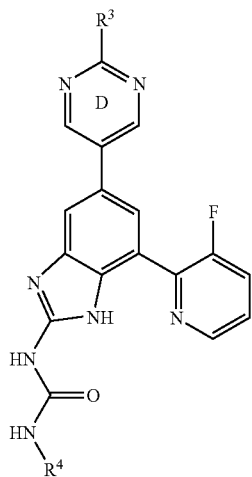

VIIE

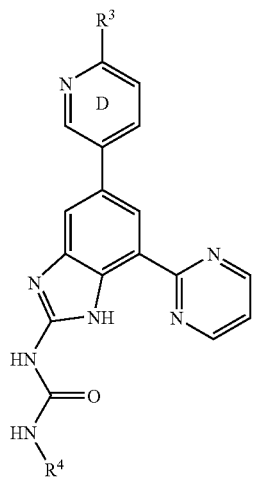

VIIF

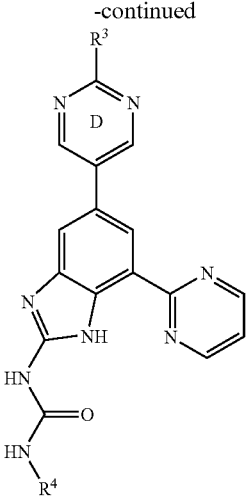

VIIG or a pharmaceutically acceptable salt thereof, wherein:
$R^3$ is $C_{1-4}$ aliphatic, wherein:
  $R^3$ is substituted with 0-3 groups independently selected from OH, $R^5$, or $OR^5$;
wherein:
  $R^5$ is $C_{1-3}$ aliphatic; and
$R^4$ is a $C_{1-3}$ aliphatic group.

According to another embodiment, the present invention relates to a compound of formula VIIH, or VIIJ:

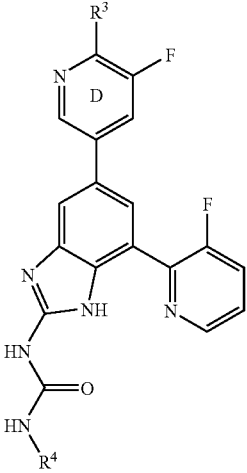

VIIH

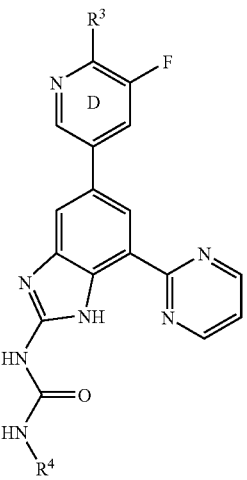

VIIJ or a pharmaceutically acceptable salt thereof, wherein:

R³ is hydrogen or C₁₋₄ aliphatic, wherein:
when R³ is C₁₋₄ aliphatic, R³ is substituted with 0-3 groups independently selected from OH, R⁵, or OR⁵;
wherein:
R⁵ is C₁₋₃ aliphatic; and
R⁴ is a C₁₋₃ aliphatic group.

According to another embodiment of compounds of formula VII, VIIA, VIIB, VIIC, VIID, VIIE, VIIF, VIIG, VIIH, and VIIJ, R⁴ is ethyl.

According to another embodiment the present invention provides a method of treating, preventing, or lessening the severity of a bacterial infection in a patient, wherein the bacterial infection is characterized by the presence of one or more of the following: Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound of formula I:

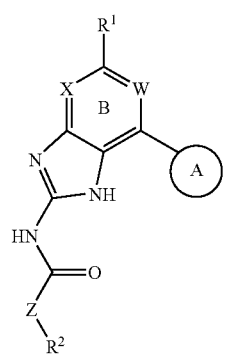

I or a pharmaceutically acceptable salt thereof, wherein:

W is selected from nitrogen, CH, or CF;
X is selected from CH or CF;
Z is O or NH;
R¹ is phenyl or a 5-6 membered heteroaryl ring having 1-3 heteroatoms independently selected from oxygen, nitrogen, or sulfur, wherein:
R¹ is substituted with 0-3 groups independently selected from —(T)ᵧ—Ar, R', oxo, C(O)R', CO₂R', OR', N(R')₂, SR', NO₂, halogen, CN, C(O)N(R')₂, NR'C(O)R', SO₂R', SO₂N(R')₂, or NR'SO₂R';

y is 0 or 1;
T is a straight or branched C₁₋₄ alkylidene chain, wherein one methylene unit of T is optionally replaced by —O—, —NH—, or —S—;
each R' is independently selected from hydrogen, C₁₋₄ aliphatic, or a 5-6 membered saturated, unsaturated, or aryl ring having 0-3 heteroatoms independently selected from nitrogen, oxygen, or sulfur, wherein:
R' is substituted with 0-3 groups independently selected from halogen, oxo, R°, N(R°)₂, OR°, CO₂R°, NR°C(O)R°, C(O)N(R°)₂, SO₂R°, SO₂N(R°)₂, or NR°SO₂R°, wherein:
each R° is independently selected from hydrogen, C₁₋₄ aliphatic, or a 5-6 membered saturated, unsaturated, or aryl ring having 0-3 heteroatoms independently selected from nitrogen, oxygen, or sulfur, and wherein:
two substituents on adjacent positions of R¹ may be taken together to form a 5-7 membered saturated, partially unsaturated, or aryl ring having 0-3 heteroatoms independently selected from nitrogen, oxygen, or sulfur;

Ar is a 3-8 membered saturated, unsaturated, or aryl ring, a 3-7 membered heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur, wherein:
Ar is substituted with 0-3 groups independently selected from R', oxo, CO₂R', OR', N(R')₂, SR', NO₂, halogen, CN, C(O)N(R')₂, NR'C(O)R', SO₂R', C(O)R', SO₂N(R')₂, or NR'SO₂R';

R² is selected from hydrogen or a C₁₋₃ aliphatic group; and

Ring A is a 5-6 membered heteroaryl ring having 1-4 heteroatoms independently selected from nitrogen, oxygen, or sulfur, provided that said ring has a hydrogen-bond acceptor in the position adjacent to the point of attachment to Ring B, wherein:
Ring A is substituted with 0-3 groups independently selected from R', oxo, CO₂R', OR', N(R')₂, SR', NO₂, halogen, CN, C(O)N(R')₂, NR'C(O)R', SO₂R', SO₂N(R')₂, or NR'SO₂R', and wherein:

two substituents on adjacent positions of Ring A may be taken together to form a 5-7 membered saturated, partially unsaturated, or aryl ring having 0-3 heteroatoms independently selected from nitrogen, oxygen, or sulfur.

According to another embodiment the present invention provides a method of treating, preventing, or lessening the severity of a bacterial infection in a patient, wherein the bacterial infection is characterized by the presence of one or more of the following: Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound of formula VII:

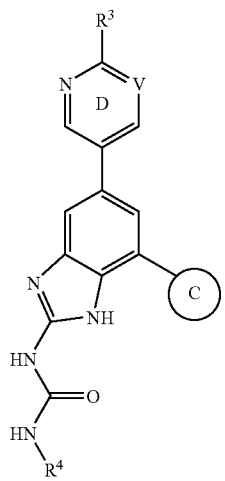

VII or a pharmaceutically acceptable salt thereof, wherein:

V is selected from nitrogen, CH, or CF;

$R^3$ is hydrogen or $C_{1-4}$ aliphatic, wherein:
    when $R^3$ is $C_{1-4}$ aliphatic, $R^3$ is substituted with 0-3 groups independently selected from OH, $R^5$, or $OR^5$;
    wherein:
        $R^5$ is $C_{1-3}$ aliphatic, wherein:
            two $R^5$ aliphatic groups may be optionally taken together with the carbon to which they are bound to form a $C_{3-4}$ cycloalkyl ring;
    provided that if $R^3$ is hydrogen, then V is not nitrogen or CH;

$R^4$ is a $C_{1-3}$ aliphatic group; and

Ring C is a 6-membered heteroaryl ring having 1-2 nitrogens, wherein:
    Ring C is substituted with 1-3 groups selected from $R^6$;
    wherein:
        each $R^6$ is independently selected from $OR^7$ or halogen; and
        $R^7$ is $C_{1-4}$ aliphatic; or Ring C is an unsubstituted 2-pyrimidine ring.

According to another embodiment, the method of the present invention comprises the step of administering to said patient a compound of formula VIIA, VIIB, or VIIC:

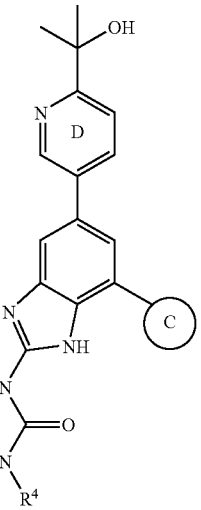

VIIA

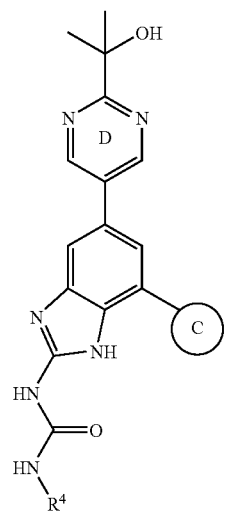

VIIB

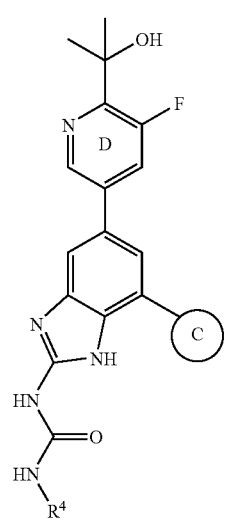

VIIC or a pharmaceutically acceptable salt thereof, wherein:

$R^4$ is a $C_{1-3}$ aliphatic group; and

Ring C is a 6-membered heteroaryl ring having 1-2 nitrogens, wherein:
Ring C is substituted with 1-3 groups selected from $R^6$; wherein:
each $R^6$ is independently selected from $OR^7$ or halogen; $R^7$ is $C_{1-4}$ aliphatic; or
Ring C is an unsubstituted 2-pyrimidine ring.

According to another embodiment of the methods of the present invention, the patient is a human.

According to another embodiment, the methods of the present invention are useful to treat patients in the veterinarian field including, but not limited to, zoo, laboratory, and farm animals including primates, rodents, and birds. Examples of said animals include, but are not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, ostriches, chickens, turkeys, ducks, and geese.

According to another embodiment of the methods of the present invention, the Methicillin resistant Staphylococci are selected from Methicillin resistant *Staphylococcus aureus*, Methicillin resistant *Staphylococcus epidermidis*, or Methicillin resistant Coagulase negative *staphylcoccus*.

According to another embodiment of the methods of the present invention, the Fluoroquinolone resistant Staphylococci are selected from Fluoroquinolone resistant *Staphylococcus aureus*, Fluoroquinolone resistant *Staphylococcus epidermidis*, or Fluoroquinolone resistant Coagulase negative *staphylcoccus*.

According to another embodiment of the methods of the present invention, the Glycopepetide resistant Staphylococci are selected from Glycopeptide intermediate resistant *Staphylococcus aureus*, Vancomycin resistant *Staphylococcus aureus*, Vancomycin intermediate *Staphylococcus aureus*, Hetero vancomycin intermediate resistant *Staphylococcus aureus*, or Hetero vancomycin resistant *Staphylococcus aureus*.

According to another embodiment of the methods of the present invention, the Macrolide-Lincosamide-Streptogramin resistant Staphylococci is Macrolide-Lincosamide-Streptogramin resistant *Staphylococcus aureus*.

According to another embodiment of the methods of the present invention, the Linezolid resistant Enterococci are selected from Linezolid resistant *Enterococcus faecalis*, or Linezolid resistant *Enterococcus faecium*.

According to another embodiment of the methods of the present invention, the Glycopepetide resistant Enterococci are selected from Vancomycin resistant *Enterococcus faecium* or Vancomycin resistant *Enterococcus faecalis*.

According to another embodiment of the methods of the present invention, the β-lactam resistant *Enterococcus faecalis* and β-lactam resistant *Enterococcus faecium*.

According to another embodiment of the methods of the present invention, the Penicillin resistant Streptococci include Penicillin resistant *Streptococcus pneumoniae*.

According to another embodiment of the methods of the present invention, the Macrolide resistant Streptococci is Macrolide resistant *Streptococcus pneumonia*.

According to another embodiment of the methods of the present invention, the Ketolide resistant Streptococci are selected from Macrolide resistant *Streptococcus pneumoniae* and Ketolide resistant *Streptococcus pyogenes*.

According to another embodiment of the methods of the present invention, the Fluoroquinolone resistant Streptococci is Fluoroquinolone resistant *Streptococcus pneumoniae*.

According to another embodiment of the methods of the present invention, the β-lactam resistant *Haemophilus* is β-lactam resistant *Haemophilus influenzae*.

According to another embodiment of the methods of the present invention, the Fluoroquinolone resistant *Haemophilus* is Fluoroquinolone resistant *Haemophilus influenzae*.

According to another embodiment of the methods of the present invention, the Macrolide resistant *Haemophilus* is Macrolide resistant *Haemophilus influenzae*.

According to another embodiment of the methods of the present invention, the Macrolide resistant *Mycoplasma* is Macrolide resistant *Mycoplasma pneumoniae*.

According to another embodiment of the methods of the present invention, the Isoniazid resistant *Mycobacterium* is Isoniazid resistant *Mycobacterium tuberculosis*.

According to another embodiment of the methods of the present invention, the Rifampin resistant *Mycobacterium* is Rifampin resistant *Mycobacterium tuberculosis*.

According to another embodiment of the methods of the present invention, the β-lactam resistant *Moraxella* is β-lactam resistant *Moraxella catarrhalis*.

According to another embodiment of the methods of the present invention, the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplama pneumoniae*, Isoniazid resistant *Mycobacterium tuberculosis*, or Rifampin resistant *Mycobacterium tuberculosis*.

According to another embodiment of the methods of the present invention, the bacterial infection is characterized by the presence of one or more of the following: Methicillin resistant *Staphylococcus aureus*, Methicillin resistant *Staphylococcus epidermidis*, Methicillin resistant Coagulase negative staphylcocci, Fluoroquinolone resistant *Staphylococcus aureus*, Fluoroquinolone resistant *Staphylococcus epidermidis*, Fluoroquinolone resistant Coagulase negative staphylcocci, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, or β-lactam resistant *Haemophilus influenzae*.

According to another embodiment of the methods of the present invention, the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplama pneumoniae*, Isoniazid resistant *Mycobacterium tuberculosis*, Rifampin resistant *Mycobacterium tuberculosis*, Methicillin resistant Coagulase negative staphylcocci, Fluoroquinolone resistant Coagulase negative staphylcocci, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *staphyloccus epidermidis*.

According to another embodiment of the present invention, the methods further comprise the step of administering to the patient one or more additional therapeutic antibacterial agents other than a compound of the present invention (see, e.g. http://www.fda.gov/cvm).

According to another embodiment of the present invention, the methods further comprise the step of administering to said patient one or more additional therapeutic agents either as part of a multiple dosage form together with said compound or as a separate dosage form wherein said one or more additional therapeutic agents include an antibiotic selected from a natural penicillin, a penicillinase-resistant penicillin, an antipseudomonal penicillin, an aminopenicillin, a first generation cephlosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidone, a rifamycin, or other antibiotics.

According to another embodiment of the present invention, the methods further comprise the step of administering to said human one or more additional therapeutic agents either as part of a multiple dosage form together with said compound or as a separate dosage form wherein said one or more additional therapeutic agents include an antibiotic selected from a natural penicillin, a penicillinase-resistant penicillin, an antipseudomonal penicillin, an aminopenicillin, a first generation cephlosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidone, a rifamycin, or other antibiotics.

According to another embodiment of the present invention, the methods further comprise the step of administering to said patient one or more additional therapeutic agents either as part of a multiple dosage form together with said compound or as a separate dosage form wherein said one or more additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, from a Cephamycin including Cefotetan and Cefoxitin, from a carbapenem including Imipenem and Meropenem, from a monobactam including Aztreonam, from a quinolone including Cinoxacin, Nalidixic acid, Oxolininc acid and Pipemidic acid, from a fluoroquinolone including Cirpofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, chloramphenicol, clindamycin, isoniazid, metronidazole, polymyxin B, pyrazinamide, and trimethoprim/sulfamethoxazole.

According to another embodiment of the present invention, the methods further comprise the step of administering to said human one or more additional therapeutic agents either as part of a multiple dosage form together with said compound or as a separate dosage form wherein said one or more additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, from a Cephamycin including Cefotetan and Cefoxitin, from a carbapenem including Imipenem and Meropenem, from a monobactam including Aztreonam, from a quinolone including Cinoxacin, Nalidixic acid, Oxolininc acid and Pipemidic acid, from a fluoroquinolone including Cirpofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, chloramphenicol, clindamycin, isoniazid, metronidazole, polymyxin B, pyrazinamide, and trimethoprim/sulfamethoxazole.

According to another embodiment of the present invention, the methods further comprise the step of administering to said patient one or more additional therapeutic agents either as part of a multiple dosage form together with said compound or as a separate dosage form wherein said one or more additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a fluoroquinolone including Cirpofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including Vancomycin, from a Rifamycin including Rifampin and from other antibiotics including isoniazid, pyrazinamide, or trimethoprim/sulfamethoxazole.

According to another embodiment of the present invention, the methods further comprise the step of administering to said human one or more additional therapeutic agents either as part of a multiple dosage form together with said compound or as a separate dosage form wherein said one or more additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a fluoroquinolone including Cirpofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including Vancomycin, from a Rifamycin including Rifampin and from other antibiotics including isoniazid, pyrazinamide, or trimethoprim/sulfamethoxazole.

According to another embodiment of the present invention, the methods further comprise the step of administering to a patient, one or more additional therapeutic agents that increase the susceptibility of bacterial organisms to antibiotics.

According to another embodiment of the present invention, the methods further comprise the step of administering to a human, one or more additional therapeutic agents that increase the susceptibility of bacterial organisms to antibiotics.

According to another embodiment of the present invention, the methods further comprise the step of administering to a patient, one or more additional therapeutic agents that increase the susceptibility of bacterial organisms to antibiotics including a biofilm inhibitor.

According to another embodiment of the present invention, the methods further comprise the step of administering to a human, one or more additional therapeutic agents that increase the susceptibility of bacterial organisms to antibiotics including a biofilm inhibitor.

Exemplary structures of formula I are set forth in Table 2 below:

TABLE 2

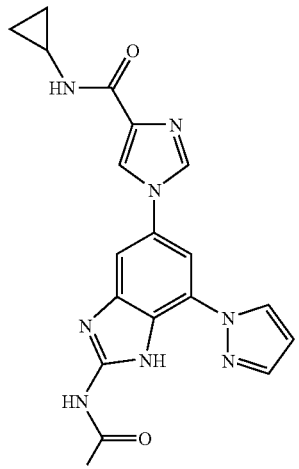

I-1

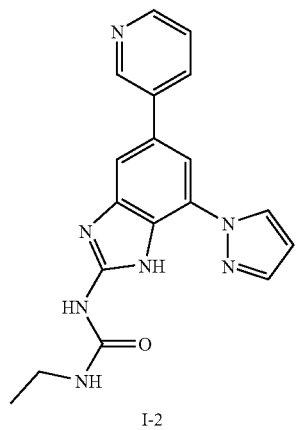

I-2

TABLE 2-continued
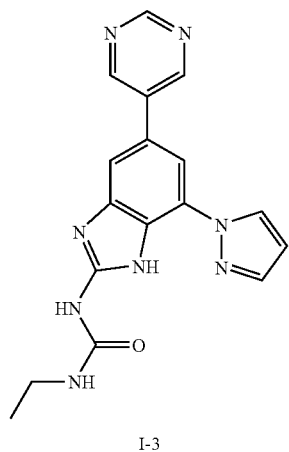
I-3
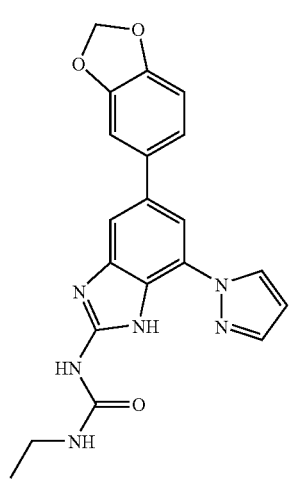
I-4
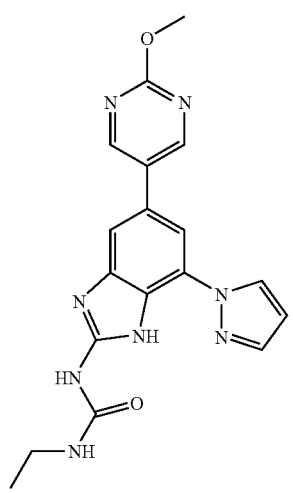
I-5
TABLE 2-continued
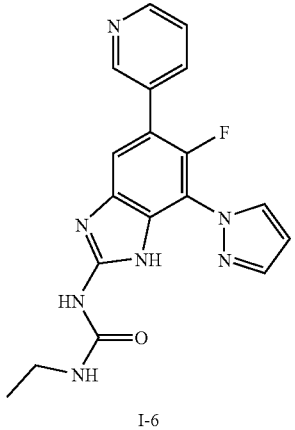
I-6
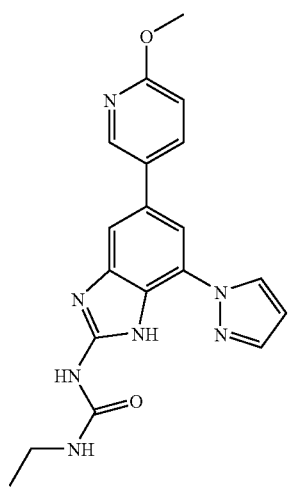
I-7
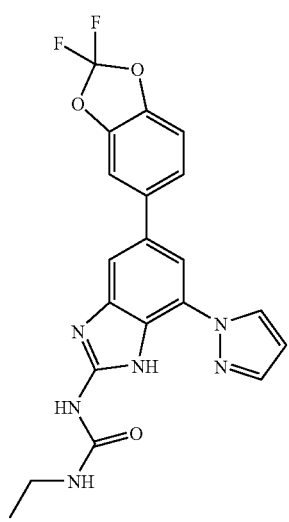
I-8

TABLE 2-continued
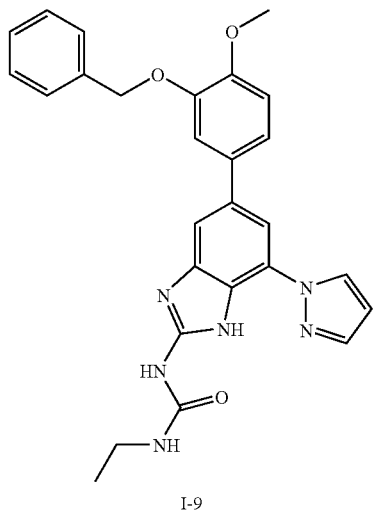
I-9
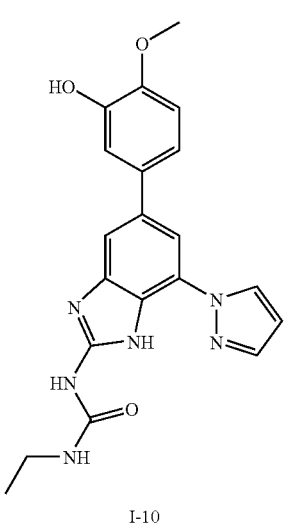
I-10
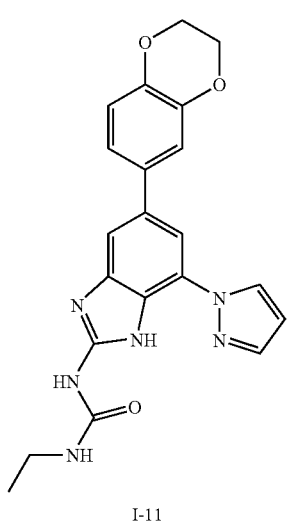
I-11
TABLE 2-continued
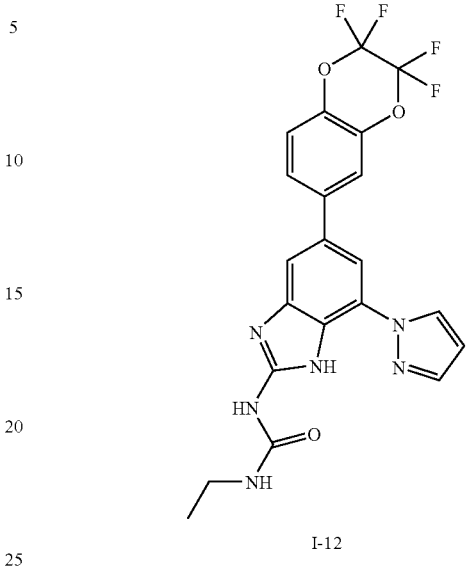
I-12
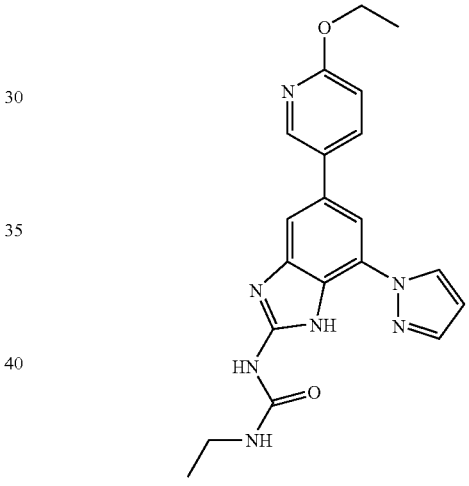
I-13
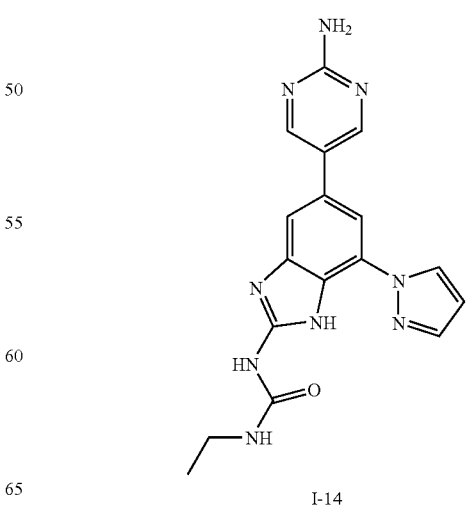
I-14

TABLE 2-continued
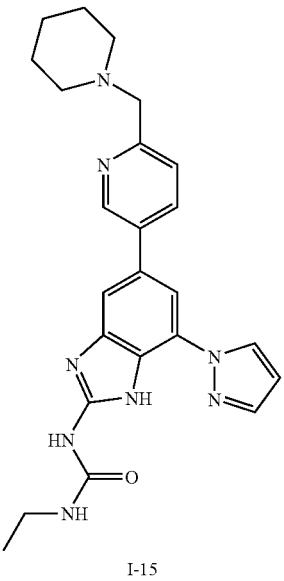
I-15
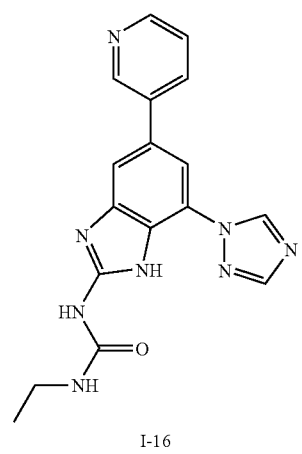
I-16
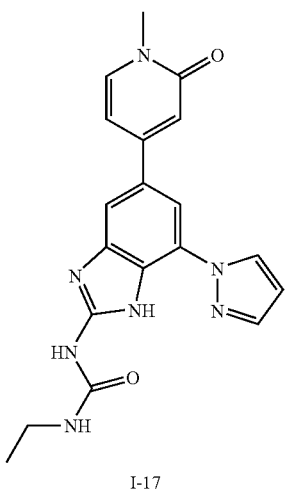
I-17
TABLE 2-continued
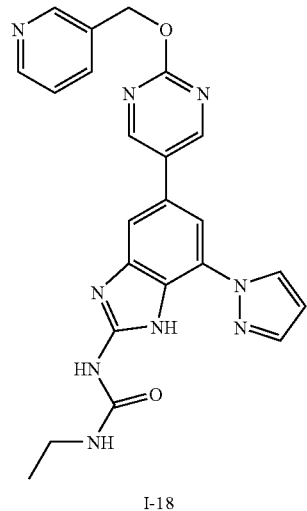
I-18
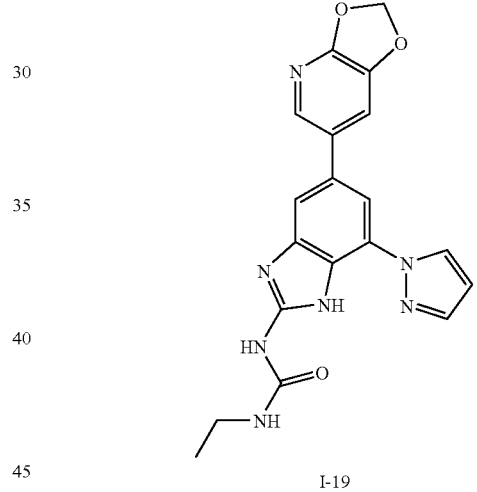
I-19
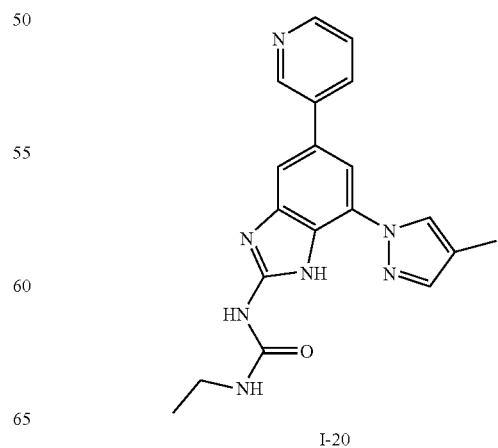
I-20

TABLE 2-continued
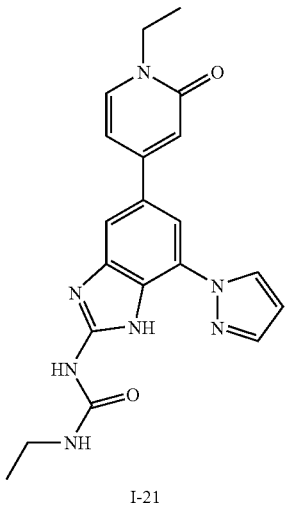
I-21
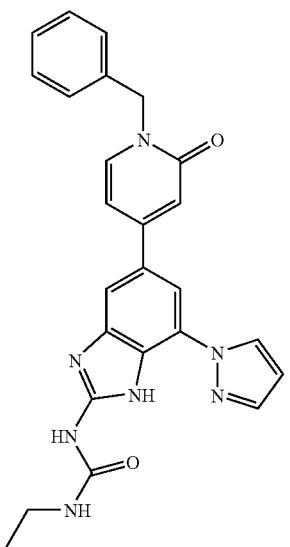
I-22
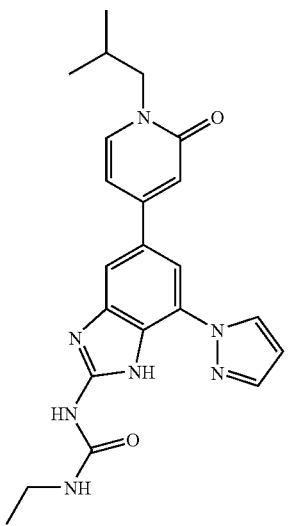
I-23
TABLE 2-continued
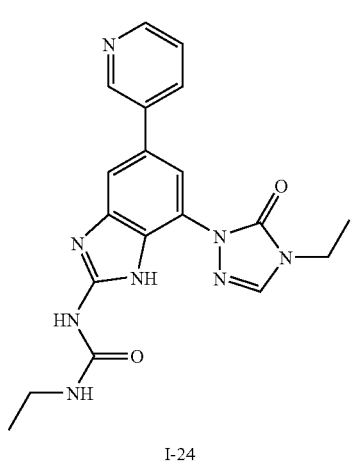
I-24
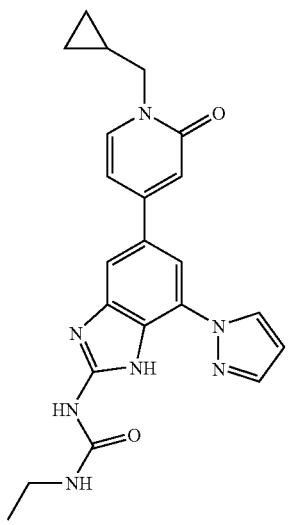
I-25
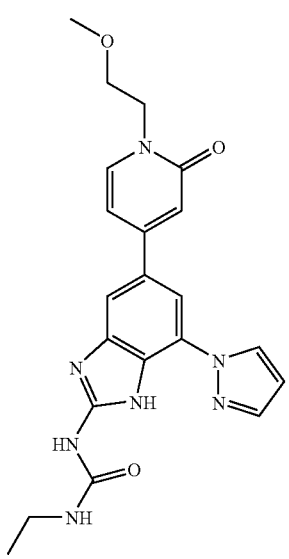
I-26

TABLE 2-continued
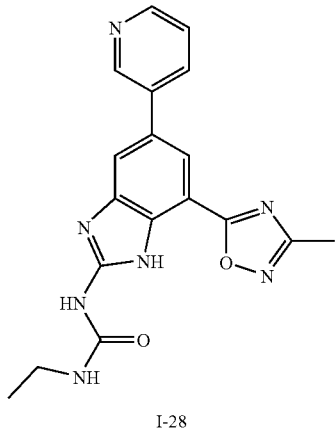
I-28
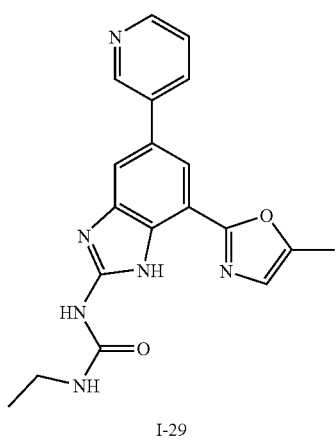
I-29
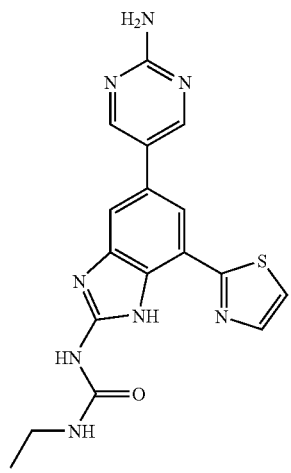
I-30
TABLE 2-continued
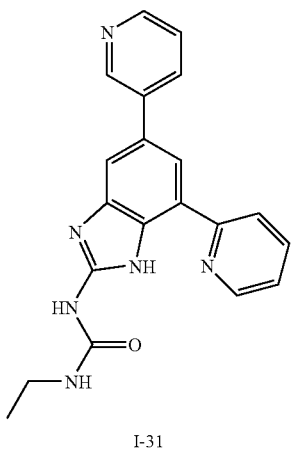
I-31
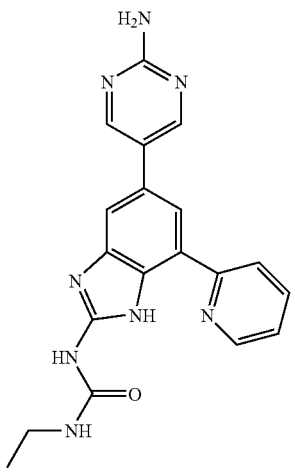
I-32
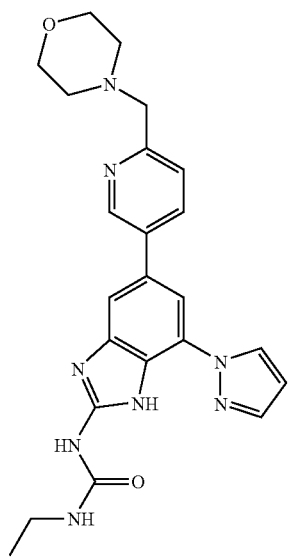
I-35

TABLE 2-continued
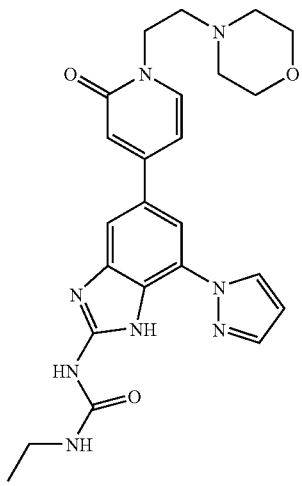
I-37
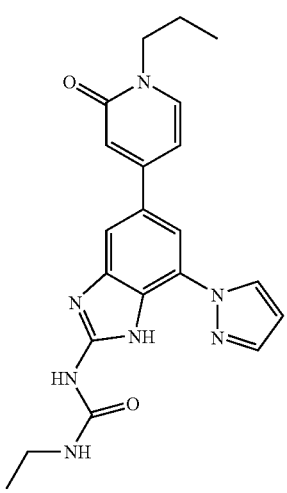
I-38
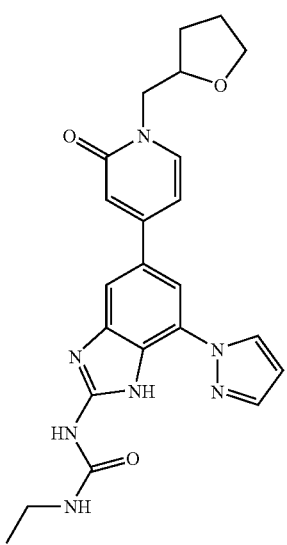
I-39
TABLE 2-continued
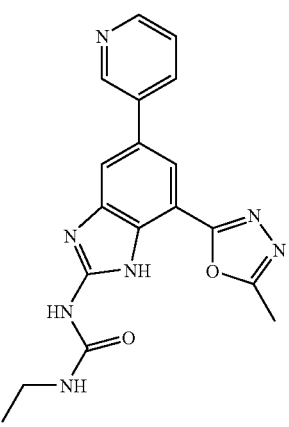
I-40
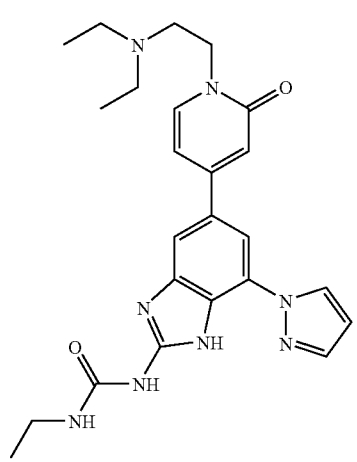
I-41
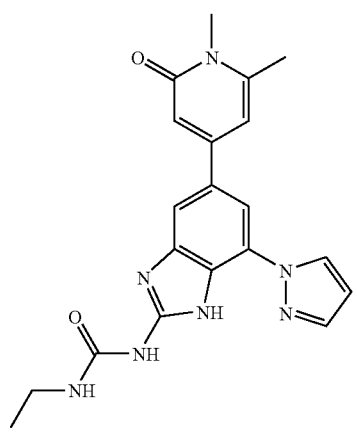
I-42

TABLE 2-continued
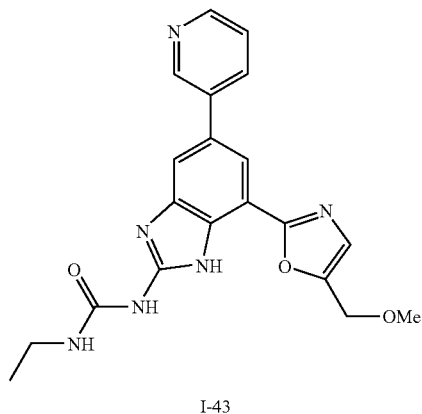
I-43
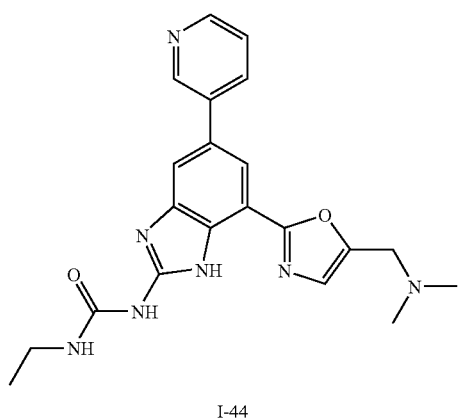
I-44
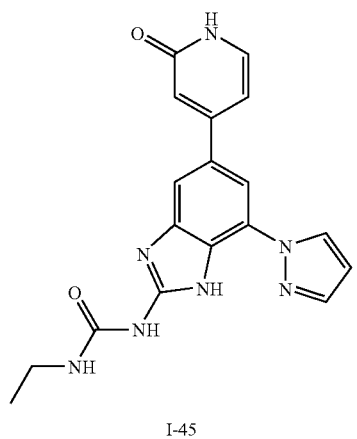
I-45
TABLE 2-continued
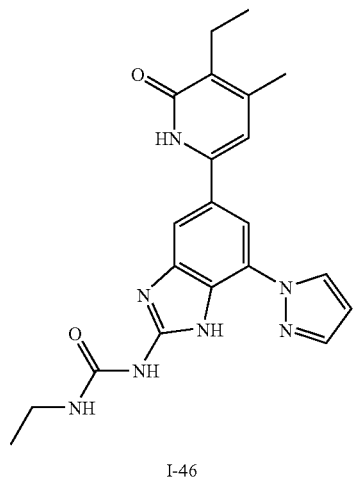
I-46
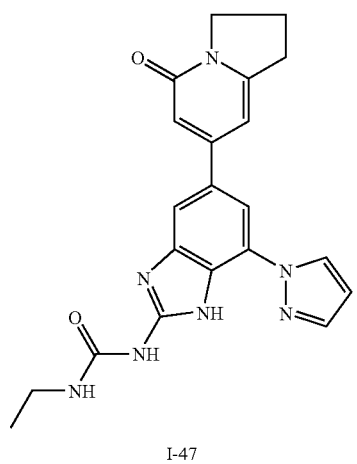
I-47
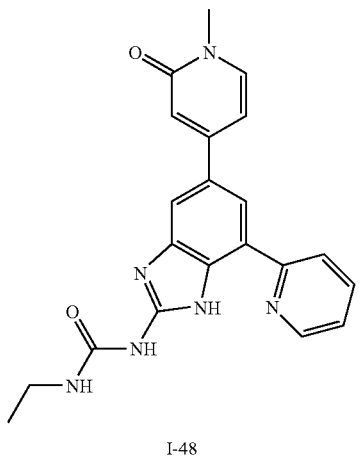
I-48

TABLE 2-continued
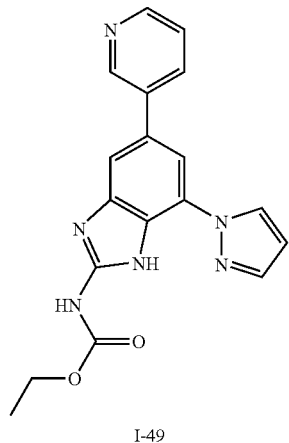
I-49
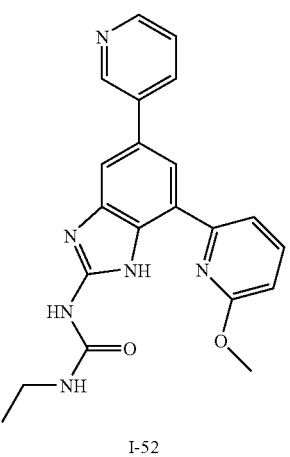
I-52
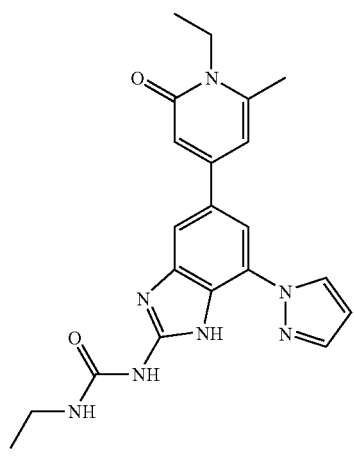
I-50
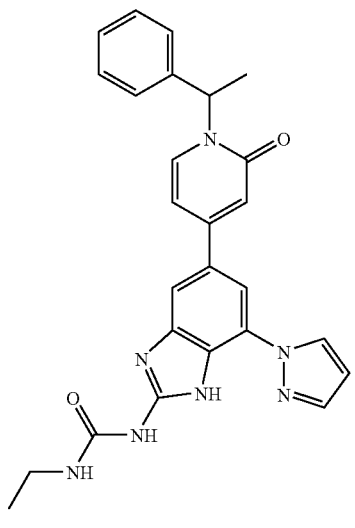
I-53
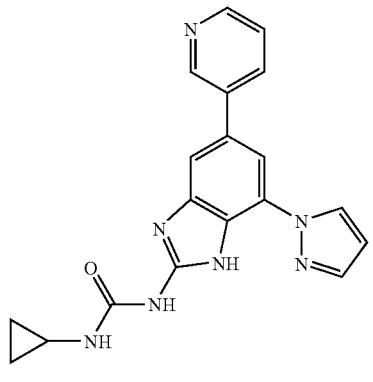
I-51
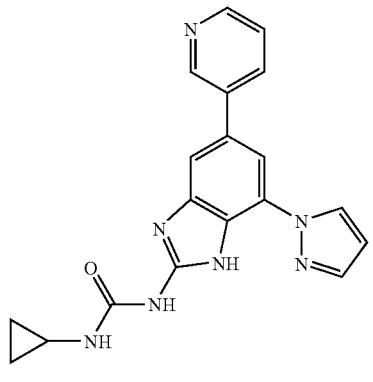
I-54

TABLE 2-continued
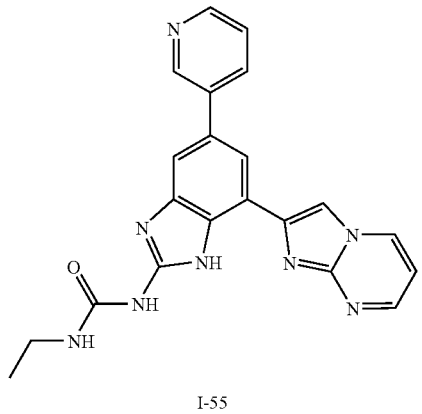
I-55
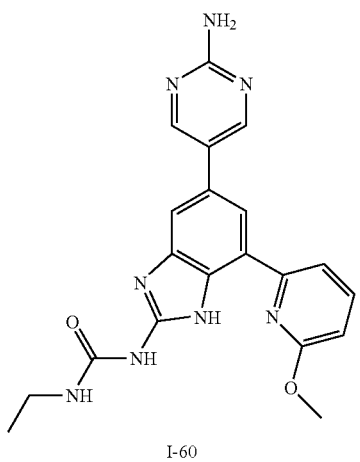
I-60
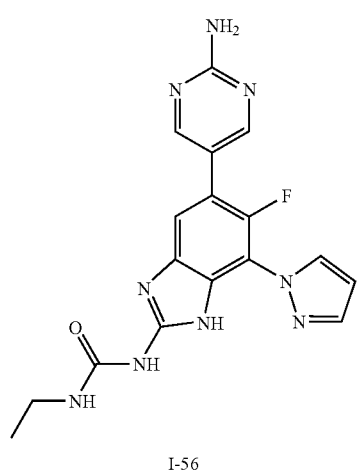
I-56
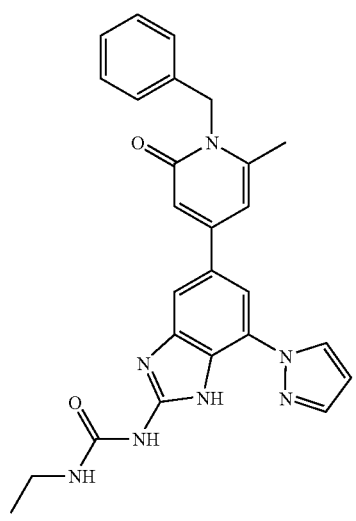
I-61
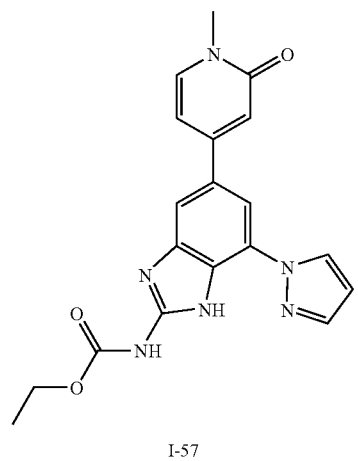
I-57
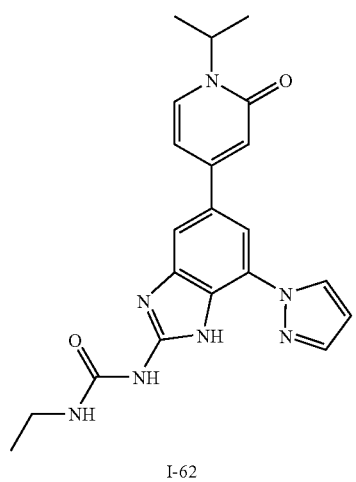
I-62

TABLE 2-continued
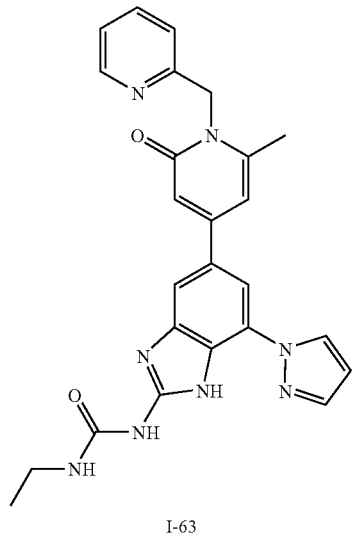
I-63
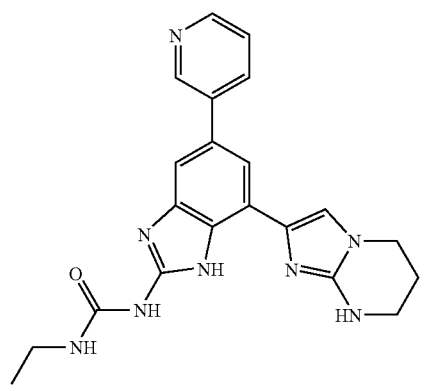
I-64
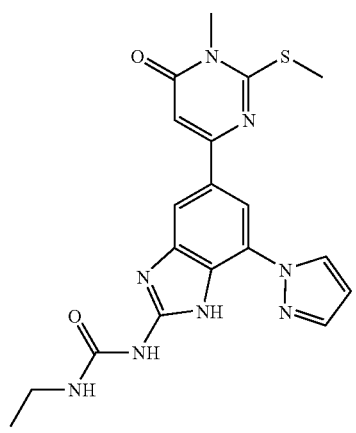
I-65
TABLE 2-continued
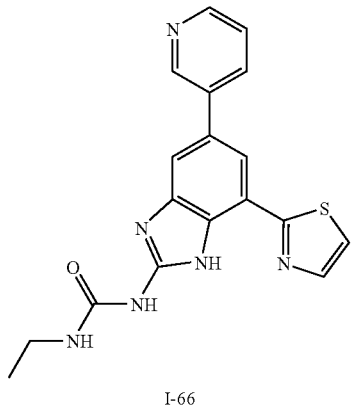
I-66
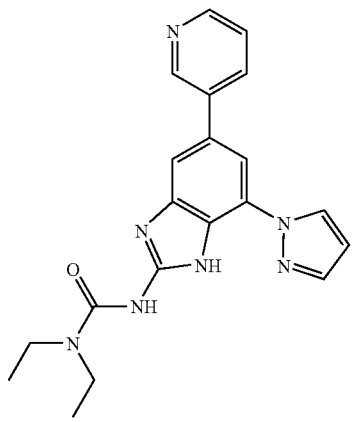
I-67
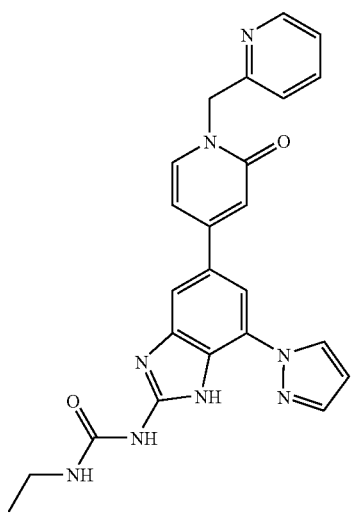
I-68

TABLE 2-continued
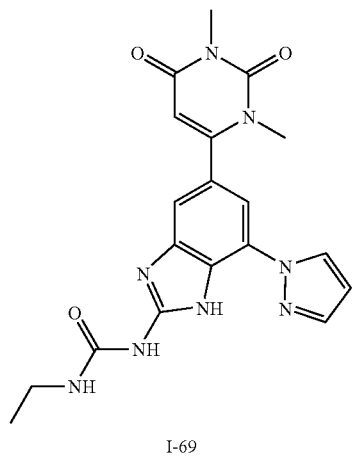
I-69
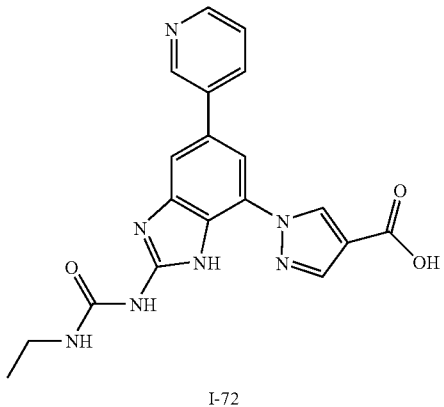
I-72
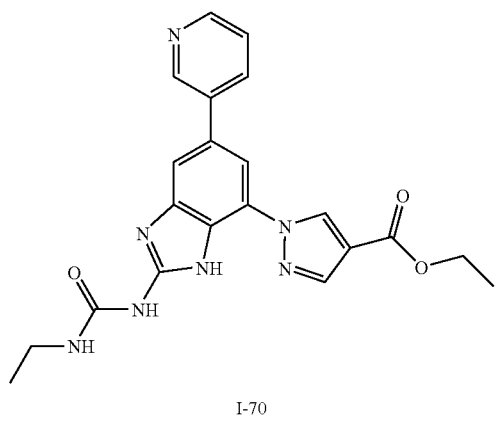
I-70
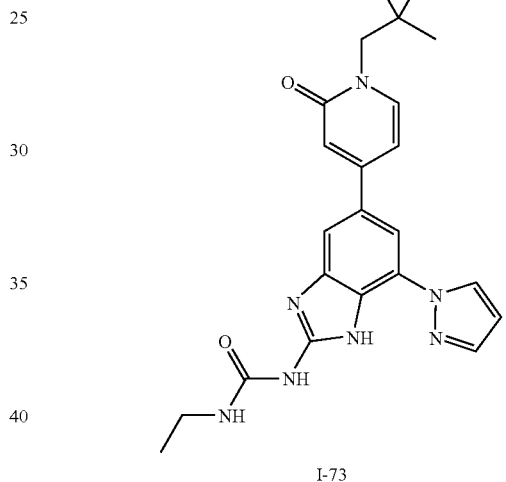
I-73
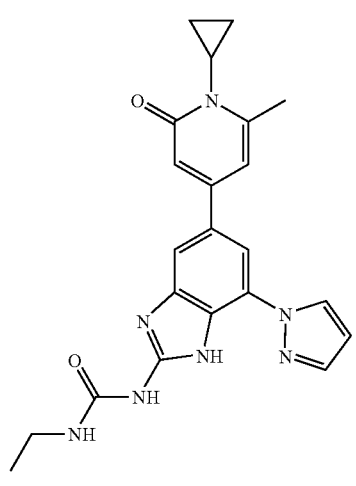
I-71
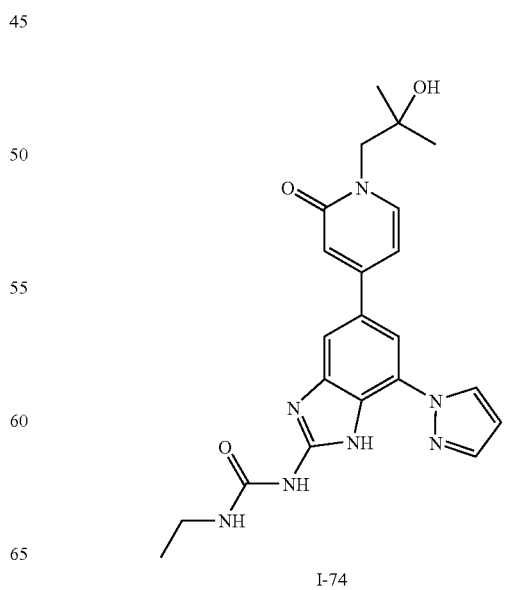
I-74

TABLE 2-continued
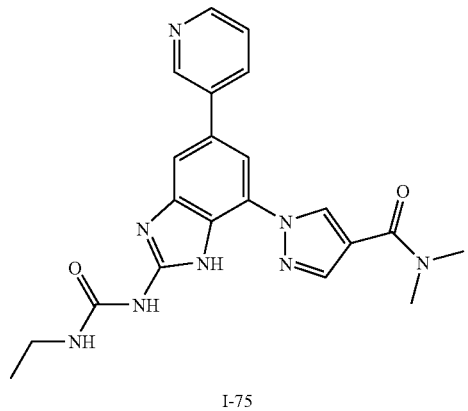
I-75
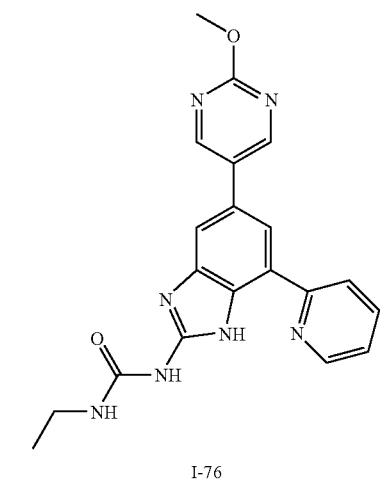
I-76
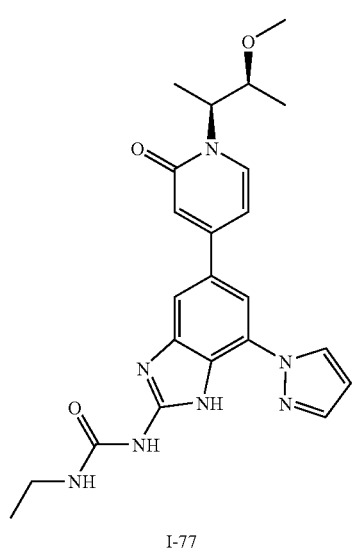
I-77
TABLE 2-continued
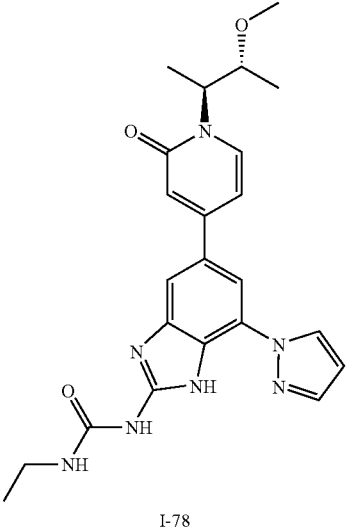
I-78
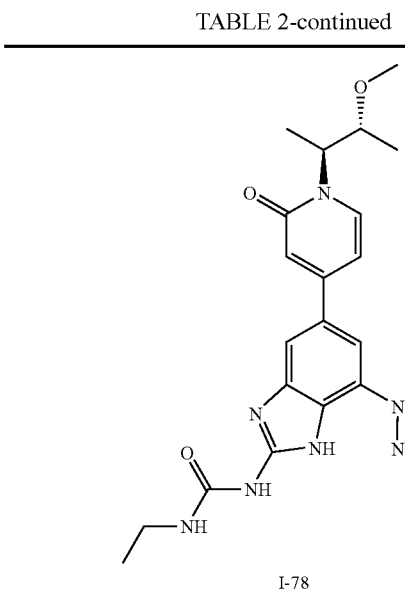
I-79
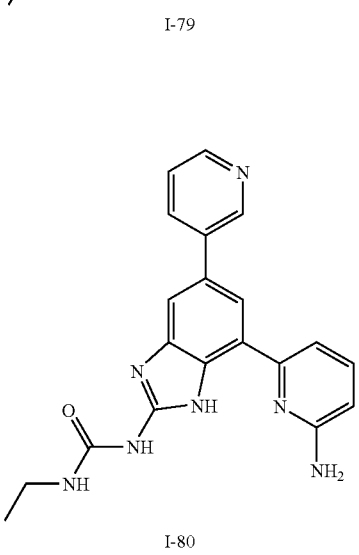
I-80

TABLE 2-continued
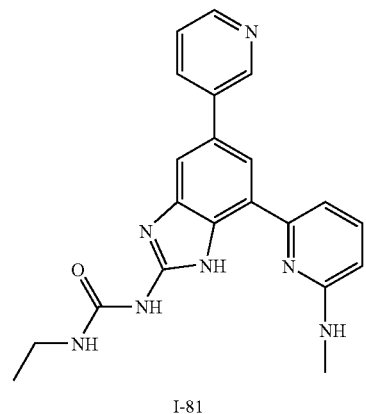
I-81
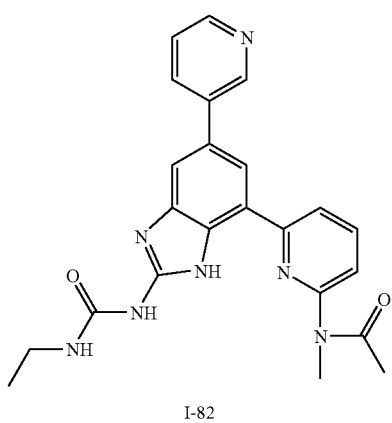
I-82
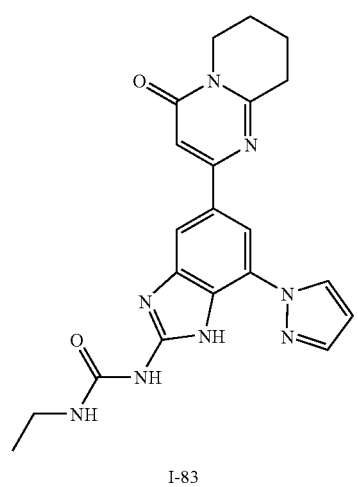
I-83
TABLE 2-continued
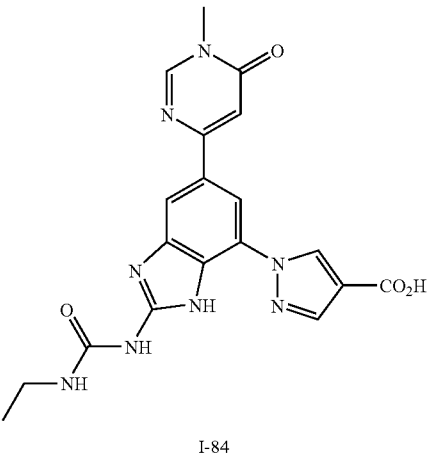
I-84
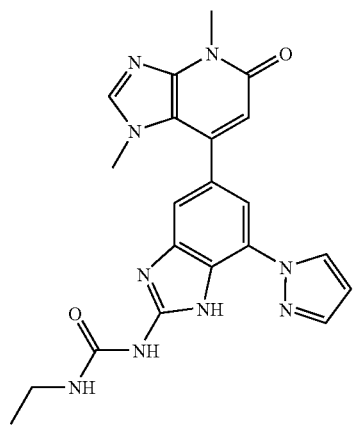
I-85
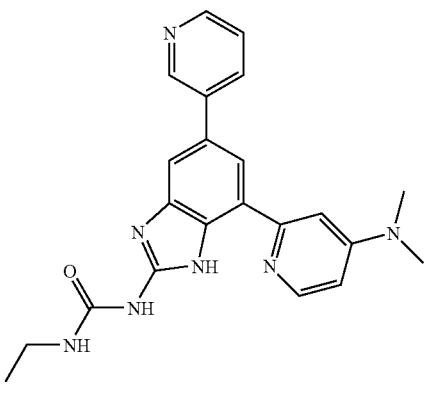
I-86

TABLE 2-continued
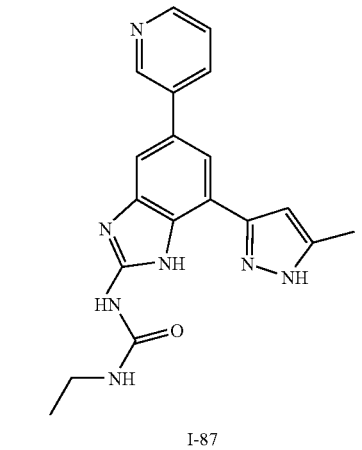
I-87
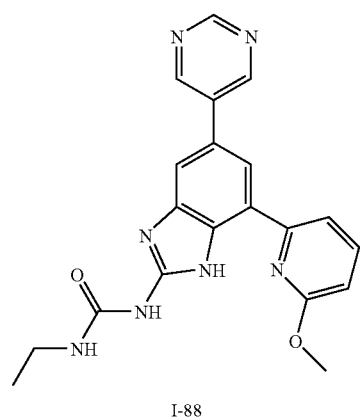
I-88
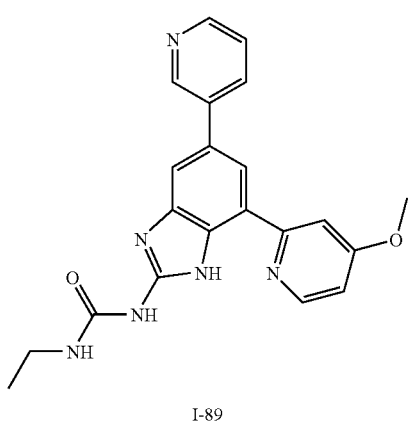
I-89
TABLE 2-continued
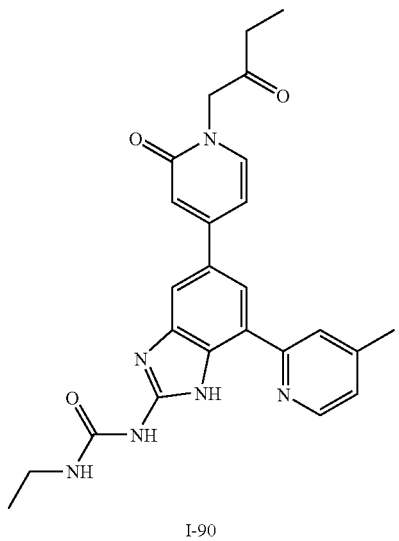
I-90
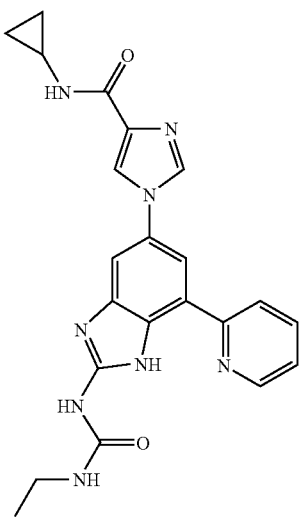
I-91
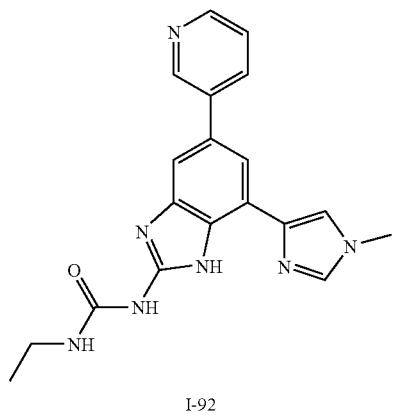
I-92

TABLE 2-continued
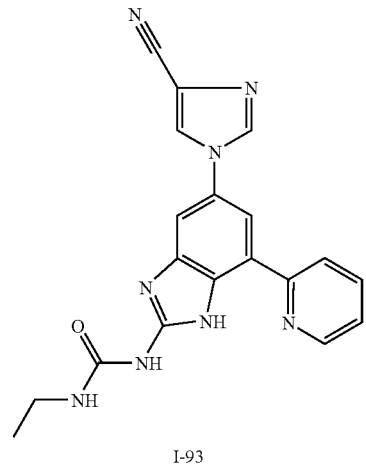
I-93
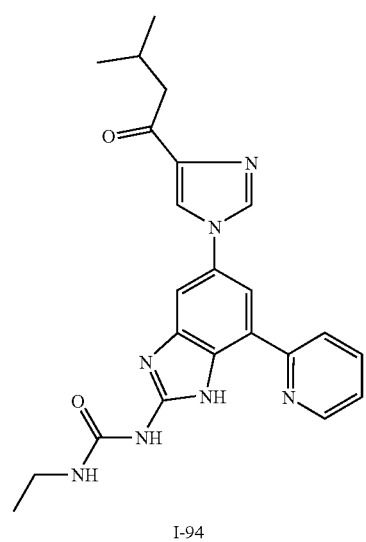
I-94
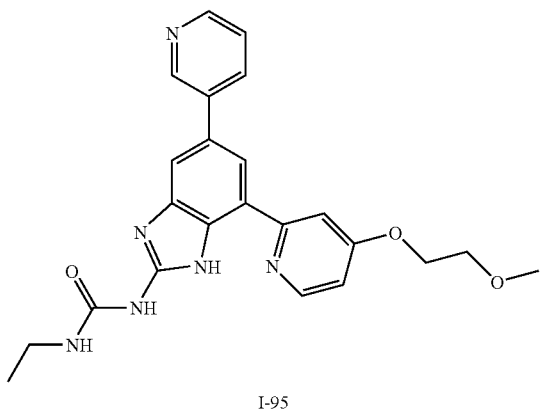
I-95
TABLE 2-continued
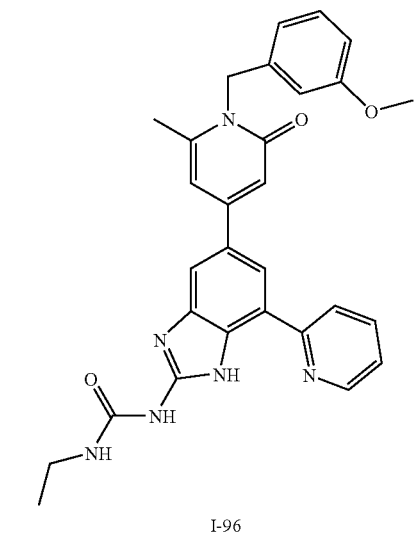
I-96
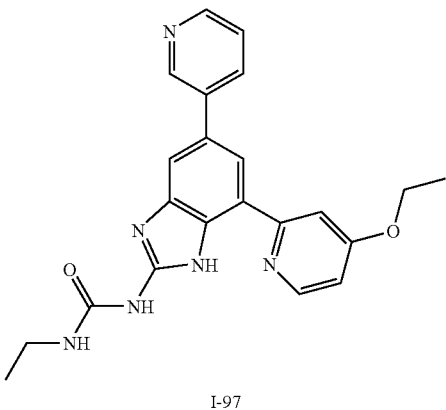
I-97
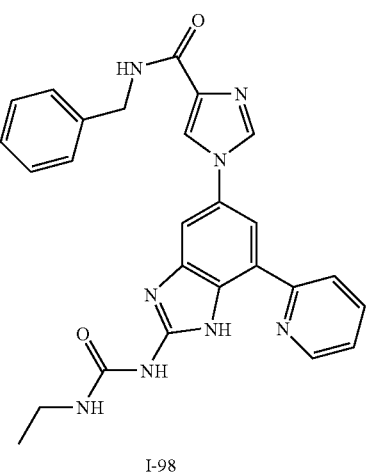
I-98

TABLE 2-continued
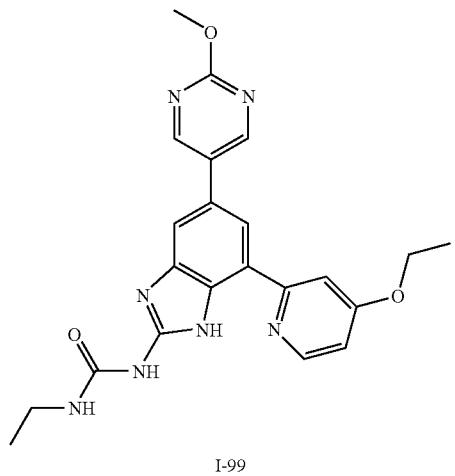
I-99
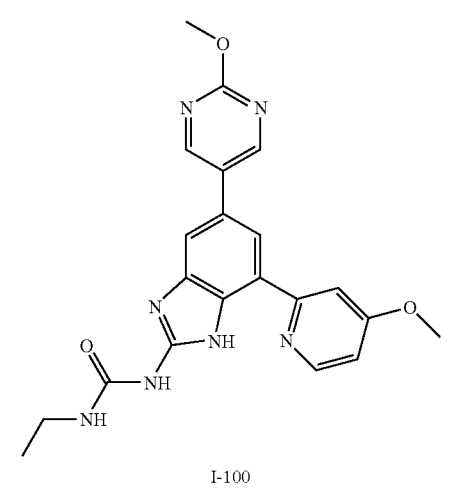
I-100
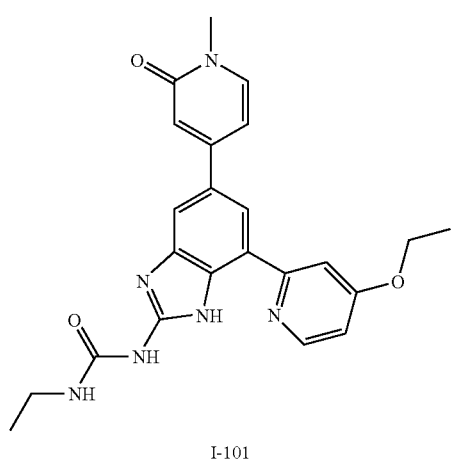
I-101
TABLE 2-continued
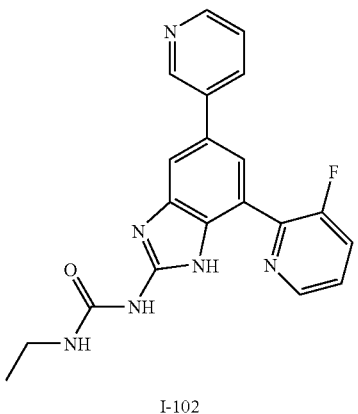
I-102
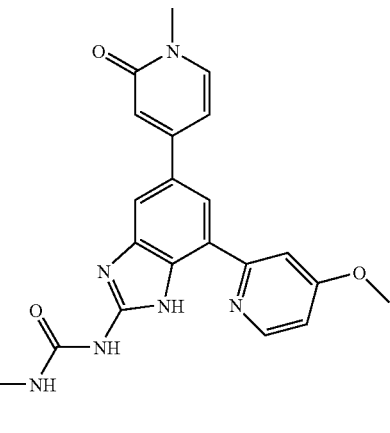
I-103
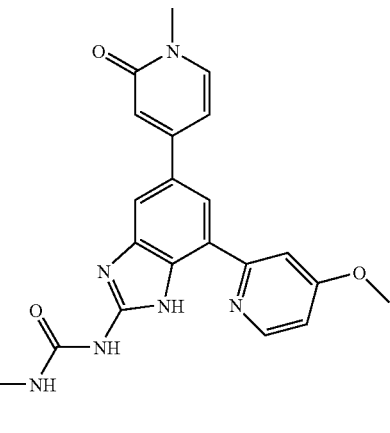
I-104

TABLE 2-continued
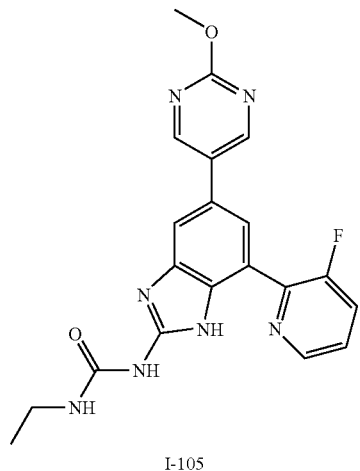
I-105
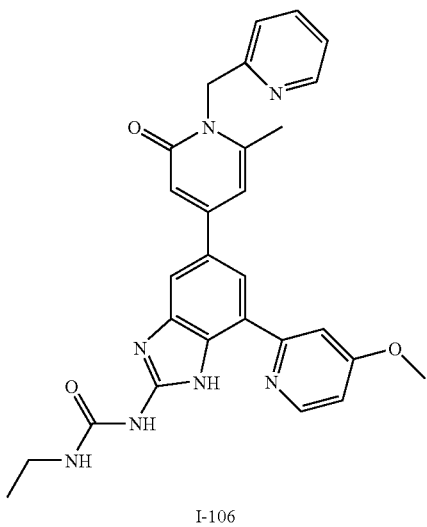
I-106
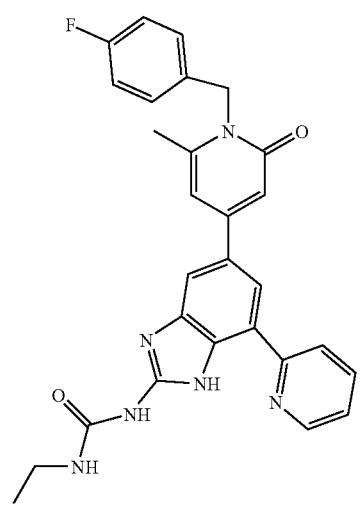
I-107
TABLE 2-continued
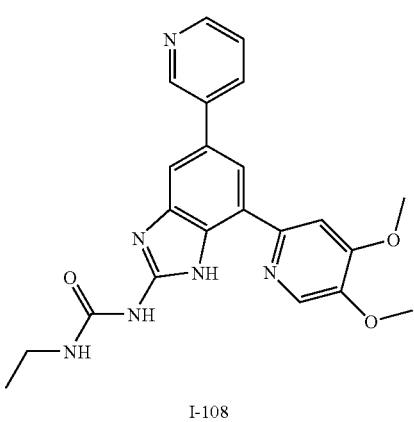
I-108
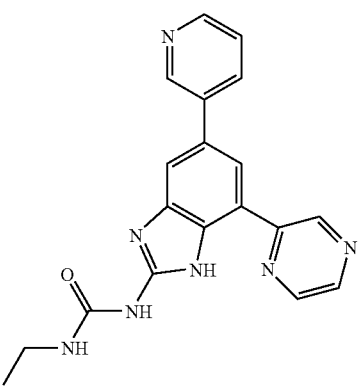
I-109
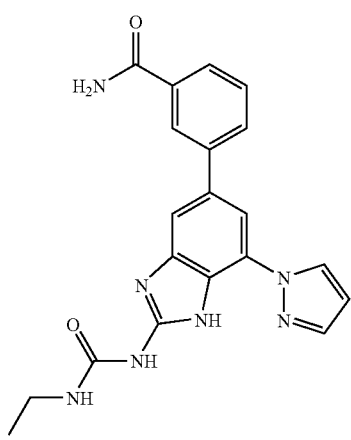
I-110

TABLE 2-continued
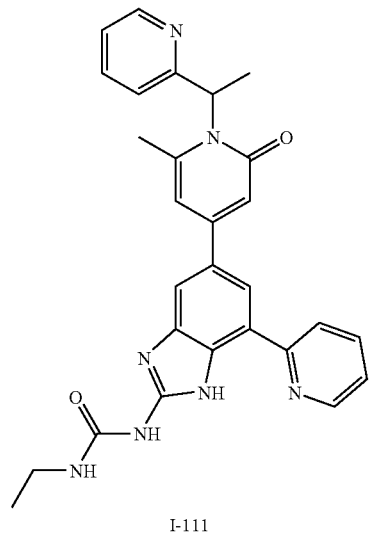
I-111
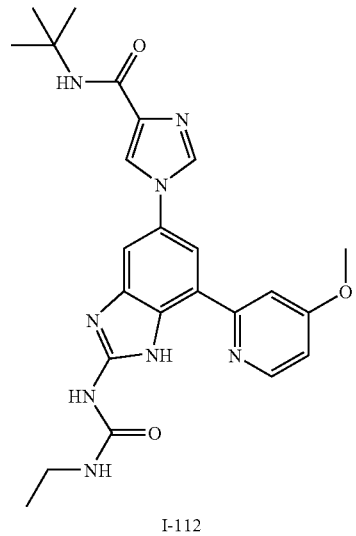
I-112
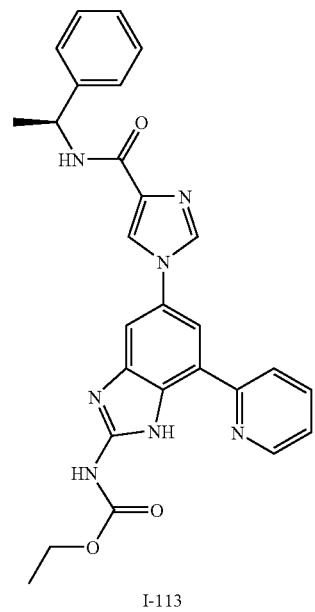
I-113
TABLE 2-continued
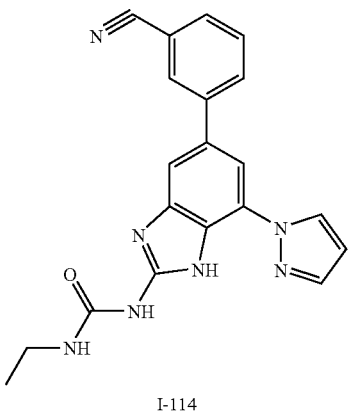
I-114
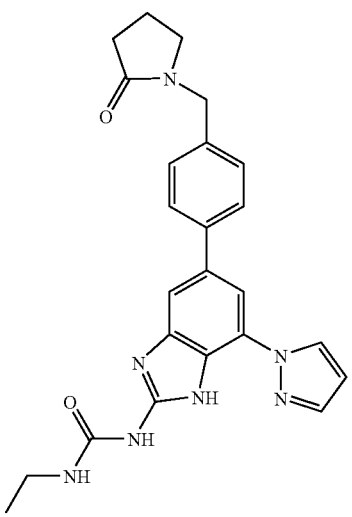
I-115
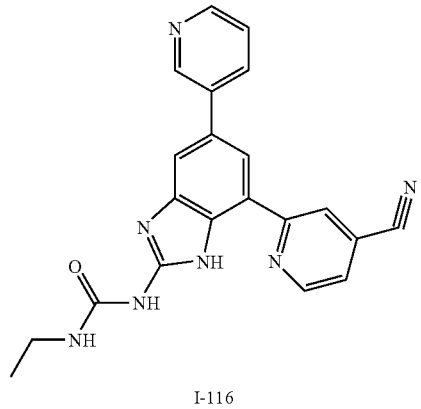
I-116

TABLE 2-continued
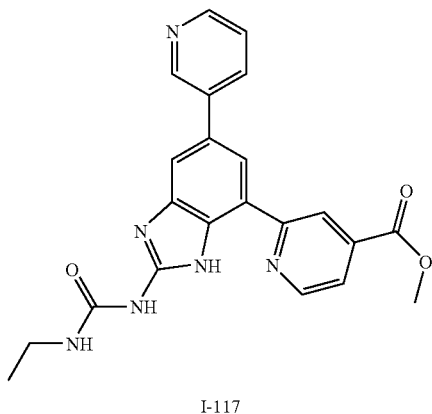
I-117
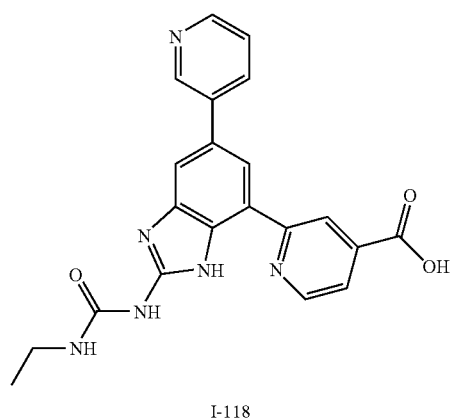
I-118
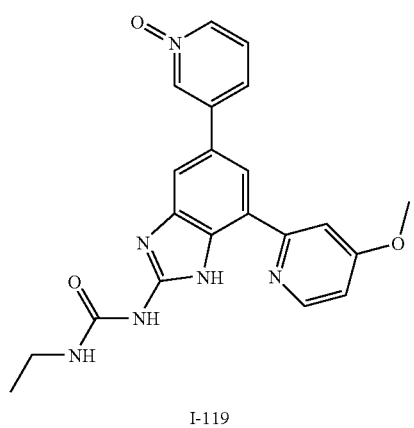
I-119
TABLE 2-continued
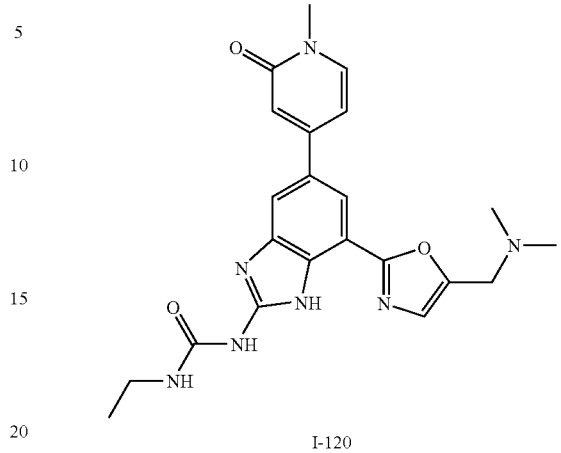
I-120
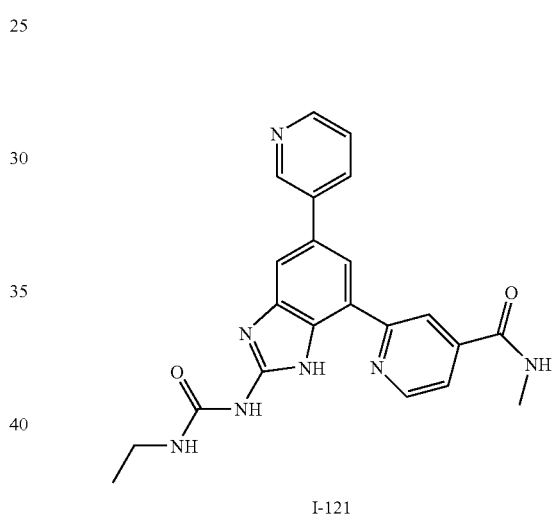
I-121
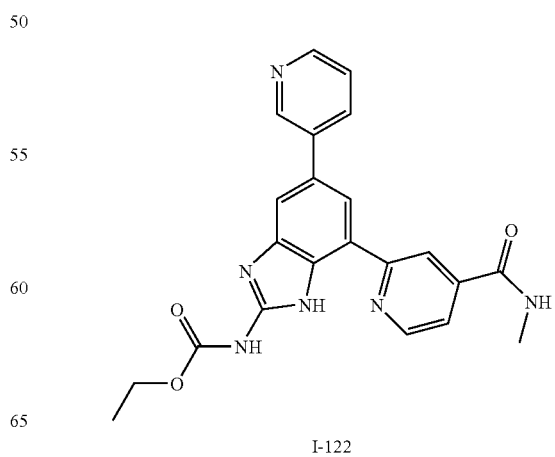
I-122

TABLE 2-continued
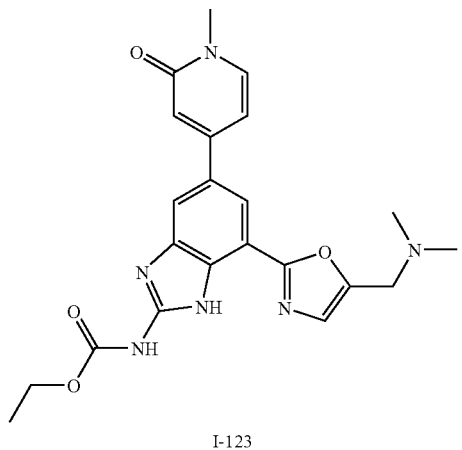
I-123
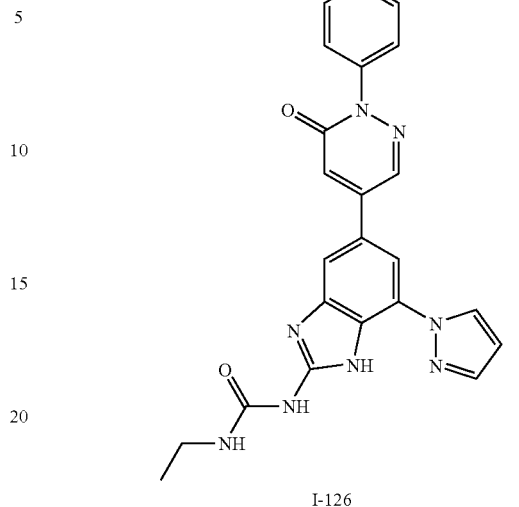
I-126
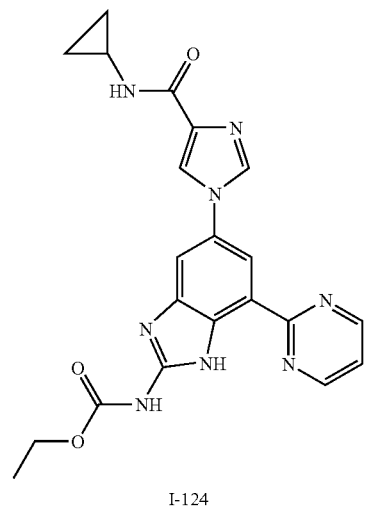
I-124
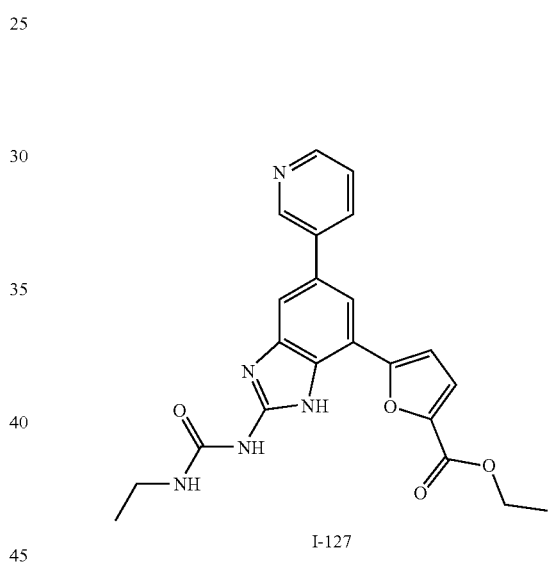
I-127
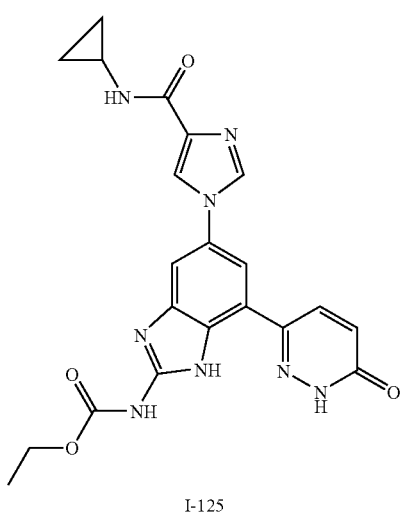
I-125
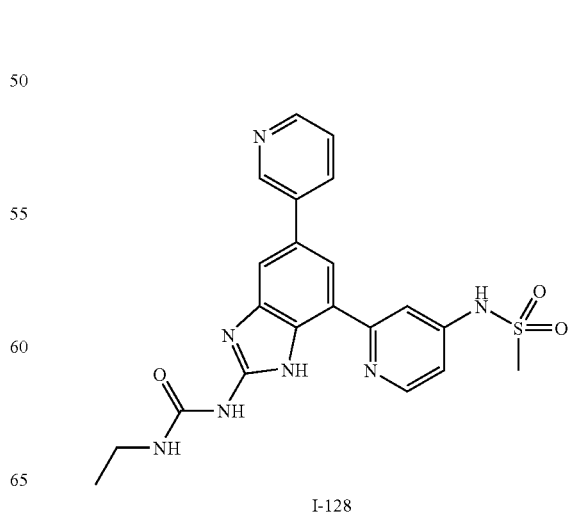
I-128

TABLE 2-continued
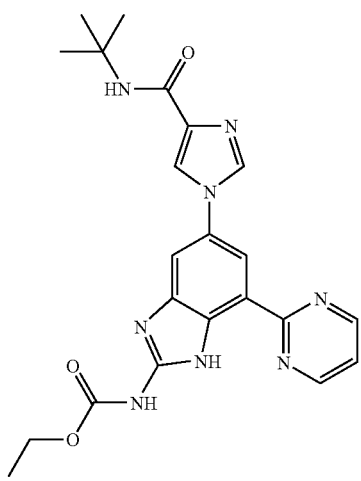
I-129
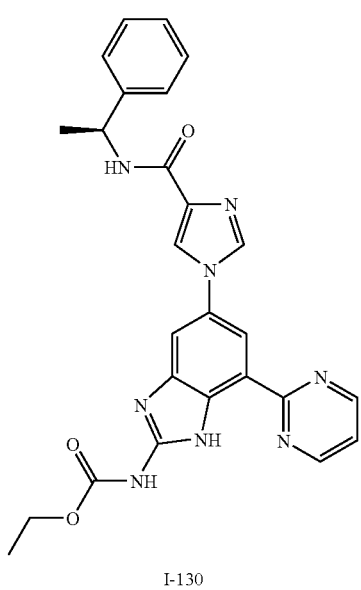
I-130
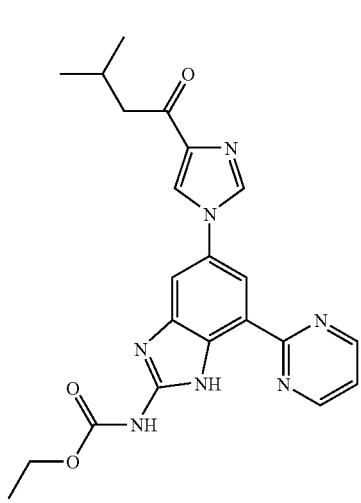
I-131
TABLE 2-continued
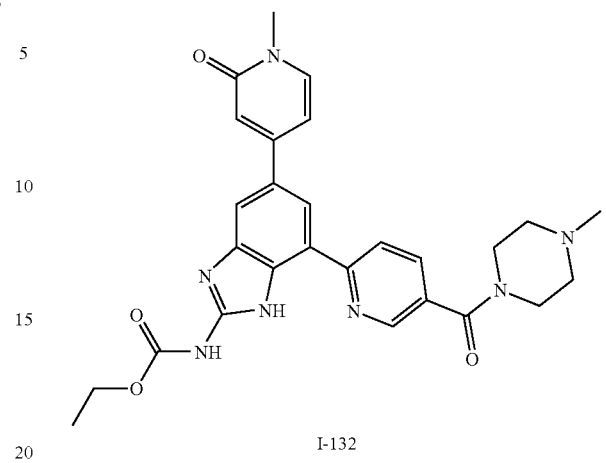
I-132
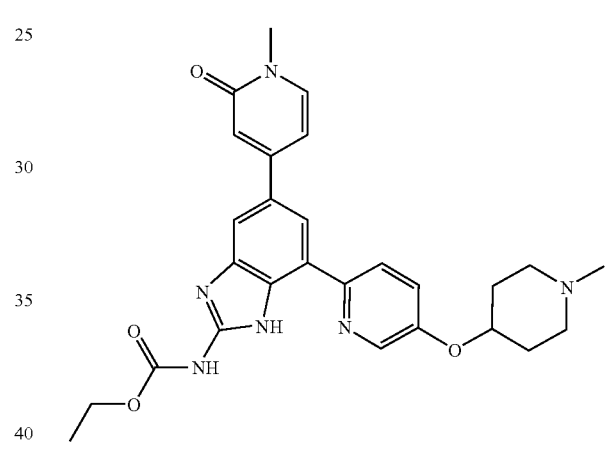
I-133
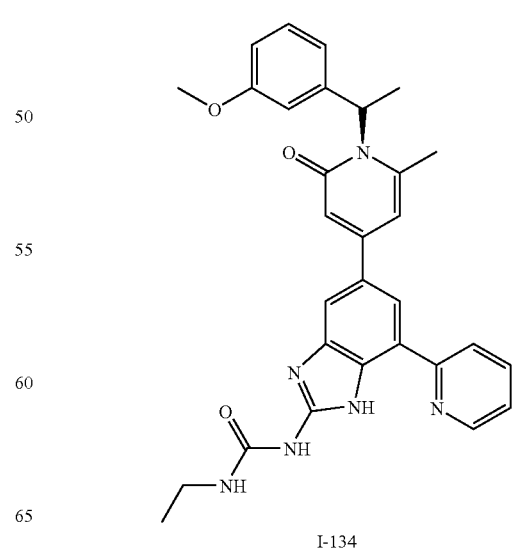
I-134

TABLE 2-continued
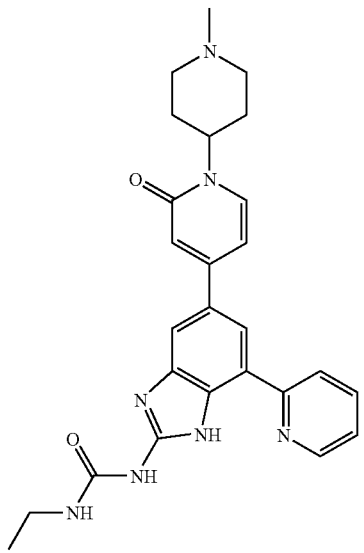
I-135
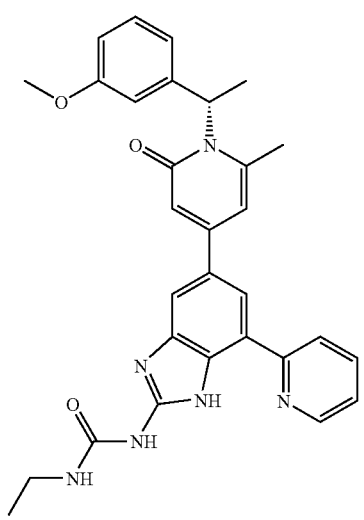
I-136
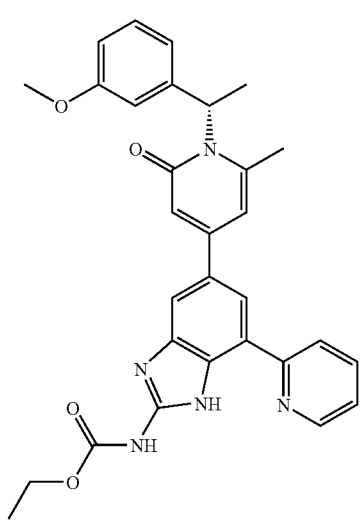
I-137
TABLE 2-continued
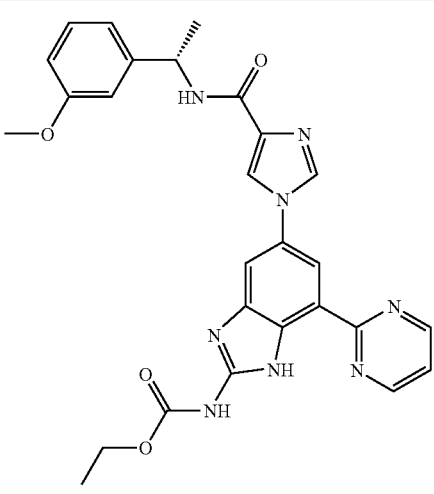
I-138
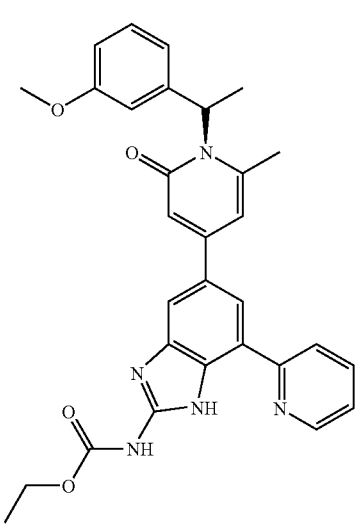
I-139
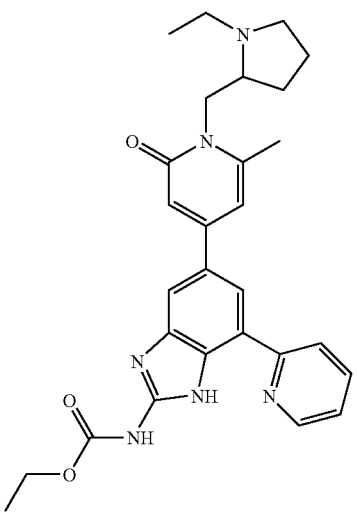
I-140

TABLE 2-continued
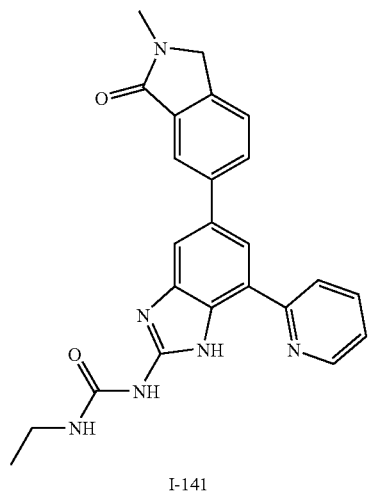
I-141
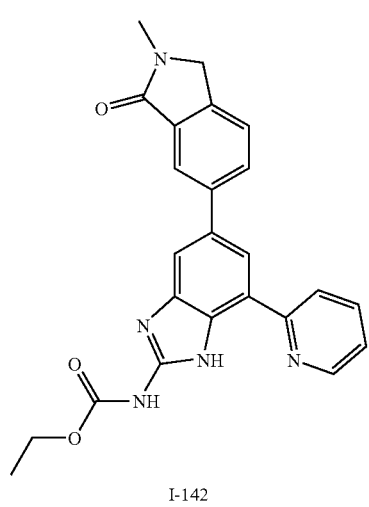
I-142
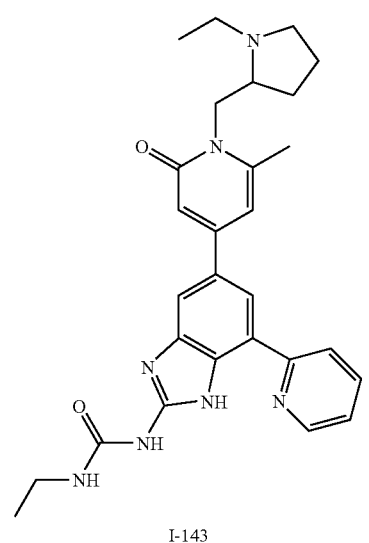
I-143
TABLE 2-continued
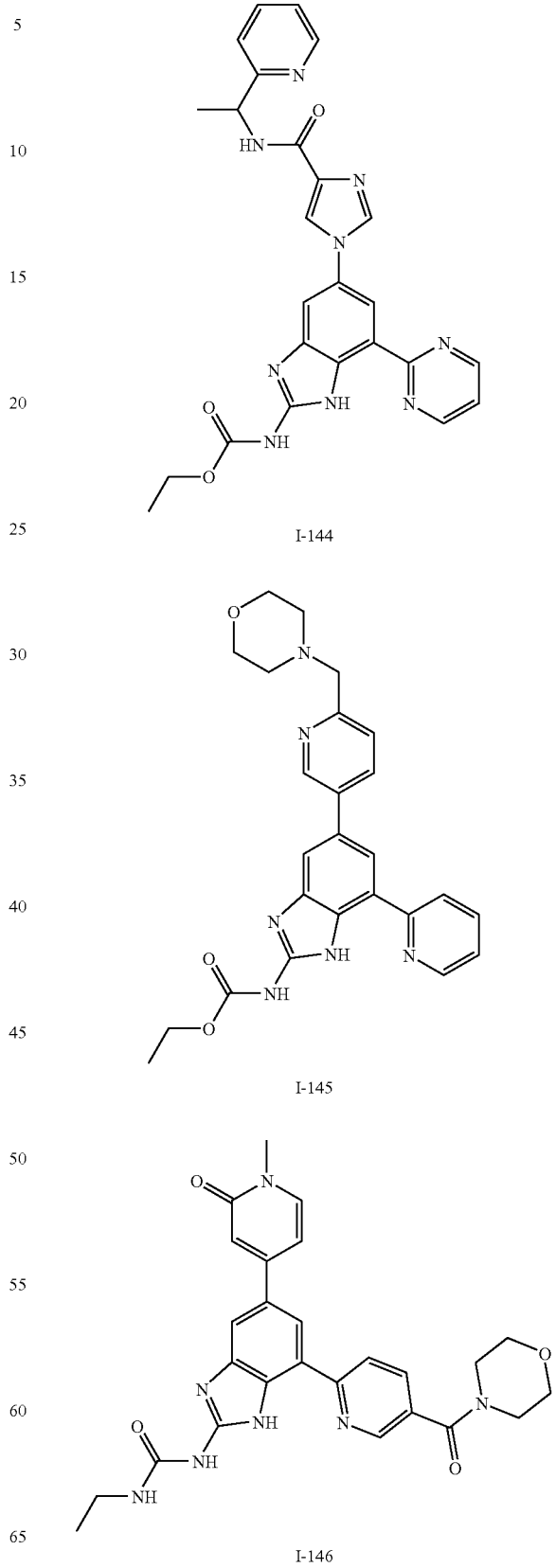
I-144
I-145
I-146

TABLE 2-continued
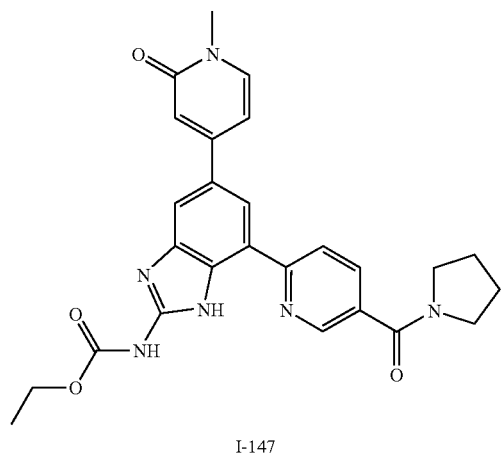
I-147
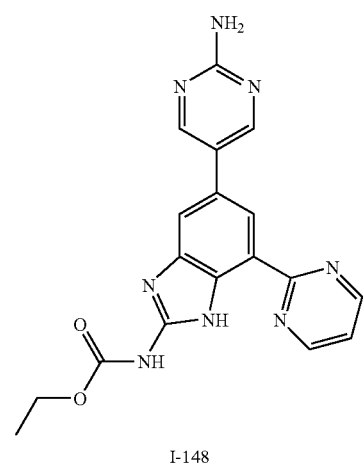
I-148
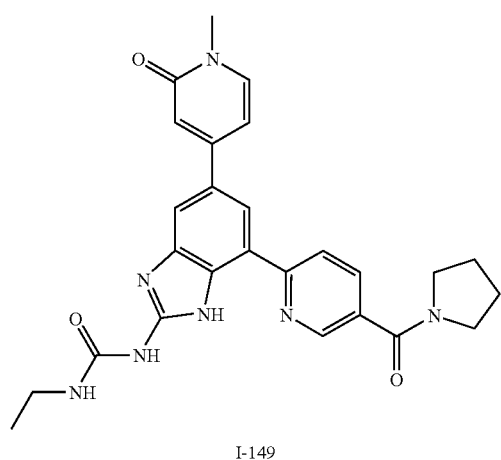
I-149
TABLE 2-continued
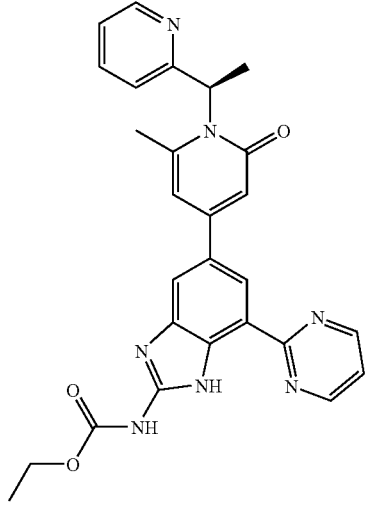
I-150
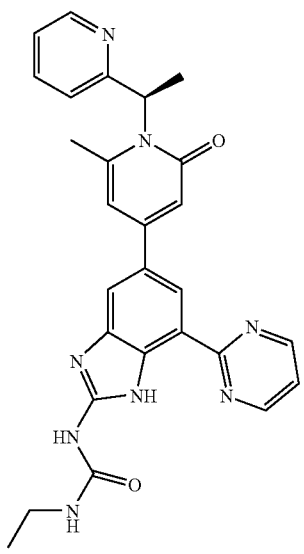
I-151
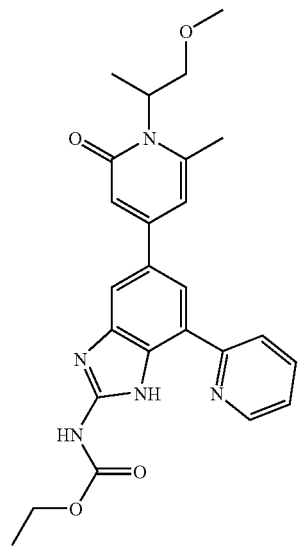
I-152

TABLE 2-continued
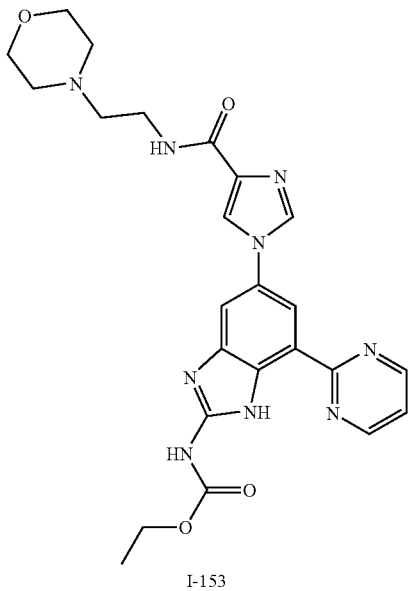
I-153
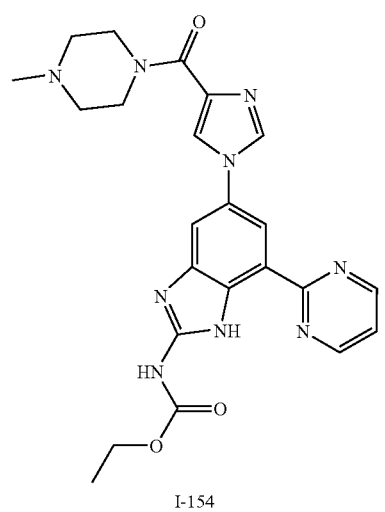
I-154
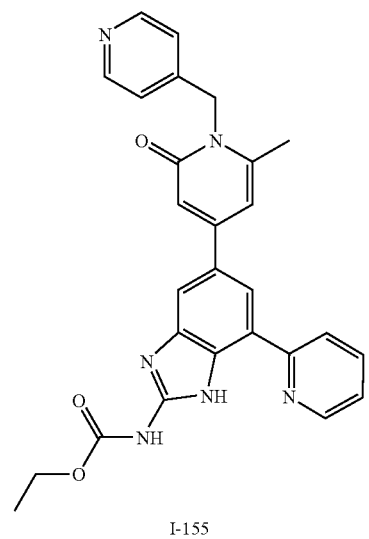
I-155
TABLE 2-continued
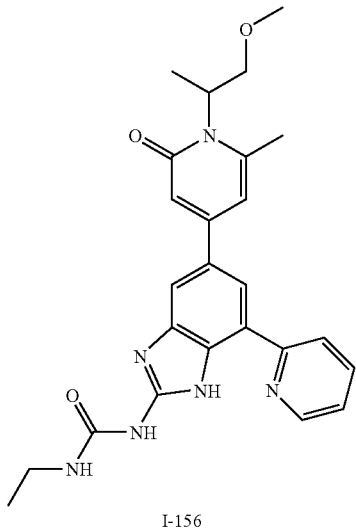
I-156
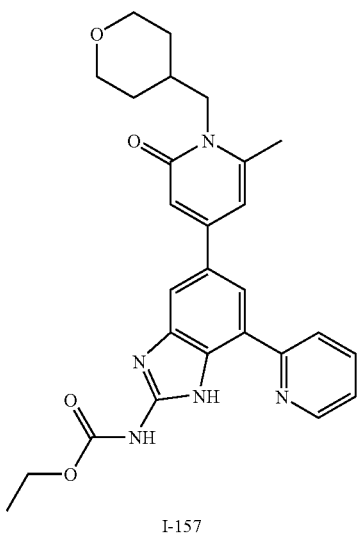
I-157
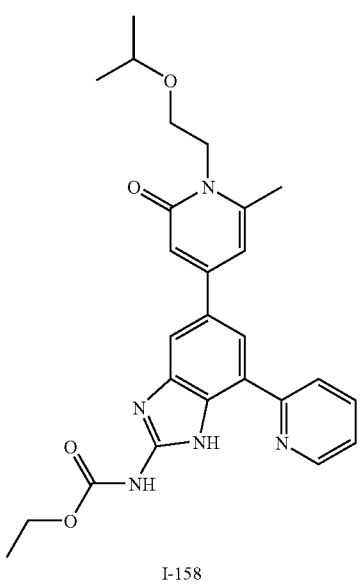
I-158

TABLE 2-continued
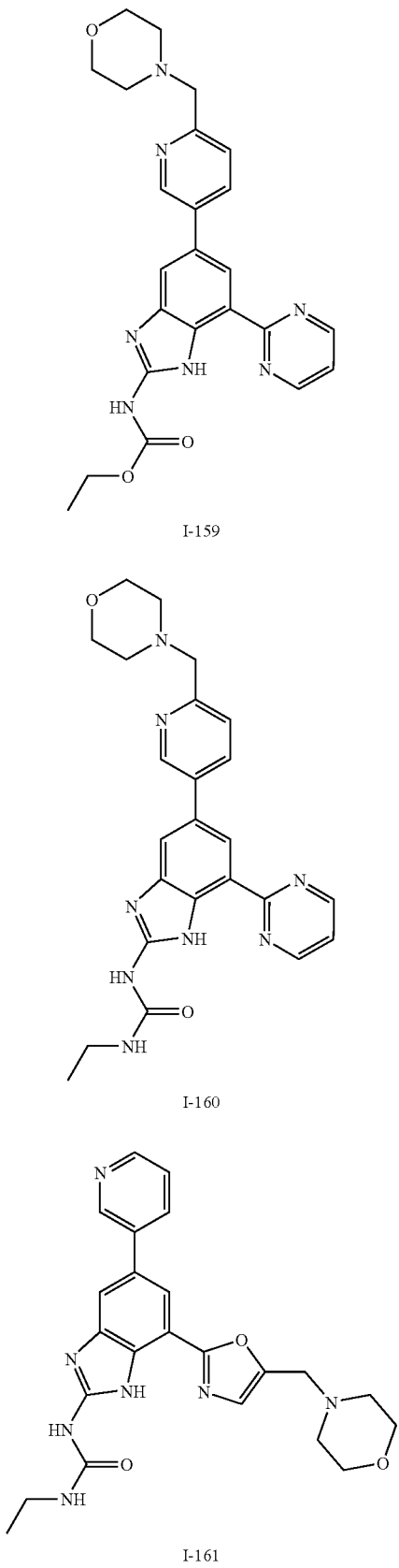
I-159
I-160
I-161
TABLE 2-continued
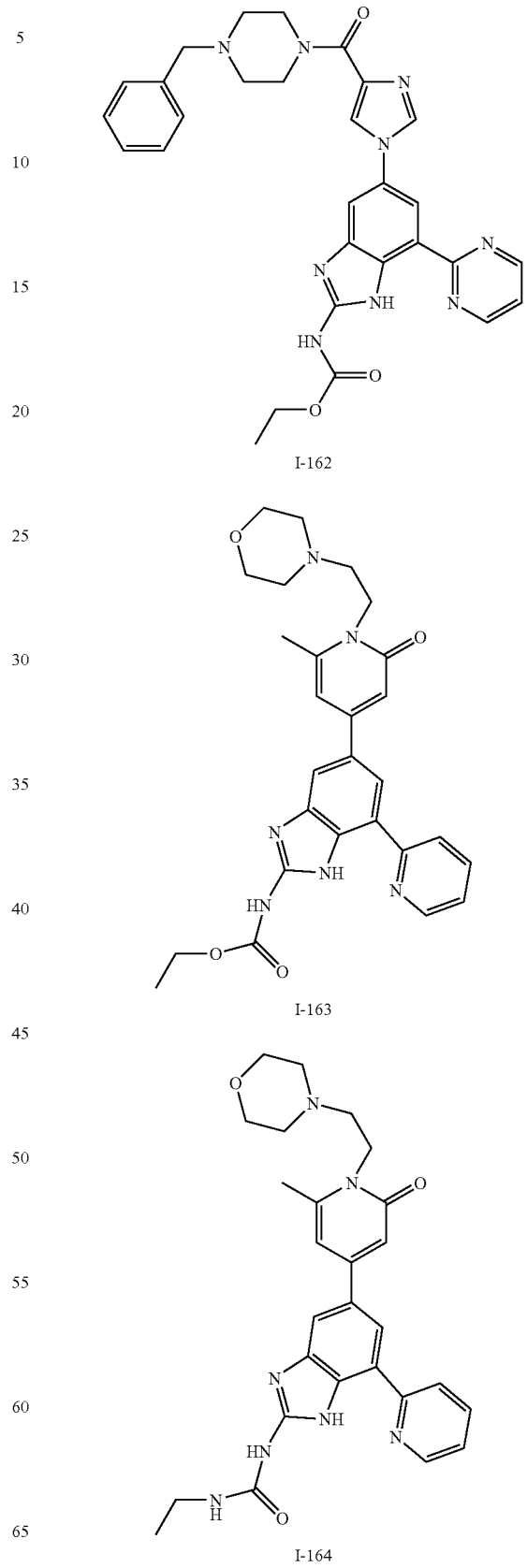
I-162
I-163
I-164

TABLE 2-continued
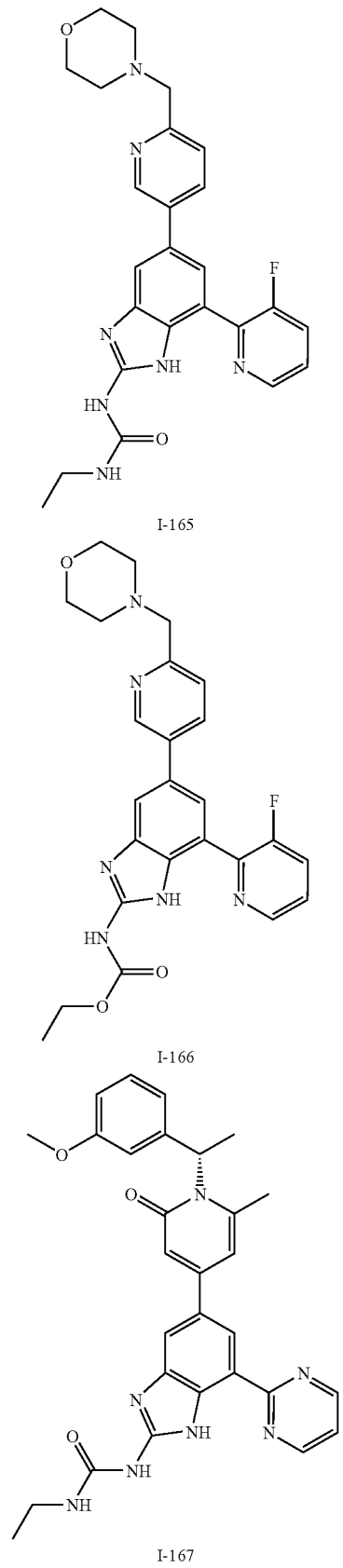
I-165
I-166
I-167
TABLE 2-continued
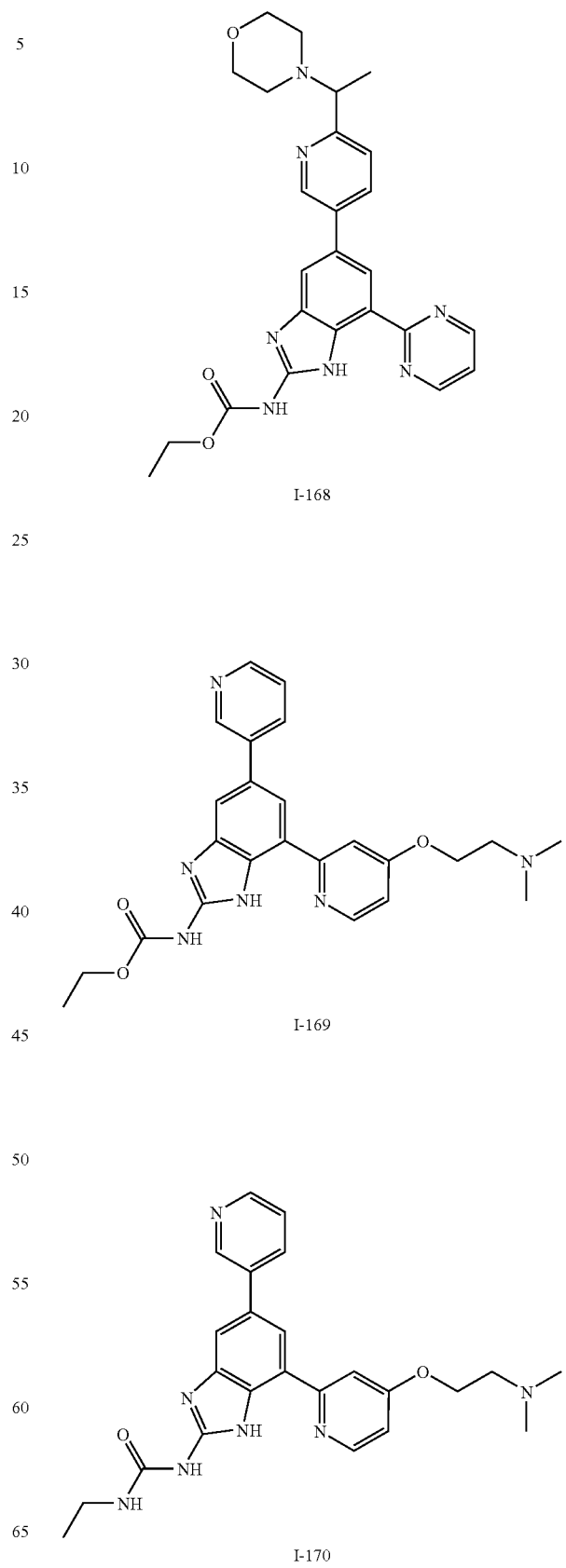
I-168
I-169
I-170

TABLE 2-continued
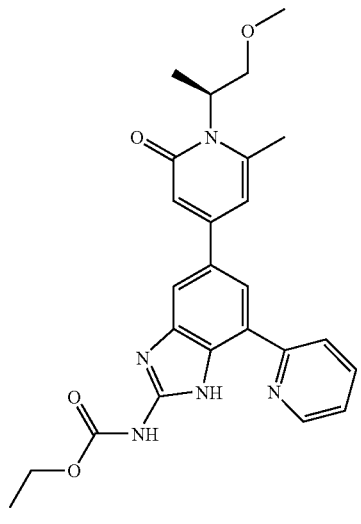
I-171
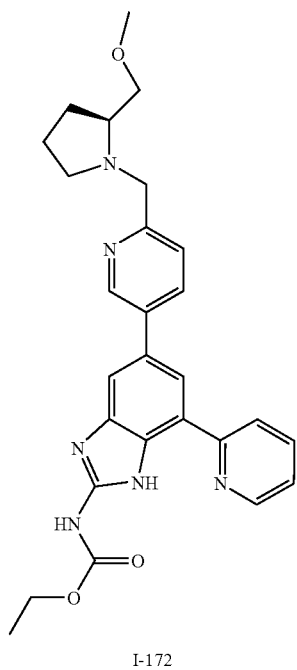
I-172
TABLE 2-continued
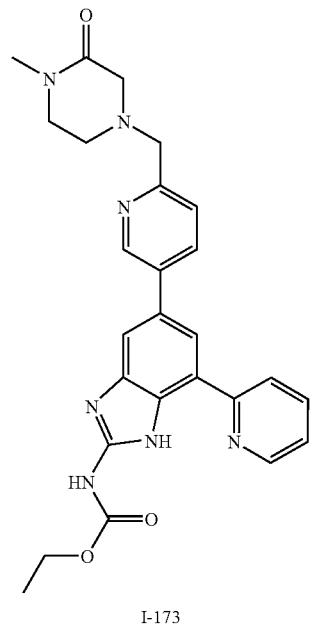
I-173
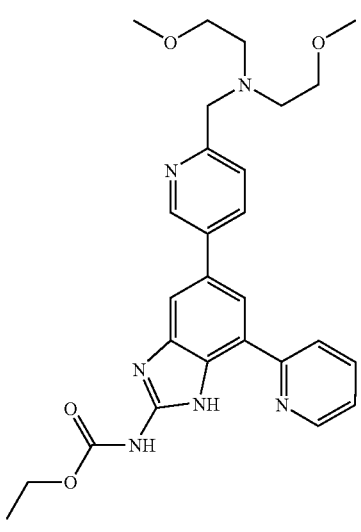
I-174

TABLE 2-continued
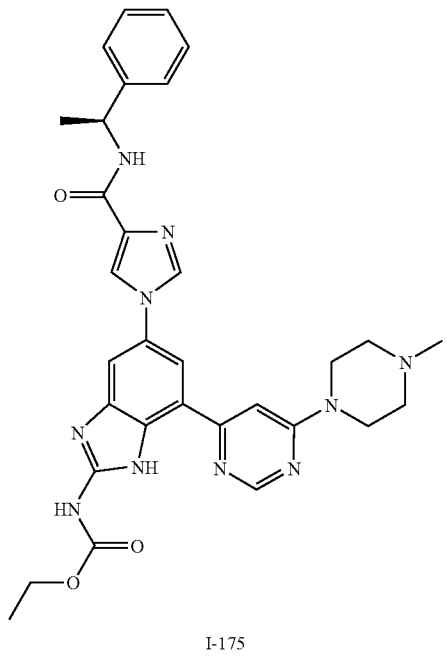
I-175
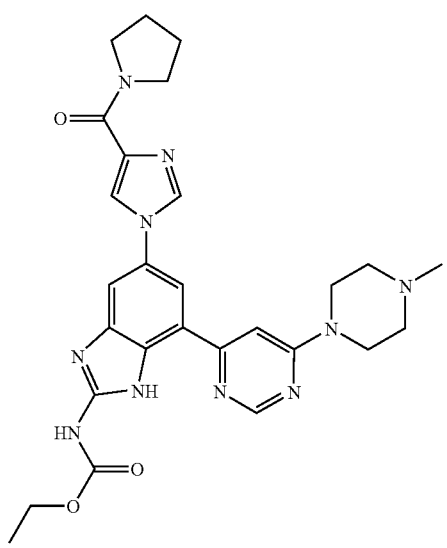
I-176
TABLE 2-continued
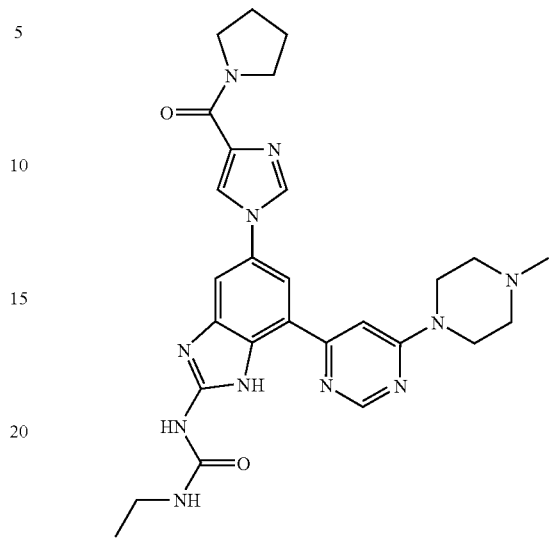
I-177
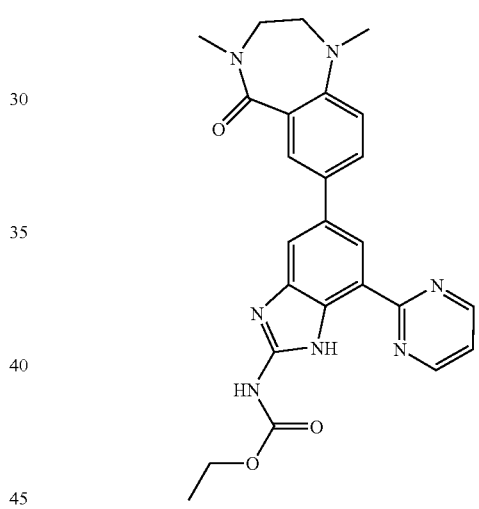
I-178
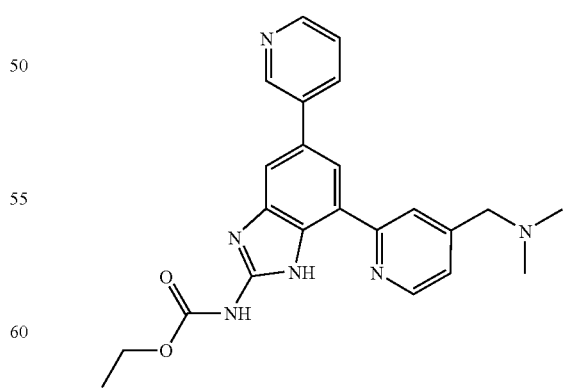
I-179

TABLE 2-continued
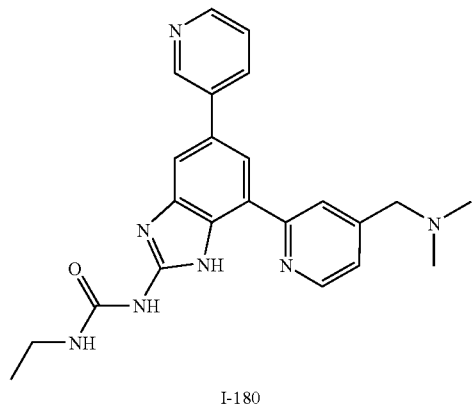
I-180
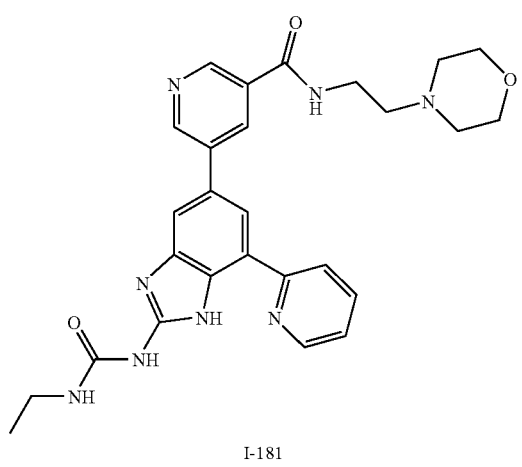
I-181
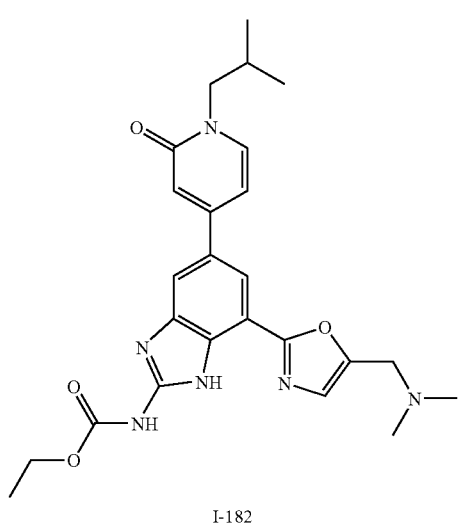
I-182
TABLE 2-continued
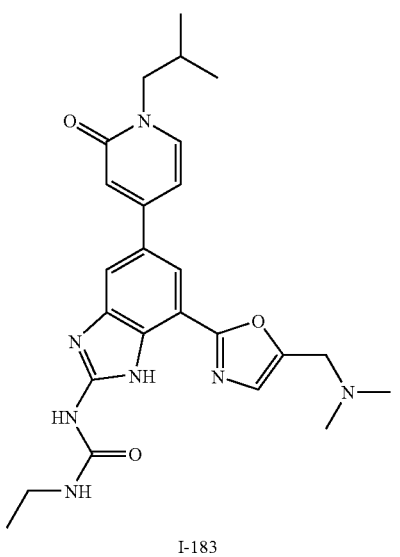
I-183
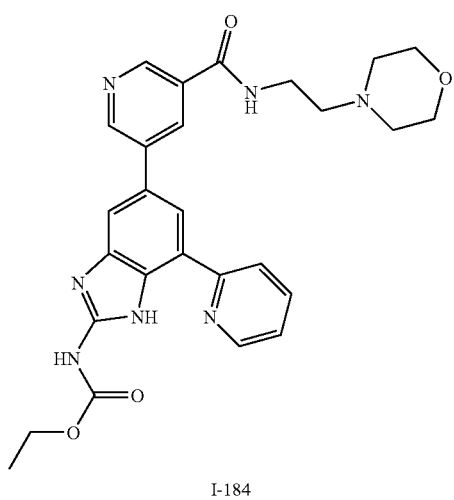
I-184
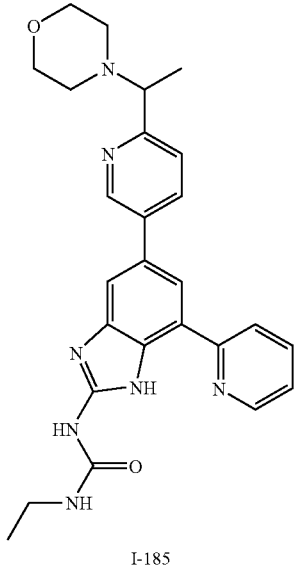
I-185

TABLE 2-continued
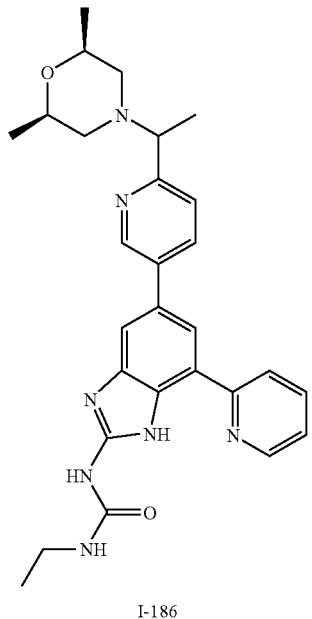
I-186
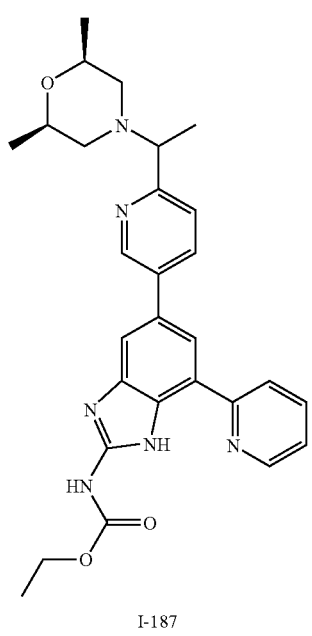
I-187
TABLE 2-continued
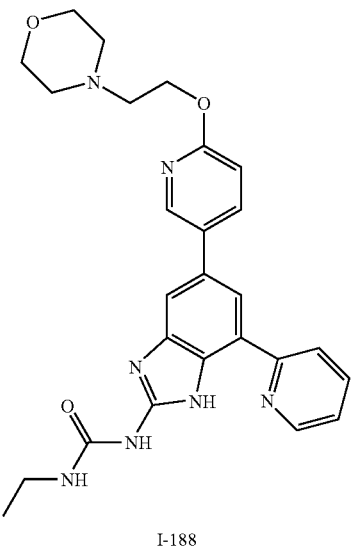
I-188
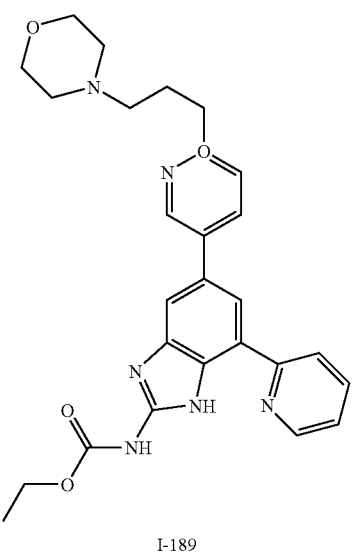
I-189
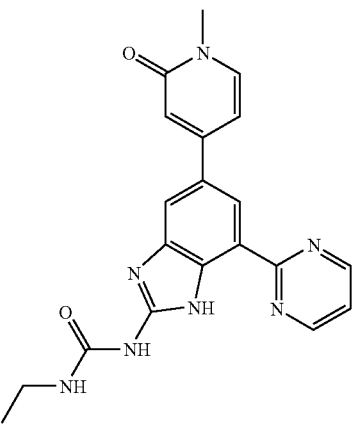
I-190

TABLE 2-continued
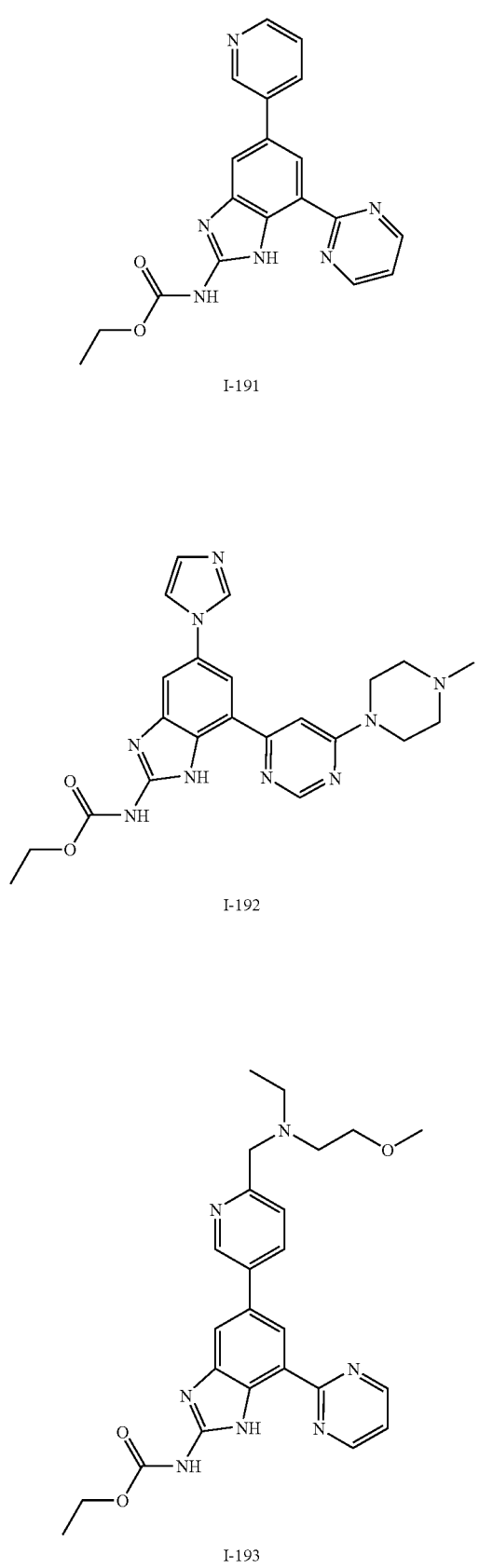
TABLE 2-continued
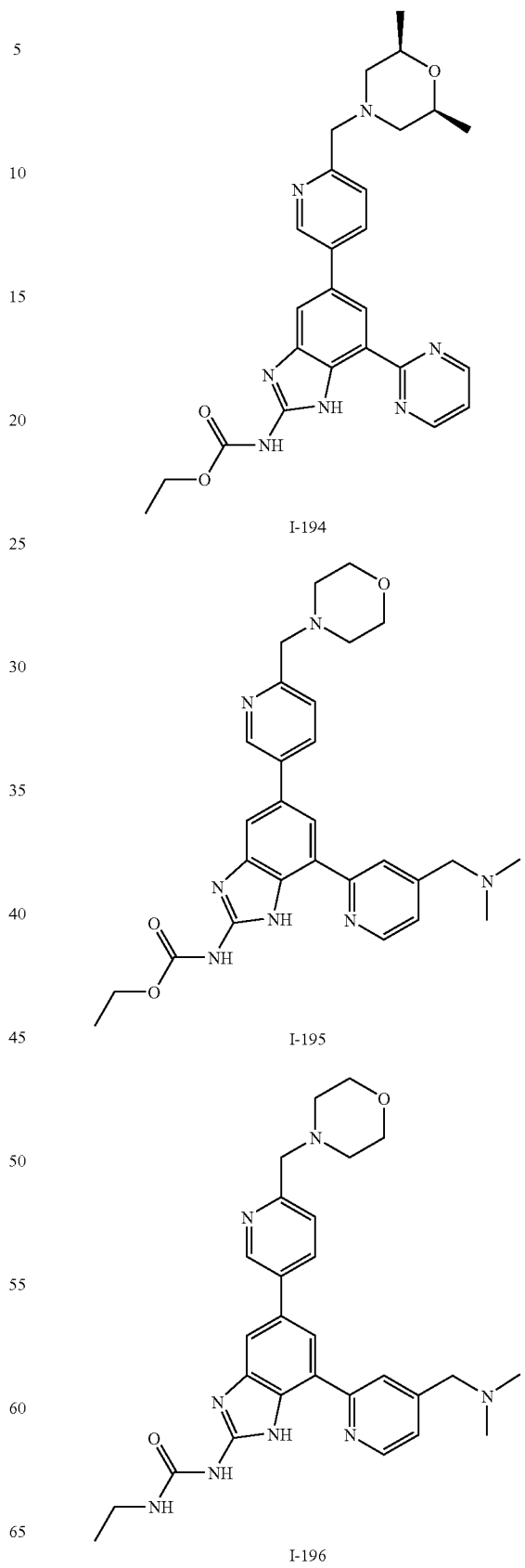

TABLE 2-continued
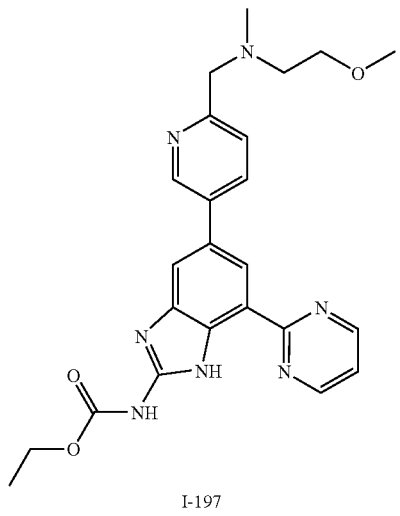
I-197
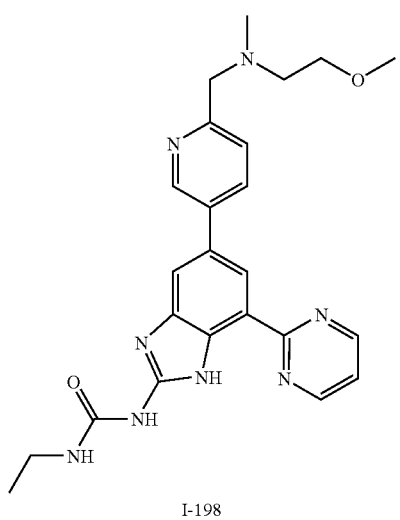
I-198
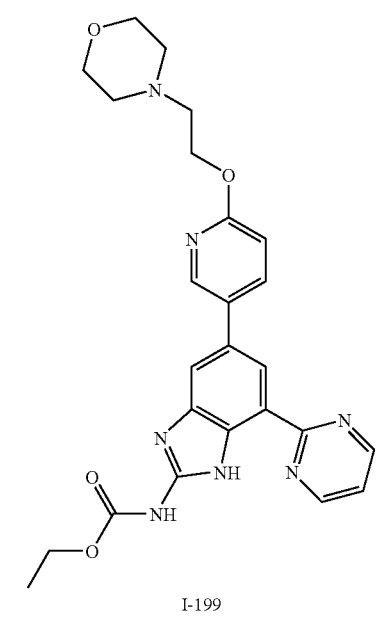
I-199
TABLE 2-continued
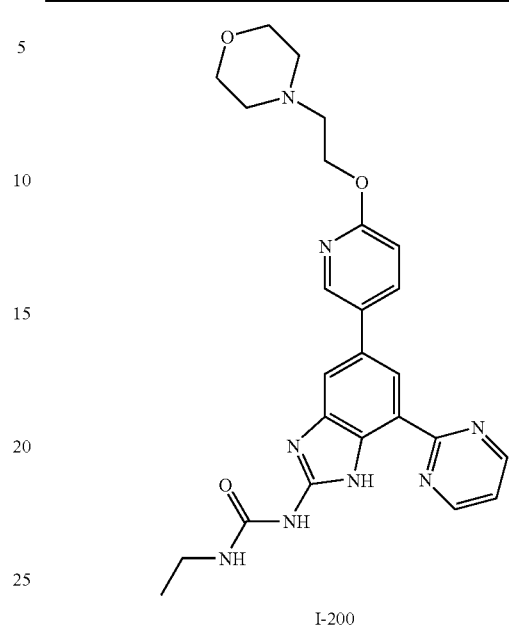
I-200
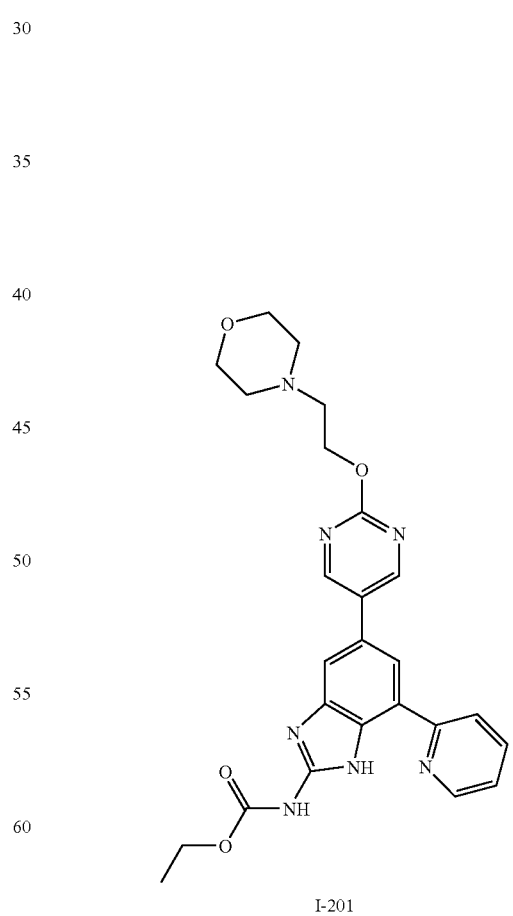
I-201

TABLE 2-continued
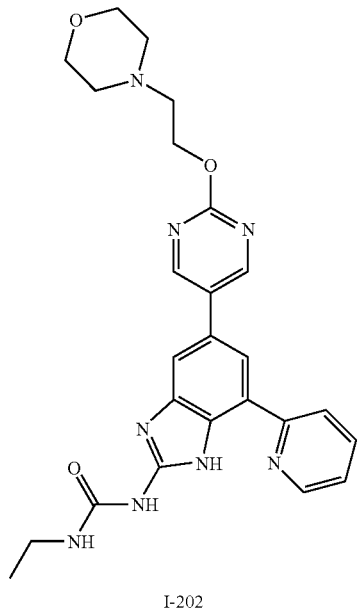
I-202
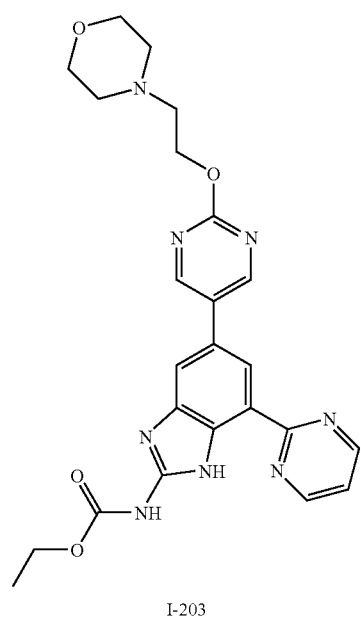
I-203
TABLE 2-continued
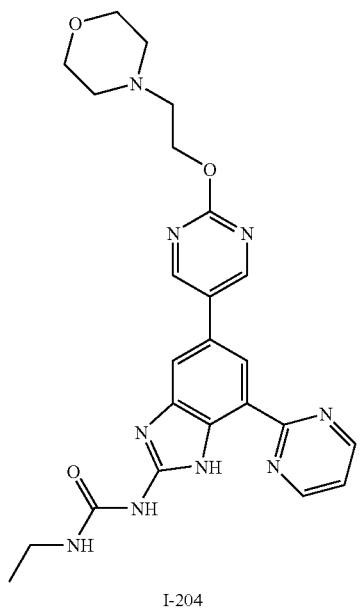
I-204
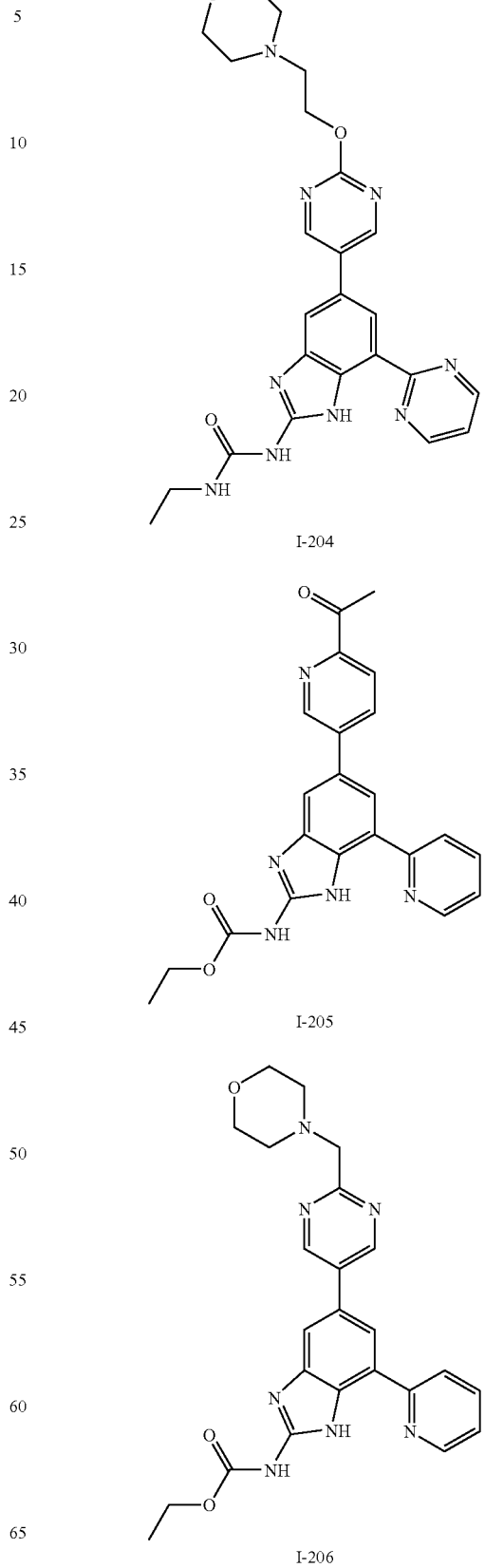
I-205
I-206

TABLE 2-continued
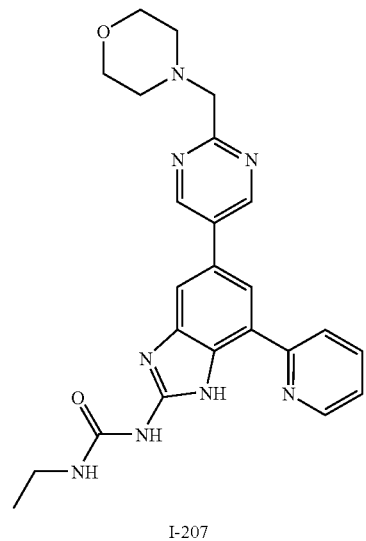
I-207
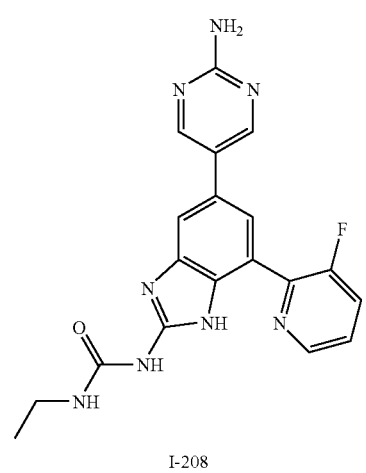
I-208
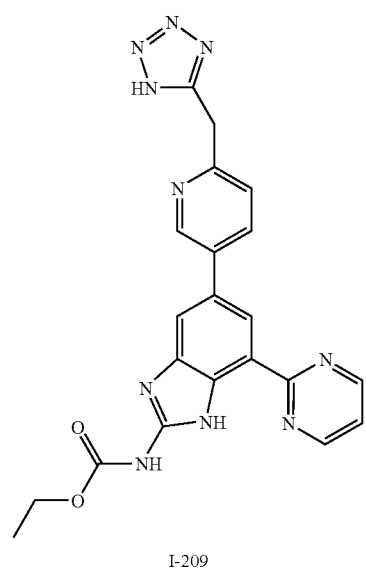
I-209
TABLE 2-continued
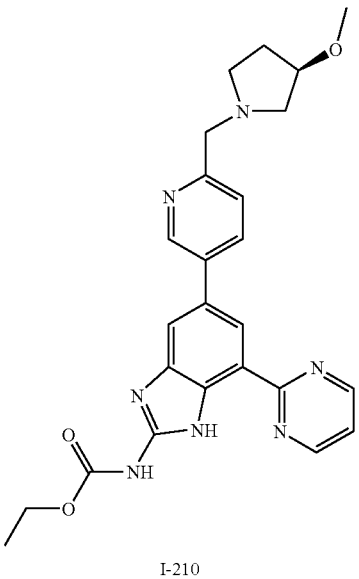
I-210
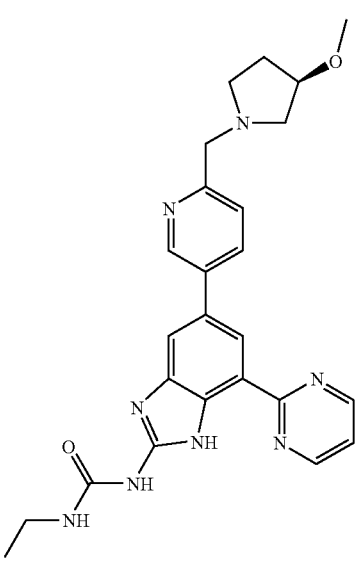
I-211

TABLE 2-continued
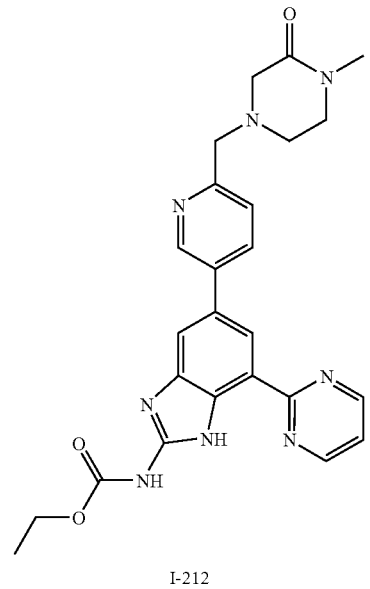
I-212
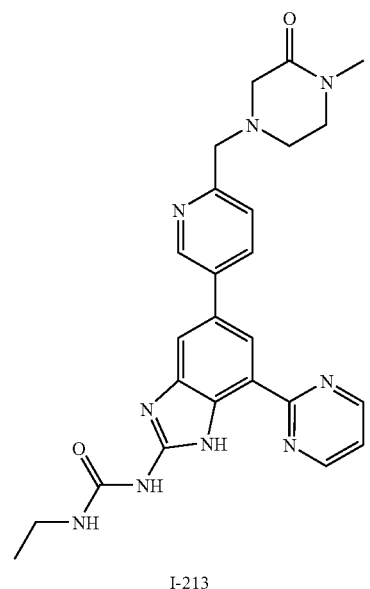
I-213
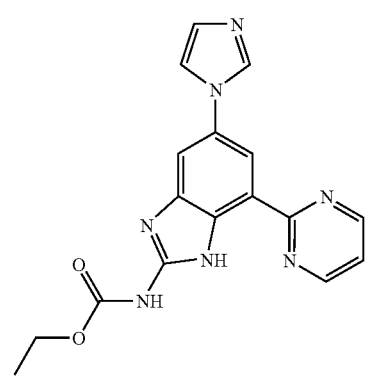
I-214
TABLE 2-continued
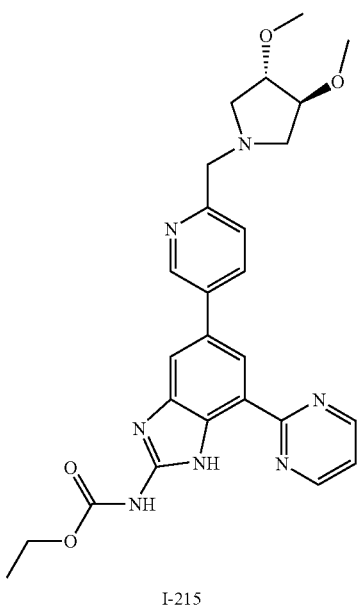
I-215
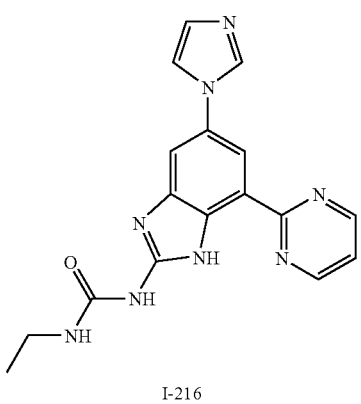
I-216
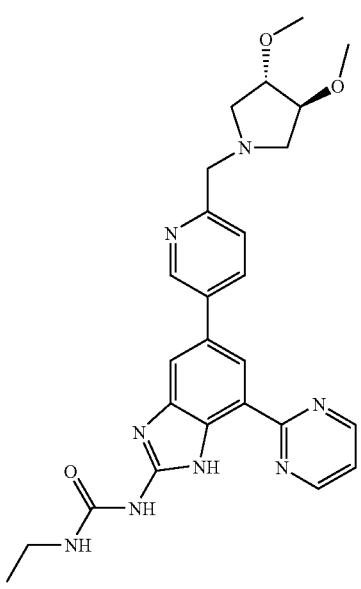
I-217

TABLE 2-continued
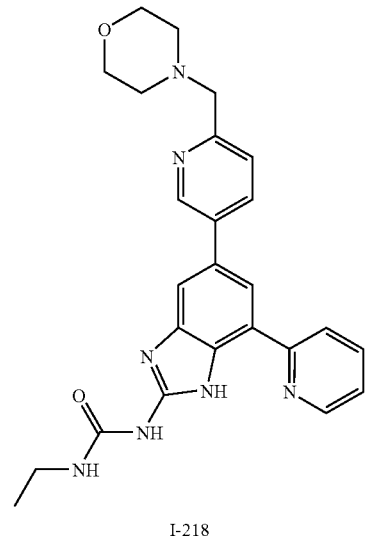
I-218
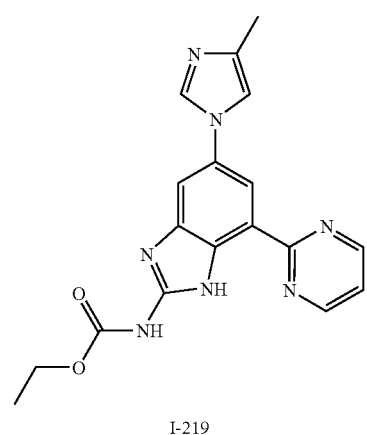
I-219
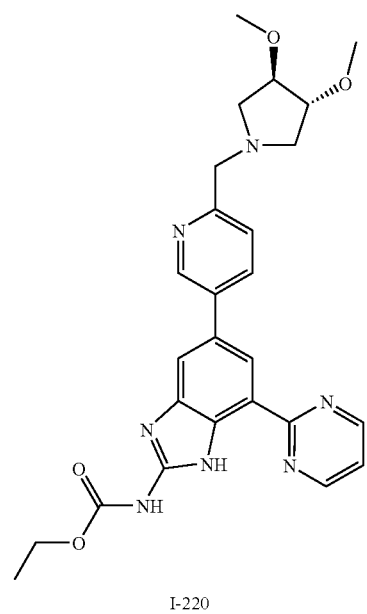
I-220
TABLE 2-continued
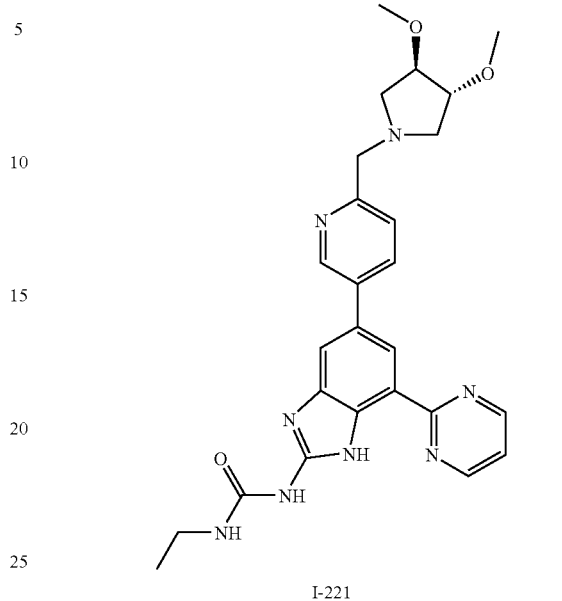
I-221
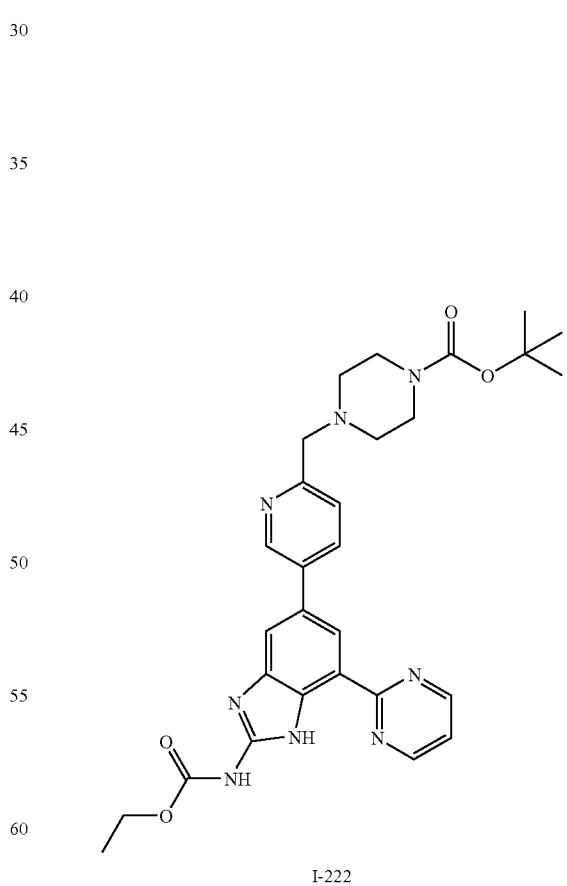
I-222

TABLE 2-continued
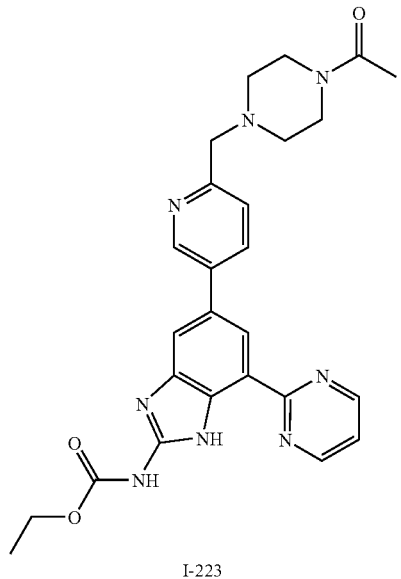
I-223
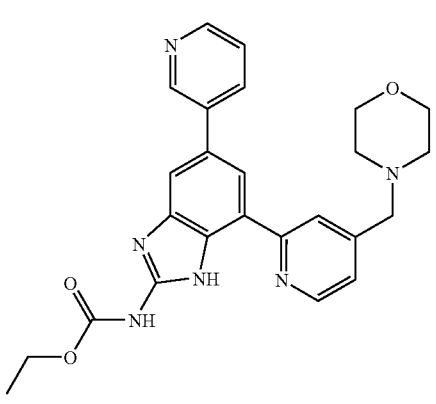
I-224
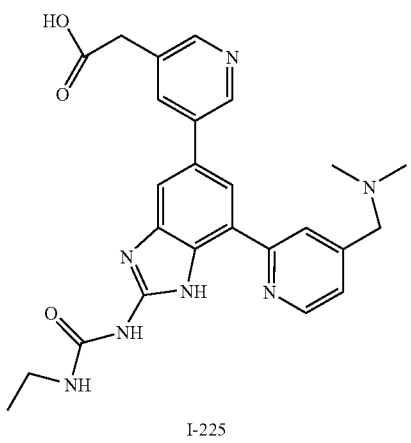
I-225
TABLE 2-continued
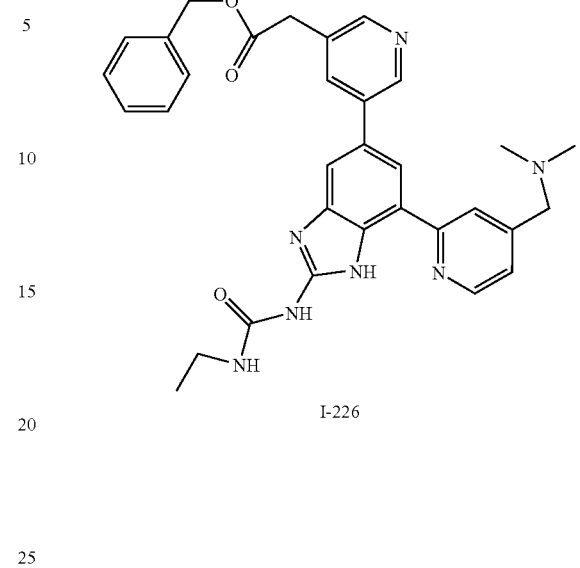
I-226
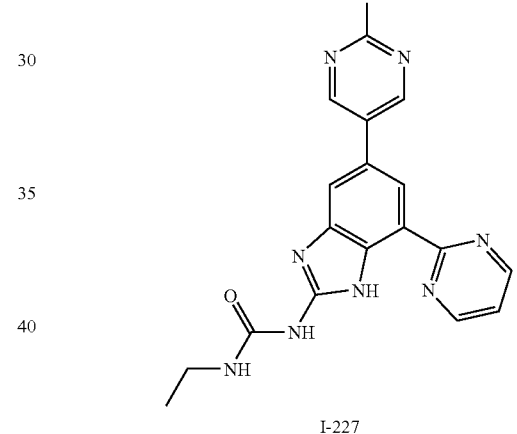
I-227
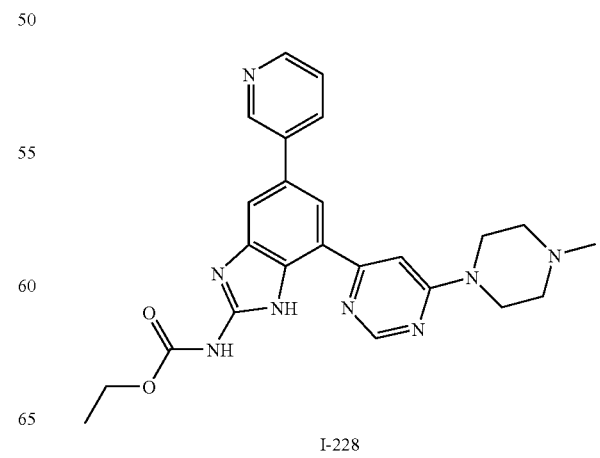
I-228

TABLE 2-continued
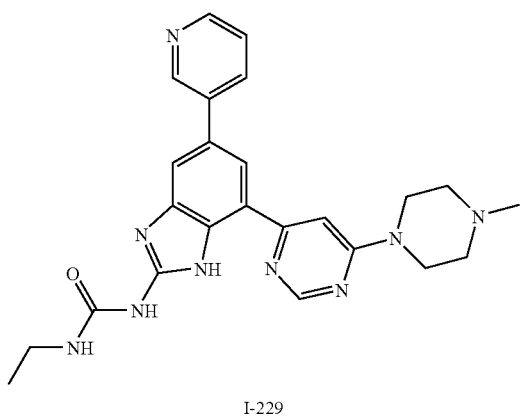
I-229
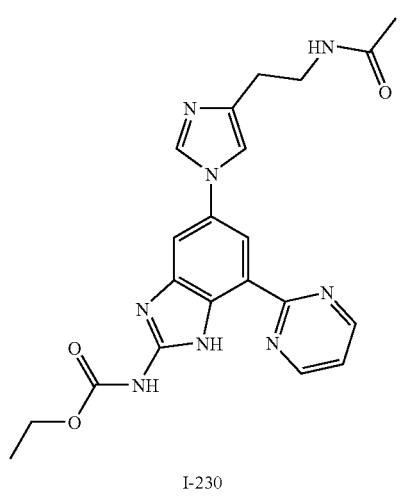
I-230
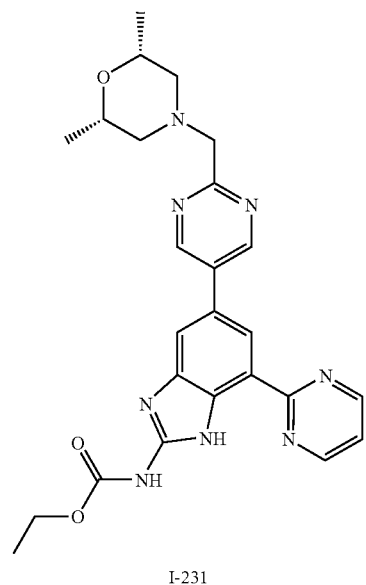
I-231
TABLE 2-continued
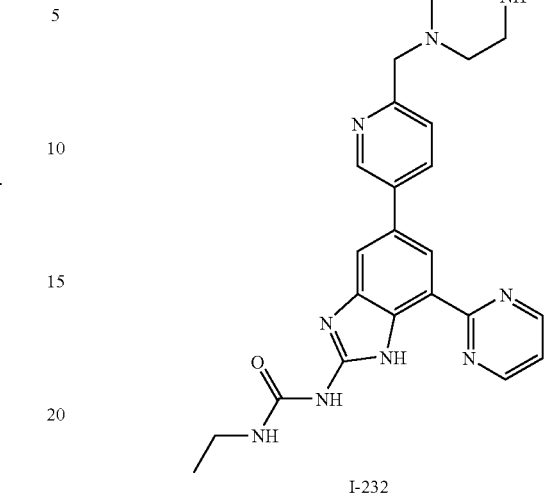
I-232
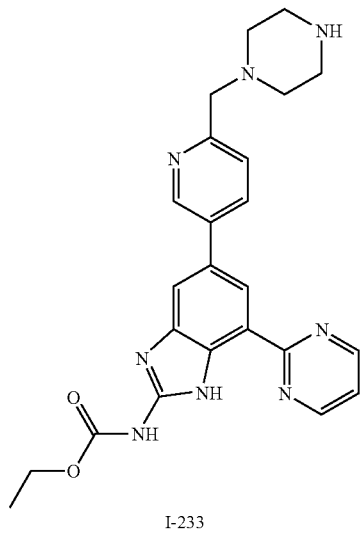
I-233
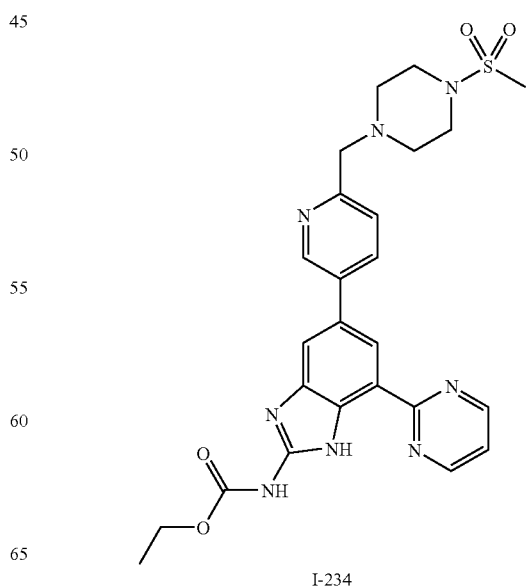
I-234

TABLE 2-continued
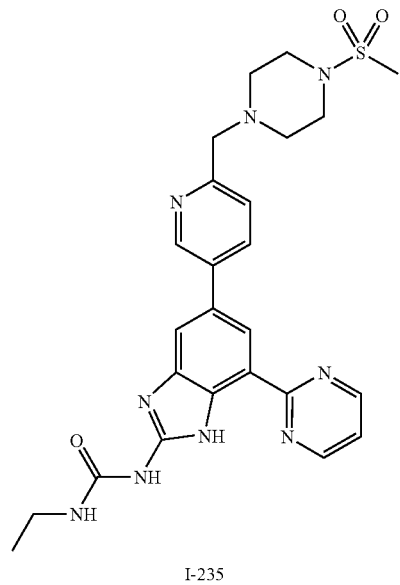
I-235
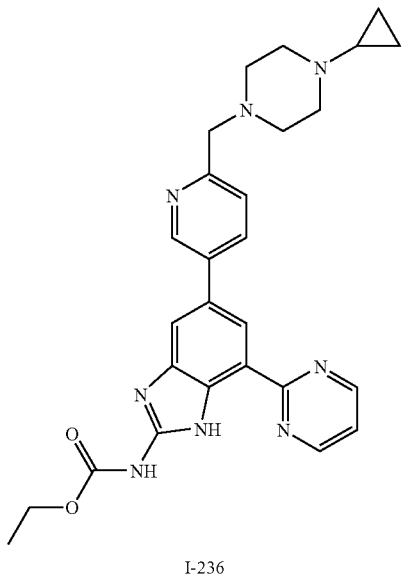
I-236
TABLE 2-continued
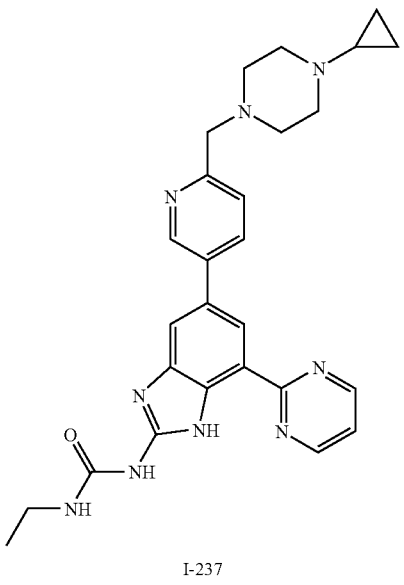
I-237
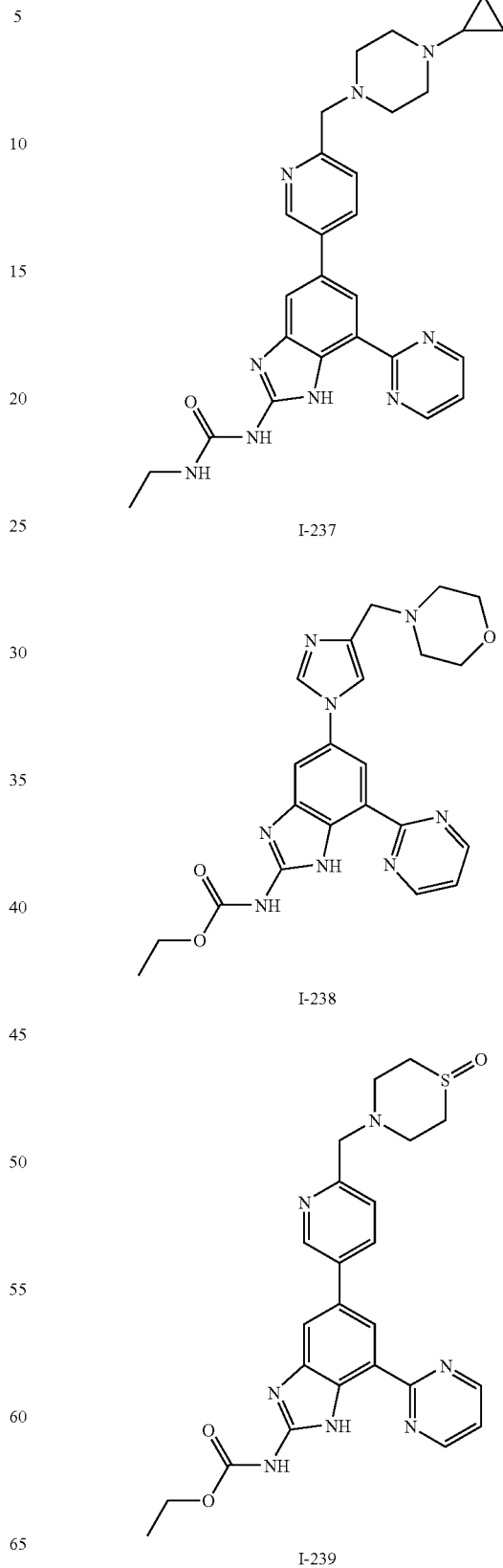
I-238
I-239

TABLE 2-continued
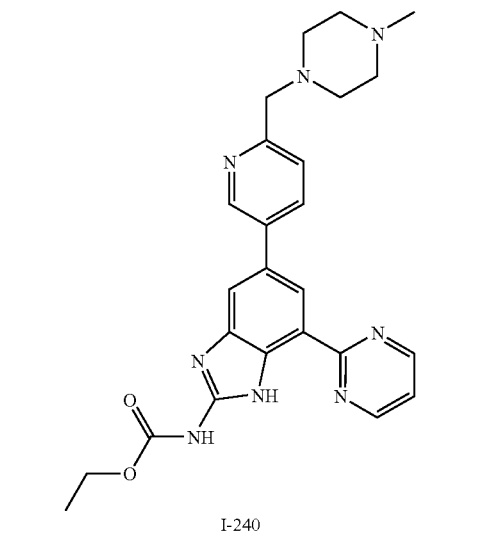
I-240
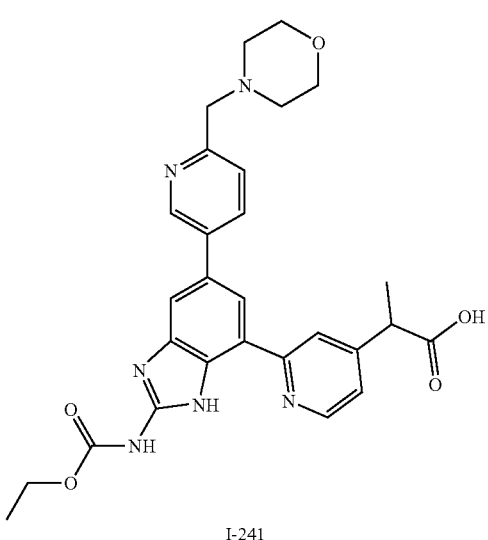
I-241
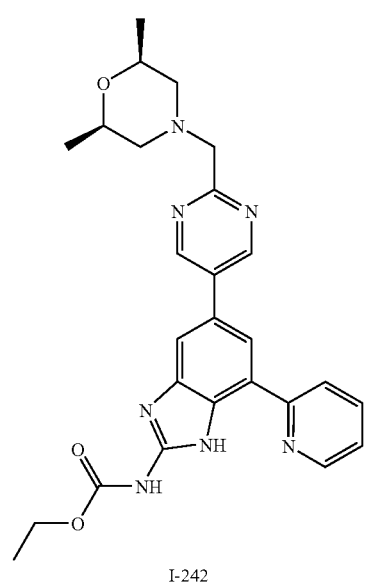
I-242
TABLE 2-continued
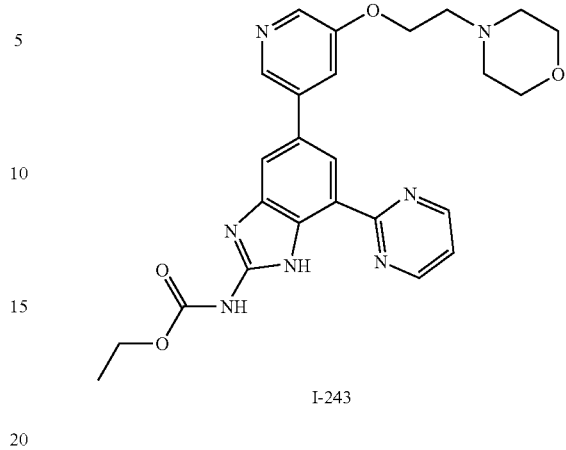
I-243
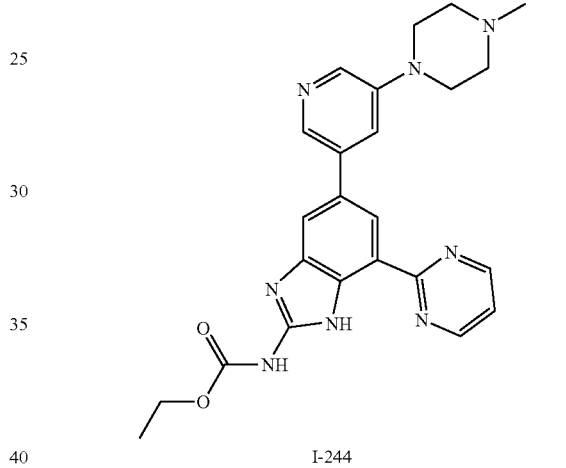
I-244
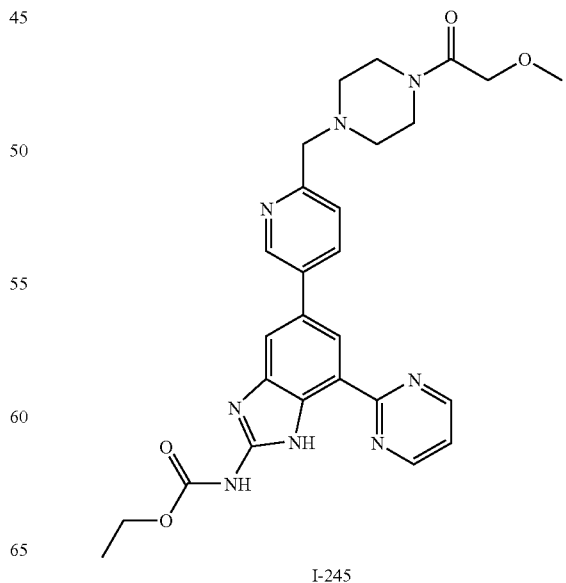
I-245

TABLE 2-continued
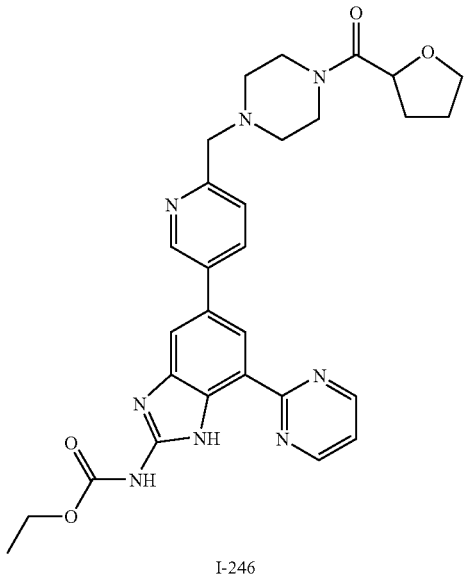
I-246
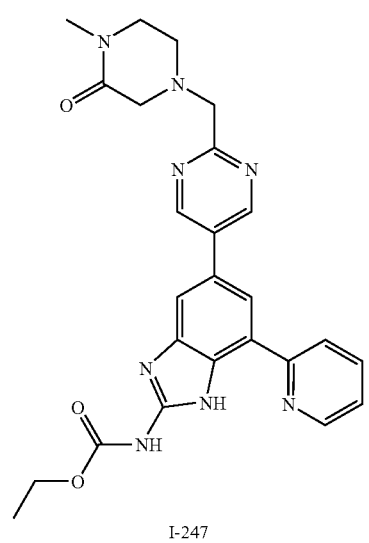
I-247
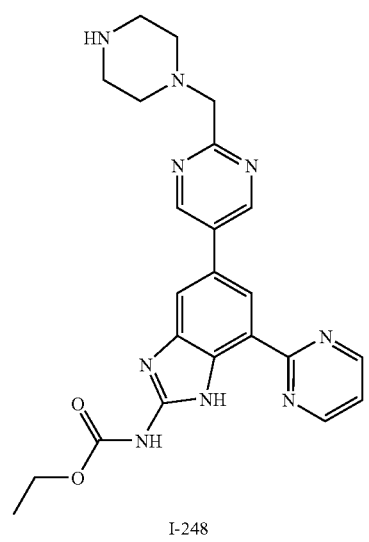
I-248
TABLE 2-continued
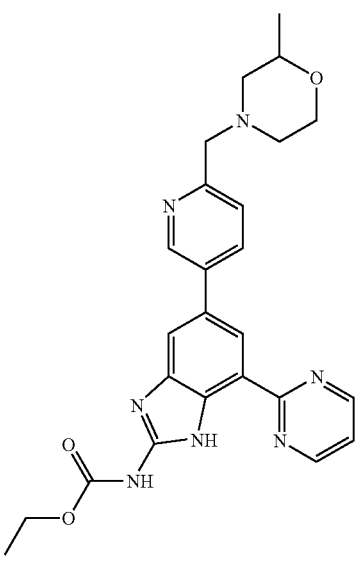
I-249
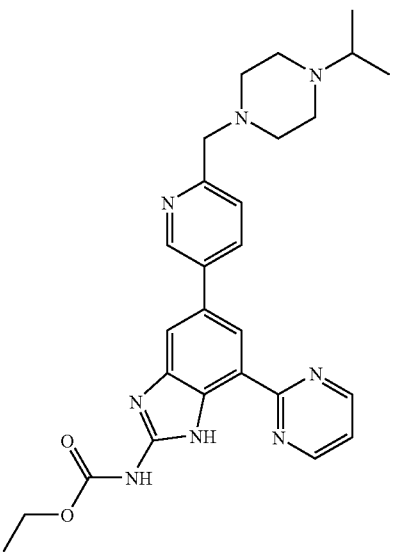
I-250

TABLE 2-continued
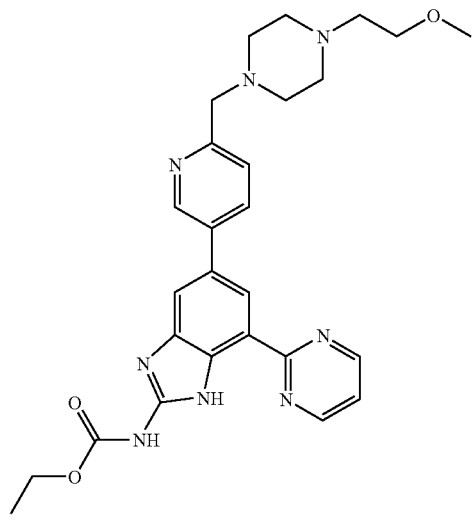
I-251
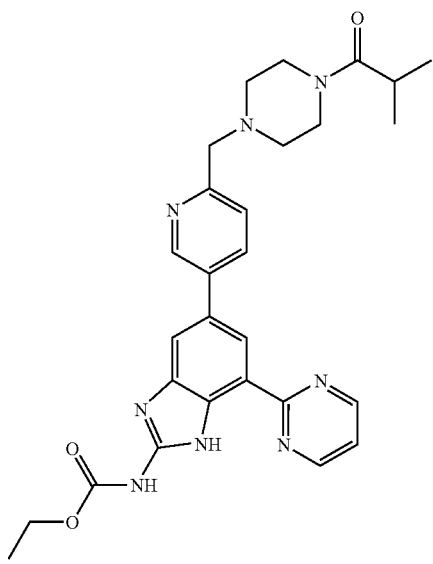
I-252
TABLE 2-continued
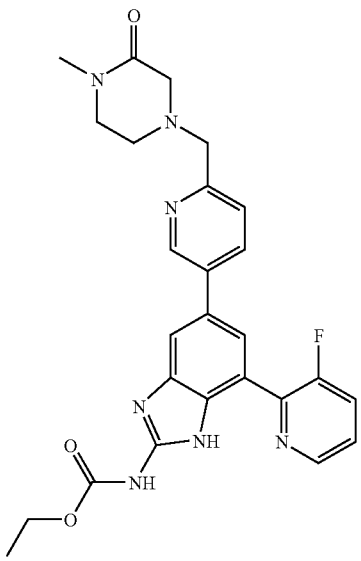
I-253
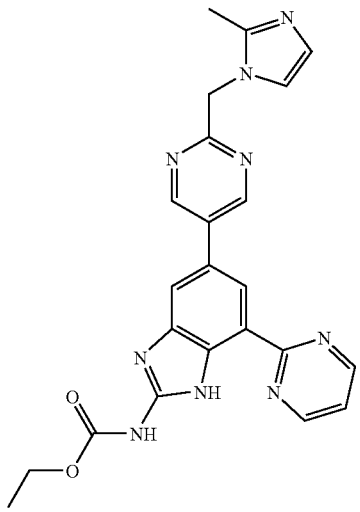
I-254

TABLE 2-continued
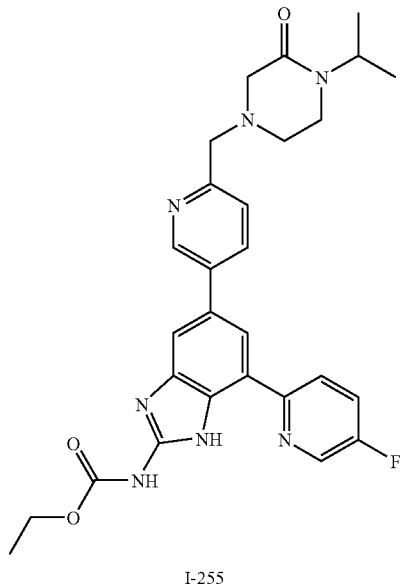
I-255
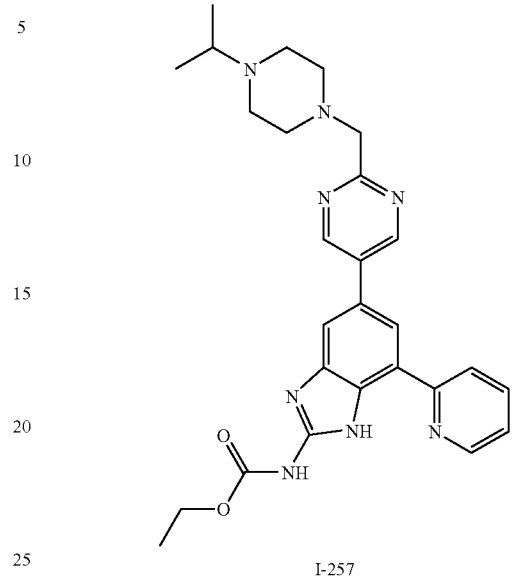
I-257
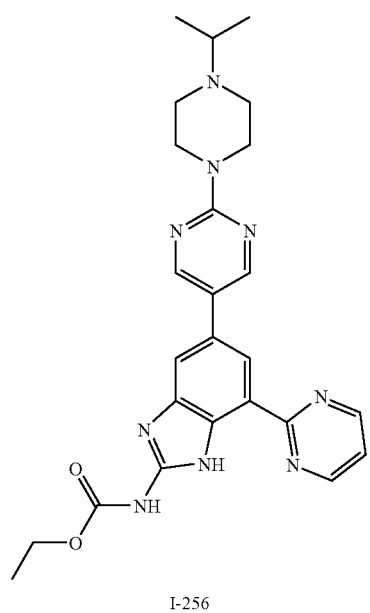
I-256
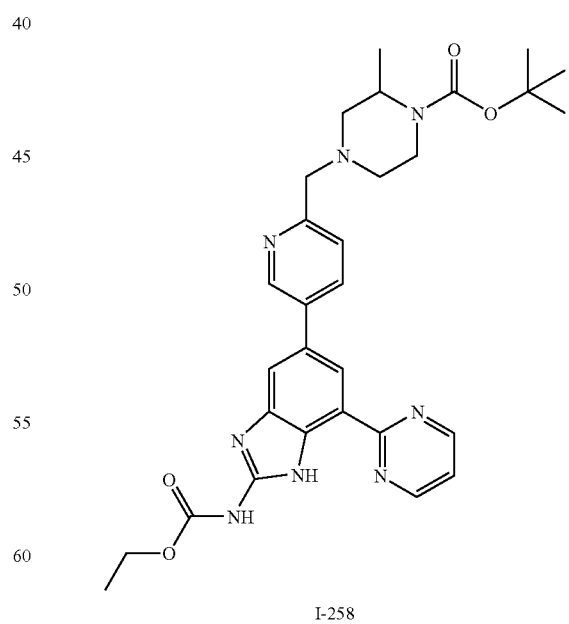
I-258

TABLE 2-continued
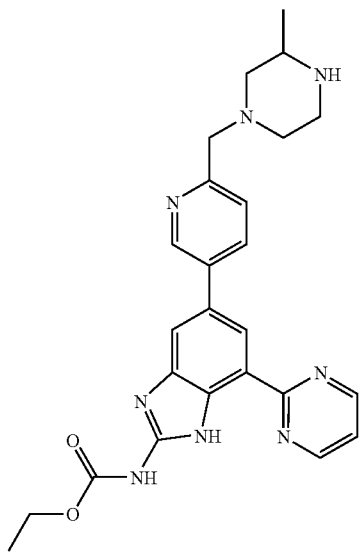
I-259
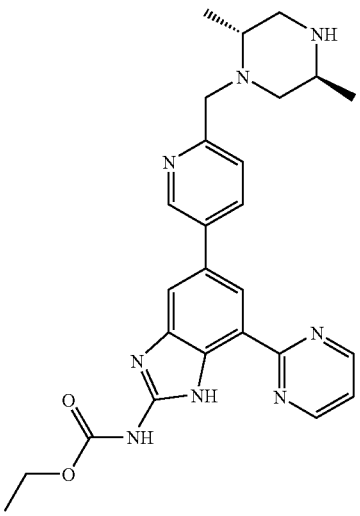
I-261
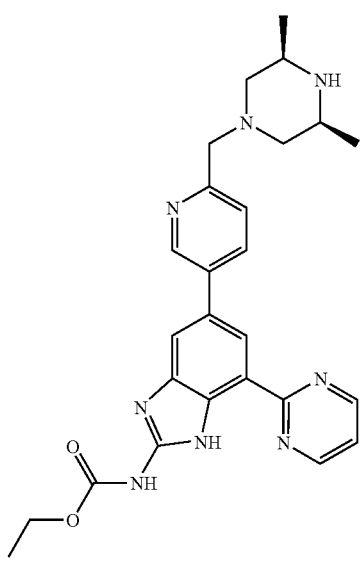
I-260
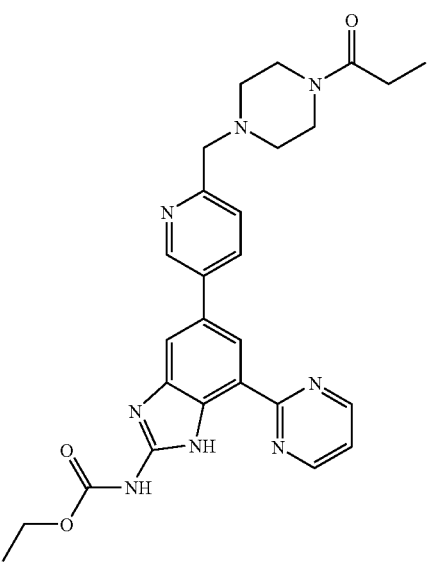
I-262

TABLE 2-continued
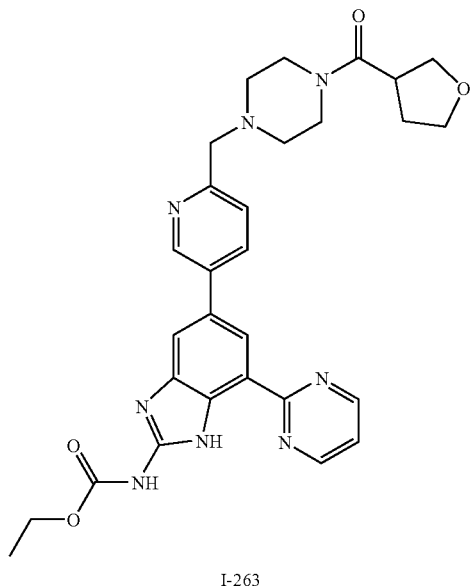
I-263
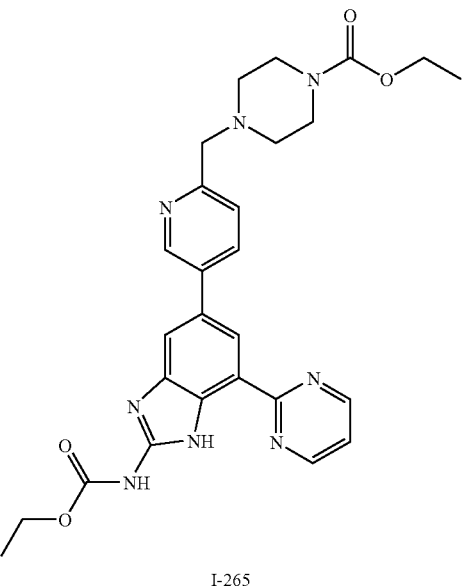
I-265
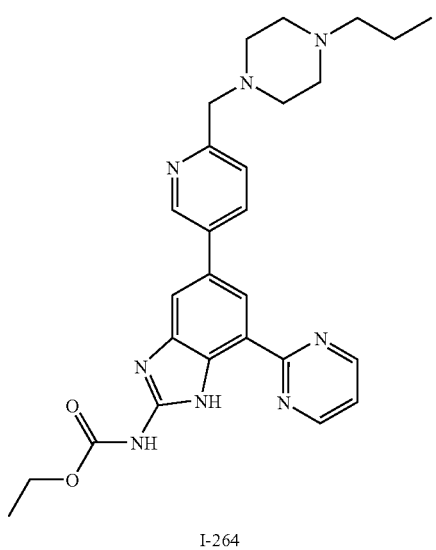
I-264
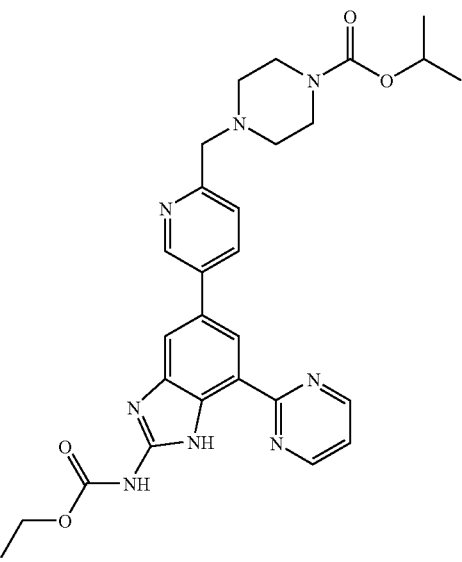
I-266

TABLE 2-continued
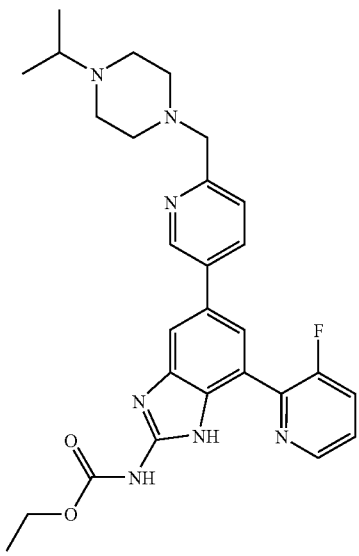
I-267
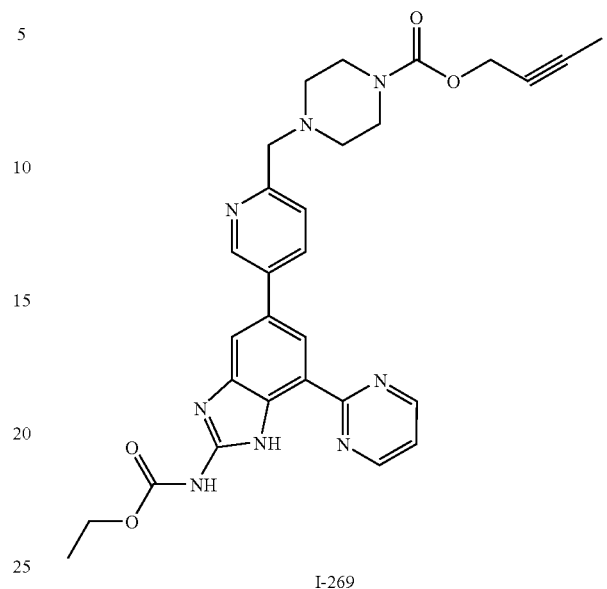
I-269
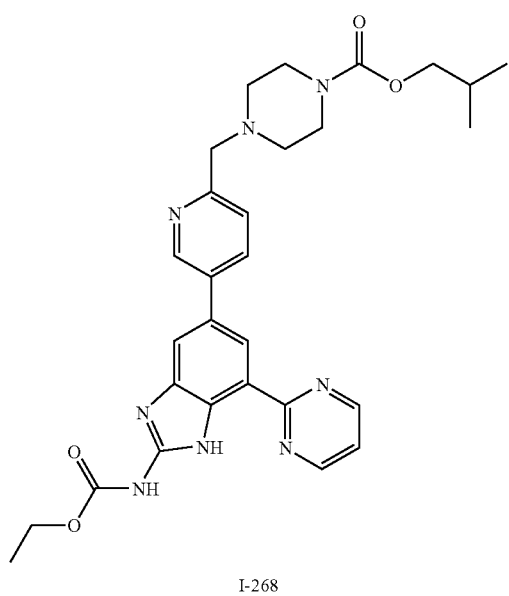
I-268
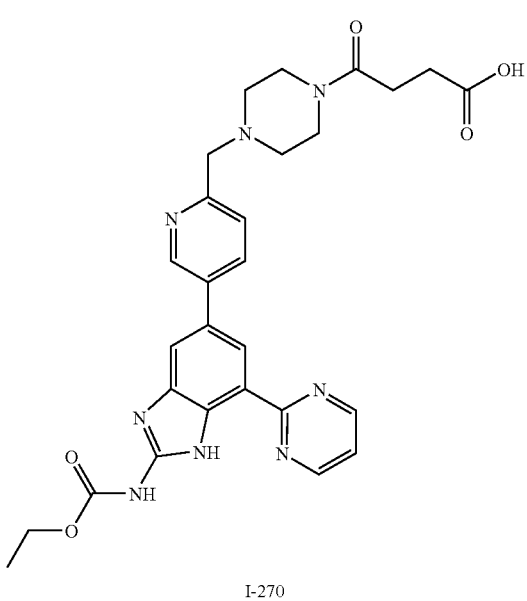
I-270

TABLE 2-continued
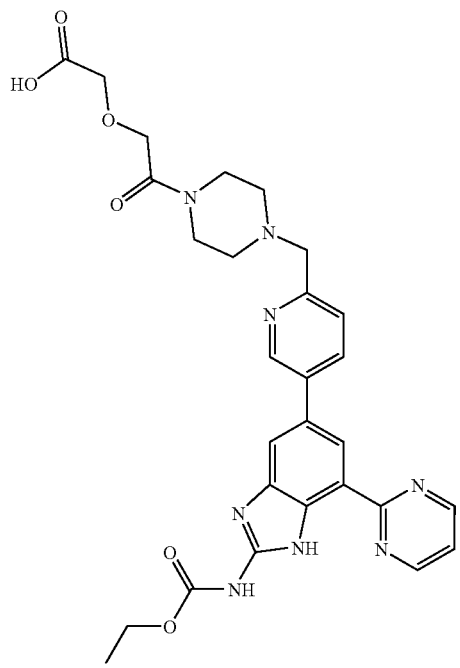
I-271
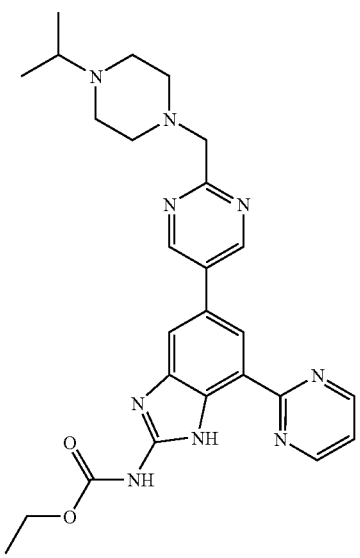
I-272
TABLE 2-continued
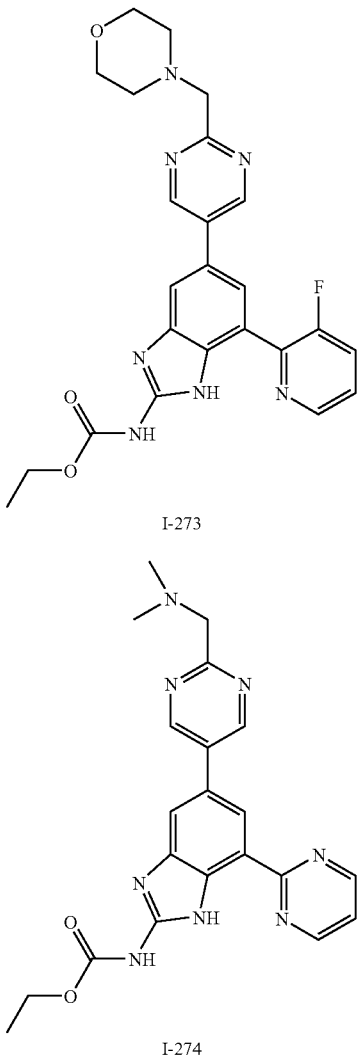
I-273
I-274
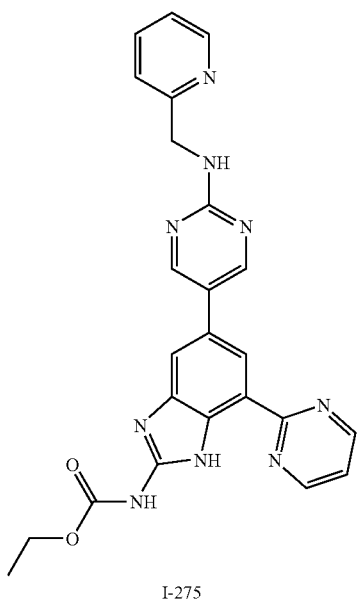
I-275

TABLE 2-continued
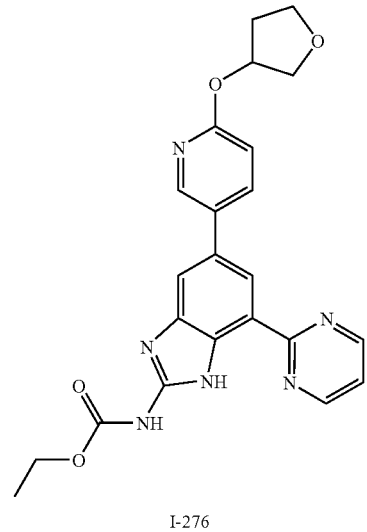
I-276
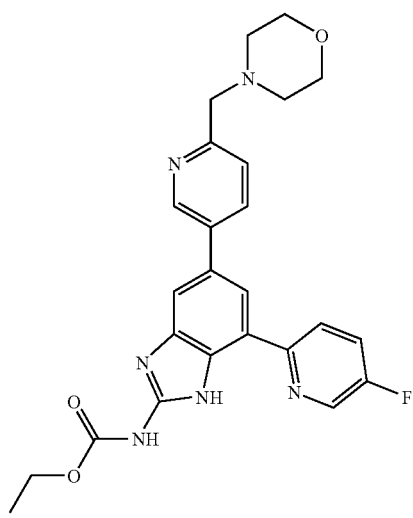
I-277
TABLE 2-continued
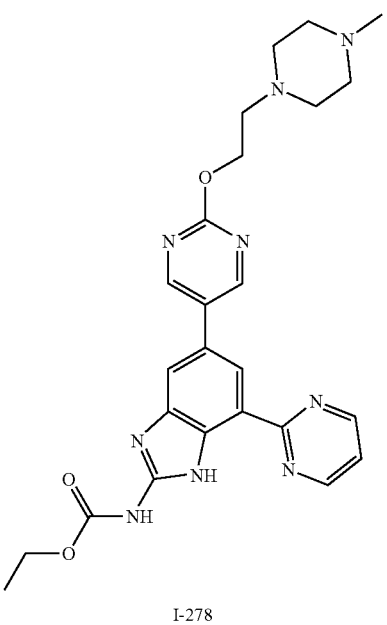
I-278
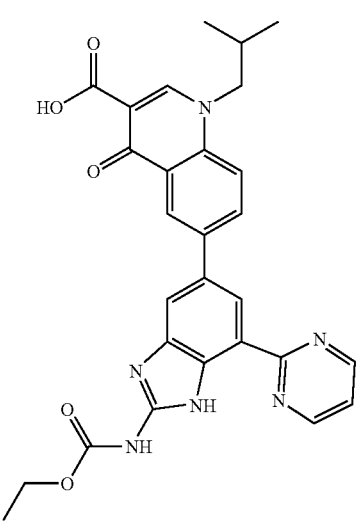
I-279

TABLE 2-continued
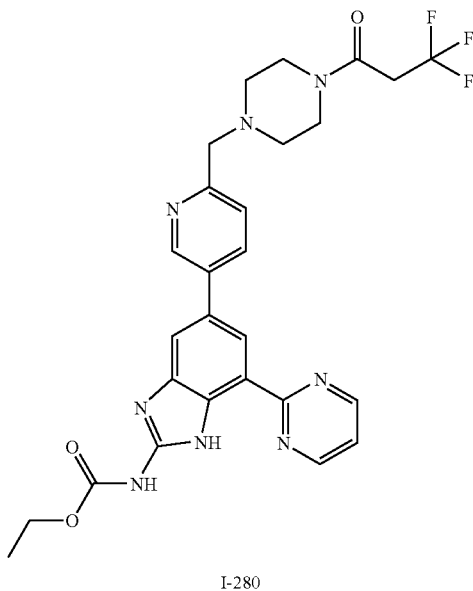
I-280
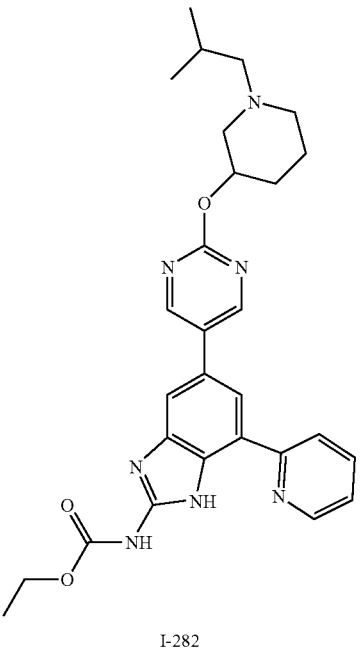
I-282
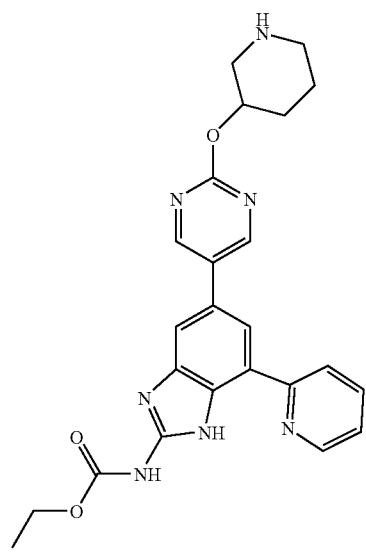
I-281
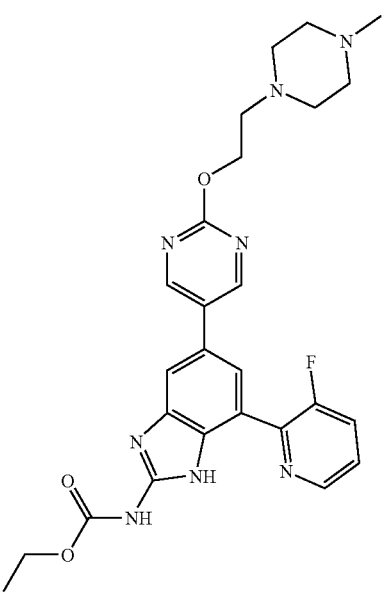
I-283

TABLE 2-continued
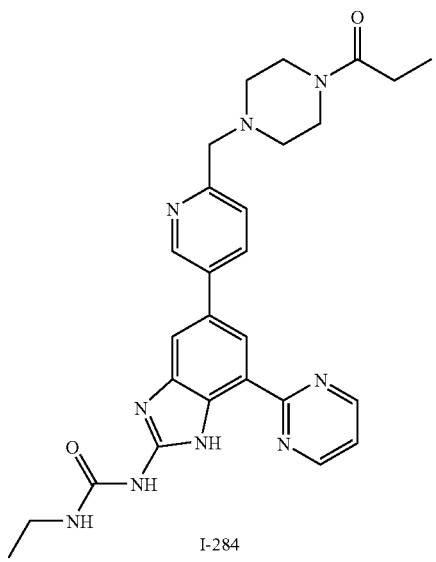
I-284
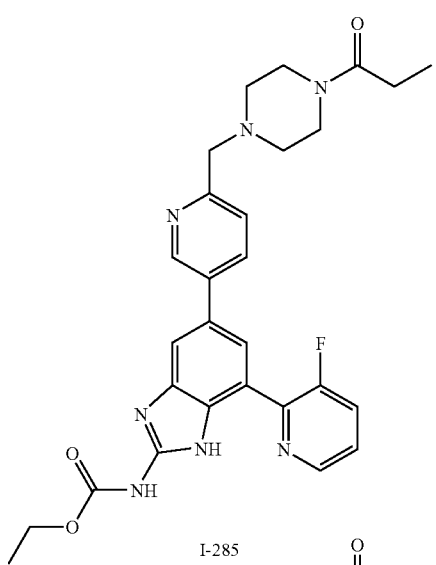
I-285
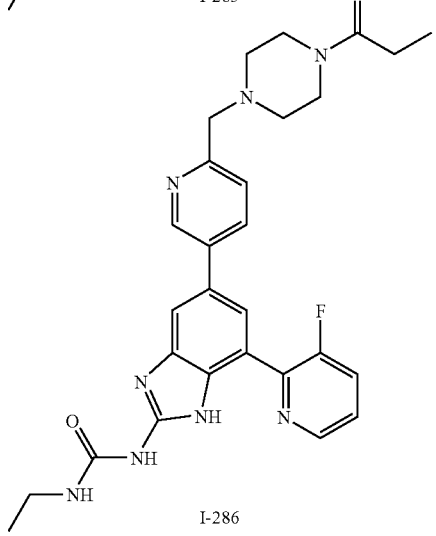
I-286
TABLE 2-continued
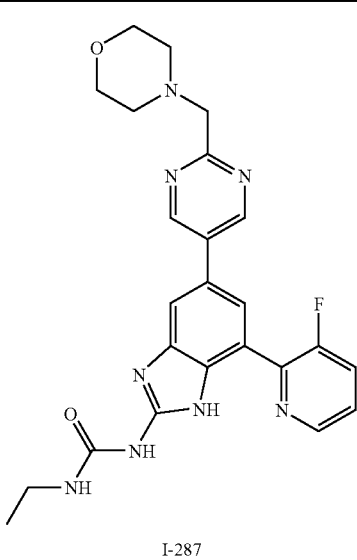
I-287
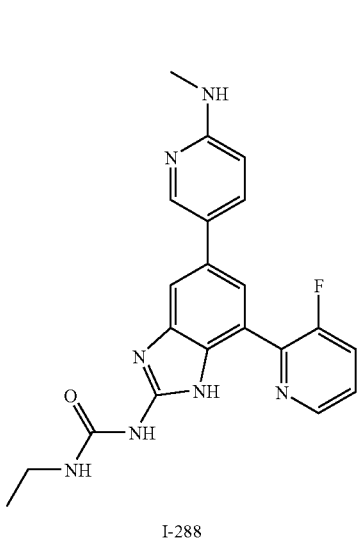
I-288
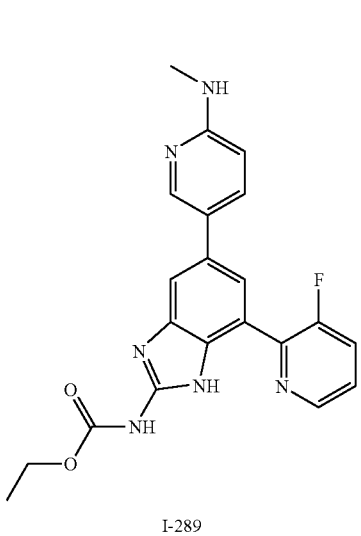
I-289

TABLE 2-continued
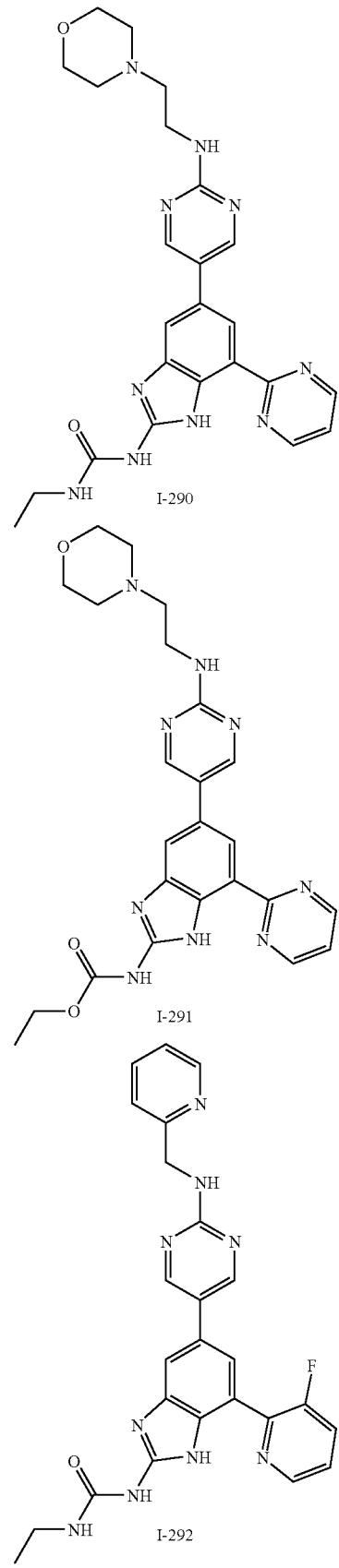
TABLE 2-continued
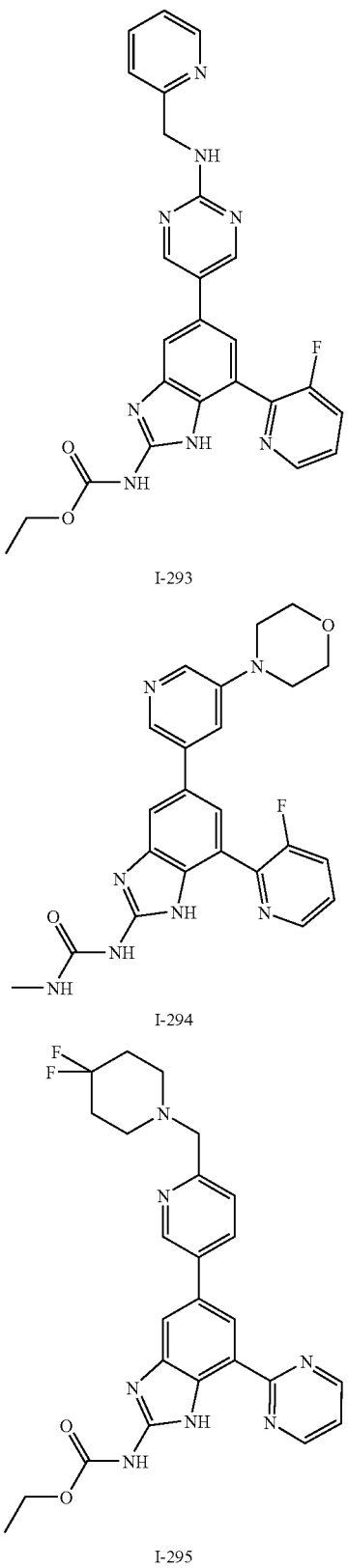

Exemplary structures of formula VII are compound numbers; I-345, I-389, I-390, I-391, I-410, I-426, I-432, I-442, I-443, I-445, I-446, I-447, I-448, I-450, I-451, I-455, I-460, I-461, I-462, I-463, I-464, I-465, I-466, I-467, I-478, I-479, I-481, I-484, I-485, I-487, I-491, I-492, I-493, I-496, I-497, I-498, I-499, I-500, I-501, and I-502 set forth in Table 2a below.

Exemplary structures of formula I are set forth in Table 2a below.

TABLE 2a

| No. | Structure |
| --- | --- |
| I-296 | 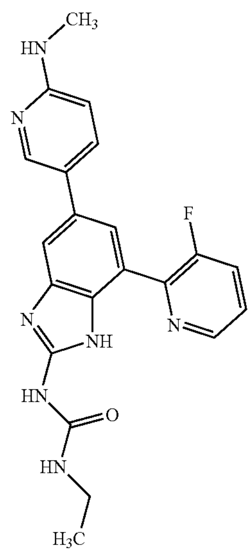 |
| I-297 | 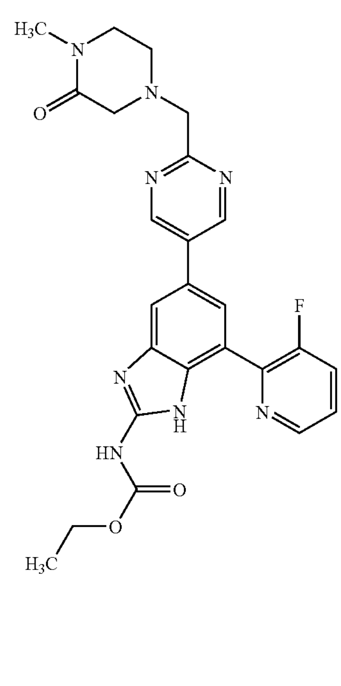 |

TABLE 2a-continued

| No. | Structure |
|---|---|
| I-298 | 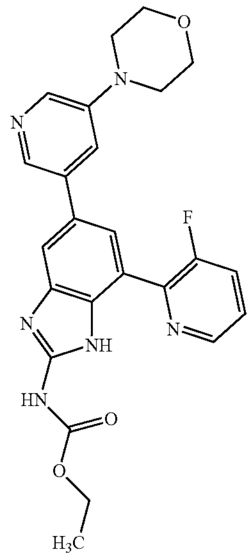 |
| I-299 | 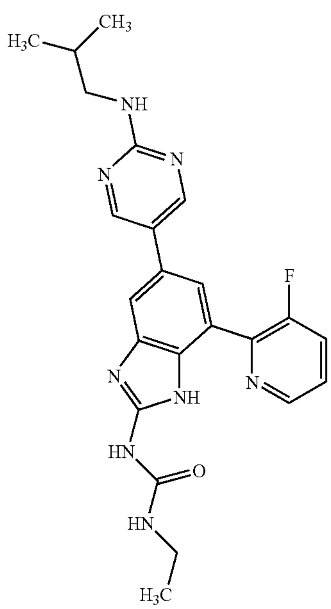 |
| I-300 | 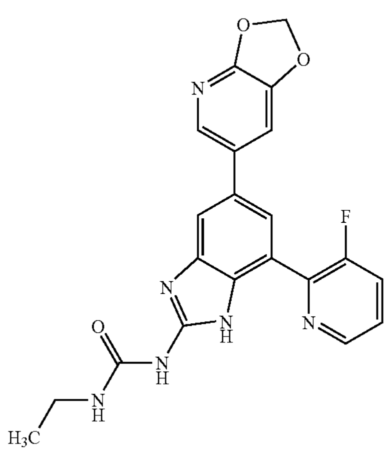 |

TABLE 2a-continued
| No. | Structure |
|---|---|
| I-301 | 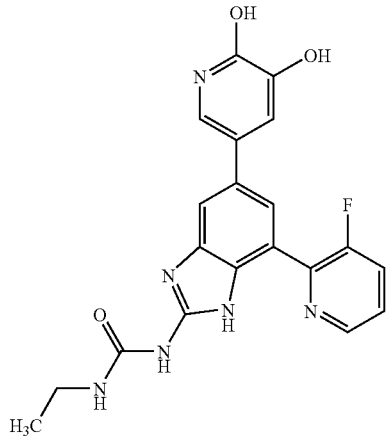 |
| I-302 | 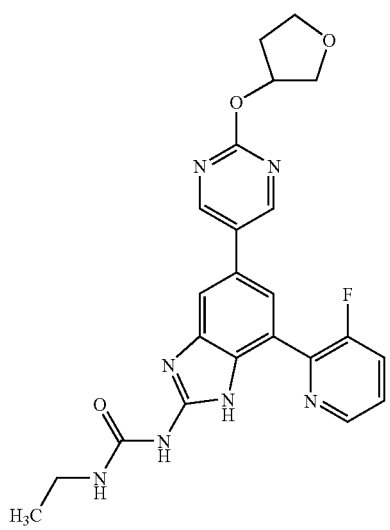 |
| I-303 | 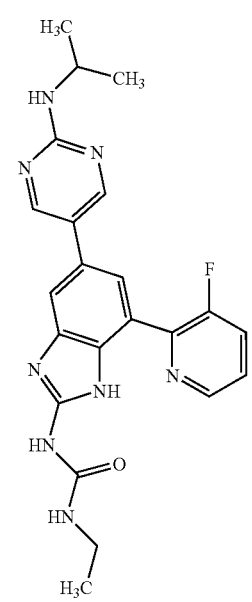 |

TABLE 2a-continued
| No. | Structure |
|---|---|
| I-304 | 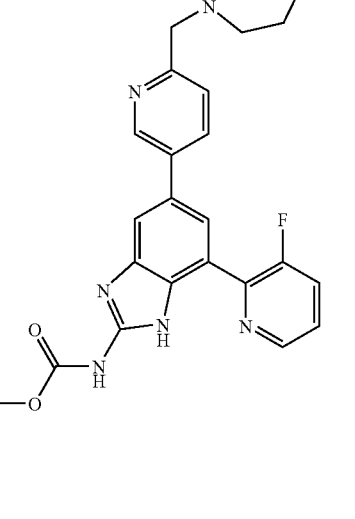 |
| I-305 | 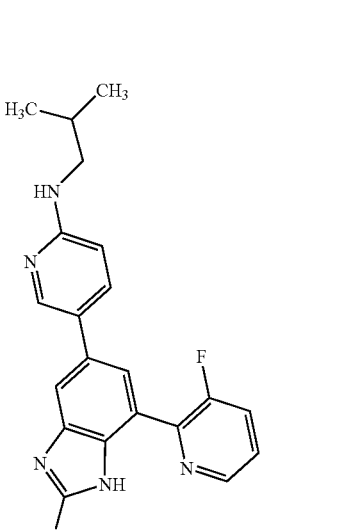 |

TABLE 2a-continued

| No. | Structure |
|---|---|
| I-306 | 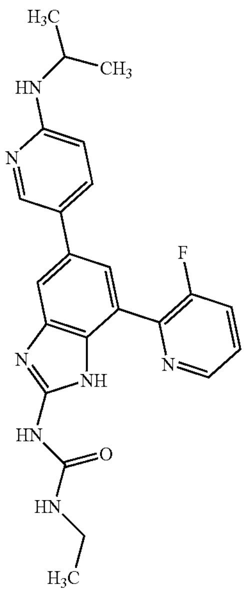 |
| I-307 | 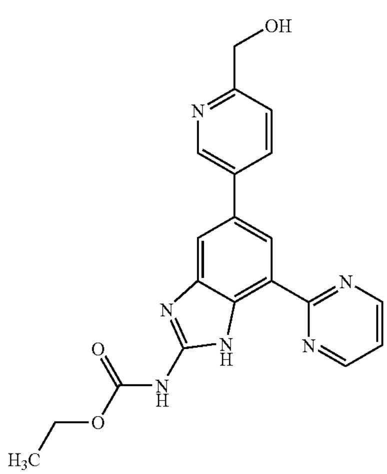 |

TABLE 2a-continued
| No. | Structure |
|---|---|
| I-308 | 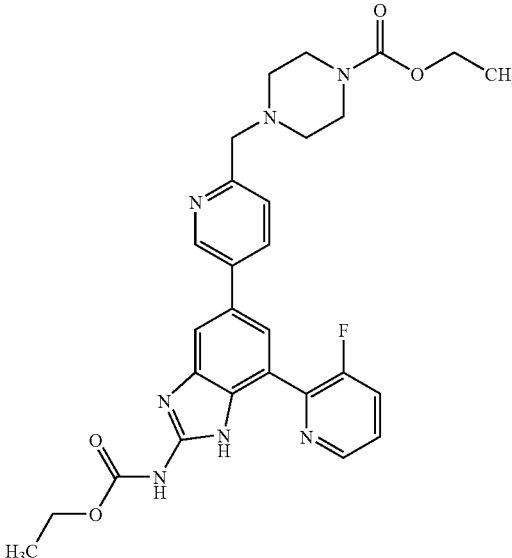 |
| I-309 | 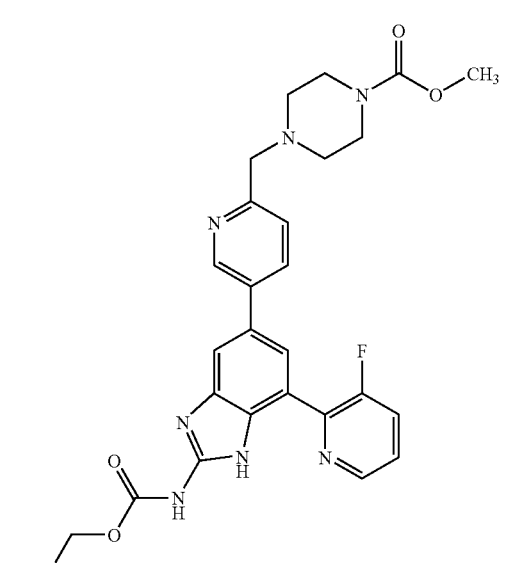 |

TABLE 2a-continued
| No. | Structure |
|---|---|
| I-310 | 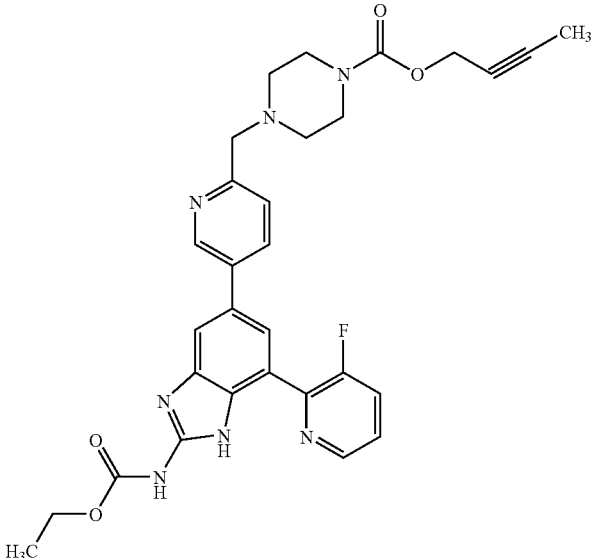 |
| I-311 | 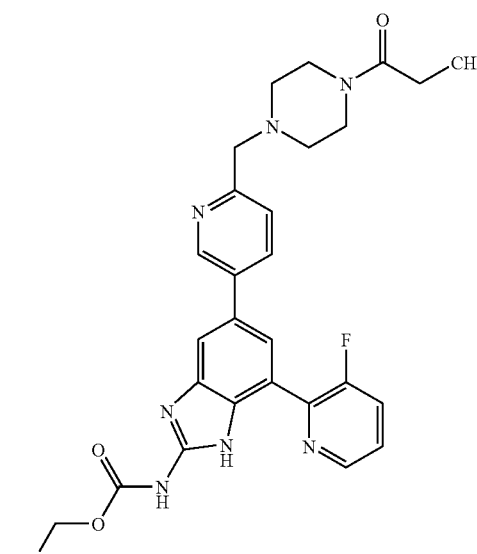 |

TABLE 2a-continued
| No. | Structure |
|---|---|
| I-312 | 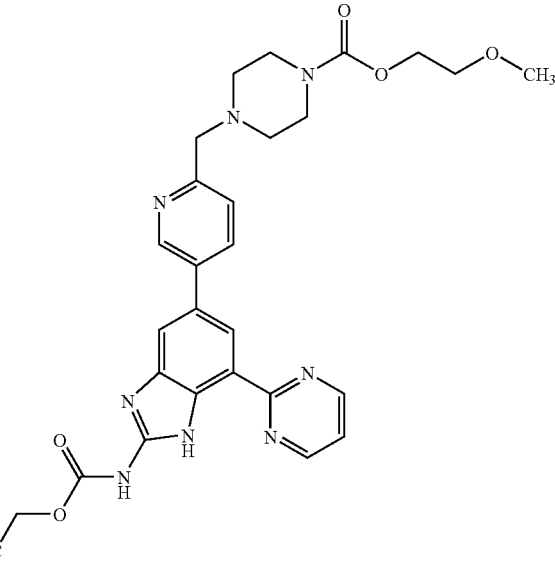 |
| I-313 | 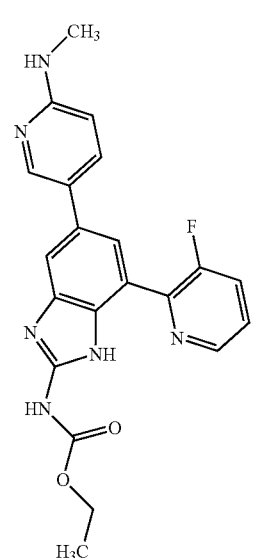 |

TABLE 2a-continued
| No. | Structure |
|---|---|
| I-314 | 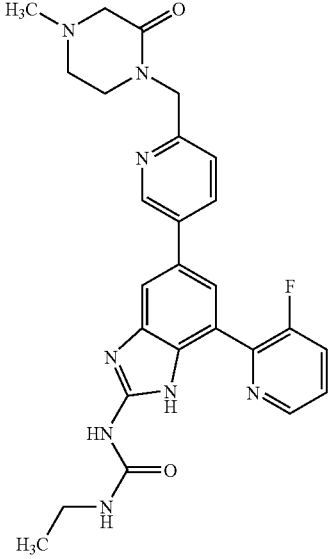 |
| I-315 | 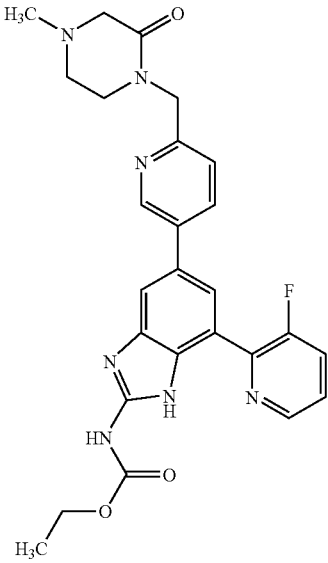 |

TABLE 2a-continued
| No. | Structure |
|---|---|
| I-316 | 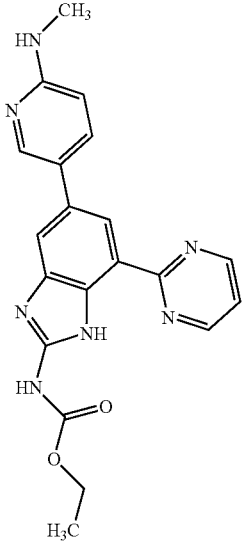 |
| I-317 | 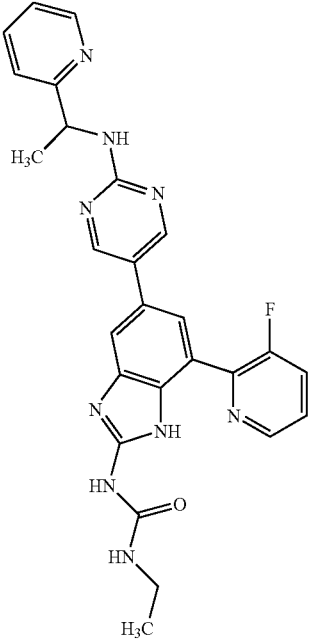 |

TABLE 2a-continued
| No. | Structure |
|---|---|
| I-318 | 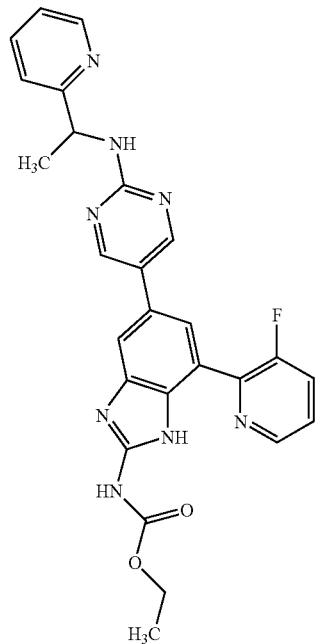 |
| I-319 | 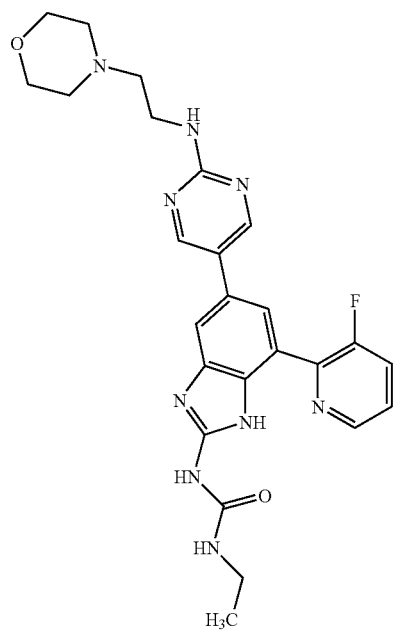 |

TABLE 2a-continued

| No. | Structure |
|---|---|
| I-320 | 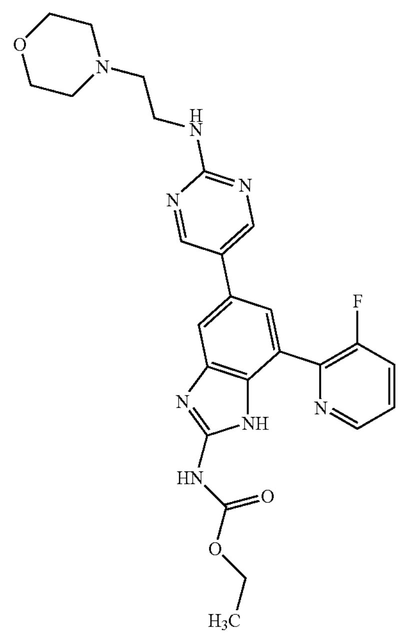 |
| I-321 | 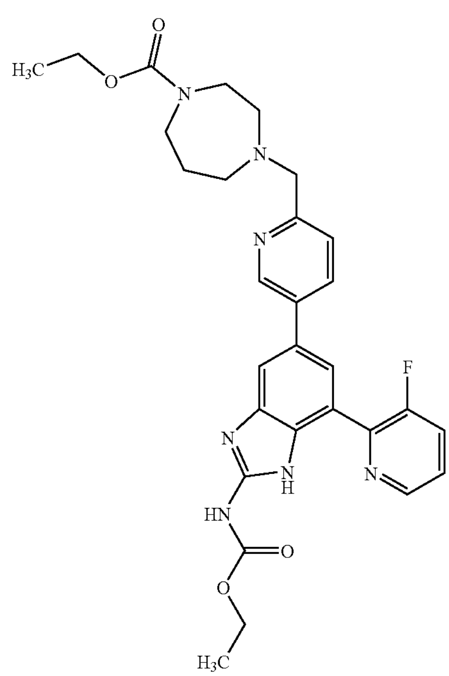 |

TABLE 2a-continued
| No. | Structure |
|---|---|
| I-322 | 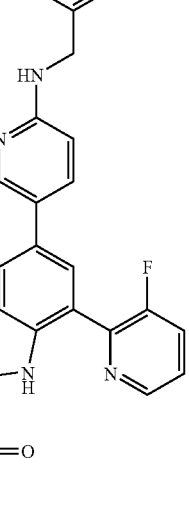 |
| I-323 | 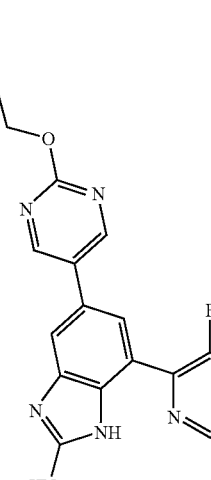 |

TABLE 2a-continued

| No. | Structure |
|---|---|
| I-324 | 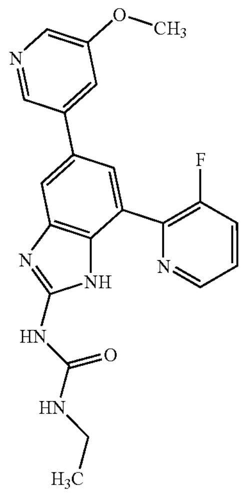 |
| I-325 | 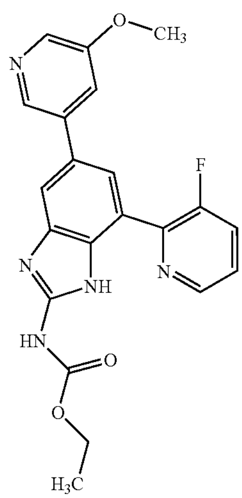 |
| I-326 | 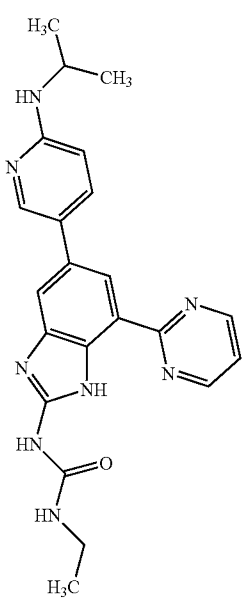 |

TABLE 2a-continued
| No. | Structure |
|---|---|
| I-327 | 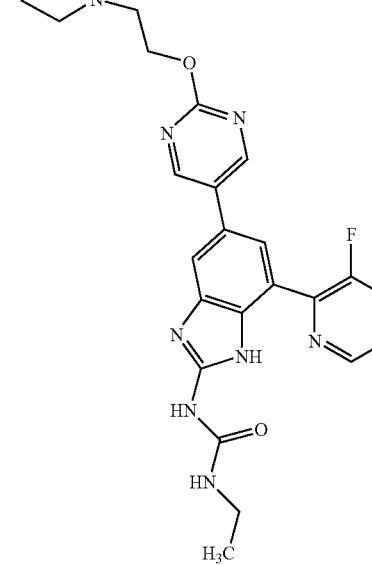 |
| I-328 | 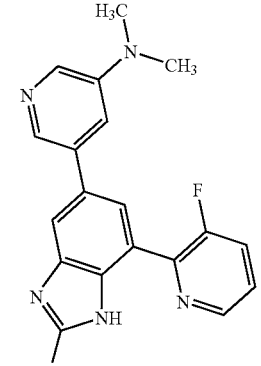 |

TABLE 2a-continued

| No. | Structure |
|---|---|
| I-329 | 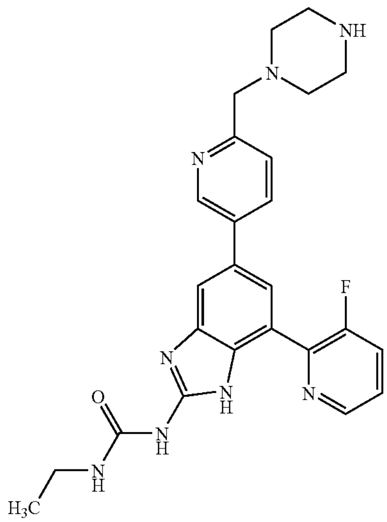 |
| I-330 | 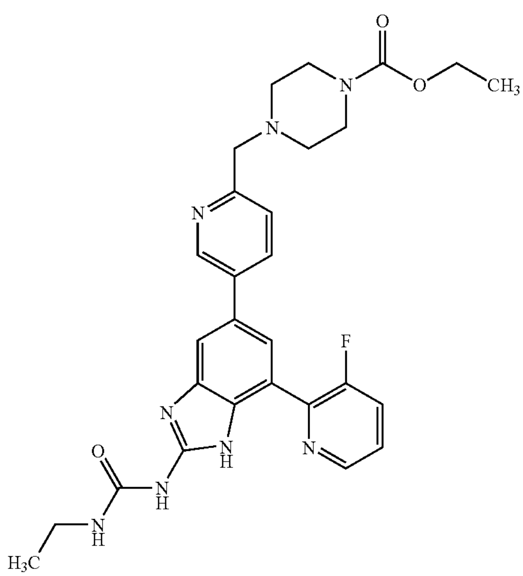 |

TABLE 2a-continued

| No. | Structure |
| --- | --- |
| I-331 | 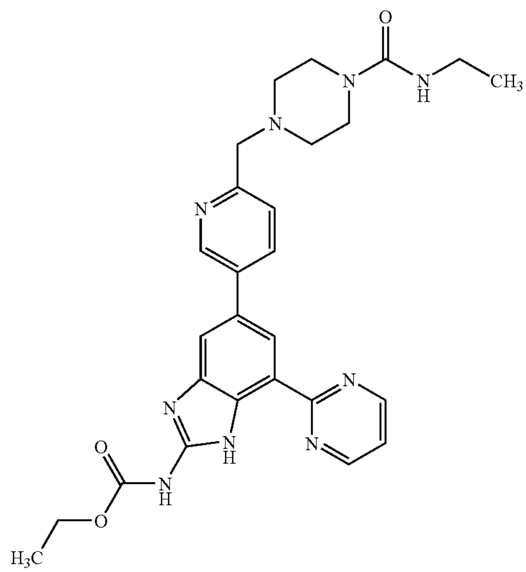 |
| I-332 | 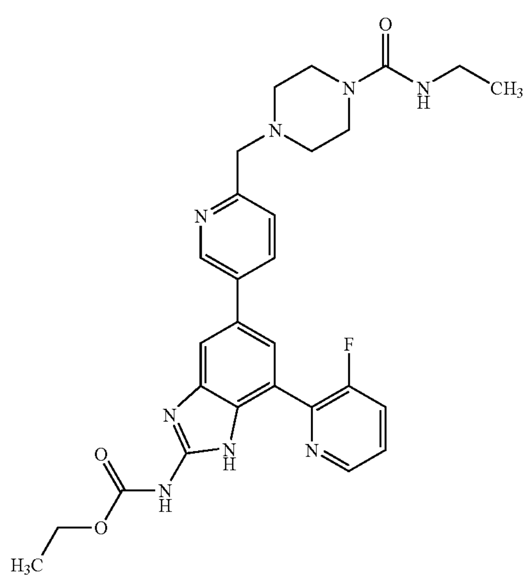 |

TABLE 2a-continued
| No. | Structure |
|---|---|
| I-333 | 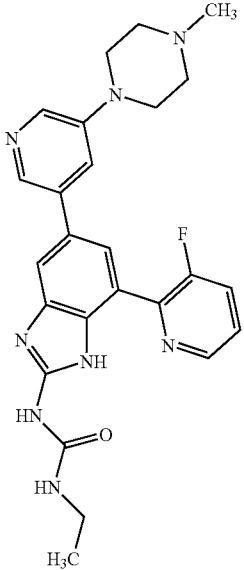 |
| I-334 | 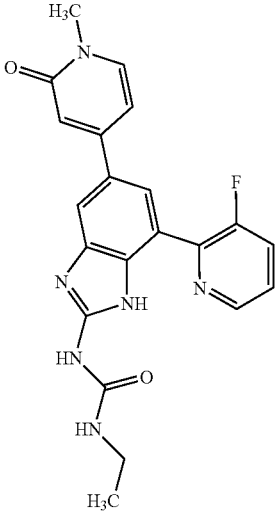 |

TABLE 2a-continued

| No. | Structure |
|---|---|
| I-335 | 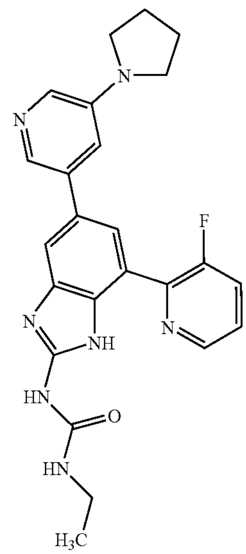 |
| I-336 | 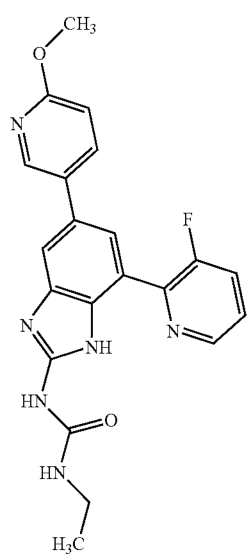 |

TABLE 2a-continued
| No. | Structure |
|---|---|
| I-337 | 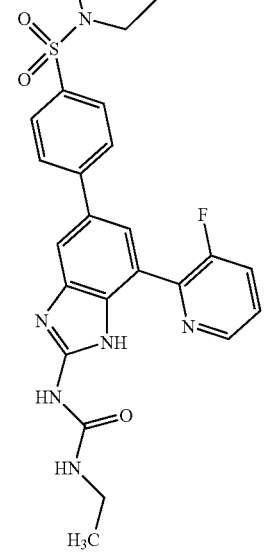 |
| I-338 | 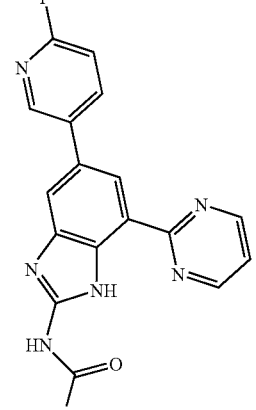 |

TABLE 2a-continued
| No. | Structure |
|---|---|
| I-339 | 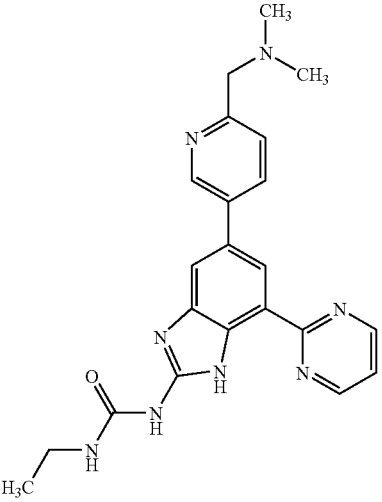 |
| I-340 | 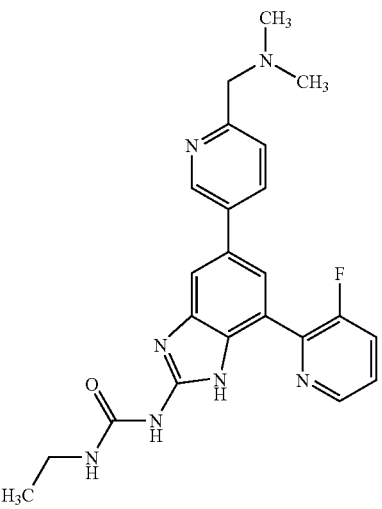 |
| I-341 | 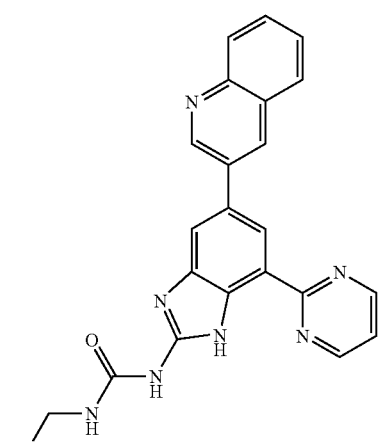 |

TABLE 2a-continued

| No. | Structure |
|---|---|
| I-342 | 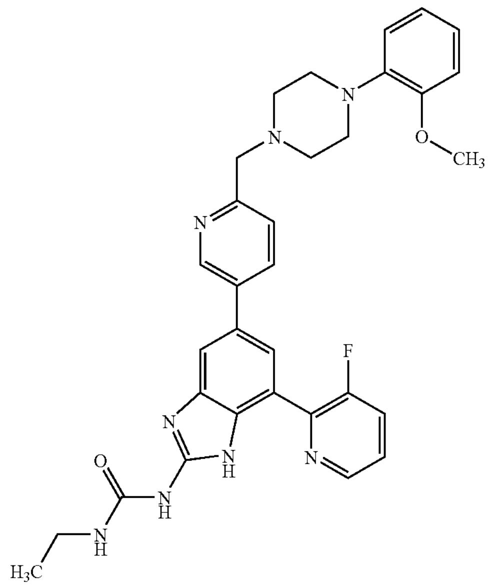 |
| I-343 | 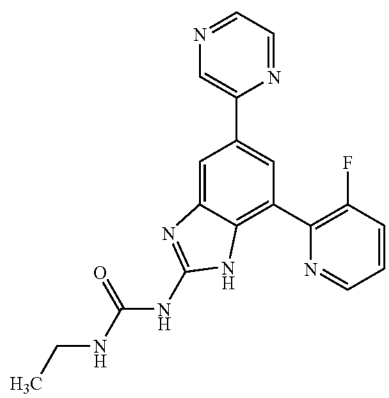 |
| I-344 | 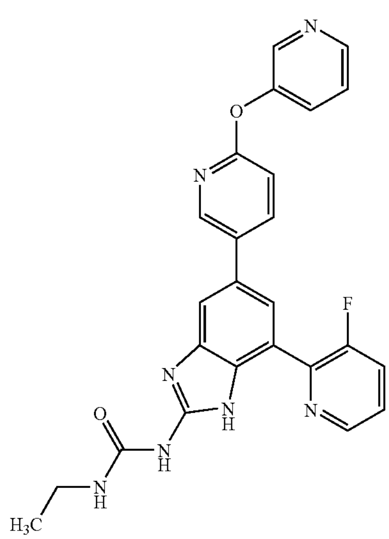 |

TABLE 2a-continued
| No. | Structure |
|---|---|
| I-345 | 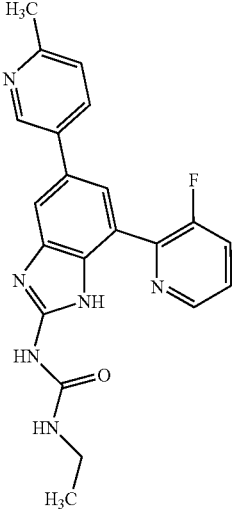 |
| I-346 | 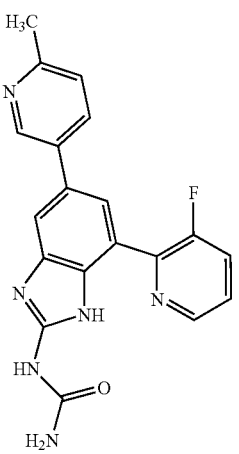 |

TABLE 2a-continued
| No. | Structure |
| --- | --- |
| I-347 | 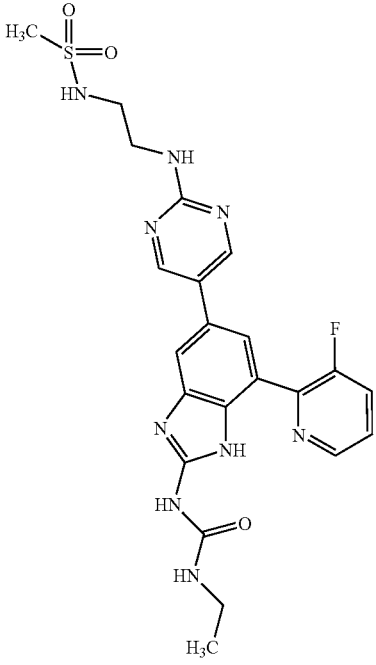 |
| I-348 | 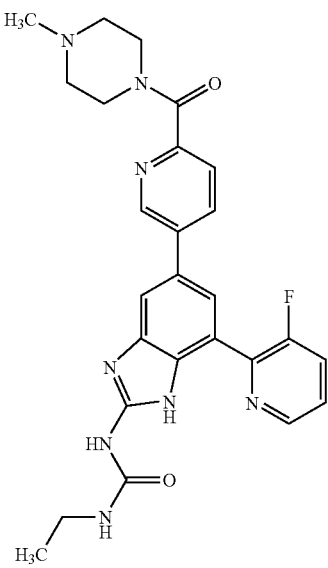 |

TABLE 2a-continued

| No. | Structure |
|---|---|
| I-349 | 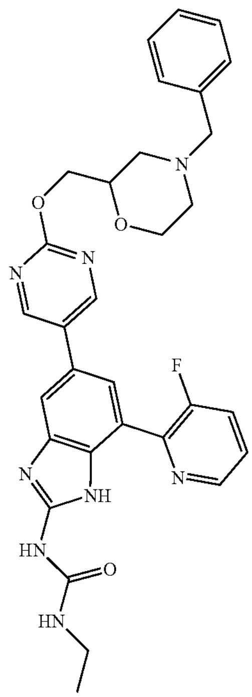 |
| I-350 | 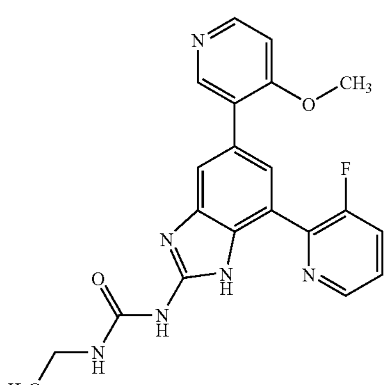 |

TABLE 2a-continued

| No. | Structure |
|---|---|
| I-351 | 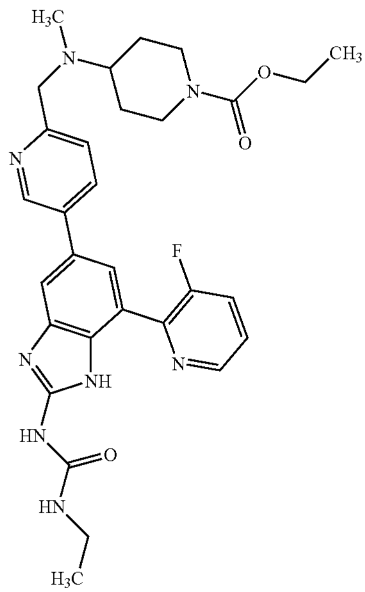 |
| I-352 | 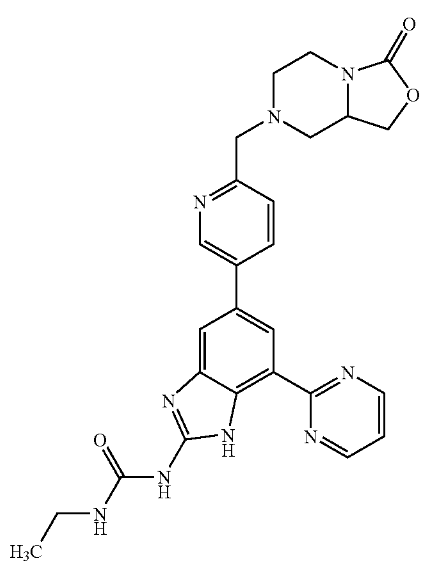 |

TABLE 2a-continued

| No. | Structure |
|---|---|
| I-353 | 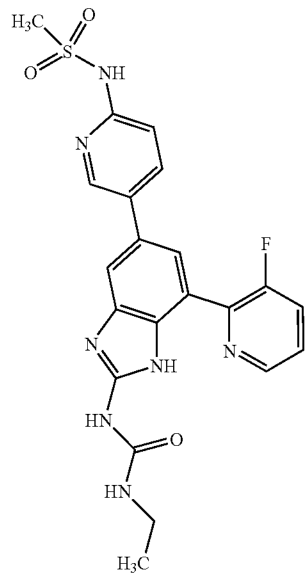 |
| I-354 | 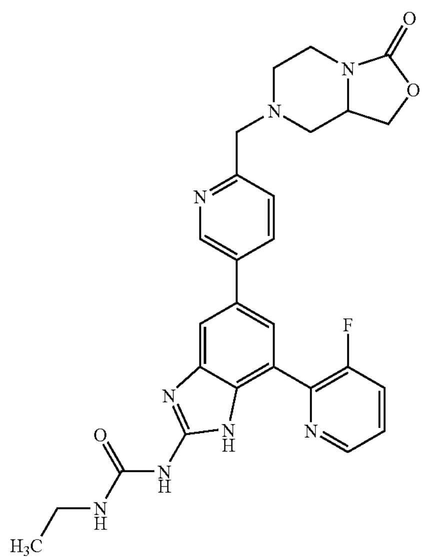 |
| I-355 | 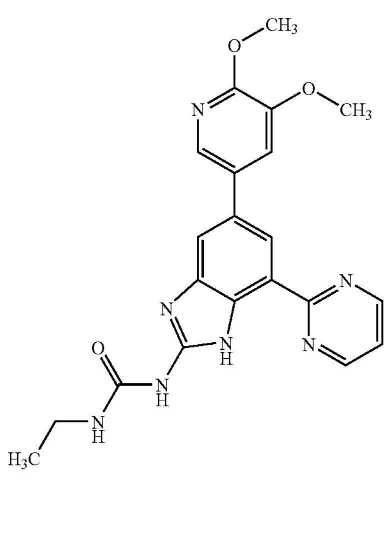 |

TABLE 2a-continued
| No. | Structure |
|---|---|
| I-356 | 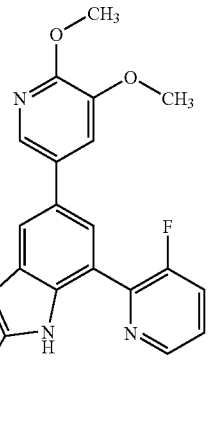 |
| I-357 | 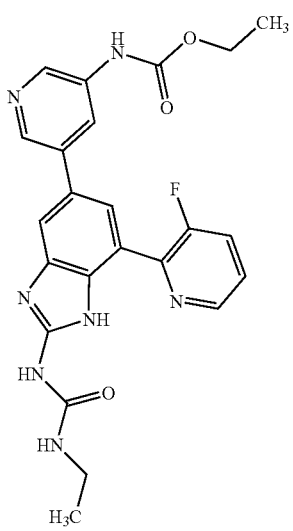 |
| I-358 | 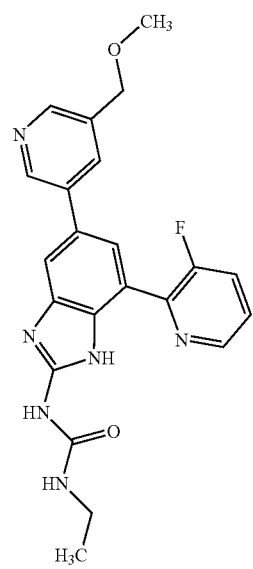 |

TABLE 2a-continued
| No. | Structure |
|---|---|
| I-359 | 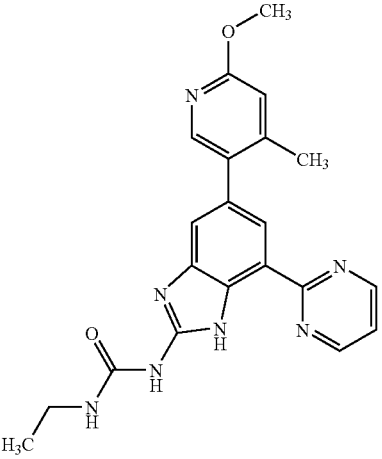 |
| I-360 | 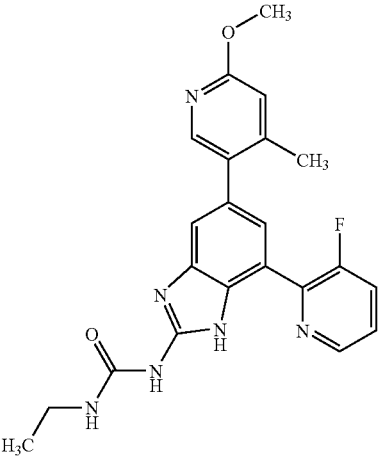 |
| I-361 | 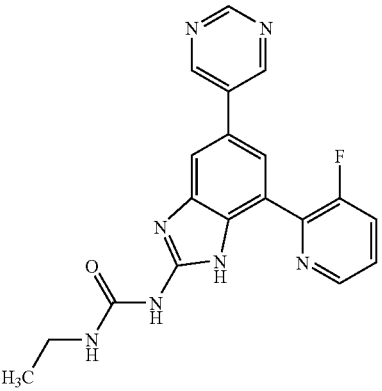 |

TABLE 2a-continued
| No. | Structure |
| --- | --- |
| I-362 | 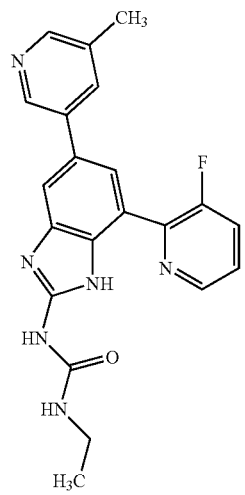 |
| I-363 | 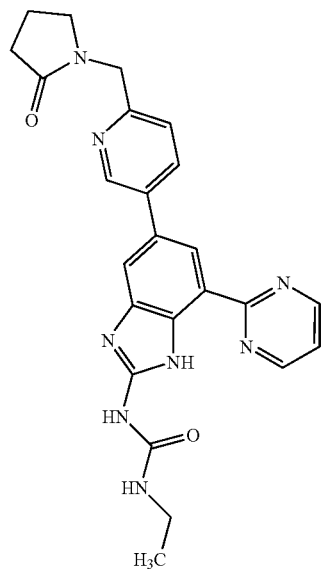 |

TABLE 2a-continued

| No. | Structure |
| --- | --- |
| I-364 | 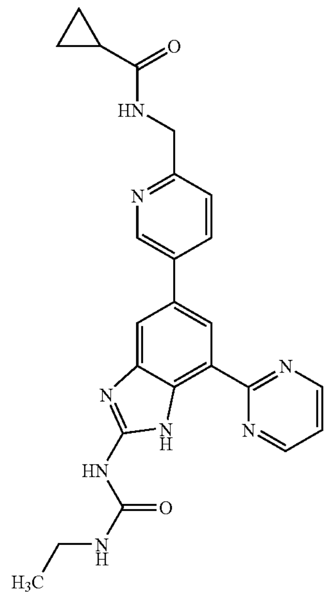 |
| I-365 | 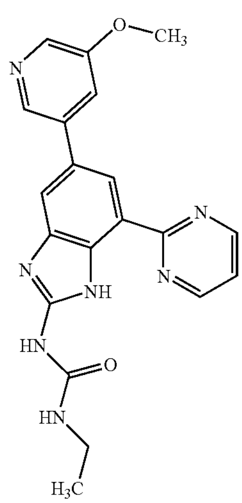 |

TABLE 2a-continued
| No. | Structure |
|---|---|
| I-366 | 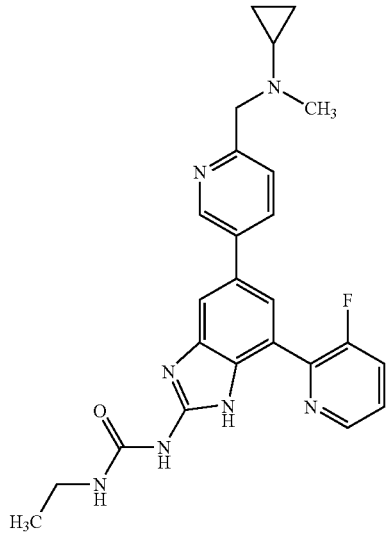 |
| I-367 | 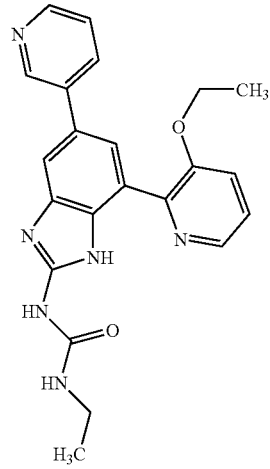 |
| I-368 | 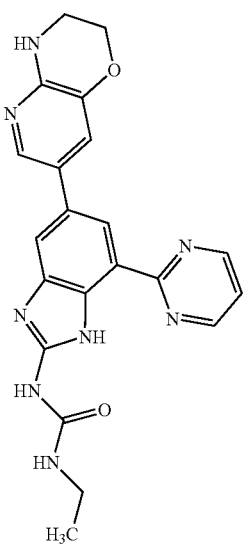 |

TABLE 2a-continued
| No. | Structure |
|---|---|
| I-369 | 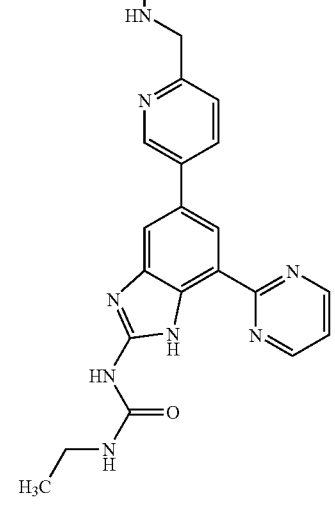 |
| I-370 | 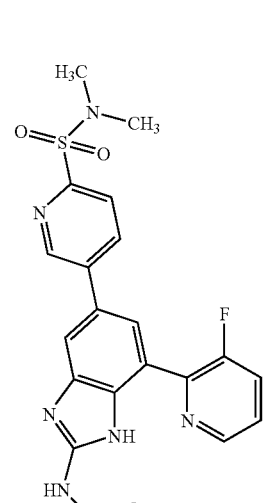 |

TABLE 2a-continued
| No. | Structure |
|---|---|
| I-371 | 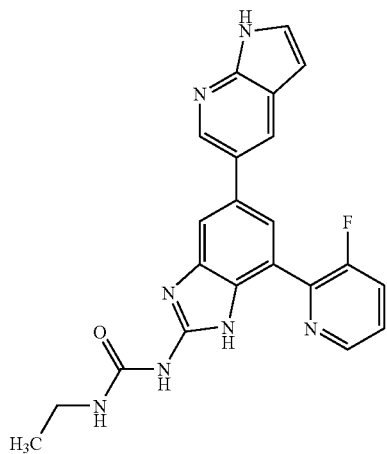 |
| I-372 | 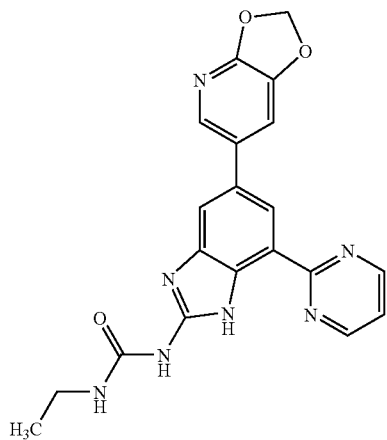 |
| I-373 | 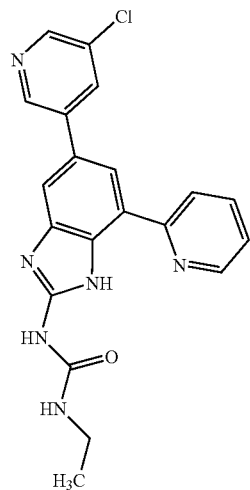 |

TABLE 2a-continued
| No. | Structure |
|---|---|
| I-374 | 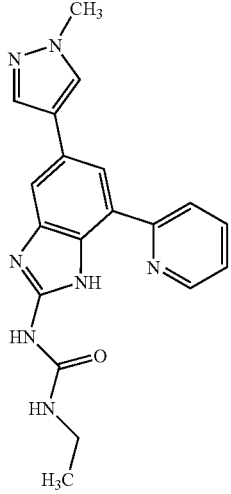 |
| I-375 | 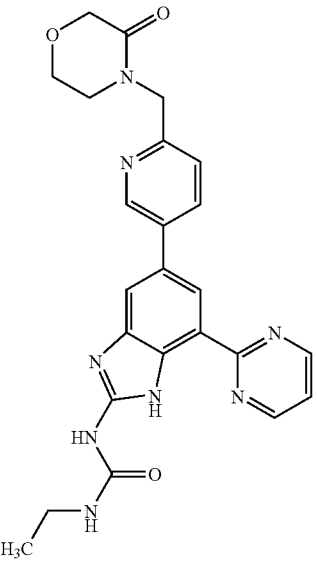 |

TABLE 2a-continued
| No. | Structure |
|---|---|
| I-376 | 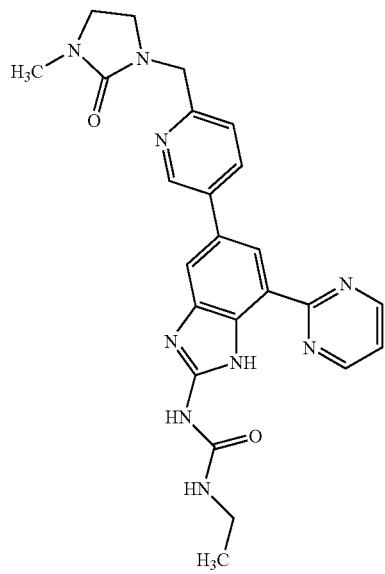 |
| I-377 | 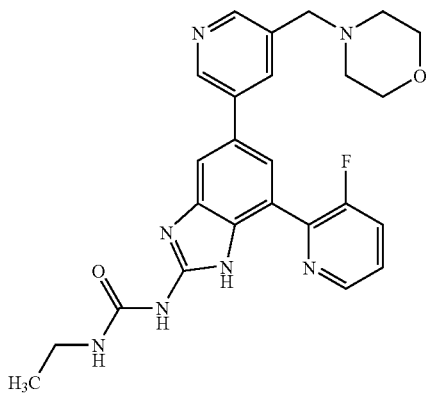 |
| I-378 | 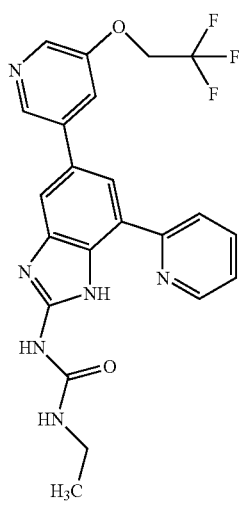 |

TABLE 2a-continued
| No. | Structure |
|---|---|
| I-379 | 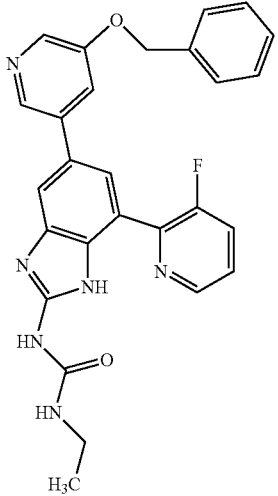 |
| I-380 | 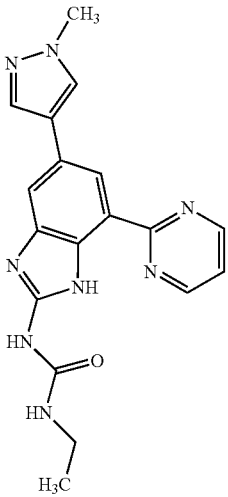 |
| I-381 | 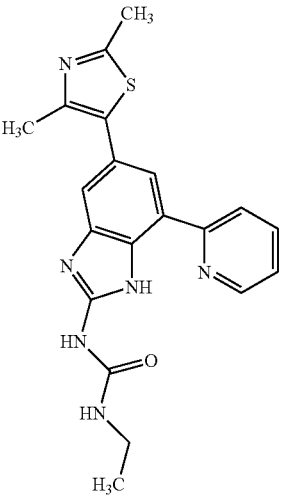 |

TABLE 2a-continued
| No. | Structure |
|---|---|
| I-382 | 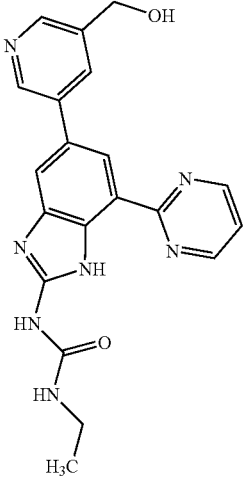 |
| I-383 | 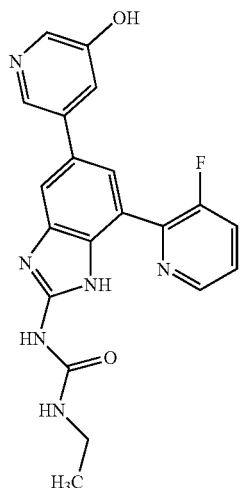 |
| I-384 | 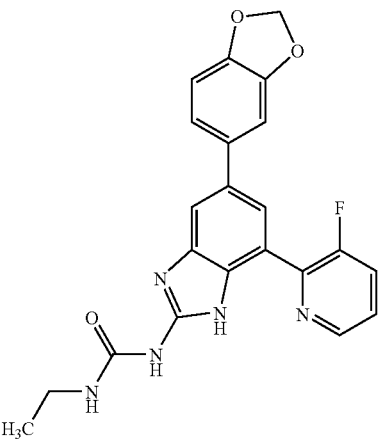 |

TABLE 2a-continued
| No. | Structure |
|---|---|
| I-385 | 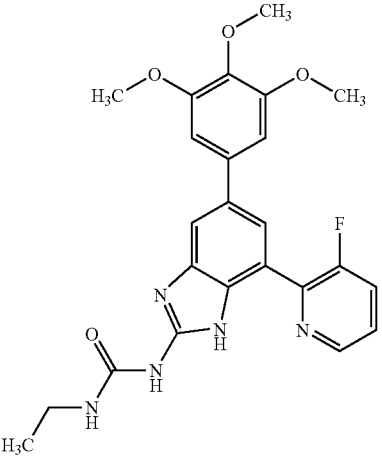 |
| I-386 | 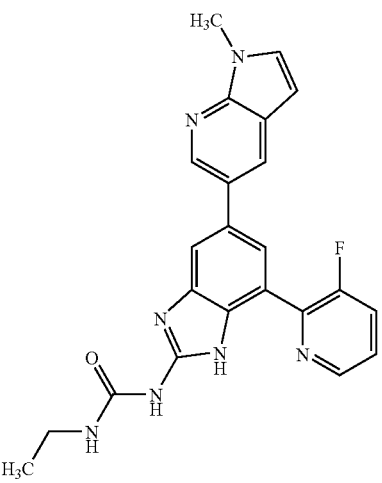 |
| I-387 | 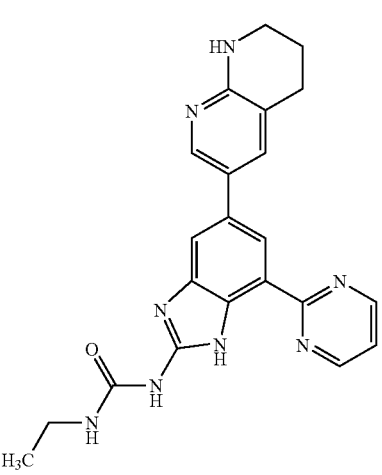 |

TABLE 2a-continued
| No. | Structure |
|---|---|
| I-388 | 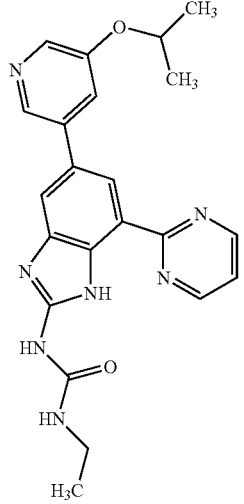 |
| I-389 | 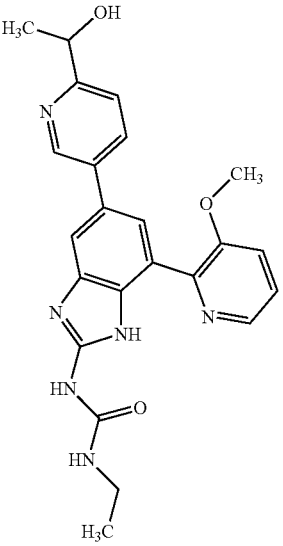 |

TABLE 2a-continued

| No. | Structure |
|---|---|
| I-390 | 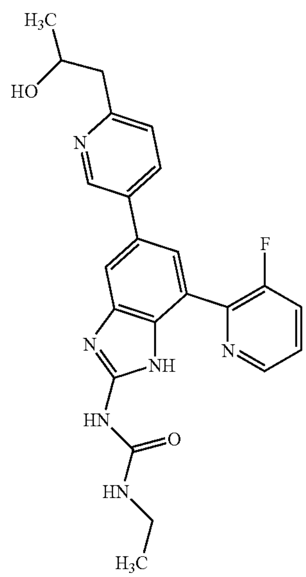 |
| I-391 | 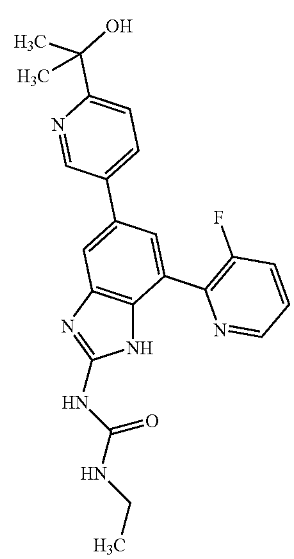 |

TABLE 2a-continued

| No. | Structure |
|---|---|
| I-392 | 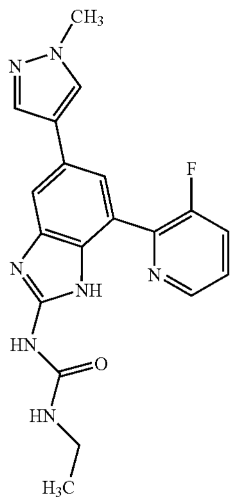 |
| I-393 | 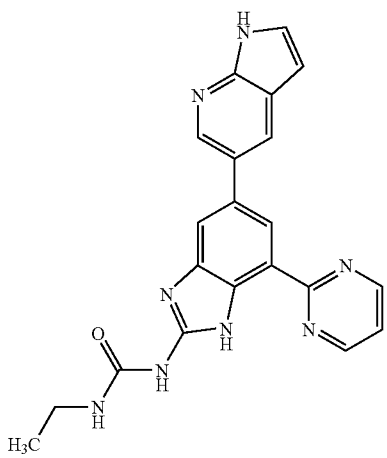 |
| I-394 | 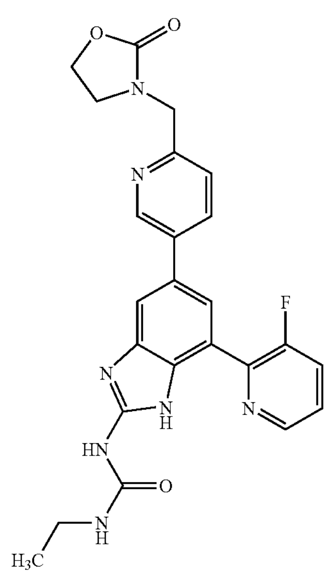 |

TABLE 2a-continued
| No. | Structure |
|---|---|
| I-395 | 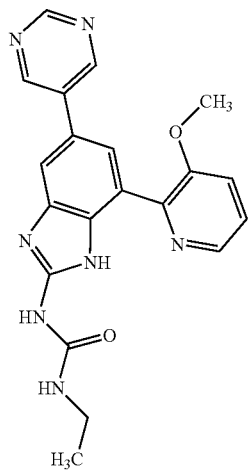 |
| I-396 | 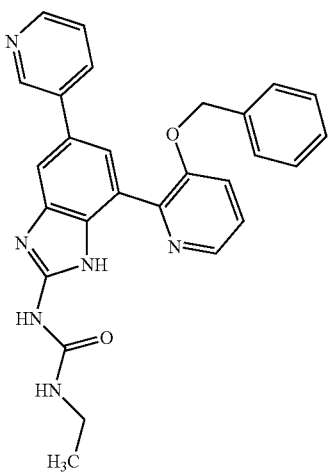 |
| I-397 | 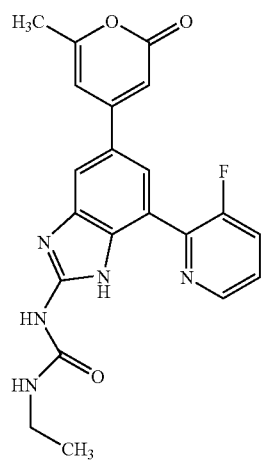 |

TABLE 2a-continued
| No. | Structure |
|---|---|
| I-398 | 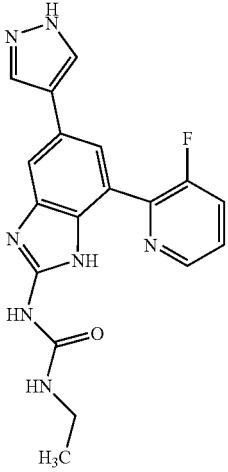 |
| I-399 | 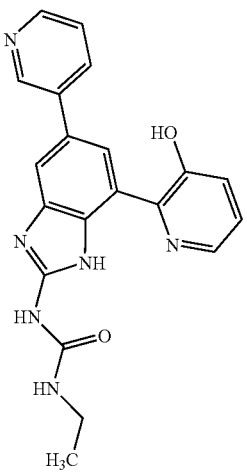 |
| I-400 | 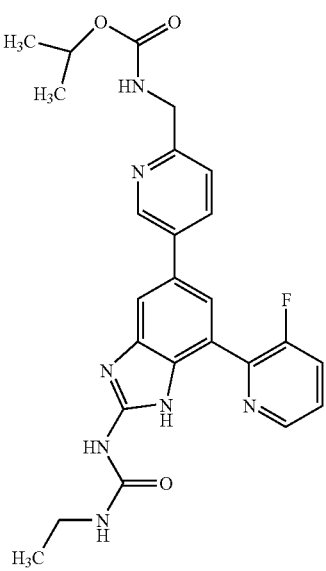 |

TABLE 2a-continued
| No. | Structure |
|---|---|
| I-401 | 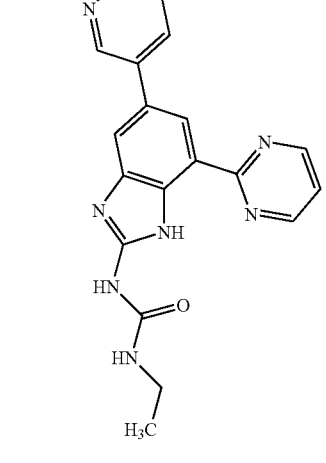 |
| I-402 | 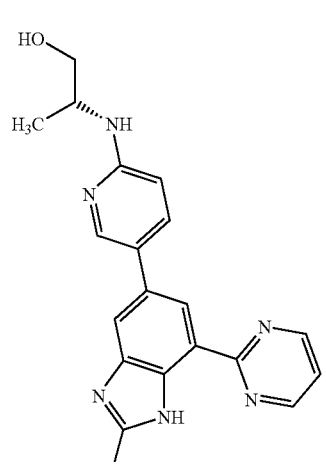 |

TABLE 2a-continued
| No. | Structure |
|---|---|
| I-403 | 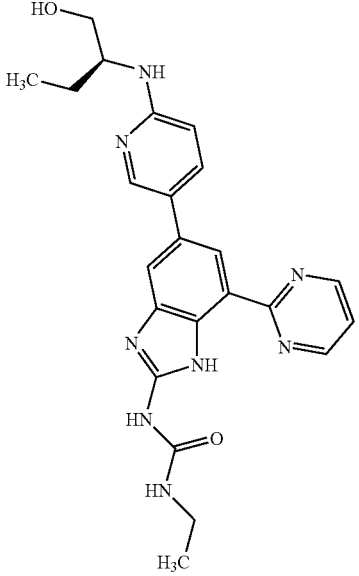 |
| I-404 | 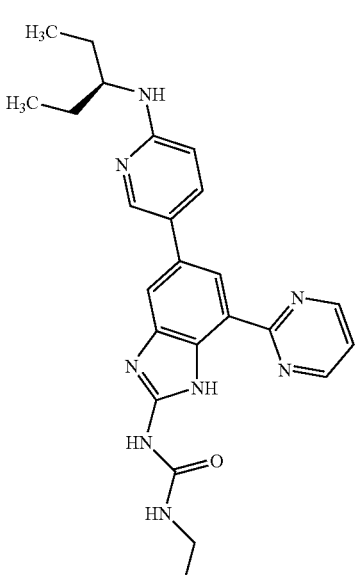 |

TABLE 2a-continued
| No. | Structure |
| --- | --- |
| I-405 | 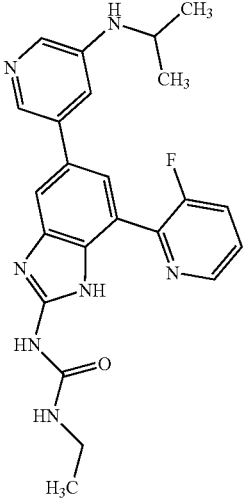 |
| I-406 | 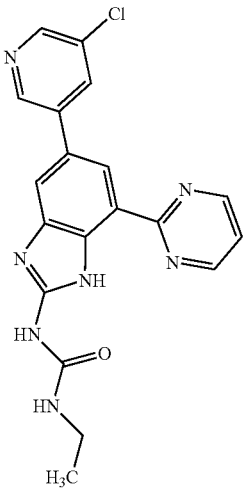 |
| I-407 | 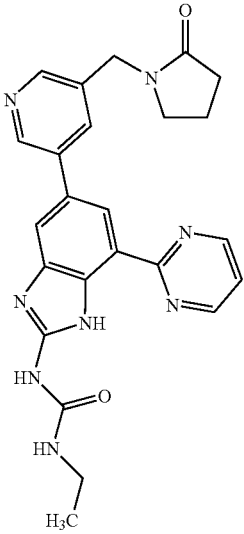 |

TABLE 2a-continued

| No. | Structure |
|---|---|
| I-408 | 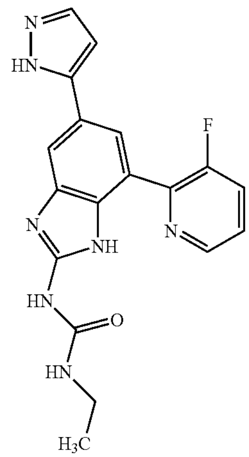 |
| I-409 | 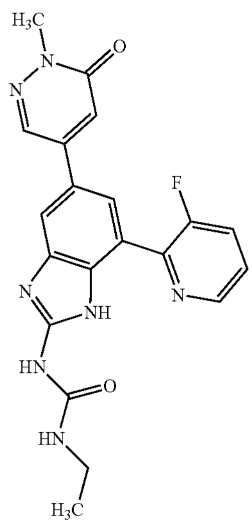 |
| I-410 | 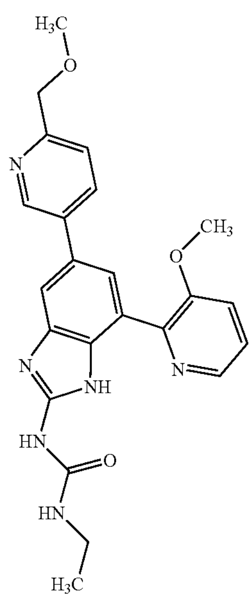 |

TABLE 2a-continued
| No. | Structure |
|---|---|
| I-411 | 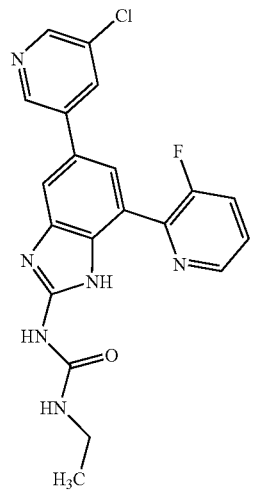 |
| I-412 | 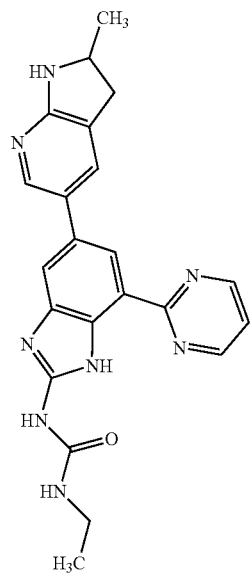 |

TABLE 2a-continued

| No. | Structure |
|---|---|
| I-413 | 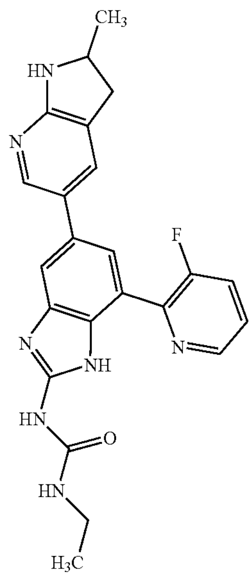 |
| I-414 | 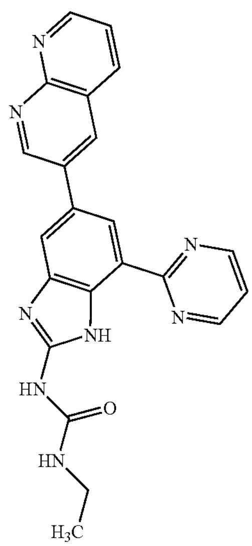 |
| I-415 | 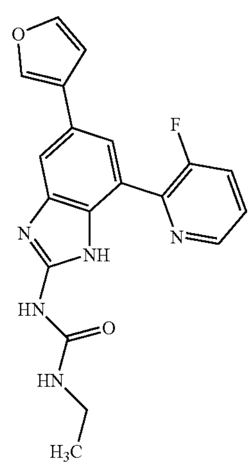 |

TABLE 2a-continued
| No. | Structure |
|---|---|
| I-416 | 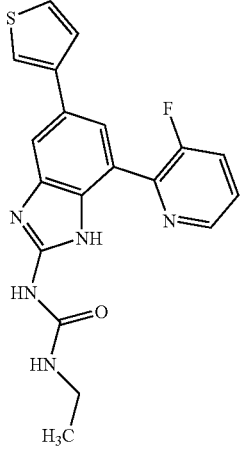 |
| I-417 | 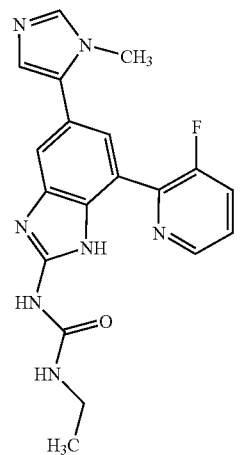 |
| I-418 | 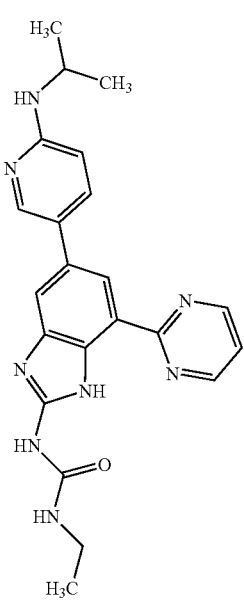 |

TABLE 2a-continued
| No. | Structure |
|---|---|
| I-419 | 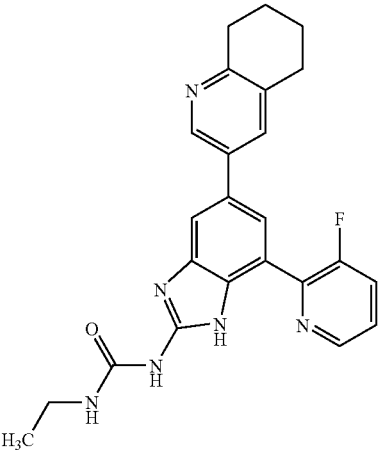 |
| I-420 | 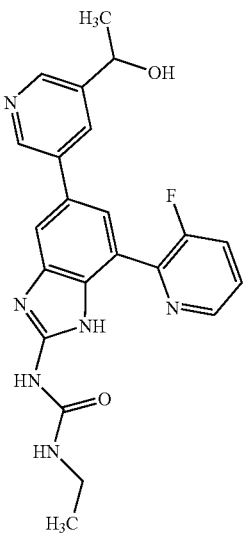 |
| I-421 | 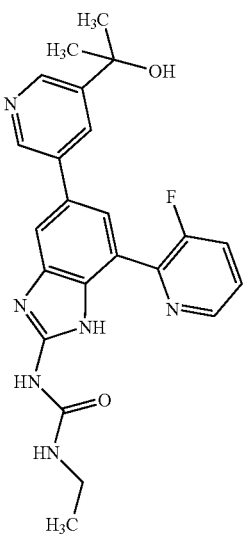 |

TABLE 2a-continued

| No. | Structure |
|---|---|
| I-422 | 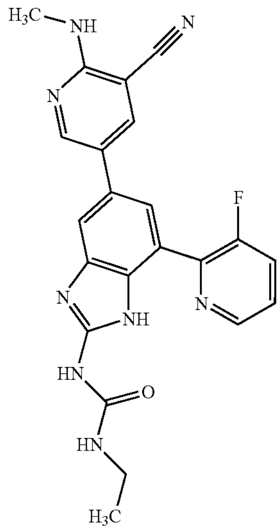 |
| I-423 | 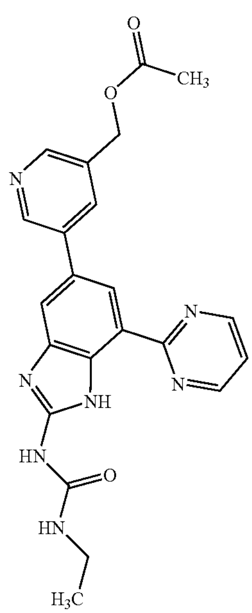 |

TABLE 2a-continued
| No. | Structure |
|---|---|
| I-424 | 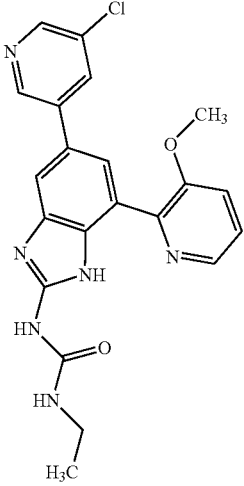 |
| I-425 | 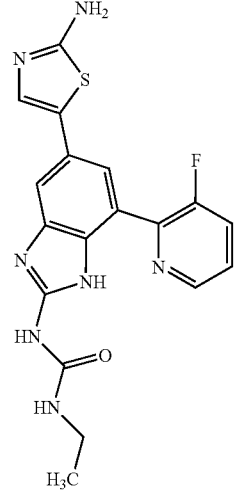 |
| I-426 | 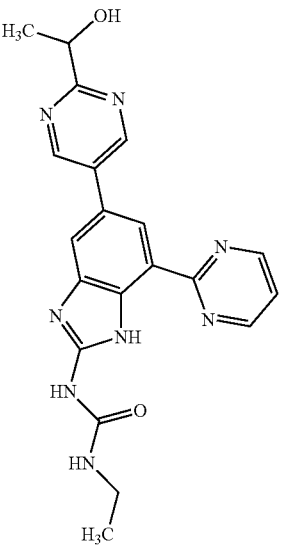 |

TABLE 2a-continued
| No. | Structure |
|---|---|
| I-427 | 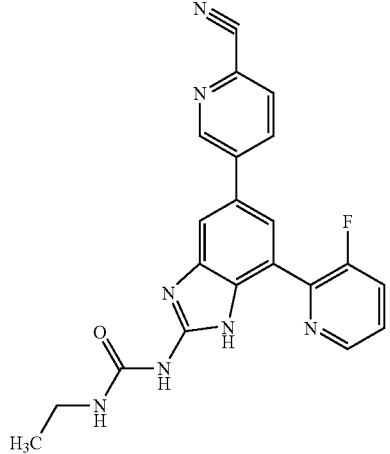 |
| I-428 | 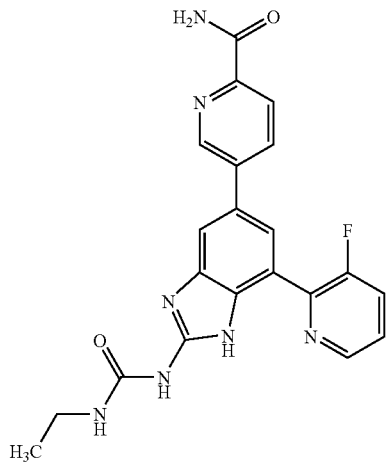 |
| I-429 | 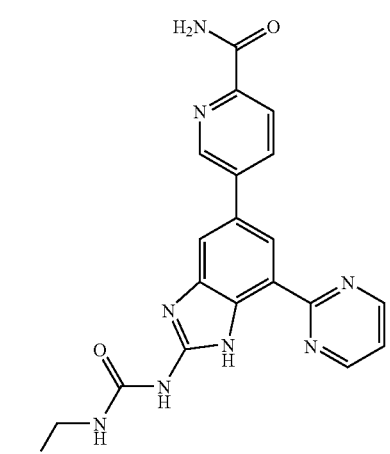 |

TABLE 2a-continued
| No. | Structure |
|---|---|
| I-430 | 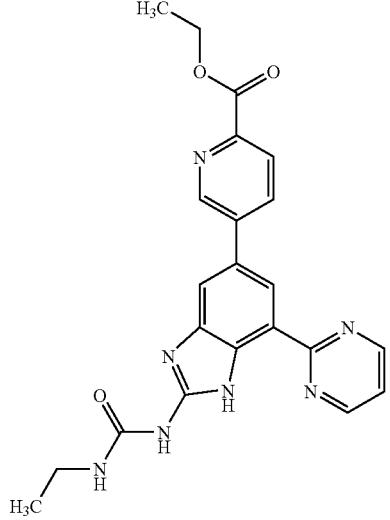 |
| I-431 | 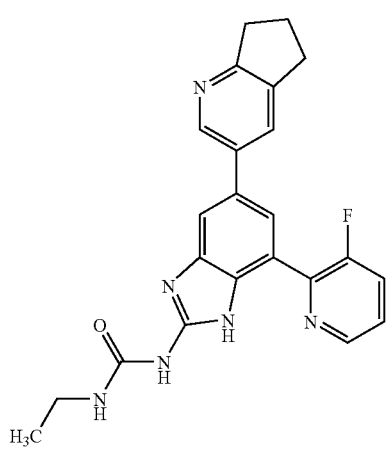 |
| I-432 | 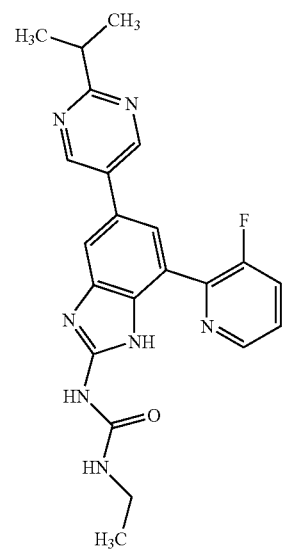 |

TABLE 2a-continued
| No. | Structure |
|---|---|
| I-433 | 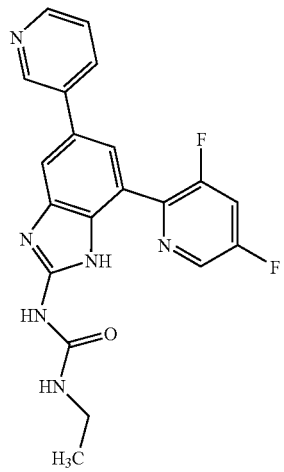 |
| I-434 | 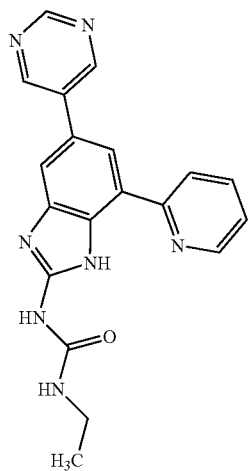 |
| I-435 | 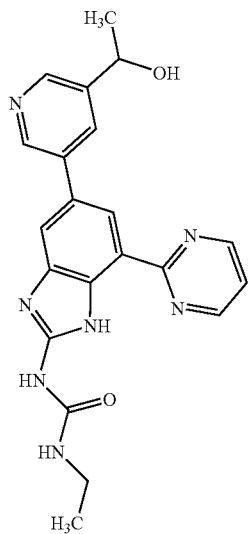 |

TABLE 2a-continued
| No. | Structure |
|---|---|
| I-436 | 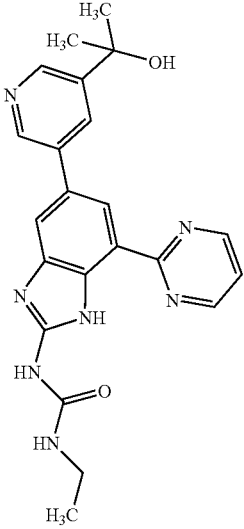 |
| I-437 | 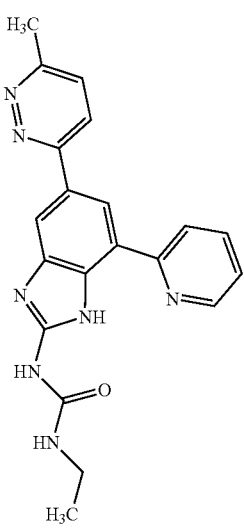 |
| I-438 | 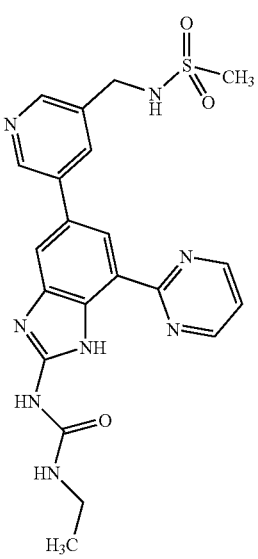 |

TABLE 2a-continued

| No. | Structure |
|---|---|
| I-439 | 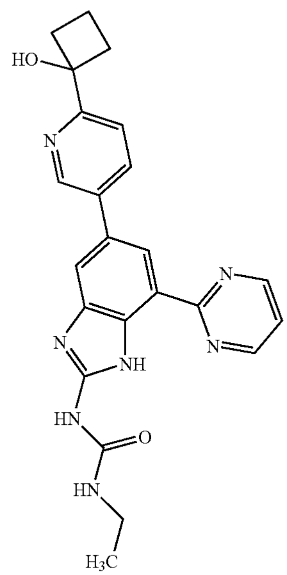 |
| I-440 | 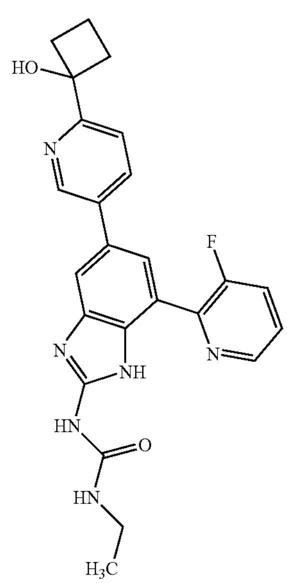 |

TABLE 2a-continued
| No. | Structure |
|---|---|
| I-441 | 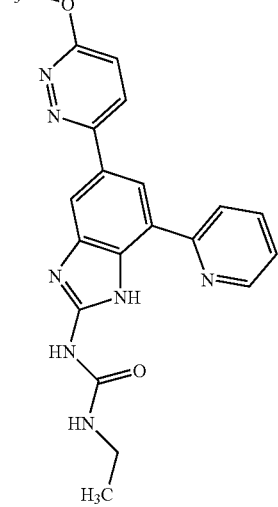 |
| I-442 | 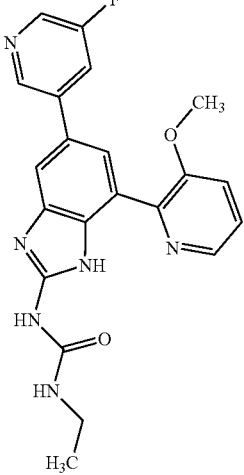 |
| I-443 | 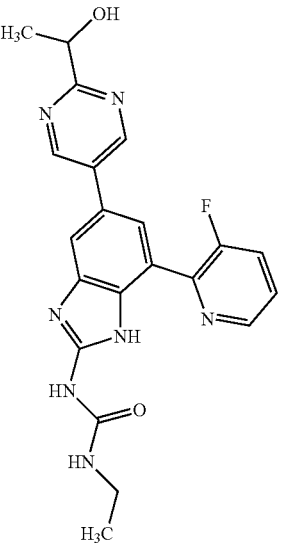 |

TABLE 2a-continued

| No. | Structure |
|---|---|
| I-444 | 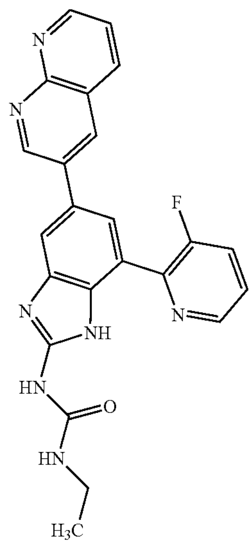 |
| I-445 | 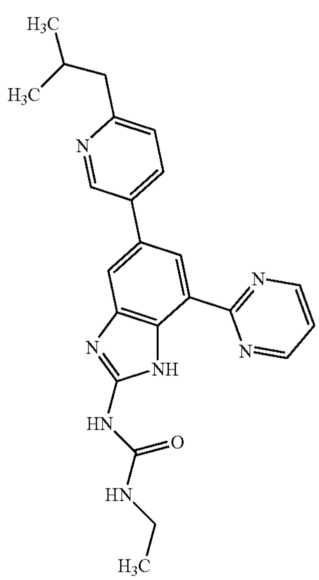 |

TABLE 2a-continued

| No. | Structure |
|---|---|
| I-446 | 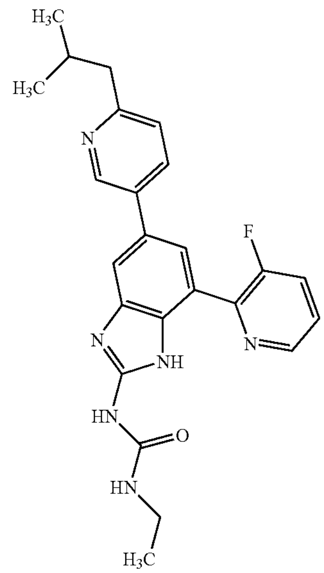 |
| I-447 | 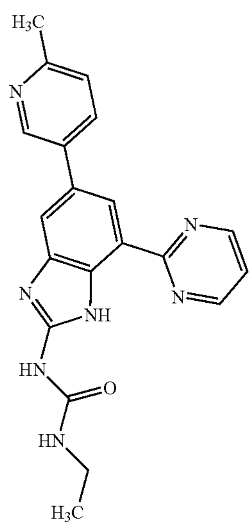 |
| I-448 | 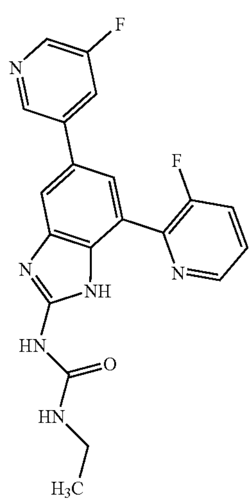 |

TABLE 2a-continued
| No. | Structure |
|---|---|
| I-449 | 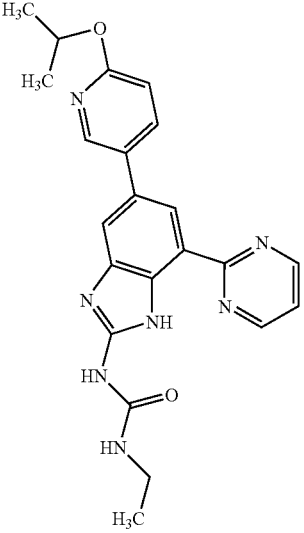 |
| I-450 | 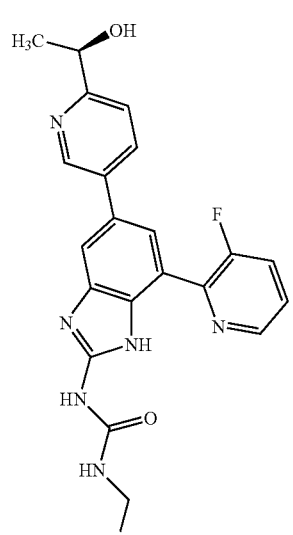 |

TABLE 2a-continued

| No. | Structure |
|---|---|
| I-451 | 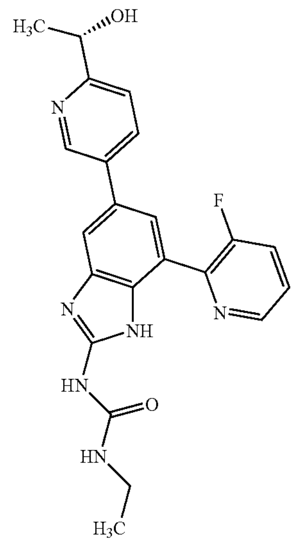 |
| I-452 | 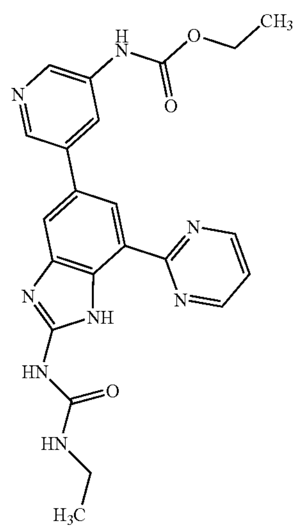 |

TABLE 2a-continued

| No. | Structure |
|---|---|
| I-453 | 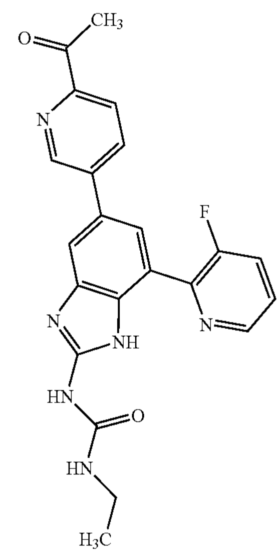 |
| I-454 | 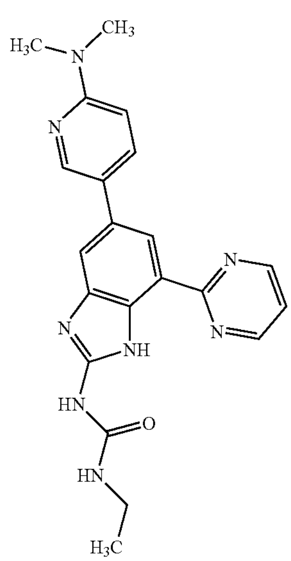 |

TABLE 2a-continued
| No. | Structure |
|---|---|
| I-455 | 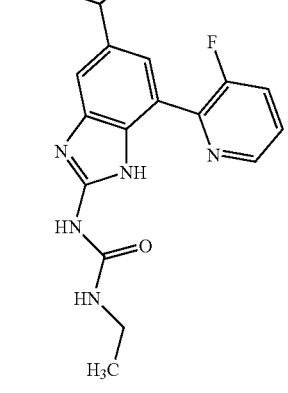 |
| I-456 | 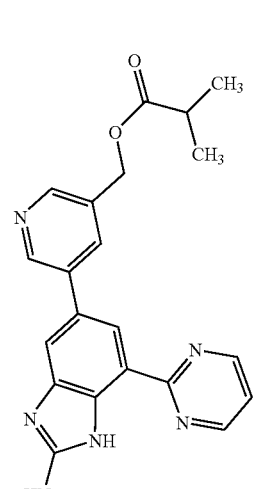 |

TABLE 2a-continued
| No. | Structure |
|---|---|
| I-457 | 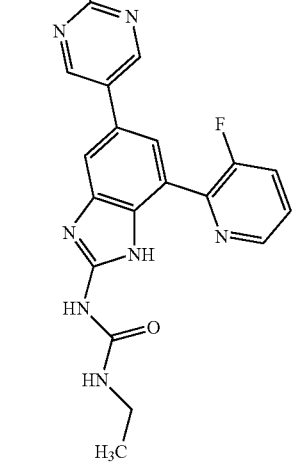 |
| I-458 | 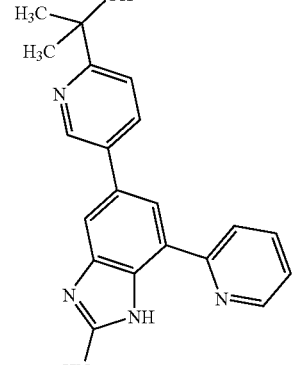 |

TABLE 2a-continued
| No. | Structure |
|---|---|
| I-459 | 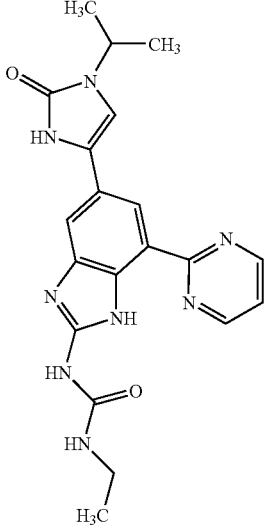 |
| I-460 | 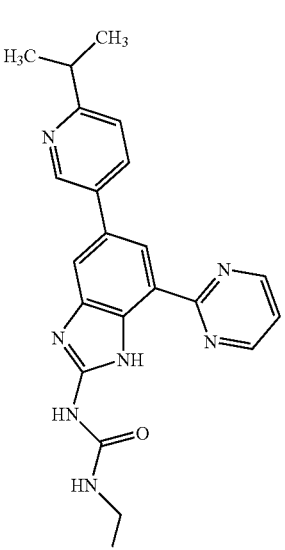 |

TABLE 2a-continued
| No. | Structure |
|---|---|
| I-461 | 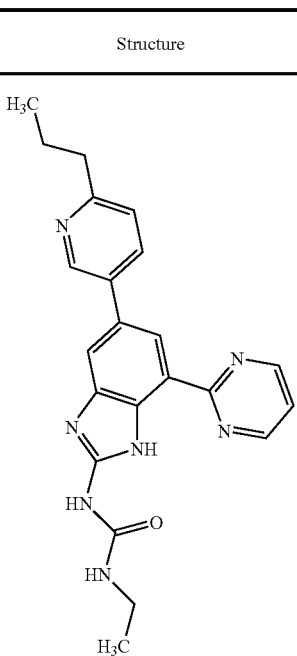 |
| I-462 | 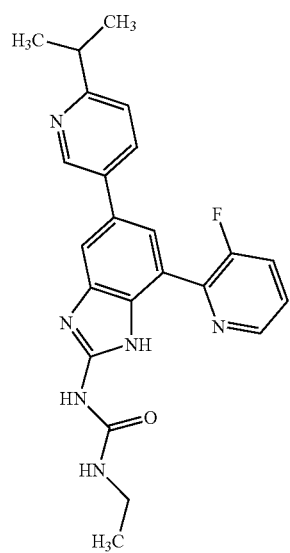 |

TABLE 2a-continued
| No. | Structure |
|---|---|
| I-463 | 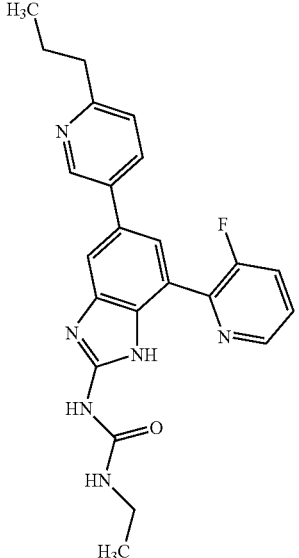 |
| I-464 | 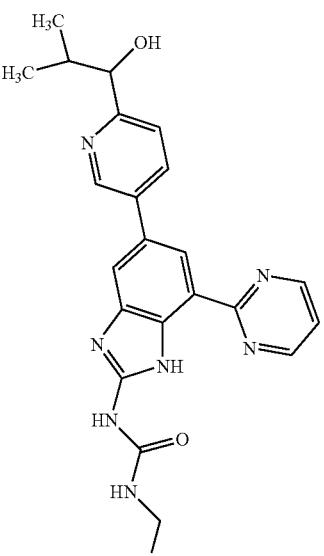 |

TABLE 2a-continued
| No. | Structure |
|---|---|
| I-465 | 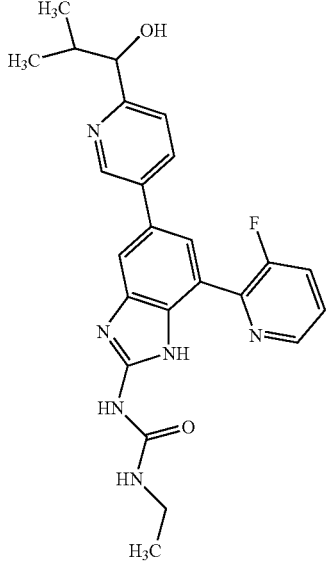 |
| I-466 | 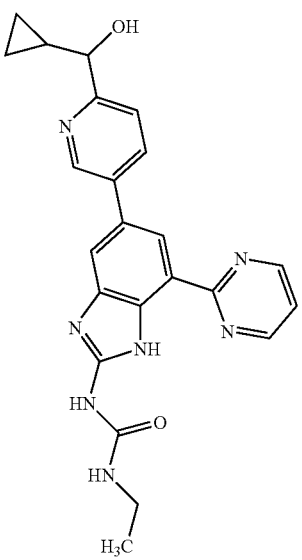 |

TABLE 2a-continued
| No. | Structure |
|---|---|
| I-467 | 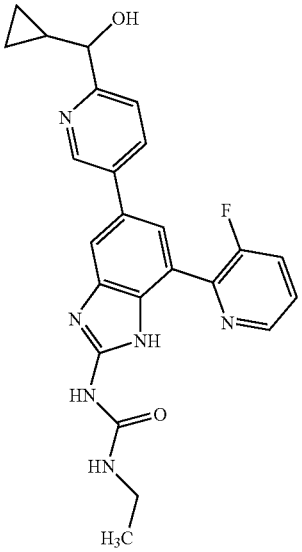 |
| I-468 | 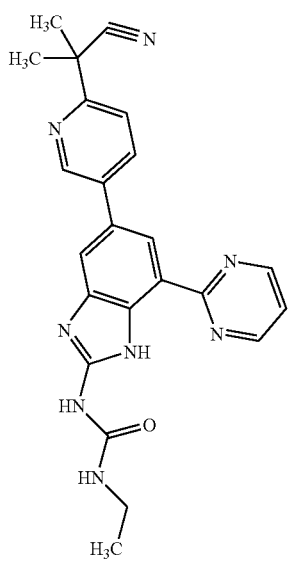 |

TABLE 2a-continued

| No. | Structure |
|---|---|
| I-469 | 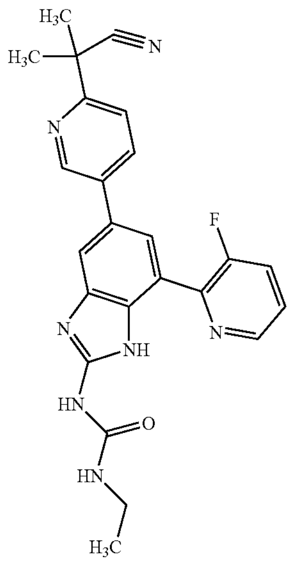 |
| I-470 | 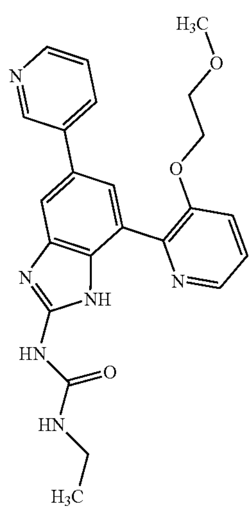 |

TABLE 2a-continued

| No. | Structure |
|---|---|
| I-471 | 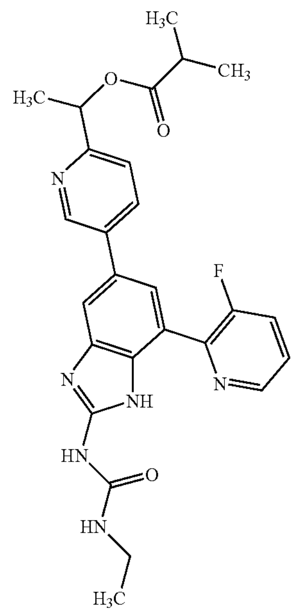 |
| I-472 | 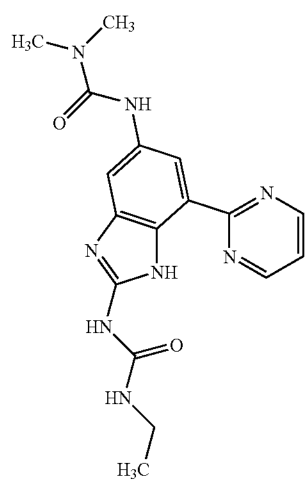 |
| I-473 | 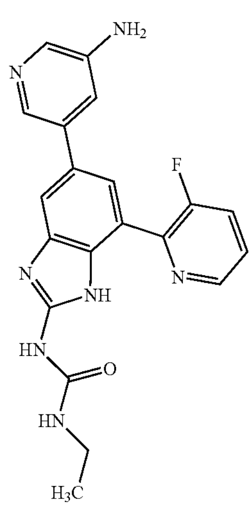 |

TABLE 2a-continued

| No. | Structure |
|---|---|
| I-474 | 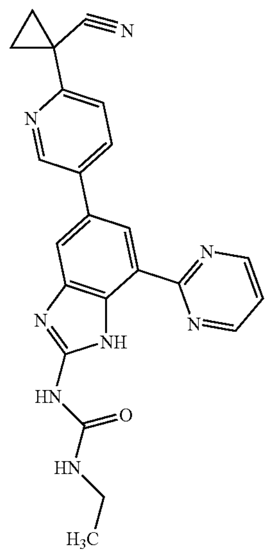 |
| I-475 | 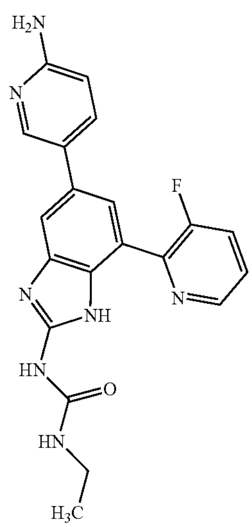 |
| I-476 | 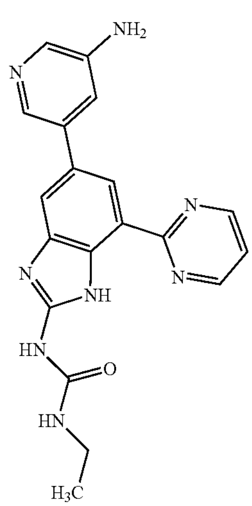 |

TABLE 2a-continued

| No. | Structure |
|---|---|
| I-477 | 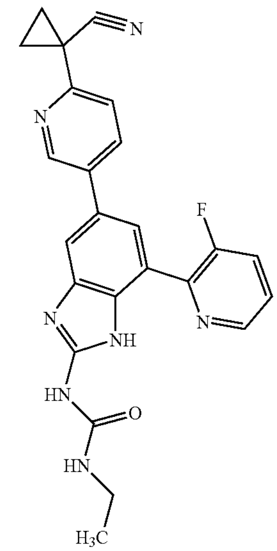 |
| I-478 | 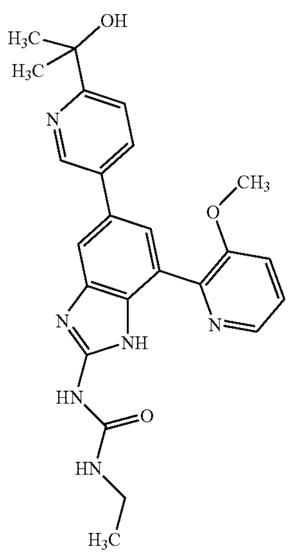 |
| I-479 | 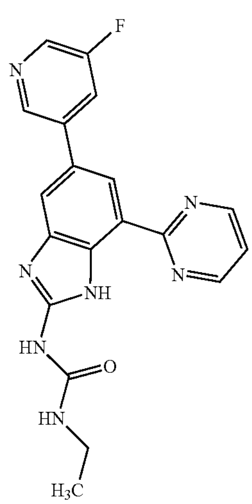 |

TABLE 2a-continued
| No. | Structure |
|---|---|
| I-480 | 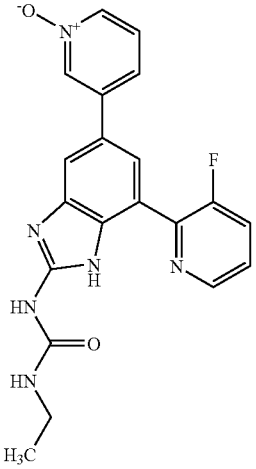 |
| I-481 | 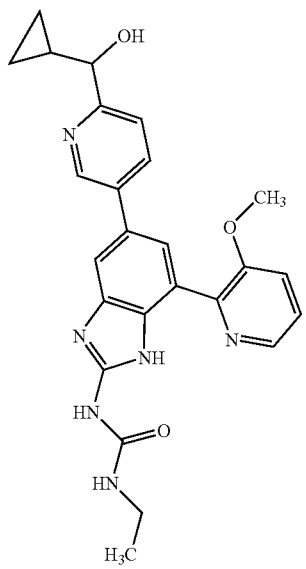 |
| I-482 | 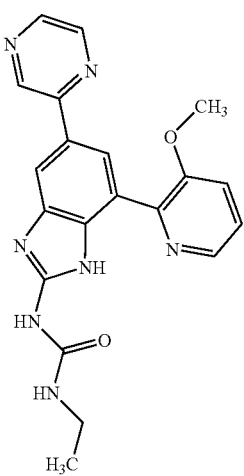 |

TABLE 2a-continued

| No. | Structure |
|---|---|
| I-483 | *(chemical structure)* |
| I-484 | *(chemical structure)* |

TABLE 2a-continued

| No. | Structure |
|---|---|
| I-485 | 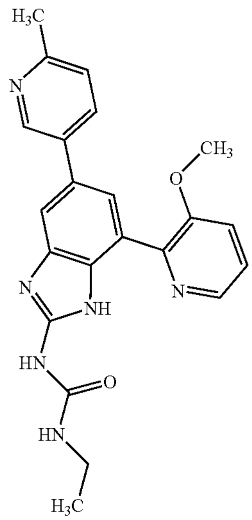 |
| I-486 | 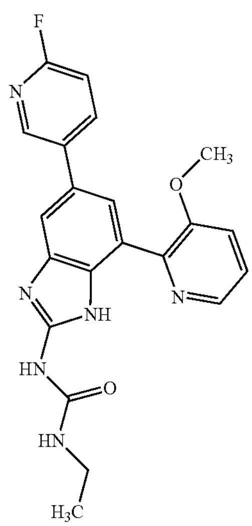 |
| I-487 | 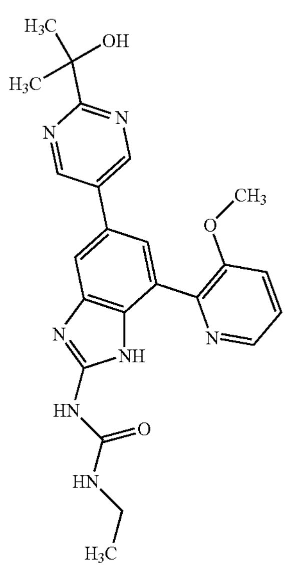 |

TABLE 2a-continued
| No. | Structure |
|---|---|
| I-488 | 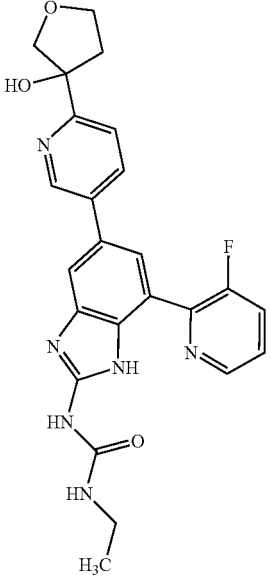 |
| I-489 | 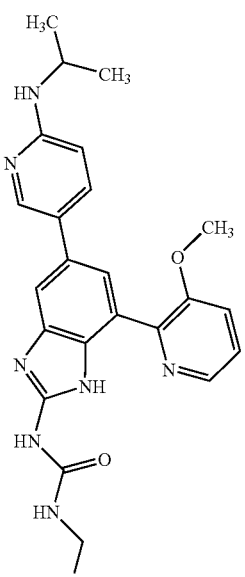 |

TABLE 2a-continued
| No. | Structure |
|---|---|
| I-490 | 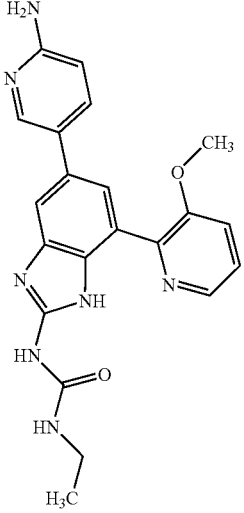 |
| I-491 | 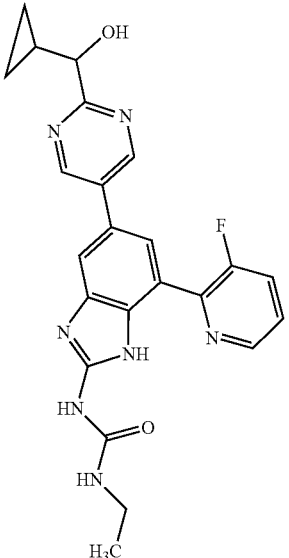 |

TABLE 2a-continued
| No. | Structure |
|---|---|
| I-492 | 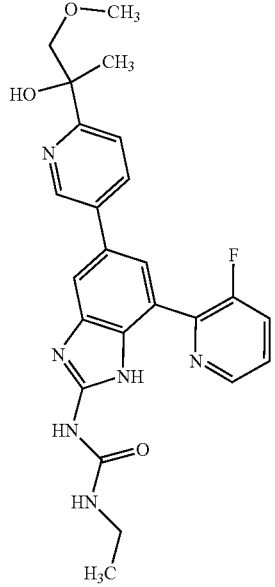 |
| I-493 | 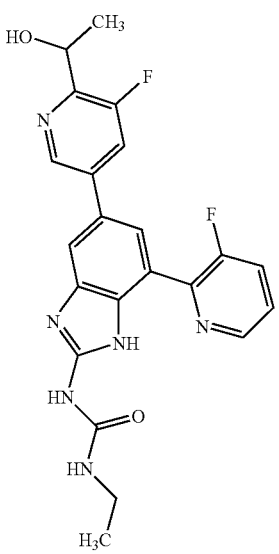 |

TABLE 2a-continued
| No. | Structure |
|---|---|
| I-494 | 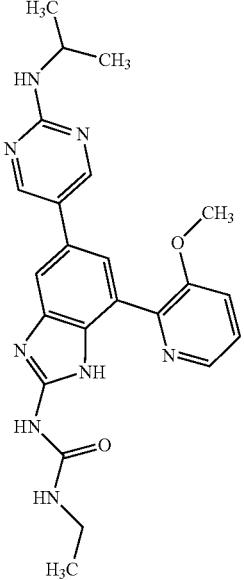 |
| I-495 | 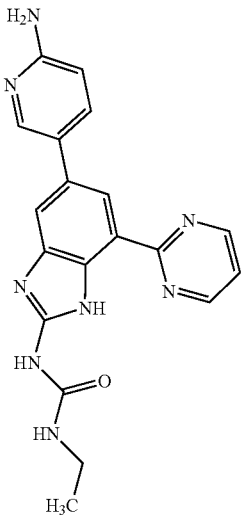 |

TABLE 2a-continued
| No. | Structure |
|---|---|
| I-496 | 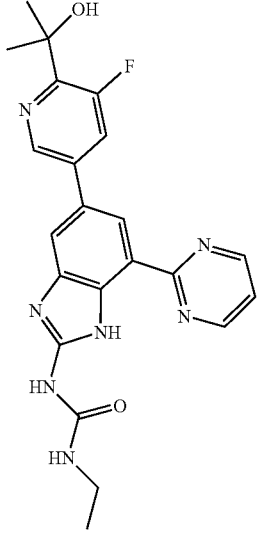 |
| I-497 | 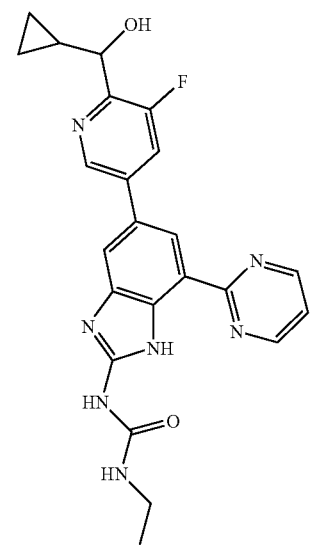 |

TABLE 2a-continued

| No. | Structure |
|---|---|
| I-498 | 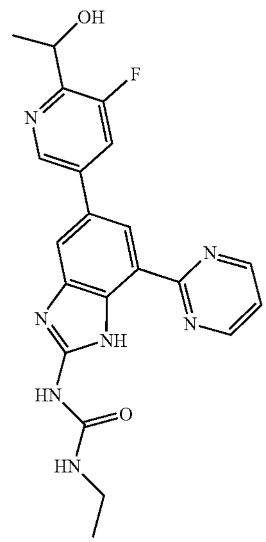 |
| I-499 | 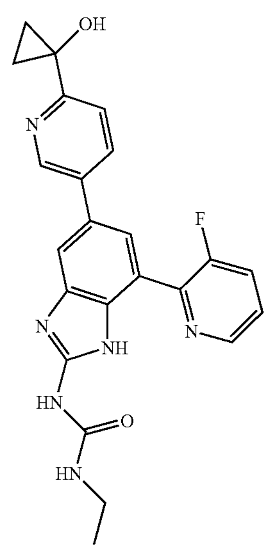 |

TABLE 2a-continued
| No. | Structure |
|---|---|
| I-500 | 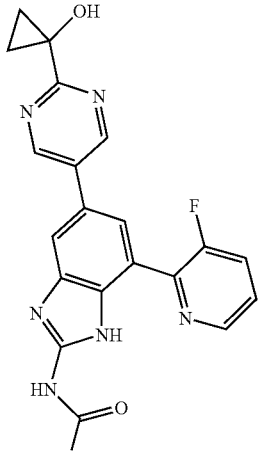 |
| I-501 | 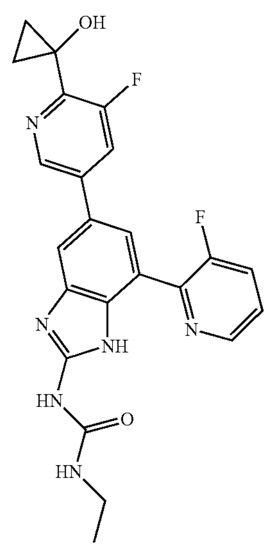 |

TABLE 2a-continued

| No. | Structure |
|---|---|
| and | |
| I-502 | (structure shown) |

The compounds of this invention may be prepared in general by methods known to those skilled in the art for analogous compounds, as illustrated by the general Schemes I, II, III, IV, and V shown below and the Examples set forth infra.

Scheme I

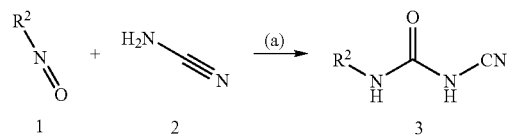

Scheme I above shows a general method for preparing N'-alkyl-N-cyanoureas 3 useful in the preparation of the compounds of the present invention wherein Z is NH. At step (a), cyanamide 2 was treated with an alkyl isocyanate in aqueous sodium hydroxide to afford, after acidification, compound 3. One of skill in the art would recognize that a variety of alkyl isocyanates would be amenable to the reaction conditions of Scheme I to form a variety of N'-alkyl-N-cyanoureas.

Scheme II

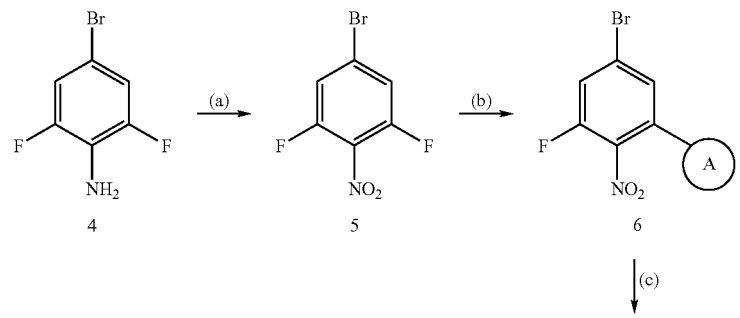

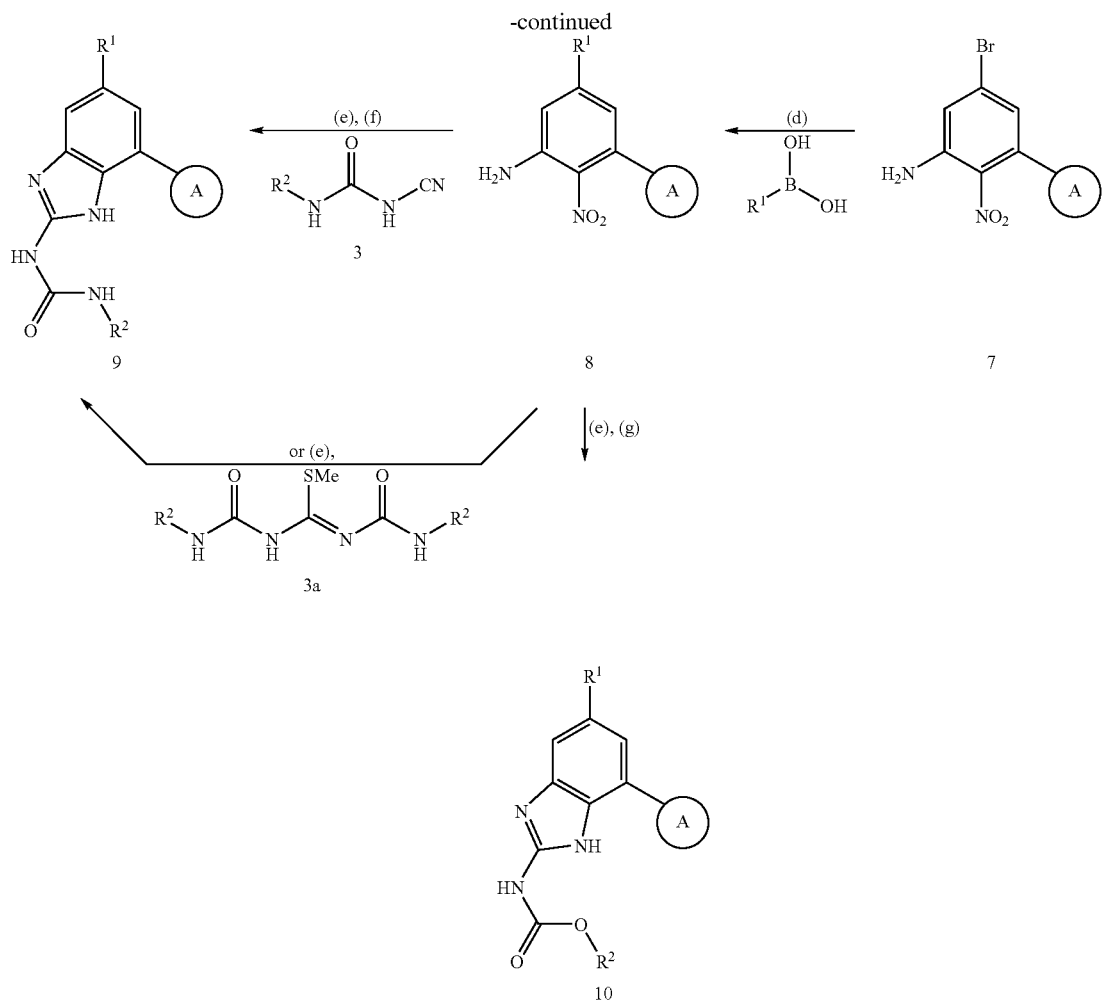

Reagents and conditions:
(a) sodium perborate, HOAc, 55° C.
(b) Ring A, NaH, THF;
(c) NH₃, MeOH, EtOH, 80° C.;
(d) R¹—B(OH)₂, Pd(PPh₃)₄, NaHCO₃, H₂O, THF, 70° C.;
(e) H₂, Pd/C, EtOAc;
(f) 3, H₂SO₄, 95° C.;
(g) 2-methyl-2-thiopseudourea, R²-chloroformate.

Scheme II above shows a general method for preparing the benzimidazole compounds of the present invention wherein Z is NH or O. The bromo-aniline 4 was treated with sodium perborate and acetic acid to form the difluoro-nitro compound 5. Compound 5 was treated with Ring A in the presence of sodium hydride to afford the bi-aryl compound 6. The remaining fluoro group of compound 6 was displaced with ammonia to form the amino compound 7. The 2-nitro-5-bromoaniline 7 was then coupled to an aryl boronic acid, at step (d), in the presence of palladium to form the tri-aryl compound 8. The nitro group of compound 8 was reduced to form a diamino compound which was either treated with an N'-alkyl-N-cyanourea 3 or with an N,N-dialkylureamido-2-methyl-2-thiopseudourea 3a to form a benzimidazole compound of formula I wherein Z is NH 9.

Alternatively, intermediate 8 may be used to form compounds of formula I wherein Z is O. Compound 10 was formed by treating 8, after reduction to the diamino compound, with 2-methyl-2-thiopseudourea and R²-chloroformate according to the method described by L. I. Kruse et al, *J. Med. Chem.* 1989, 32, 409-417. One of ordinary skill in the art would recognize that the reactions depicted in Scheme II above are amenable to a variety of R¹ and Ring A groups of the present invention.

In an alternative method, intermediate 8 was treated with either N,N-diethlycarboxy-2-methyl-2-thiopseudourea or N,N-diethlyureamido-2-methyl-2-thiopseudourea to form compounds 10 and 9, respectively. The syntheses of both N,N-diethlycarboxy-2-methyl-2-thiopseudourea and N,N-diethlyureamido-2-methyl-2-thiopseudourea are described in the Examples set forth infra.

Scheme III

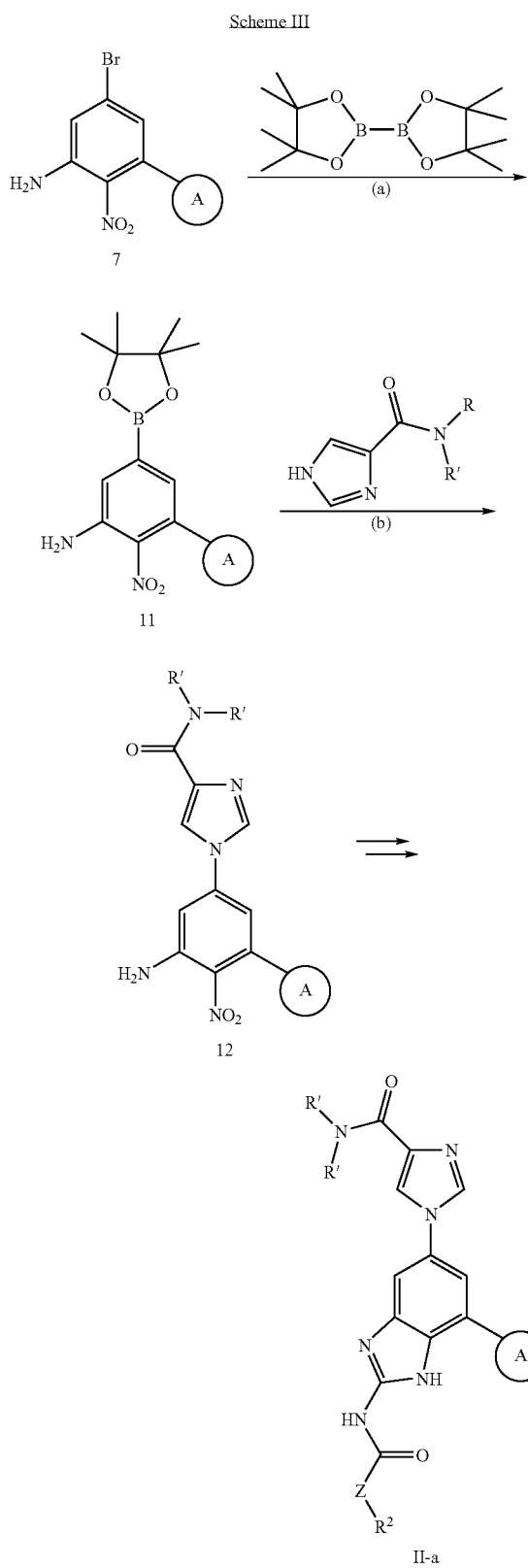

Reagents and conditions:
(a) Pd(dppf)Cl$_2$/KOAc, DMSO, 80° C.; and
(b) Cu(OAc)$_2$/pyridine, DMF.

Scheme III above shows a general method for preparing compounds of formula II-a using methods substantially similar to those described by Kiyomori, A.; Marcoux, J.-F.; Buchwald, S. L., *Tetrahedron Letters*, vol. 40, (1999) 2657-2660. Compound 7 was treated with diboronic ester in the presence of Pd(dppf)/potassium acetate in DMSO at 80° C. to afford intermediate 11. Compound 11 was treated with 4-C(O)N(R')$_2$-imidazole in the presence of copper acetate to form the 4-C(O)N(R')$_2$-imidazol-1-yl compound 12. Compounds of formula II-a were prepared from compound 12 as described in Scheme II, steps (e), (f), and (g).

Although 4-C(O)N(R')$_2$-imidazole was used to exemplify, one of ordinary skill in the art would recognize that a variety of R$^1$ groups are amenable to the displacement reaction at step (c) to form a variety of compounds of the present invention. Generally, the boronate intermediate 11 may be treated with a variety of R$^1$-halides or R$^1$-triflates, using methods well known to one of ordinary skill in the art, to form intermediate compounds 12' as shown below. Using the methods recited herein and those known to one of ordinary skill in the art, compounds 12' are useful for preparing compounds 9 and 10 of the present invention as depicted above at Scheme II.

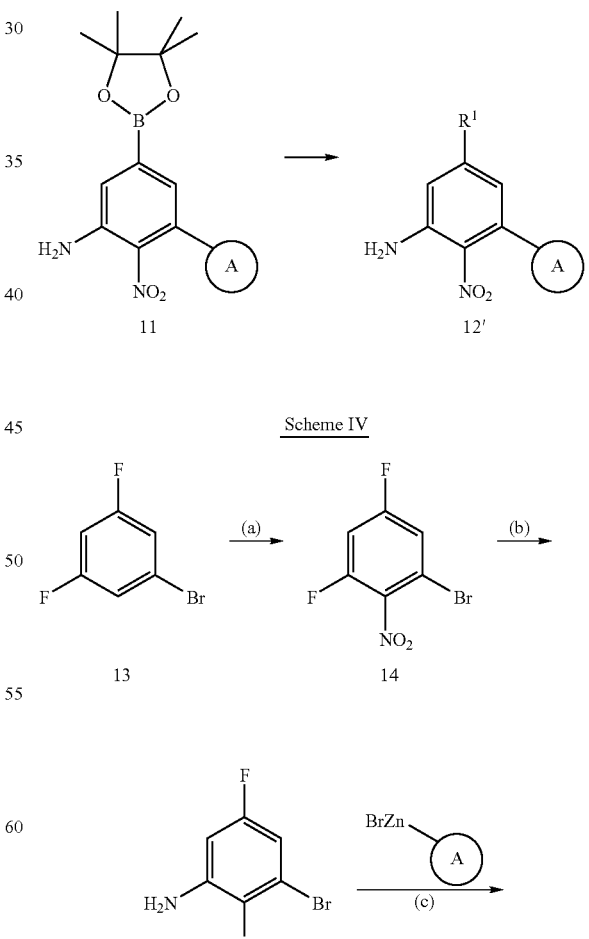

-continued

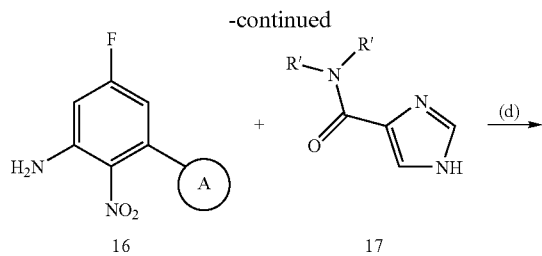

16    17

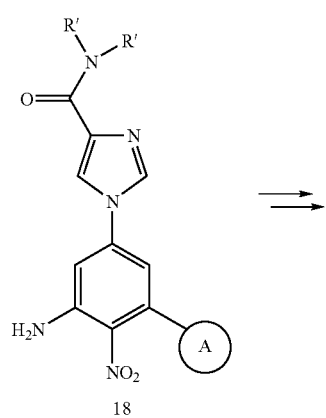

18

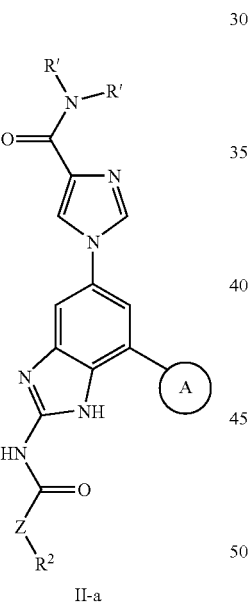

II-a

Reagents and conditions:
(a);
(b) NH₄OH/dioxane, reflux;
(c) Pd(PPh₃)₄/THF, reflux; and
(d) Na₂CO₃/DMF, heat.

Scheme IV above shows an alternate method for preparing compounds of formula II-a. Compound 13 was nitrated to form 14. Compound 14 was treated with ammonium hydroxide to form the amino compound 15. The bromo group of compound 15 was treated with the BrZn-Ring A reagent in the presence of Pd(PPh₃)₄ in THF to form compound 16. Compound 16 was treated with the 4-C(O)N(R')₂-imidazole in the presence of sodium carbonate to form the 4-C(O)N(R')₂-imidazol-1-yl compound 18. Compounds of formula II-a were then prepared from compound 18 as described in Scheme II, steps (e), (f), and (g).

Scheme V

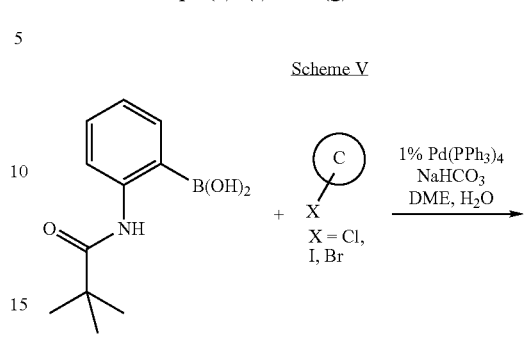

19    20

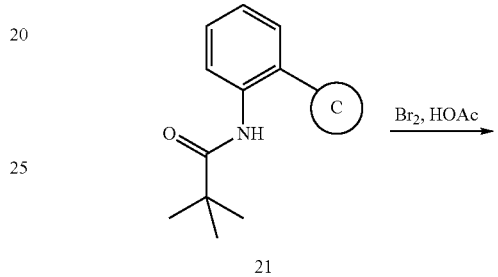

21

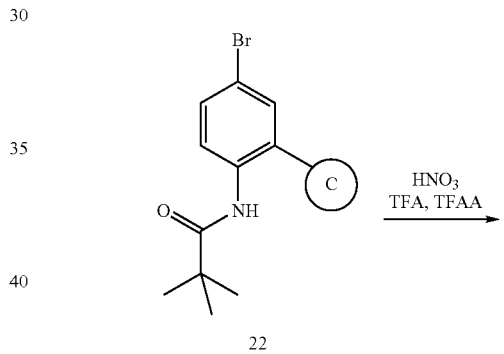

22

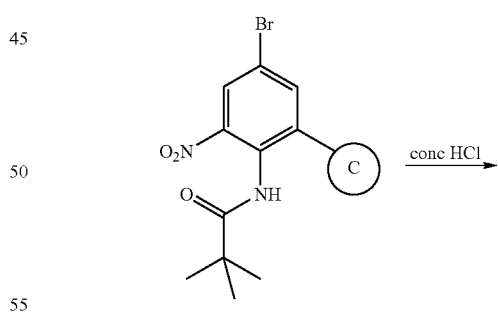

23

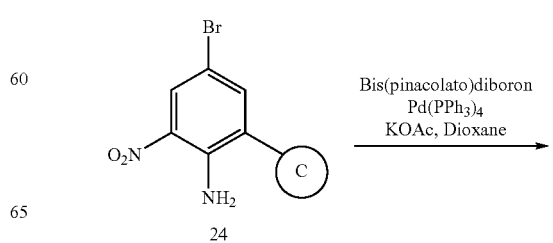

24

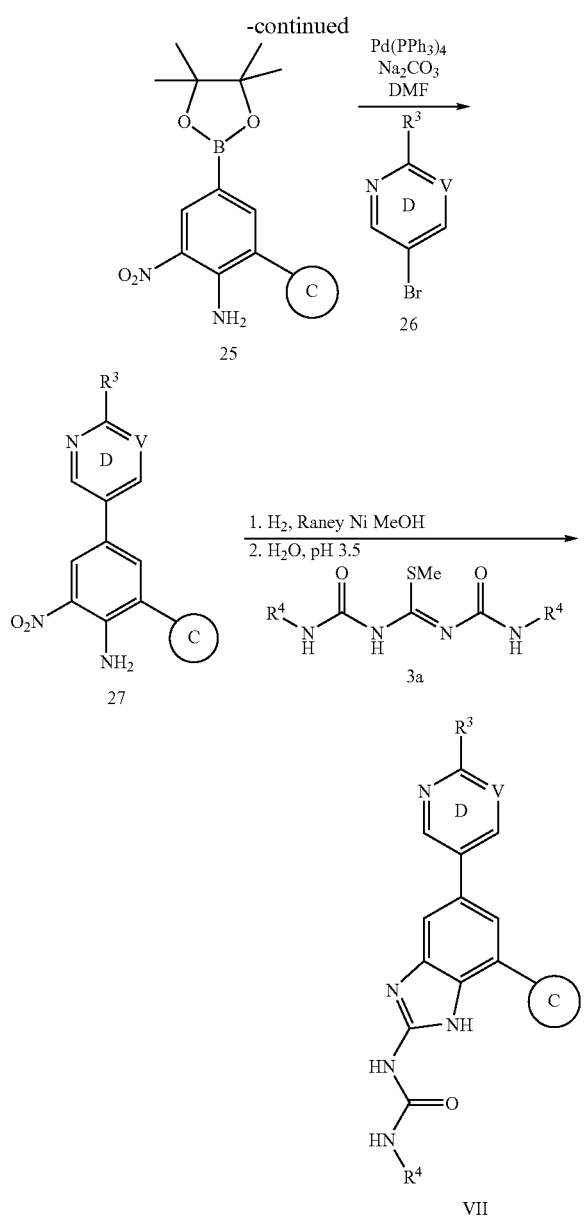

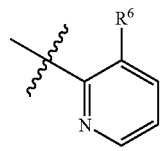

opseudourea 3a afforded benzimidazole compounds of formula VII. Compounds of formula VII wherein Ring C is:

and $R^6$ is OMe are either prepared from compounds of formula 20, using scheme V, wherein formula 20 is 2-bromo-3-methoxypyridine (prepared according to methods known in the art from commercially available 2-bromo-3-hydroxy pyridine) or by the displacement of a 3-fluoro pyridine intermediate 24 (in scheme V) with methoxide in methanol.

One of skill in the art would recognize that a variety of compounds of the present invention may be prepared according to the general method of Schemes I, II, III, IV, and V, according to methods known in the art, and the synthetic Examples set forth below.

The compounds of this invention are potent inhibitors of gyrase and Topo IV as determined by enzymatic assay. These compounds have also been shown to have antimicrobial activity in an antimicrobial susceptibility assay. The activity of a compound utilized in this invention as an inhibitor of gyrase or Topo IV may be assayed in vitro, in vivo or in a cell line according to methods known in the art. The details of the conditions used for both the enzymatic and the antimicrobial susceptibility assays are set forth in the Examples below.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit gyrase, Topo IV, or to measurably decrease bacterial quantity, in a biological sample or in a patient. Preferably the composition of this invention is formulated for administration to a patient in need of such composition. Most preferably, the composition of this invention is formulated for oral administration to a patient.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of gyrase and/or Topo IV activity in a biological sample is useful for a variety of purposes that are known to one of skill in the art. Examples of such purposes include, but are not limited to, blood transfusion, organ-transplantation, biological specimen storage, and biological assays.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen Scheme V above shows a general method for preparing compounds of formula VII. Compound 19 (purchased commercially from CB Research) underwent Suzuki-type coupling with commercial reagents (purchased from Aldrich or Manchester Organics Limited) of type 20 to form intermediate 21. Compound 21 was brominated with bromine in acetic acid to form bromide 22, then nitrated with nitric acid in the presence of TFA and TFAA to form intermediate 23. Acidic hydrolysis of compound 23 provided aniline 24. The bromo group of compound 24 was converted into boronate ester 25 in the presence of Pd(PPh$_3$)$_4$ in buffered dioxane. Compound 25 underwent Suzuki-type coupling with intermediate 26 (prepared from the di-bromoheteroaryl ring D [commercially available from Aldrich, etc.] according to the procedure of Wang, X. et al., *Tetrahedron Letters*, vol. 41, (2000) 4335-4338) to prepare nitro aniline intermediate 27. Raney-nickel reduction of the nitro group in compound 27, followed by treatment with N,N-dialkylureamido-2-methyl-2-thiphosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in gyrase, or Topo IV, activity between a sample comprising said composition and gyrase, or Topo IV, and an equivalent sample comprising gyrase, or Topo IV in the absence of said composition.

As used herein, the term "measurably decrease bacterial quantity", as used herein means a measurable change in the number of bacteria between a sample containing said composition and a sample containing only bacteria.

A "pharmaceutically acceptable salt" means any non-toxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of gyrase and/or Topo IV.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} \text{ alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus faecalis, Enterococcus faecium, Klebsiella pneumoniae, Enterobacter* sps. *Proteus* sps. *Pseudomonas aeruginosa, E. coli, Serratia marcesens, Staphylococcus aureus*, Coag. Neg. *Staph, Haemophilus influenzae, Bacillus anthracis, Mycoplasma pneumoniae, Moraxella catarralis, Chlamydia pneumoniae, Legionella pneumophila, Mycobacterium tuberculosis, Staphylococcus epidermidis, Staphylococcus saprophyticus*, or *Heliobacter pylori*.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of resistant bacterial infections caused by bacteria such as Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplama pneumoniae*, Isoniazid resistant *Mycobacterium tuberculosis*, Rifampin resistant *Mycobacterium tuberculosis*, Methicillin resistant Coagulase negative staphylcocci, Fluoroquinolone resistant Coagulase negative staphylcocci, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *staphylococcus epidermidis*.

Typically, the pharmaceutical compositions of this invention will be administered from about 1 to 5 times per day or alternatively, as a continuous infusion. Or, alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I or formula VII and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated". Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, or an agent which increases the susceptibility of bacterial organisms to antibiotics.

Agents that increase the susceptibility of bacterial organisms to antibiotics are known. For example, U.S. Pat. No. 5,523,288, U.S. Pat. No. 5,783,561 and U.S. Pat. No. 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in *Microbiological Reviews* (1992) pp. 395-411, and the sensitization of gram-negative bacteria has been described by Tsubery, H., et al, in *J. Med. Chem.* (2000) pp. 3085-3092.

According to another embodiment, the invention provides a method for treating or lessening the severity of a bacterial infection in a patient comprising the step of administering to said patient a composition according to the present invention.

According to another embodiment, the invention provides a method of inhibiting gyrase in a biological sample.

According to another embodiment, the invention provides a method of inhibiting Topo IV in a biological sample.

According to another embodiment, the invention provides a method of decreasing bacterial quantity in a biological sample.

According to another embodiment, the invention provides a method of decreasing bacterial quantity in a biological sample, but further comprising the step of contacting said biological sample with an agent that increases the susceptibility of bacterial organisms to antibiotics.

The pharmaceutical compositions and methods of this invention will be useful generally for controlling bacterial infections in vivo. Examples of bacterial organisms that may be controlled by the compositions and methods of this invention include, but are not limited to, the following organisms: *Streptococcus pneumoniae, Streptococcus pyogenes, Enterococcus faecalis, Enterococcus faecium, Klebsiella pneumoniae, Enterobacter* sps., *Proteus* sps., *Pseudomonas aeruginosa, E. coli, Serratia marcesens, Staphylococcus aureus,* Coag. Neg. *Staph, Haemophilus infuenzae, Bacillus anthracis, Mycoplasma pneumoniae, Moraxella catarralis, H. influenzae, Chlamydia pneumoniae, Legionella pneumophila, Mycobacterium tuberculosis, Helicobacter pylori, Staphylococcus epidermidis. Chlamydia pneumoniae, Legionella pneumophila, Mycobacterium tuberculosis, Staphylococcus saprophyticus,* or *Heliobacter pylori.*

In another embodiment, the pharmaceutical compositions and methods of this invention will be useful generally for controlling bacterial infections in vivo caused by the following the following organisms: *Streptococcus pneumoniae, Streptococcus pyogenes, Enterococcus faecalis, Enterococcus faecium, Staphylococcus aureus,* Coag. Neg. *Staph, Haemophilus influenzae, Bacillus anthracis, Mycoplasma pneumoniae, Moraxella catarralis, H. influenzae, Chlamydia pneumoniae, Legionella pneumophila, Mycobacterium tuberculosis, Helicobacter pylori, Staphylococcus epidermidis. Chlamydia pneumoniae, Legionella pneumophila, Mycobacterium tuberculosis, Staphylococcus saprophyticus,* or *Heliobacter pylori.*

In another embodiment, the pharmaceutical compositions and methods of this invention will be useful generally for controlling bacterial infections in vivo caused by the following the following organisms: *Streptococcus pneumoniae, Streptococcus pyogenes, Enterococcus faecalis, Enterococcus faecium, Staphylococcus aureus,* Coag. Neg. *Staph, Bacillus anthracis, Staphylococcus epidermidis, Staphylococcus saprophyticus,* or *Mycobacterium tuberculosis.*

The compositions and methods will therefore be useful for controlling, treating or reducing the advancement, severity or effects of nosocomial or non-nosocomial infections. Examples of nosocomial uses include, but are not limited to, urinary tract infections, respiratory infections such as pneumonia, surgical wound infections, and blood stream infections (also known as bacteremia). Examples of non-nosocomial uses include but are not limited to urinary tract infections, pneumonia, prostatitis, skin and soft tissue infections, intra-abdominal infections, and therapy for febrile neutropenic patients.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

The compounds of this invention may be employed in a conventional manner for controlling bacterial infections levels in vivo and for treating diseases or reducing the advancement or severity of effects that are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

The compounds of formula I or formula VII may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula I or formula VII and another therapeutic or prophylactic agent.

The additional therapeutic agents described above may be administered separately, as part of a multiple dosage regimen, from the inhibitor-containing composition. Alternatively, these agents may be part of a single dosage form, mixed together with the inhibitor in a single composition.

In order that this invention be more fully understood, the following examples are set forth. These examples are for the purpose of illustration only and are not to be construed as limiting the scope of the invention in any way.

EXAMPLES

Example 1

5-Bromo-1,3-difluoro-2-nitro-benzene: To a suspension of sodium perborate tetrahydrate (1.04 g, 5 mmol) in acetic acid (20 mL), stirred at 55° C., was added a solution of 4-bromo-2,6-difluoroaniline in acetic acid (10 mL) over 1 hour in a dropwise fashion. After stirring at 55° C. for an additional 3 hours, the solution was allowed to cool to room temperature and filtered. The filtrate was poured into ice, and extracted twice with ethyl acetate. The combined organic extracts were washed successively with 5×100-mL portions of water, brine, dried ($MgSO_4$), and concentrated in vacuo. The resulting residue was purified by column chromatography over silica gel eluted with ethyl acetate:hexanes (1:20) to afford 780 mg of the title compound as a tan solid. $^1$H NMR (CDCl$_3$) δ 7.32 (dt, 2H).

Example 2

1-(5-Bromo-3-fluoro-2-nitro-phenyl)-1H-pyrazole: To a suspension of sodium hydride (44 mg, 1.1 mmol, 60% oil dispersion) in THF (4 mL), stirred at 0° C., was added a solution of pyrazole (72 mg, 1.05 mmol) in THF (1 mL). The resulting mixture was stirred at 0° C. for 5 minutes and a solution of 5-bromo-1,3-difluoro-2-nitro-benzene (238 mg, 1 mmol) in THF (1 mL) was added. The mixture was stirred at room temperature for 1 hour, quenched by addition of water (1 mL), then partitioned between water (20 mL) and ethyl acetate (50 mL). The organic layer was washed with brine, dried (MgSO$_4$), and concentrated in vacuo. The residue was purified by column chromatography over silica gel eluted with ethyl acetate:hexanes (1:6), to afford 240 mg (86%) of the title compound. $^1$H NMR (CDCl$_3$) δ 6.55 (t, 1H), 7.45 (d, 1H), 7.60 (s, 1H), 7.80 (m, 2H). MS M+1 287, M+1+2 289.

Example 3

5-Bromo-2-nitro-3-pyrazol-1-yl-phenylamine: To a solution of 1-(5-bromo-3-fluoro-2-nitro-phenyl)-1H-pyrazole (240 mg, 0.84 mmol) in ethanol (3 mL) was added ammonia (3 mL, 2N in methanol. The resulting mixture was heated in a sealed tube at 80° C. for 16 hours then concentrated in vacuo. The residue was purified by column chromatography over silica gel eluted with ethyl acetate:hexanes (1:3) to afford 205 mg (86%) of the title compound as a yellow solid. $^1$H NMR (CDCl$_3$) δ 5.20 (br s, 2H), 6.50 (t, 1H), 6.9 (d, 1H), 7.1 (d, 1H), 7.7 (d, 1H), 7.8 (d, 1H). MS M+1 283, M+1+2 285.

Example 4

2-Nitro-3-pyrazol-1-yl-5-pyridin-3-yl-phenylamine: To a solution of 5-bromo-2-nitro-3-pyrazol-1-yl-phenylamine (200 mg, 0.71 mmol) in THF (8 mL) was added, successively, 3-pyridyl-diethyl borane (157 mg), (tetrakistriphenylphosphine) palladium(0) (84 mg), and sodium carbonate (1.1 mL, 2.2 mmom of 2M aqueous). The resulting mixture was stirred at 70° C. overnight then cooled to room temperature. The reaction mixture was diluted with ethyl acetate (100 mL) and washed with water (50 mL), brine (50 mL), dried (MgSO$_4$) then concentrated in vacuo. The resulting residue was purified by column chromatography over silica gel eluted with a gradient of ethyl acetate:hexanes (1:3, 1:2, 1:0, 2:1, 4:1, 8:1), to afford 120 mg (60%) of the title compound as a yellow solid. $^1$H NMR (DMSO-d$_6$) δ 6.45 (br, s 2H), 6.55 (t, 1H), 7.1 (s, 1H), 7.25 (s, 1H), 7.55 (m, 1H), 7.7 (s, 1H), 8.1 (dt, 1H), 8.3 (d, 1H), 8.7 (d, 1H), 8.9 (s, 1H).

Example 5

1-Ethyl-3-(7-pyrazol-1-yl-5-pyridin-3-yl-1H-benzoimidazol-2-yl)-urea (I-2): A suspension of 2-nitro-3-pyrazol-1-yl-5-pyridin-3-yl-phenylamine (120 mg, 0.40 mmol) and 10% palladium on carbon (12 mg) in ethyl acetate (10 mL) was placed in a Parr hydrogenator under a hydrogen pressure of 45 psi. The mixture was shaken for 16 hours, filtered and the filtrate concentrated in vacuo. The resulting residue was diluted with H$_2$SO$_4$ (1.6 mL or 1N), and N'-ethyl-N-cyanourea (0.8 mL, 1M) was added. The mixture was heated at 95° C. for 4 hours then concentrated in vacuo. The residue was purified by preparative HPLC to afford 75 mg of the title compound as the bis-TFA salt which was converted to the free base to afford the title compound. $^1$H NMR (DMSO-d$_6$) δ 1.1 (t, 3H), 3.2 (m, 2H), 7.0 (m, 1H), 7.3 (d, 1H), 7.5 (m, 1H), 7.55 (s, 1H), 8.0 (d, 1H), 8.55 (dd, 1H), 8.85 (s, 1H), 10.1 (s, 1H), 12.0 (s, 1H). LC/MS one peak, M+1 348.23, M−1 346.18.

Example 6

N'-Ethyl-N-cyanourea: To a 20° C. solution of sodium hydroxide (1.5 M aqueous, 50 mL, 75.02 mmol) was added cyanamide (8.5 g, 202.25 mmol) then ethyl isocyanate (4 mL, 50.56 mmol) was added in a dropwise fashion over 10 minutes. After stirring for 30 minutes, additional sodium hydroxide (3M, 25 mL, 75.02 mmol) and ethyl isocyanate (4 mL, 50.56 mmol) were added. The resulting solution was then aged for a minimum of 30 minutes before using directly without isolation.

Example 7

4-(Pyridin-3-yl)-2-nitroaniline: To a solution of 4-bromo-2-nitroaniline (4.8 g, 22 mmol) in DME (100 mL) was added pyridine-3-boronic acid 1,3-propanediol cyclic ester (4 g, 24 mmol), sodium bicarbonate (45 mL, 1M), and tetrakis(triphenylphosphine)palladium (0.5 eq). The resulting mixture was heated at 90° C. for 8 hours then cooled to room temperature. The solids were collected, washed with water, 5% EtOAc in Hexane and dried to afford the title compound (5 g). $^1$H NMR (CDCl$_3$) δ 8.8 (d, 1H), 8.55 (m, 1H), 8.35 (d, 1H), 7.85 (dd, 1H), 7.65 (dd, 1H), 7.35 (m, 1H), 6.95 (d, 1H), 6.25 (br s, 2H).

Example 8

2-Bromo-6-nitro-4-pyridin-3-yl-phenylamine: To a solution of 4-(pyridin-3-yl)-2-nitroaniline (1.3 g, 9 mmol) in HOAc (25 mL) was added bromine (1.58 g, 9.9 mmol) in HOAc (5 mL). The resulting mixture was stirred at room temperature for one hour and then quenched with ice-water. The solids were collected, washed with water and dried. The solids in EtOAc was then washed with NaOH (2N; 20 mL), water, brine and concentrated in vacuo. The concentrate was purified by chromatography [Silica Gel, ethyl acetate: hexanes (1:1)] to afford the title compound (0.8 g). $^1$H NMR (CDCl$_3$) δ 8.83 (d, 1H), 8.55 (m, 1H), 8.41 (d, 1H), 8.15 (d, 1H), 7.96 (m, 1H), 7.41 (m, 1H), 6.80 (br s, 2H). (M+1) 294.

Example 9

2-Nitro-6-pyridin-2-yl-4-pyridin-3-yl-phenylamine: A mixture of 2-bromo-6-nitro-4-pyridin-3-yl-phenylamine (100 mg, 1 eq), 2-pyridylznic bromide (6 eq) and tetrakis (triphenylphosphine)palladium (0.1 eq) in THF (10 mL) was heated at 100° C. for 18 hours. The reaction was quenched with water (2 mL). The product was extracted with EtOAc (20×3). The combined organic layer was then concentrated in vacuo and the residue was purified by chromatography (Silica Gel, EtOAC) to afford the title compound (75 mg) as a yellow solid. (M+1) 293.

Example 10

3-Pyridin-2-yl-5-pyridin-3-yl-benzene-1,2-diamine: To a solution of 2-nitro-6-pyridin-2-yl-4-pyridin-3-yl-phenylamine (75 mg, 0.26 mmol) in ethyl acetate (20 mL) was added 10% palladium on carbon (50 mg). The resulting suspension was placed in a Parr hydrogenation apparatus under 40 psi hydrogen gas while shaking at ambient temperature for one hour. The catalyst was removed by filtration and the filtrate concentrated in vacuo to afford compound the title compound (50 mg, 0.19 mmol).

Example 11

1-Ethyl-3-(7-pyridin-2-yl-5-pyridin-3-yl-1H-benzoimidazol-2-yl)-urea (I-31): To a solution 3-pyridin-2-yl-5-pyridin-3-yl-benzene-1,2-diamine (50 mg, 0.19 mmol) and sulfuric acid (0.76 mL, 1 N) in water (1 mL) was added N'-ethyl-N-cyanourea (0.76 mL, 1 M). Enough sulfuric acid was added dropwise to achieve pH 3. The resulting mixture was heated at 100° C. for 8 hours. The reaction mixture was then cooled to ambient temperature. The solids were collected, washed with water and dried. The solids were purified by chromatography (Silica Gel, EtOAc, then 10% MeOH in EtOAc) to afford compound 5 (27 mg). $^1$H NMR (CDCl$_3$) δ 8.92 (d, 1H), 8.80 (m, 1H), 8.52 (m, 1H), 8.30 (m, 1H), 8.21 (d, 1H), 8.04 (s, 1H), 7.94 (m, 1H), 7.75 (s, 1H), 7.56 (d, 1H), 7.37 (m, 2H), 3.36 (q, 2H), 1.24 (t, 3H). (M+1) 359.

Example 12

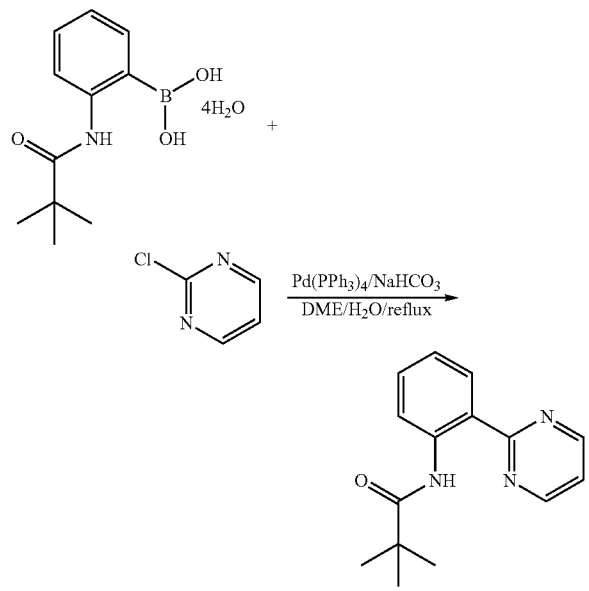

2,2-Dimethyl-N-(2-pyrimidin-2-yl-phenyl)-propionamide: A 5 L flask was charged with the above depicted boronic acid as a tetrahydrate (281.4 grams, 960 mmoles), 2-chloropyrimidine (100 g, 874 mmoles), NaHCO$_3$ (146.8 grams, 1.746 moles), and Pd(PPh$_3$)$_4$ (10.0 grams, 8.72 mmoles). Water (1 L) and dimethoxyethane (1 L) were added, and the mixture was heated slowly to 83° C. (internal temperature) over a 1 hour period with overhead stirring. After ~2 hours all solids had dissolved. The reaction was allowed to stir for 8 hours. The mixture was cooled to room temperature and stirred overnight after which time a thick precipitate had formed. The crude mixture was diluted with water (2 L) and stirred for an additional 2 hours after which time the mixture was filtered and the solids were washed sequentially with water, 0.1 N NaOH, and water again. The solids were then dried under high vacuum at 50° C. to afford the title compound (~233 grams) as a tan powder.

Example 13

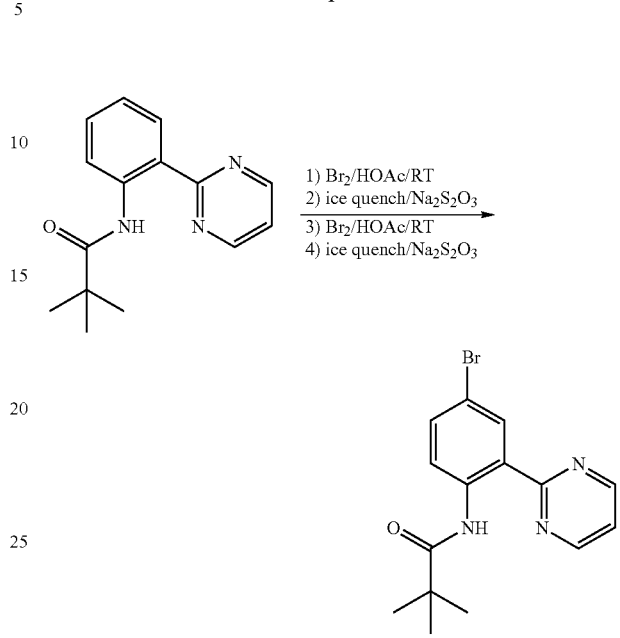

N-(4-Bromo-2-pyrimidin-2-yl-phenyl)-2,2-dimethyl-propionamide: To a room temperature suspension of 2,2-dimethyl-N-(2-pyrimidin-2-yl-phenyl)-propionamide (~117 grams, 437 mmoles) in acetic acid (1 L) was added bromine (67 mL, 1.31 moles) as a solution in 100 mL of acetic acid over a 1 hour period. The heterogenous mixture was stirred at room temperature for 5 hours over which time a thick precipitate formed. The mixture was then poured over ice, diluted with 1N Na$_2$S$_2$O$_3$ (2 L), and stirred for 1 hour. The solids were filtered, resuspended in water (2 L), stirred for 1 hour, then filtered and washed with water again. The resulting solids were pumped to dryness at 50° C., resuspended in HOAc (1 L), and treated with bromine (22 mL, 430 mmoles) in acetic acid solution (20 mL) over a 20 minute period. The resulting heterogenous mixture was stirred for 5 hours, then quenched and treated as described above. The resulting solids were vacuum dried at 50° C. to afford the title compound (165 grams) as a tan powder.

Example 14

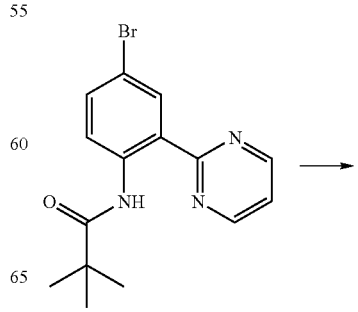

-continued

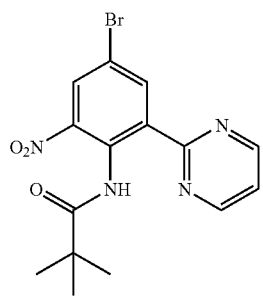

N-(4-Bromo-2-nitro-6-pyrimidin-2-yl-phenyl)-2,2-dimethyl-propionamide: To a 5° C. suspension of N-(4-bromo-2-pyrimidin-2-yl-phenyl)-2,2-dimethyl-propionamide (32.6 grams, 97.5 mmoles) in TFA (400 mL) was added 90% nitric acid (70 mL, 1.46 mmoles) over a 30 minute period. The mixture was then allowed to warm to room temperature and stir for a total of 2 hours. The crude reaction (now homogenous) was poured into ice producing a pasty mass. The mixture was diluted to 2 L total volume with water, treated with 500 mL of methanol, and vigorously stirred for 12 hours. The resulting solids were filtered, washed with copious amounts of water, then vacuum dried at 50° C. to afford the title compound (29.9 grams, 81% yield) as a tan powder.

Example 15

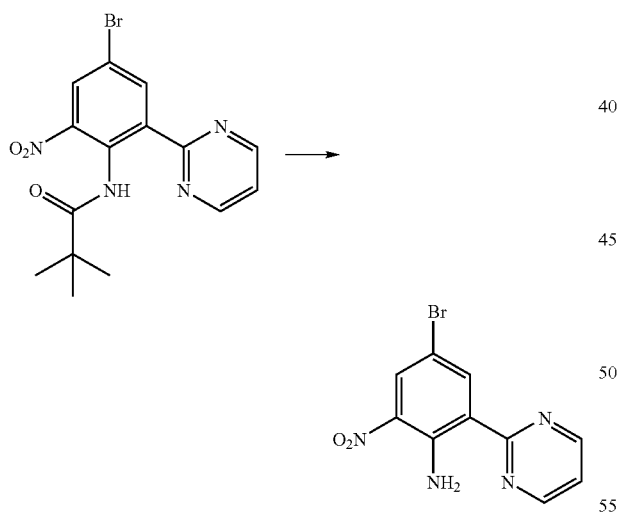

4-Bromo-2-nitro-6-pyrimidin-2-yl-phenylamine: A suspension of N-(4-bromo-2-nitro-6-pyrimidin-2-yl-phenyl)-2,2-dimethyl-propionamide (29.9 grams, 78.8 mmoles) in conc. HCl (200 mL) was refluxed for 8 hours. The partially homogeneous crude reaction was then cooled to room temperature, diluted with water (500 mL), and the resulting precipitate was stirred for 1 hour. The solids were then filtered, washed with water, and vacuum dried at 50° C. to afford the title compound (21.1 grams, 91% yield) as an orange powder.

Example 16

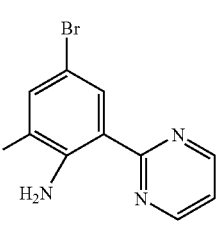

2-Nitro-6-pyrimidin-2-yl-4-(4,4,5,5-tetramethyl-[1,3,2]dioxaborolan-2-yl)-phenylamine: A mixture of 4-bromo-2-nitro-6-pyrimidin-2-yl-phenylamine (1.82 g, 6.2 mmol), bis(pinacolato)diboron (3.144 g, 12.4 mmol), PdCl$_2$dppf$_2$ (453 mg, 0.6 mmol) and KOAc (3.03 g, 31 mmol) in dioxane (60 ml) was heated at 105° C. for 2.5 hours. The reaction was filtered and washed with dichloromethane. The combined filtrates were concentrated under vacuum and water (100 ml) was added to the residue. Extraction with dichloromethane (3×50 ml), drying and concentration gave a residue, which was washed with ether-hexane to afford the title compound (2.07 g, 98%).

Example 17

N-[2-(3-Fluoro-pyridin-2-yl)-phenyl]-2,2-dimethyl-propionamide: A 3 L flask was charged with the above depicted boronic acid as a tetrahydrate (92.1 grams, 314 mmoles), chlorofluoropyridine (37.6 g, 286 mmoles), NaHCO$_3$ (48.0 grams, 572 mmoles), and Pd(PPh$_3$)$_4$ (3.3 grams, 2.86 mmoles). Water (300 mL) and dimethoxyethane (300 mL)

were added, and the mixture was heated slowly to 83° C. (internal temperature) over a 1 hour period with overhead stirring. After ~2 hours all solids had dissolved. The reaction was allowed to stir for 10 hours. The mixture was cooled to room temperature and stirred overnight after which time a thick gum had formed. The crude mixture was diluted with water (2 L) and stirred for an additional 2 hours. The mixture was then allowed to rest without stirring until the gum had settled to the bottom of the flask. The liquid phase was removed via vacuum, then replaced with 0.1 N NaOH and stirred for 15 minutes. The gum was allowed to settle and the liquid removed via vacuum. The gum was then similarly washed three times with water, then transferred to a 1 neck flask as an acetone solution. The mixture was concentrated in vacuo and azeotroped five times with ethyl acetate.

Example 18

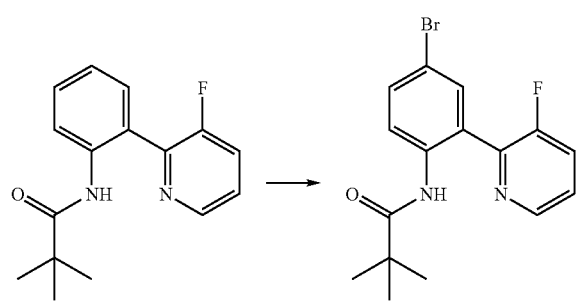

N-[4-Bromo-2-(3-fluoro-pyridin-2-yl)-phenyl]-2,2-dimethyl-propionamide: To a room temperature suspension of N-[2-(3-fluoro-pyridin-2-yl)-phenyl]-2,2-dimethyl-propionamide (~77 mmoles) in acetic acid (300 mL) was added bromine (12 mL, 228 mmoles) as a solution in 50 mL of acetic acid over a 1 hour period. The heterogenous mixture was stirred at room temperature for 5 hours over which time a thick precipitate formed. The mixture was then poured over ice, diluted with 1N Na₂S₂O₃ (500 mL), and stirred for 1 hour. The solids were filtered, re-suspended in water (2 L), stirred for 1 hour, then filtered and washed with water again. The resulting solids were pumped to dryness at 50° C., re-suspended in HOAc (400 mL), and treated with bromine (4 mL, 76 mmoles) in acetic acid solution (20 mL) over a 20 minute period. The resulting heterogenous mixture was stirred for 5 hours, then quenched and treated as described above. The resulting solids were vacuum dried at 50° C. to afford the title compound (19.1 grams, 72%) as a tan powder.

Example 19

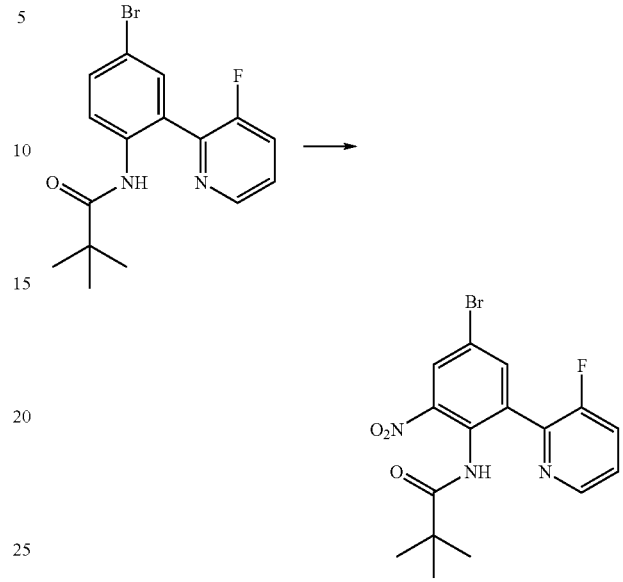

N-[4-Bromo-2-(3-fluoro-pyridin-2-yl)-6-nitro-phenyl]-2,2-dimethyl-propionamide: To a suspension of N-[4-bromo-2-(3-fluoro-pyridin-2-yl)-phenyl]-2,2-dimethyl-propionamide (6.45 grams, 18.4 mmoles) in TFA (100 mL) and TFAA (25.5 mL, 183.6 mmole), at 0° C., was added a TFA solution (30 mL) of 90% fuming nitric acid (2.46 mL, 55.1 mmoles) over a 45 minute period. The mixture was then stirred at 0° C. for a total of 4 hours. The crude reaction (now homogenous) was poured into ice producing a pasty mass. The mixture was diluted to 500 mL total volume with water, treated with 50 mL of methanol, and vigorously stirred for 12 hours. The resulting solids were filtered, washed with copious amounts of water, then dried in vacuo at 50° C. to afford the title compound (6.1 grams, 82% yield) as a tan powder.

Example 20

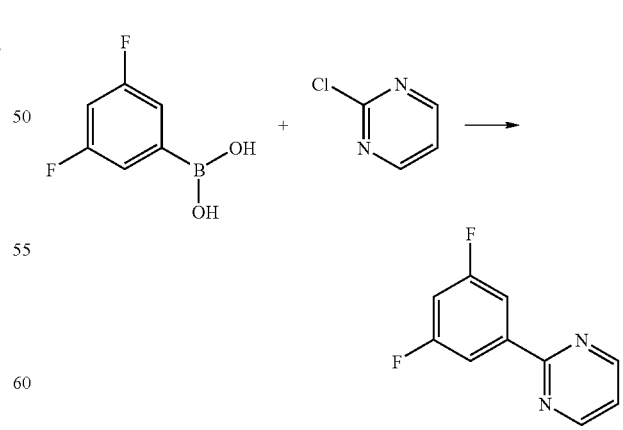

2-(3,5-Difluoro-phenyl)-pyrimidine: A solution of the difluoroboronic acid (5.4 g, 34.1 mmoles) and 2-chloropyrimidine (3.0 g, 26.2 mmoles) in ethanol (50 mL) was treated with Na₂CO₃ (3.6 g, 34.1 mmoles) and Pd(PPh₃)₄ (1.5 g, 1.31 mmoles) then heated at reflux for 3 days. The resulting mixture was then diluted with EtOAc, Silica gel added, and the resulting slurry stirred for 3 hours at room temperature. The crude mixture was then filtered through a silica gel pad with EtOAc, concentrated in vacuo, and flash chromatographed (silica gel, 19/1-14/1-9/1-7/1 hexanes/EtOAc gradient) to afford the title compound (1.38 g, 27%) as a white solid. $^1$H NMR (dmso-d$_6$, 500 MHz): 8.95 (d, 2H); 7.98 (m, 2H); 7.57 (dd, 1H); 7.48 (m, 1H).

Example 21

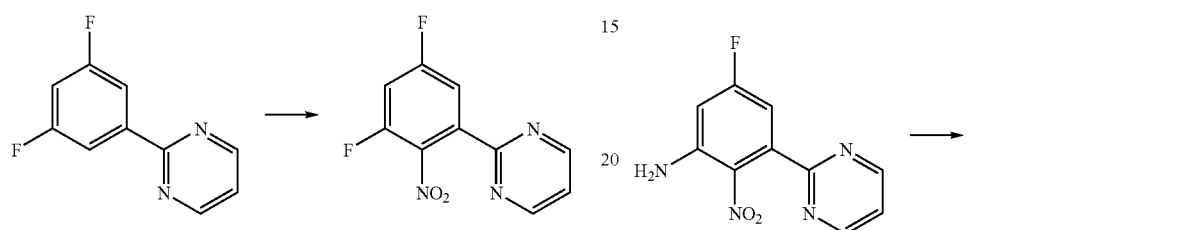

2-(3,5-Difluoro-2-nitro-phenyl)-pyrimidine: To a room temperature solution of 2-(3,5-difluoro-phenyl)-pyrimidine (1.2 g, 6.24 mmole) in H$_2$SO$_4$ (3 mL) was added 90% HNO$_3$ (0.375 mL, 9.37 mmoles) over 10 seconds via syringe. The resulting mixture was stirred at room temperature for 1 hour then poured into ice. The resulting heterogeneous mixture was then diluted with water, warmed to room temperature, and filtered. The solids were washed with water and dried in vacuo to afford the title compound (1.53 g, 100%) as a tan solid. $^1$H NMR (dmso-d$_6$, 500 MHz): 8.92 (d, 2H); 8.67 (m, 1H); 7.94 (m, 1H); 7.65 (dd, 1H).

Example 22

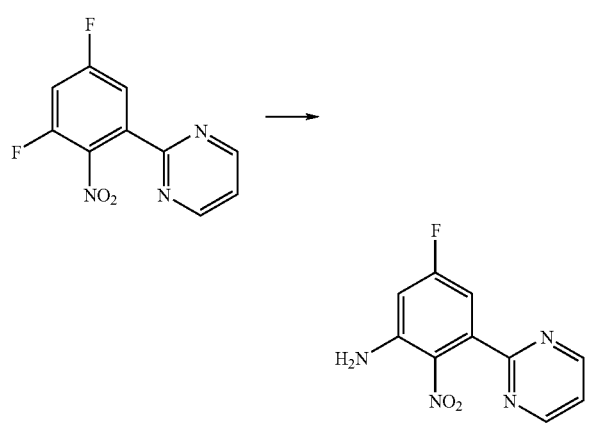

5-Fluoro-2-nitro-3-pyrimidin-2-yl-phenylamine: To a solution of 2-(3,5-difluoro-2-nitro-phenyl)-pyrimidine (1.5 g, 6.32 mmoles) in dioxane (10 mL) was added tBuNH$_2$ (6.6 mL, 63.24 mmoles) at room temperature. The mixture was heated to 100° C. in a sealed tube for 10 hours. The mixture was then cooled to room temperature, poured into water, and the solids stirred for 1 hour. The mixture was filtered, solids washed with water until filtrate was clear. The crude product was then diluted in MeOH, 6N HCl added, and the resulting mixture heated at reflux for 3 hours. The reaction was cooled to room temperature and poured into ice. The resulting heterogeneous mixture was warmed to room temperature, filtered, solids washed with water until filtrate ran clear, and dried in vacuo to afford the title compound (1.33 g, 90%) as an orange powder. $^1$H NMR (dmso-d$_6$, 500 MHz): 8.87 (d, 2H); 7.52 (dd, 1H); 7.08 (dd, 1H); 6.86 (dd, 1H); 6.60 (s, 2H).

Example 23

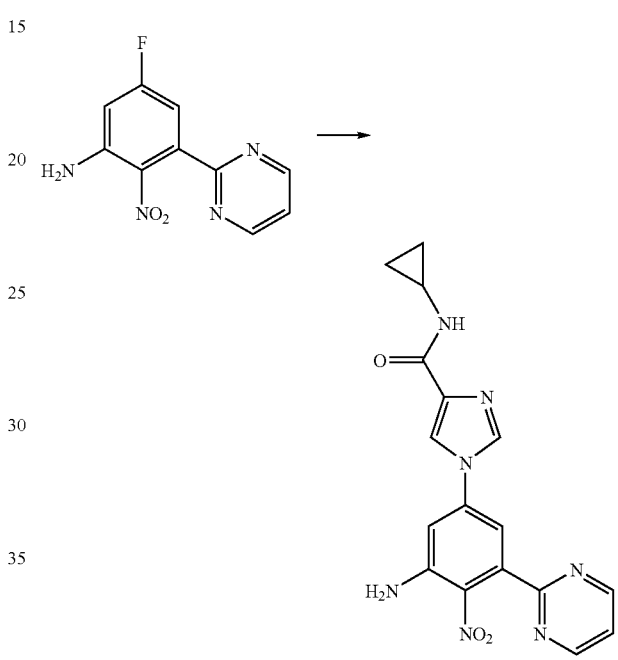

1-(3-Amino-4-nitro-5-pyrimidin-2-yl-phenyl)-1H-imidazole-4-carboxylic acid cyclopropylamide: To a mixture of 5-fluoro-2-nitro-3-pyrimidin-2-yl-phenylamine (650 mg, 2.77 mmole) in DMF (5 mL) was added 17 (545 mg, 3.6 mmoles) and Na$_2$CO$_3$ (381 mg, 3.60 mmoles) at room temperature. The resulting mixture was heated to 125° C. for 6 hours, then cooled to room temperature. The resulting mixture was diluted with water and the yellow precipitate was stirred for 1 hour. The crude reaction was filtered and the solids washed with water until the filtrate ran clear. The washed solids were then dried in vacuo to afford the title compound (960 mg, 95%) as a yellow powder. $^1$H NMR (dmso-d$_6$, 500 MHz): 8.91 (d, 1H); 8.42 (s, 1H); 8.29 (s, 1H); 8.08 (d, 1H); 7.52 (dd, 1H); 7.36 (d, 1H); 7.29 (d, 1H); 6.59 (s, 2H); 2.89 (m, 1H); 0.072 (m, 2H); 0.64 (m, 2H).

Example 24

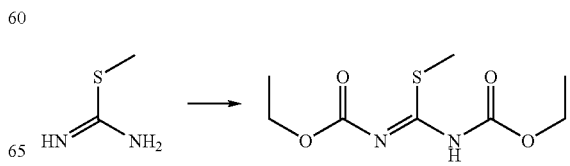

N,N-Diethlycarboxy-2-methyl-2-thiopseudourea: To a mixture of 2-methyl-2-thiopseudourea sulfate (22.8 g, 81.9 mmol) in methylene chloride (200 mL) was added triethylamine (34.5 mL, 245.7 mmol) and ethyl chloroformate (20.65 g, 245 mmol). After stirring over night the mixture was washed with water, brine then dried over sodium sulfate, filtered and concentrated in vacuo to a pungent oil which was flash chromatagraphed (10% ethyl acetate/hexanes) to provide the title compound (16.68 g, 86.9% Y) as a colorless oil which solidified on standing. $^1$H NMR (500 Mhz, CDCl$_3$) ∂1.3 (q, 6H), 2.41 (s, 3H), 4.22 (m, 4H).

Example 25

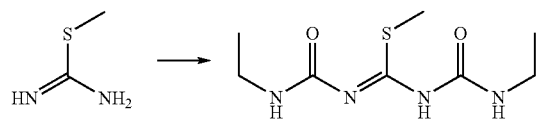

N,N-Diethlyureamido-2-methyl-2-thiopseudourea: To a mixture of 2-methyl-2-thiopseudourea sulfate (2.0 g, 7.18 mmol) in water (3 mL) was added ethyl isocyanate (1.137 mL, 14.37 mmol) followed by dropwise 6N NaOH to a stable pH 8. After 1 hour at pH8 the biphasic solution was diluted with aqueous saturated sodium bicarbonate and extracted into ethyl acetate (3×100 mL). The combined organic layers were washed with brine and dried over sodium sulfate, filtered then concentrated in vacuo to afford the title compound as a pungent oil (1.54 g, 92.7%). TLC (50% Ethyl acetate/methylene chloride) and $^1$H NMR suggests that the material is a mixture of mono and diacyl pseudourea. $^1$H NMR (500 Mhz, CDCl$_3$) ∂1.18 (m2, 6H), 2.31 and 2.41 (2s, 3H), 3.28 (m, 4H).

Example 26

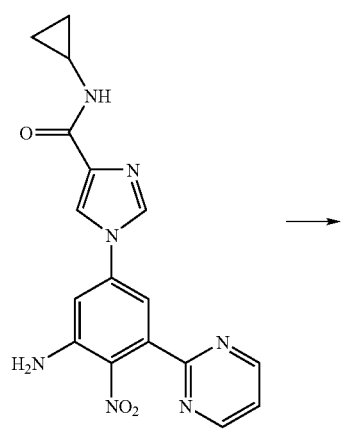

-continued

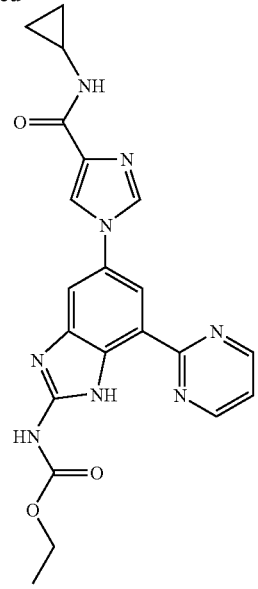

[5-(4-Cyclopropylcarbamoyl-imidazol-1-yl)-7-pyrimidin-2-yl-1H-benzoimidazol-2-yl]-carbamic acid ethyl ester: To a solution of 1-(3-amino-4-nitro-5-pyrimidin-2-yl-phenyl)-1H-imidazole-4-carboxylic acid cyclopropylamide (65 mg, 0.178 mmoles) in MeOH (10 mL) was added Ra—Ni (2 drops of water slurry, catalytic) and the resulting suspension was placed under 45 psi of H$_2$ (Parr shaker) for 2 hours. The resulting mixture was then filtered, concentrated, diluted with 3 mL of pH=3.5 buffer (made from 1M H$_2$SO$_4$ with enough NaOAc to raise pH to 3.5), and treated with N,N-diethlycarboxy-2-methyl-2-thiopseudourea (0.267 mL of a 1M solution of N,N-diethylcarboxy-2-methyl-2-thiopseudourea in dioxane) at room temperature. The resulting mixture was refluxed for 5 hours resulting in a heterogeneous suspension. The reaction was cooled to room temperature, diluted with water and enough NH$_4$OH to raise the pH to ~6.0. The solids were then filtered and washed sequentially with water, 2/1 water/ethanol, EtOAc, and then hexanes. The resulting solids were suspended in MeOH, 2 equivalents of methanesulfonic acid was added, and concentrated in vacuo to afford the title compound (75, 70%) as an off-white solid. $^1$H NMR (dmso-d$_6$, 500 MHz): 9.28 (s, 1H); 9.08 (d, 1H); 8.8-7.4 (v. broad s, 4H); 8.67 (s, 1H); 8.53 (s, 1H); 8.46 (d, 1H); 8.05 (d, 1H); 7.59 (dd, 1H); 4.33 (q, 2H); 2.88 (m, 1H); 2.35 (s, 6H); 1.34 (t, 3H); 0.76 (m, 2H); 0.61 (m, 2H).

We have prepared other compounds of formula I by methods substantially similar to those described in Schemes I through IV, Examples 1 through 26, and by methods known in the art. The characterization data for these compounds is summarized in Table 3 below and includes LC/MS (observed) and $^1$H NMR data.

$^1$H NMR data is summarized in Table 3 below wherein $^1$H NMR data was obtained at 500 MHz in deuterated DMSO, unless otherwise indicated, and was found to be consistent with structure. Compound numbers correspond to the compound numbers listed in Table 2.

$^1$H NMR data is also summarized in Table 3a below wherein $^1$H NMR data was obtained at 500 MHz in the deuterated solvents indicated therein, and was found to be consistent with the structure. Compound numbers correspond to the compound numbers listed in Table 2a.

TABLE 3

Characterization Data for Selected Compounds of Formula I

| Compound No. I- | M − 1(obs) | M + 1(obs) | ¹H NMR |
|---|---|---|---|
| 16 | 347.2 | 349.2 | 1.1(t, 3H) 3.2(q, 2H) 6.8(t, 1H) 7.5(m, 1H), 7.7(s, 1H) 7.9(s, 1H) 8.1(d, 1H) 8.3(s, 1H) 8.6(d, 1H) 8.9(s, 1H)9.6(s1H) 10.3(s, 1H) |
| 20 | 360.3 | 362.3 | (CD$_3$OD): 8.89(dd, 1H), 8.51(dd, 1H); 8.42-8.29(br. s, 1H), 8.18(ddd, 1H); 7.94-7.77(br. s, 1H); 7.63(br. s); 7.58(br. s, 1H); 7.53(dd, 1H); 3.32(q, 2H); 2.21(s, 3H); 1.23(t, 3H) |
| 24 | 391.3 | 393.3 | 1.13(t, 3H), 1.3(t, 3H) 3.24(q, 2H), 3.37(q, 2H), 7.82(s, 1H), 7.82(s1H), 7.96(t, 1H)8.19(s, 1H), 8.56(s, 1H), 8.62(d, 1H), 8.82(d, 1H), 9.15(s, 1H), 11.02(s, 1H) |
| 42 | 390.3 | 392.2 | 1.13(t, 3H) 2.45(s, 3H) 3.23(q, 2H) 3.46(s, 3H) 6.58(m, 4H), 7.78(m, 3H) 9.11(s, 1H) 10.51(s, 1H) 12.18(s, 1H) |
| 43 | — | — | 1.15(t, 3H), 3.25(m, 2H), 3.35(s, 3H), 4.6(s, 2H), 7.4(br s, 1H), 7.55(s, 1H), 7.8(m, 1H), 8.0(d, 1H), 8.05(d, 1H), 8.6(m, 1H), 8.7(m, 1H), 9.2(s, 1H), 10.4(br s, 1H) |
| 49 | — | — | 1.3(t, 3H), 4.3(q, 2H), 6.65(t, 1H), 7.75(d, 1H), 7.85(dd, 1H), 7.9(s, 1H), 8.05(d, 1H), 8.5(d, 1H), 8.75(dd, 1H), 9.1(s, 1H0, 11.7(br s, 1H), |
| 50 | 377.2 | 379.1 | 1.23(t, 3H), 2.89(s, 3H), 3.36(q, 2H), 7.93(d, 1H), 8.16(d, 1H), 8.26(d, 1H), 8.33(d, 1H), 8.86(d, 1H), 8.97(d, 1H), 9.30(d, 1H) |
| 51 | — | — | 1.1(t, 3H), 1.25(t, 3H), 3.25(q, 2H), 3.37(s, 3H), 4.05(q, 2H), 6.6(m, 4H), 7.65(s, 1H), 7.9(m, 2H) 9.1(br s, 1H), 10.2(br s, 1H), 11.8(br s, 1H) |
| 54 | — | — | 0.5(m, 2H), 0.8(m, 2H), 2.7(m, 1H), 6.4(br s, 1H), 6.7(m, 1H), 7.75(s, 1H), 7.8(m, 1H), 7.85(s, 1H), 8.05(m, 1H), 8.5(brs, 1H), 8.7(m, 1H), 9.05(s, 1H), 9.15(s, 1H), 10.2(br s, 1H) |
| 55 | — | — | 1.15(t, 3H), 3.25(m, 2H), 7.25(m, 1H), 7.5(br s, 1H), 7.7(m, 1H), 7.85(s, 1H), 8.3(s, 1H), 8.4(m, 1H), 8.7(m, 2H), 8.85(s, 1H), 9.1(s, 1H), 9.15(dd, 1H), 10.5(br s, 1H), |
| 57 | 377.1 | 379.2 | 9.08(d, 1H); 8.48(br. s, 1h); 8.13,(d, 1H); 7.95(d, 1H); 7.88(s, 1H); 7.25(d, 1H); 6.75(d, 1H); 6.64(s, 1H);, 6.62(dd, 1H); 6.4-5.7(br. s, 2H); 5.69(q, 2H); 3.48(s, 3H); 1.48(t, 3H) |
| 61 | — | — | 1.13(t, 3H) 2.38(s, 3H) 3.24(q, 2H) 5.36(s, 2H) 6.71(m, 2H), 6.83(s, 1H) 7.18(d, 2H) 7.28(t, 1H) 7.38(m, 2H) 7.76(s, 1H) 7.92(s, 2H), 8.30(s, 1H) 9.08(s, 1H) 11.50(s, 1H) |
| 62 | 404.3 | 406.3 | 12.15, 11.81(s, 1H), 10.34, 9.99(s, 1H), 9.13, 8.99(s, 1H), 7.99-7.81(m, 3H), 7.68(s, 1H), 7.30-6.59(m, 4H), 5.09(m, 1H), 3.23(t, 2H), 1.33 9(d, 6H), 1.13(t, 3H) |
| 63 | — | — | 1.15(t, 3H) 2.44(s, 3H) 3.25(q, 2H) 5.44(s, 2H) 6.70(m, 3H), 7.40(d, 1H) 7.49(t, 1H) 7.75(s, 1H) 7.85(m, 1H) 7.97(s, 2H) 8.12(s, 1H) 8.60(d, 1H) 9.09(s, 1H) 11.21(s, 1H) |
| 64 | — | — | 1.2(t, 3H), 2.2(m, 2H), 3.3(m, 2H), 3.65(m, 2H), 4.1(t, 2H), 7.75(s, 1H), 7.84(s, 1H), 7.87(s, 1H), 7.8(m, 1H0, 8.5(m, 1H), 8.65(m, 1H), 9.0(s, 1H) |
| 65 | 423.1 | 425.1 | (MeOH-d$_4$ &CDCl$_3$): 8.30-7.85(m, 4H), 6.78(s, 1H), 6.58(s, 1H), 3.60(s, 3H), 3.37(q, 2H), 2.80(s, 3H), 1.25(t, 3H) |

TABLE 3-continued

Characterization Data for Selected Compounds of Formula I

| Compound No. I- | M − 1(obs) | M + 1(obs) | ¹H NMR |
|---|---|---|---|
| 67 | — | — | 1.15(t, 6H), 3.45(q, 4H), 6.7(s, 1H), 7.7(m, 2H), 7.9(s, 1H), 8.1(s, 1H), 8.4(m, 1H), 8.7(m, 1H), 9.1(m, 2H), 10.6(br s, 1H), |
| 68 | 453.2 | 455.2 | 12.17, 11.81(s, 1H), 10.35, 9.99(s, 1H), 9.13, 9.00(s, 1H), 8.52(s, 1H), 7.99-7.69(m, 5H), 7.32-7.27(m, 2H), 6.93-6.59(m, 4H), 5.23(s, 2H), 3.22(q, 2H), 1.13(t, 3H) |
| 69 | 407.3 | 409.2 | (MeOH-d₄, HCl salt)): 8.62(s, 1H), 7.96-7.93(m, 2H), 7.59(s, 1H), 6.67(s, 1H), 5.81(s, 1H), 3.45, 3.39(s, 3H), 3.36(q, 2H), 3.28, 3.20(s, 3H), 1.23(t, 3H) |
| 70 | — | — | 1.15(t, 3H), 1.35(t, 3H), 3.25(q, 2H), 4.3(q, 2H), 7.1(br s, 1H), 7.85(s, 1H), 8.05(m, 1H), 8.2(s, 1H), 8.3(s, 1H), 8.8(m, 1H), 8.85(d, 1H), 9.25(s, 1H0, 9.65(s, 1H), 10.7(br s, 1H), |
| 71 | 416.2 | 418.2 | 0.84(m, 2H) 1.14(m, 5H) 2.55(s, 3H) 2.91(m, 1H) 3.26(q, 2H) 6.59(s, 1H) 6.65(s, 1H) 6.69(s, 1H) 7.65(s, 1H) 7.81(m, 1H) 7.97(s, 1H) 8.07(s, 1H) 9.07(s, 1H) 11.59(s, 1H) |
| 72 | — | — | 1.1(t, 3H), 3.2(q, 2H), 7.1(br s, 1H), 7.8(s, 1H), 8.0(m, 1H), 8.2(s, 1H), 8.25(s, 1H), 8.7(m, 1H), 8.8(m, 1H), 9.2(s, 1H), 9.6(s, 1H), 10.7(br s, 1H), |
| 73 | 448.2 | 450.2 | (CD₃OD): 1.18-1.26(m, 9H), 3.27(s, 3H), 3.36(q, 2H), 4.21(s, 2H), 6.65-6.68(m, 1H), 6.90-6.94(m, 1H), 6.98-7.01(m, 1H), 7.78-7.84(m, 2H), 7.93-7.96(m, 1H), 8.09-8.11(m, 1H), 8.74-8.76(m, 1H) |
| 74 | 434.3 | 436.3 | (CD₃OD): 1.21-1.27(m, 9H), 3.36(q, 2H), 4.17(s, 2H), 6.65-6.68(m, 1H), 6.95-6.99(m, 1H), 7.00-7.03(m, 1H), 7.79-7.82(m, 1H), 7.89(d, 1H), 7.94-7.96(m, 1H), 8.09-8.11(m, 1H), 8.73-8.76(m, 1H) |
| 75 | — | — | 1.1(t, 3H), 3.0(br s, 3H), 3.25(m, 5H), 7.0(br s, 1H), 7.75(m, 2H), 8.05(s, 1H), 8.15(s, 1H), 8.45(m, 1H), 8.7(m, 1H), 9.1(s, 1H), 9.4(s, 1H), 10.4(br s, 1H), |
| 77 | 448.3 | 450.2 | (CD₃OD): d 1.24(t, 3H), 1.27(d, 3H), 1.47(d, 3H), 3.36(q, 2H), 3.37(s, 3H), 3.58-3.67(m, 1H), 5.21-5.28(m, 1H), 6.68-6.71(m, 1H), 7.80(d, 1H), 7.85(s, 1H), 7.95-7.99(m, 2H), 8.27(s, 1H), 8.38(d, 1H), 8.78-8.82(m, 1H). |
| 78 | 448.3 | 450.3 | (CD₃OD): d 1.24(t, 3H), 1.31(d, 3H), 1.51(d, 3H), 3.38(q, 2H), 3.42(s, 3H), 3.66-3.73(m, 1H), 5.44-5.51(m, 1H), 6.68-6.71(m, 1H), 7.94(d, 1H), 7.96-7.98(m, 1H), 8.03(s, 1H), 8.07(s, 1H), 8.32(s, 1H), 8.43(d, 1H), 8.81-8.86(m, 1H). |
| 79 | 434.3 | 436.2 | (CD₃OD): d 1.24(t, 3H), 1.32(d, 3H), 1.50(d, 3H), 3.37(q, 2H), 3.93-4.02(m, 1H), 5.14-5.22(m, 1H), 6.67-6.71(m, 1H), 7.90(d, 1H), 7.95-7.98(m, 1H), 8.02(s, 1H), 8.04(s, 1H), 8.32(s, 1H), 8.41(d, 1H), 8.81-8.85(m, 1H). |
| 82 | 428.2 | 430.1 | 9.0(m, 1H), 8.6(d, 1H), 8.4(m, 1H), 8.1-8.2(m, 2H), 8.0(m, 1H), 7.8(m, 1H), 7.5(m, 2H), 6.6(s, 1H), 4.8(s, 1H), 2.55(s, 3H), 3.25(m, 2H), 2.1(s, 3H), 1.1(t, 3H) |
| 83 | 417.1 | 419.1 | 11.01(br. s, 1H); 9.10(d, 1H); 8.37,(s, 1H); 8.19(s, 1H); 7.97(s, 1H); 7.78(br. s, 1H); 7.58(m, 1H); 7.08,(s, 1H); 6.68(m, 1H); 3.88(dd, 2H); 3.22(dq, 2H); 2.99(dd, 2H);, 1.91(ddd, 2H); 1.85(ddd, 2H); 1.11(t, 3H). |

TABLE 3-continued

Characterization Data for Selected Compounds of Formula I

| Compound No. I- | M − 1(obs) | M + 1(obs) | ¹H NMR |
|---|---|---|---|
| 84 | 377.2 | 379.2 | (MeOD-d$_3$): 8.72(br s, 1H), 8.58(s, 1H), 8.40(s, 1H), 8.19(s, 1H), 7.95(s, 1H), 7.14(s, 1H), 6.68(s, 1H), 3.60(s, 3H), 3.21(q, 2H), 1.24(t, 3H). |
| 85 | 430.2 | 432.2 | (MeOD-d$_3$, salt): 8.64(d, 1H), 8.14(s, 1H), 8.00(s, 1H), 7.97(d, 1H), 7.64(s, 1H), 6.66(dd, 1H), 6.51(s, 1H), 3.89(s, 3H), 3.48(s, 3H), 3.37(q, 2H), 1.24(t, 3H) |
| 87 | 360.1 | 362.1 | MeOD-d$_3$, 1.24(t, 3H), 2.42(s, 3H), 3.38(q, 2H), 6.87(s, 1H), 7.94(s, 1H), 8.15(m, 2H), 8.85(d, 1H), 8.98(d, 1H), 9.30(s, 1H) |
| 88 | 388 | 390 | 9.27(s, 2H). 9.20(S, 1H), 8.27(s, 1H). 8.10(m, 1H), 7.94(s, H), 7.92(d, 1H), 6.95(d, 1H), 4.10(s, 3H), 3.25(m, 2H), 1.11(t, 3H) |
| 89 | 386.9 | 389.2 | (CD$_3$OD) 8.92-6.96(m, 9ArH), 3.99(s, 3H), 3.36(q, 2H), 1.24(t, 3H) |
| 90 | 457.1 | 459.2 | — |
| 91 | 429.2 | 431.2 | (CD$_3$OD): 8.97(s, 1H); 8.89(d, 1H); 8.49(d, 1H); 8.37(m, 2H); 8.22(ddd, 1H); 7.93(d, 1H); 7.64(dd, 1H); 3.38(q, 2H); 2.91(m, 1H); 1.25(t, H): 0.88(m, 2H); 0.67(m, 2H). |
| 92 | 360.13 | 362.19 | 1.15(t, 3H), 3.25(m, 2H), 3.9(s, 3H), 7.15(m, 1H), 7.65(m, 1H), 7.8(s, 1H), 8.0(s, 1H), 8.2(m, 1H), 8.3(m, 1H), 8.65(m, 1H), 9.0(m, 2H), 10.3(br s, 1H) |
| 93 | 371 | 373 | 1.12(t, 3H), 3.25(m, 2H), 4.2(bs, 2H), 7.0.2-7.25(m, 1H), 7.5(m, 1H), 7.81(m, 1H), 8.08(t, 1H), 8.22(m, 1H), 8.61-8.48(m, 2H), 8.4(d, 1H), 8.46(s, 1H). |
| 94 | 430 | 432 | 0.92(d, 6H), 1.12(m, 3H), 2.23(m.1H), 2.83(d, 2H), 3.35(m, 2H), 7.5(m, 1H), 7.61(bs, 1H), 7.89(s, 1H), 8.1(m, 1H), 8.4(s, 1H), 8.58(m, 1H), 8.78(bs, 1H), 8.3(d, 1H). |
| 95 | 431.03 | 433.2 | (CD$_3$OD) 1.2(7, 3H), 3.3(q, 2H), 3.8(m, 2H), 4.6(m, 2H), 7.4(m, 1H), 7.8(m, 1H), 8.0(s, 1H), 8.3(m, 2H), 8.5(m, 1H), 8.7(m, 2H), 9.1(s, 1H) |
| 96 | 507.2 | 509.2 | (CD$_3$OD): 8.9(d, 1H), 8.55(d, 1H), 8.4(s, 1H), 8.3(m, 1H), 8.0(s, 1H), 7.7(m, 1H), 7.3(t, 1H), 7.0(s, 2H), 6.85(d, 1H), 6.7(d, 2H), 5.5(s, 2H), 3.7(s, 3H), 3.3(q, 2H), 2.5(s, 3H), 1.25(t, 3H) |
| 97 | 401 | 403 | 9.1(s, 1H), 8.6(d, 2H), 8.3(m, 1H), 8.1(s, 1H), 7.9(s, 1H), 7.8(s, 1H) 7.5(m, 1H), 7.0(d, 1H), 4.3(m, 2H), 3.3(m, 2H), 1.4(t, 3H), 1.1(t, 3H). |
| 98 | 497.03 | 499.18 | , 1.16(t, 3H) 3.25(q, 2H) 4.44(d, 2H) 7.17(t, 2H) 7.38(t, 2H)7.53(t, 1H) 7.79(m, 1H) 7.87(s, 1H) 8.10(t, 1H) 8.32(s, 1H)8.51(s, 1H) 8.57(d, 1H) 8.77(s, 1H) 8.82(d, 1H) 8.94(t, 1H)11.10(br s, 1H) |
| 99 | 432 | 434 | — |
| 100 | 418.25 | 420.15 | 1.1(t, 3H), 3.2(m, 2H), 3.95(s, 3H), 4.1(s, 2H), 7.2(br s, 1H), 7.25(brs, 1H), 7.9(s, 1H), 8.2(m, 1H), 8.25(s, 1H), 8.7(d, 1H), 9.05(s, 2H), 10.4(br s, 1H) |
| 101 | 431 | 433 | 8.65(d, 1H), 8.28(s, 1H), 8.24(s, 1H), 7.98(d, 1H), 7.78(d, 1H), 7.38(m, 1H), 6.93(s, 1H), 6.89(dd, 1H), 4.51(q, 2H), 3.63(s, 3H), 3.35(q, 2H), 1.55(t, 3H), 1.22(t, 3H) |
| 102 | 375 | 377 | 8.86(d, 1H), 8.69(m, 1H), 8.52(d, 1H), 8.16(m, 2H), 7.79(m, 2H), 7.56(m, 1H), 7.50(m, 1H), 3.55(m, 2H)1.23,(t, 3H |
| 103 | 430 | 432.1 | 8.87(br. s, 1H); 8.81(d, 1H); 8.66(br. s., 1H); 8.49(s, 1H); 8.39(br. s, 1H); 8.25(d, 1H); 8.09(ddd, 1H); 7.87(d, 1H); |

TABLE 3-continued

Characterization Data for Selected Compounds of Formula I

| Compound No. I- | M − 1(obs) | M + 1(obs) | ¹H NMR |
|---|---|---|---|
| | | | 7.52(dd, 1H); 5.3(very br. s, 5 H); 4.29(q, 2H); 2.85(m, 1H); 1.31(t, 3H); 0.72(m, 2H); 0.63(m, |
| 104 | 417.19 | 419.14 | 1.1(t, 3H), 3.2(q, 2H), 3.45(s, 3H), 4.1(s, 3H), 6.7(dd, 1H), 6.85(d, 1H), 7.15(br s, 1H), 7.35(br s, 1H), 7.8(d, 1H), 7.95(s, 1H), 8.2(s, 1H), 8.4(br s, 1H), 8.7(d, 1H), 10.5(br s, 1H) |
| 105 | 406 | 408 | 8.97(br. s, 2H); 8.60(d, 1H); 7.99(br. s., 1H); 7.96(m, 1H); 7.81(br. s., 1H); 7.57(m, 1H); 3.98(s, 3H); 3.25(m, 2H); 1.11(t, 3H). |
| 106 | 508.2 | 510.2 | 1.1(t, 3H), 2.4(s, 3H), 3.2(q, 2H), 4.1(s, 3H), 5.4(s, 2H), 6.65(s, 1H), 6.75(s, 1H), 7.15(br s, 1H), 7.3(m, 2H), 7.35(m, 1H), 7.8(m, 1H), 7.95(s, 1H), 8.25(s, 1H), 8.35(br s, 1H), 8.5(m, 1H), 8.75(m, 1H), 10.5(br s, 1H) |
| 107 | 495.2 | 497.2 | 8.8(m, 1H), 8.2(m, 1H), 7.9(s, 1H), 7.8(m, 1H), 7.4(m, 2H), 7.35(d, 2H), 7.25(d, 2H), 6.7-6.8(m, 2H), 5.3(2, 2H), 4.0(m, 1H), 3.4(q, 2H), 2.4(s, 3H), 1.1(t, 3H) |
| 108 | 417 | 419 | 9.12(br. s, 1H); 8.60(d, 1H); 8.39(m, 1H); 8.36(s, 1H); 8.25(s, 1H); 7.89(s, 1H); 7.70(dd, 1H); 7.41(m, 1 H); 4.13(s, 3H); 3.98(s, 3H); 3.26(m, 2H); 1.15(t, 3H). |
| 109 | 358.3 | 360.1 | (CD₃OD) 9.61(d, 1H), 9.22(d, 1H), 8.83-8.79(m, 3H), 8.65(d, 1H), 8.47(d, 1H), 8.02(dd, 1H), 8.00(s, 1H), 3.37(q, 2H), 1.24(t, 3H) |
| 110 | 388.3 | 390.2 | (CDCl₃) 14.05(br s, 1H), 12.85(br s, 1H), 8.37(t, 1H), 7.97(d, 1H), 7.88(d, 1H), 7.79-7.74(m, 2H), 7.63(dd, 1H), 7.46(d, 1H), 6.62(dd, 1H), 5.75(br s, 1H), 3.45-3.40(m, 2H), 1.27(t, 3H) |
| 111 | 492.3 | 494.1 | 10.3(s, 1H), 8.9(d, 1H), 8.6(m, 1H), 8.5(d, 1H), 8.2(s, 1H), 8.05(t, 1H), 7.8-7.9(m, 2H), 7.5(m, 2H), 7.4(d, 1H), 7.3(m, 1H), 6.7(s, 1H), 6.6(s, 1H), 3.3(q, 2H), 1.9(d, 3H), 1.1-1.2(t, 3H). |
| 112 | 475.2 | 477.2 | 10.62(s, 1H); 8.74(d, 1H); 8.65(s, 1H); 8.40(s, 1H); 8.28(s, 1H); 8.23(s, 1H); 7.87(s, 1H); 7.43(s, 1H); 7.32(m, 2H); 5.52-4.41(br. s, 3H); 4.10(s, 3H); 3.24(dt, 2H); 1.41(s, 9H); 1.13(t, 3H). |
| 113 | 494.2 | 496.2 | (CD₃OD) 9.06(s, 1H); 8.93(d, 1H); 8.71(d, 1H); 8.50(m, 2H); 8.39(s, 1H); 8.00(s, 1H); 7.87(dd, 1H); 7.42(d, 2H); 7.35(dd, 2H); 7.25(dd, 1H); 5.27(q, 1H); 4.41(q, 2H); 1.62(d, 3H); 1.42(t, 3H) |
| 114 | 370.2 | 372.2 | 12.09&12.74(s, 1H), 10.25&9.94(s, 1H), 9.12&8.94(s, 1H), 8.35-6.58(m, 9H), 3.24(m, 2H), 1.13(t, 3H) |
| 115 | 442.1 | 444.3 | (CD₃OD) 8.65(d, 1H), 7.94(s, 1H), 7.91(d, 1H), 7.72(d, 2H), 7.66(s, 1H), 7.40(d, 2H), 6.63(dd, 1H), 4.52(s, 2H), 3.40(t, 2H), 3.35(q, 2H), 2.47(t, 2H), 2.09-2.03(m, 2H), 1.24(t, 3H) |
| 116 | 382 | 384 | — |
| 117 | 415 | 417 | 9.17(br. s, 1H); 9.0(m, 1H); 8.98(d, 1H); 8.72(d, 1H); 8.55(m, 1H); 8.38(s, 1H); 7.94(s, 1H); 7.86(d, 1H); 7.79(m, 1H); 3.97(s, 3H); 3.27(m, 2H); 1.15(t, 3H). |
| 118 | 401 | 403 | — |
| 119 | 403.3 | 405.2 | (CD₃OD): 8.78(s, 1H), 8.67(d, 1H), 8.37(d, 1H), 8.24(d, 1H), 8.22(s, 1H), 8.04(d, 1H), 7.91(s, 1H), 7.67(dd, 1H), 7.40(dd, 1H), 4.22(s, 3H), 3.34(q, 2H), 1.23(t, 3H) |
| 120 | 434.32 | 436.23 | 1.1(t, 3H), 2.8(s, 6H), 3.2(m, 2H), 3.4(s, 3H), 4.6(s, 2H), 6.6(d, 1H), 6.8(s, |

TABLE 3-continued

Characterization Data for Selected Compounds of Formula I

| Compound No. I- | M − 1(obs) | M + 1(obs) | $^1$H NMR |
|---|---|---|---|
| | | | 1H), 7.2(br s, 1H), 7.6(s, 1H), 7.8(d, 1H), 7.9(s, 1H), 7.95(s, 1H), 10.0(br s, 1H), 10.2(br s, 1H) |
| 121 | 414 | 416 | (CD$_3$OD): 9.40(br. s, 1H); 9.07(d, 1H); 8.98(d, 1H); 8.91(d, 1H); 8.80(s, 1H); 8.60(s, 1H); 8.24(dd, 1H); 8.11(d, 1H); 7.84(dd, 1H); 3.35(m, 2H); 3.01(s, 3H); 1.25(t, 3H). |
| 122 | 415 | 417 | — |
| 123 | 435.28 | 437.26 | 1.3(t, 3H), 2.8(s, 6H), 3.5(s, 3H), 4.2(q, 2H), 4.6(s, 2H), 6.6(dd, 1H), 6.7(s, 1H), 7.7(s, 1H), 7.8(d, 1H), 8.0(m, 2H), 10.1(br s, 1H), 11.7(br s, 1H) |
| 124 | 431.2 | 433.2 | 9.28(s, 1H); 9.08(d, 1H); 8.8-7.4(v. broad s, 4H); 8.67(s, 1H); 8.53(s, 1H); 8.46(d, 1H); 8.05(d, 1H); 7.59(dd, 1H); 4.33(q, 2H); 2.88(m, 1H); 2.35(s, 6H); 1.34(t, 3H); 0.76(m, 2H); 0.61(m, 2H). |
| 125 | 447.4 | — | 9.10(s, 1H); 8.60(d, 1H); 8.47(m, 2H); 7.95(s, 1H); 7.83(s, 1H); 7.12(d, 1H); 5.2-3.6(br. m, 7H); 2.86(M, 1H); 1.30(t, 3H); 0.75(m, 2H); 0.64(m, 2H) |
| 126 | 439.2 | 441.2 | (CDCl$_3$) 13.89(br s, 1H), 12.89(br s, 1H), 8.28(d, 1H), 8.25(d, 1H), 7.96(d, 1H), 7.74(s, 1H), 7.69-7.43(m, 6H), 7.40(s, 1H), 6.64(dd, 1H), 6.11(br s, 1H), 3.46-3.40(m, 2H), 1.27(t, 3H) |
| 127 | 418.2 | 420.2 | (CD$_3$OD) 9.72(d, 1H), 8.87(d, 1H), 8.82(d, 1H), 8.11(d, 1H), 8.09(d, 1H), 7.85(d, 1H), 7.39(d, 1H), 7.36(d, 1H), 4.43(q, 2H), 3.35(q, 2H), 1.44(t, 3H), 1.24(t, 3H) |
| 128 | 449.8 | 452.1 | (CD$_3$OD) 9.21(d, 1H), 8.83(ddd, 1H), 8.81(dd, 1H), 8.68(d, 1H), 8.26(d, 1H), 8.18(d, 1H), 8.07(dd, 1H), 8.05(d, 1H), 7.50(dd, 1H), 3.36(q, 2H), 3.34(s, 3H), 1.23(t, 3H) |
| 129 | — | — | 9.31(s, 1H); 9.08(d, 2H); 8.63(s, 1H); 8.43(d, 1H); 8.02(d, 1H); 7.89(s, 1H); 7.57(t, 1H); 8.8-6.6(very br. s, 4H); 4.31(q, 2H); 2.32(s, 6H); 1.42(s, 9H); 1.33(t, 3H). |
| 130 | 495.4 | 497.2 | 9.07(d, 2H); 8.73(d, 1H); 8.56(s, 1H); 8.44(d, 1H); 8.03(d, 1H); 7.57(t, 3H); 7.44(d, 2H); 7.36(dd, 2H); 7.26(dd, 1H); 6.95-5.90(very broad s., 5H); 5.18(dt, 1H); 4.32(q, 2H); 2.32(s, 6H); 1.53(d, 3H); 1.33(t, 3H). |
| 131 | 432 | 434 | (CD$_3$OD) 1.08(d, 6H), 1.43(t, 3H), 2.33(m, 1H), 2.91(d, 2H), 4.45(q, 2H), 7.53(t, 1H), 8.08(s, 1H), 8.79(s, 1H)<8.94(s, 1H), 9.05(d, 2H), 9.5(s, 1H). |
| 132 | 514.23 | 516.23 | 8.84(d, 1H), 8.81-8.83(m, 1H), 8.35(s, 1H), 8.06(dd, 1H), 7.90(dd, 1H), 7.80(d, 1H), 6.80(br s, 1H), 6.70(d, 1H), 4.30(q, 2H), 3.42-3.54(m, 4H), 3.48(s, 3H), 3.12-3.17(m, 4H), 2.81(d, 3H), 1.32(t, 3H) ppm |
| 133 | 501.33 | 503.26 | — |
| 134 | 521.6 | 523.2 | (CD$_3$OD) 8.82(s, 1H), m 8.46(d, 1H), 8.30(s, 1H), 8.13(dd, 1H), 7.90(s, 1H), 7.55(dd, 1H), 7.28(dd, 1H), 6.86-6.77(m, 4H), 6.74(s, 1H), 3.77(s, 3H), 3.36(q, 2H), 2.41(br s, 3H), 1.97(d, 3H), 1.24(t, 3H) |
| 135 | 470.3 | 472.5 | (CD$_3$OD) 8.85(br s, 1H), 8.45(d, 1H), 8.34(dd, 1H), 8/26(dd, 1H), 8.13(ddd, 1H), 7.96(dd, 1H), 7.56(dd, 1H), 7.43(dd, 1H), 7.29&7.20(s, 1H), 5.49(m, 1H), 3.66-3.25(m, 4H), 3.38(q, 2H), 2.94(2s, 3H), 2.52(m, 1H), 2.38(m, 1H), 2.15(m, 1H) |

TABLE 3-continued

Characterization Data for Selected Compounds of Formula I

| Compound No. I- | M − 1(obs) | M + 1(obs) | ¹H NMR |
|---|---|---|---|
| 136 | 521.3 | 523.3 | (CD$_3$OD) 8.81(d, 1H), 8.43(d, 1H), 8.27(s, 1H), 8.11(ddd, 1H), 7.88(s, 1H), 7.54(dd, 1H), 7.28(dd, 1H), 6.87(d, 1H), 6.84(d, 1H), 6.81(s, 1H), 4.42(q, 2H), 3.78(s, 3H), 2.50(br s, 3H), 2.00(d, 3H), 1.41(t, 3H) |
| 137 | 522.6 | 524.2 | (CD$_3$OD) 8.90(d, 1H), 8.81(d, 1H), 8.49(dd, 1H), 8.41(s, 1H), 8.06(s, 1H), 7.84(dd, 1H), 7.29(dd, 1H), 6.99(br s, 1H), 6.92(s, 1H), 6.87(d, 1H), 6.84(d, 1H), 6.81(s, 1H), 4.42(q, 2H), 3.78(s, 3H), 2.50(br s, 3H), 2.00(d, 3H), 1.41(t, 3H) |
| 138 | 525 | 527 | 1.2(t.3H). 1.5(d, 3H), 3.73(s, 3H), 4.3(q, 2H), 5.13(m, 1H), 6.8(d, 1H), 7.0(m, 2H), 7.24(t, 1H), 7.53(t, 1H), 7.93(s, 1H), 8.24(s, 1H), 8.32(m, 2H), 8.4(s, 1H), 9.08(s, 1H), 11.79(bs, 1H), 12.18(s, 1H). |
| 139 | 522.5 | 524.2 | (CD$_3$OD): 8.86(d, 1H), 8.74(d, 1H), 8.41(dd, 1H), 8.35(s, 1H), 7.99(s, 1H), 7.78(dd, 1H), 7.28(dd, 1H), 6.85(d, 1H), 6.83(d, 1H), 6.80(s, 2H), m 6.76(s, 1H), 4.41(q, 2H), 3.77(s, 3H), 2.41(br s, 3H), 1.97(d, 3H), 1.41(t, 3H) |
| 140 | 499 | 501 | — |
| 141 | 425.3 | 427.2 | (CD$_3$OD) 8.8(d, 1H), 8.35(d, 1H), 8.2(s, 1H), 8.1(t, 1H), 8.0(s, 1H), 7.9(d, 1H), 7.8(s, 1H), 7.65-7.7(dd, 1H), 7.5(t, 1H), 7.49(d, 1H), 4.6(s, 2H), 4.45(s, 1H), 3.4(q, 2H), 3.2(s, 3H), 3.15(s, 1H), 1.2(t, 3H) |
| 142 | 426.3 | 428.2 | (CD$_3$OD): 8.8(d, 1H), 8.6(d, 1H), 8.3(m, 2H), 8.1(s, 1H), 8.0(d, 1H), 7.9(s, 1H), 7.7(d, 1H), 4.6(s, 2H), 4.45(s, 1H), 4.4-4.5(q, 2H), 3.3(s, 3H), 3.15(s, 1H), 1.4(t, 3H) |
| 143 | 498 | 500 | — |
| 144 | 497 | 499 | (CD$_3$OD) 1.42(t, 3H), 1.84(d.3H), 4.49(q, 2H), 6.43(q, 1H). 7.58(t, 1H), 8.03(t, 1H), 8.08(s, 1H0, 8.23(d, 1H), 8.67(t, 1H), 8.73(s, 1H), 8.39(d, 2H), 8.88(d, 2H), 9.06(s, 2H). |
| 145 | 457 | 459 | (CD$_3$OD) 1.4(t, 3H), 3.48(d, 4H), 3.99(s, 4H), 4.41(s, 2H), 7.7(d, 1H), 8.07(s, 1H) 8.05(m, 3H), 8.73(s, 1H), 8.9(s, 1H), 9.12(s, 1H). |
| 146 | — | 502.21 | (CD$_3$OD) 8.89(s, 1H), 8.49(d, 1H), 8.45(s, 1H), 8.22(d, 1H), 8.11(d, 1H), 8.06(s, 1H), 7.47(br d, 1H), 7.36(br s, 1H), 3.91(s, 3H), 3.68-3.89(br m, 8H), 3.38(q, 2H), 1.25(t, 3H) ppm |
| 147 | — | 487.2 | (CD$_3$OD) 8.99(s, 1H), 8.54(d, 1H), 8.46(s, 1H), 8.27(d, 1H), 8.01(s, 1H), 7.85(br s, 1H), 6.97(br s, 1H), 6.91(br s, 1H), 4.47(q, 2H), 3.66-3.69(m, 5H), 3.59-3.62(m, 2H), 2.01-2.06(m, 2H), 1.96-2.00(m, 2H), 1.43(t, 3H) ppm |
| 148 | 375 | 377 | (CD$_3$OD): 9.02(t, 2H), 8.98(s, 2H), 8.82(d, 1H), 8.05(d, 1H), 7.54(t, 1H), 4.48(q, 2H), 1.44(t, 3H) |
| 149 | — | 486.22 | (CD$_3$OD) 8.98(s, 1H), 8.44(m, 1H), 8.38(br s, 1H), 8.19(br d, 1H), 8.02(br s, 1H), 7.98(br s, 1H), 7.15(br s, 1H), 7.13(br s, 1H), 3.79(br s, 3H), 3.67(m, 2H), 3.61(m, 2H), 3.37(q, 2H), 2.05(m, 2H), 2.00(m, 2H), 1.25(t, 3H) p |
| 150 | 494.3 | 496.2 | (CD$_3$OD) 9.0(d, 1H), 8.8(s, 1H), 8.6(d, 1H), 8.2(t, 1H), 7.95(s, 1H), 7.8(d, 1H), 7.65(t, 1H), 7.5(t, 1H), 6.9(s, 1H), 6.6(s, 1H), 6.1(m, 1H), 4.4(q, 2H), 2.7(s, 3H), 2.05(d, 3H), 1.4(t, 3H) |

TABLE 3-continued

Characterization Data for Selected Compounds of Formula I

| Compound No. I- | M − 1(obs) | M + 1(obs) | $^1$H NMR |
|---|---|---|---|
| 151 | 493.4 | 495.2 | (CD$_3$OD) 8.95(d, 2H), 8.6(s, 1H), 8.5(d, 1H), 8.1(t, 1H), 7.8(s, 1H), 7.7(d, 1H), 7.5(t, 1H), 7.4(t, 1H), 6.8(s, 1H), 6.6(s, 1H), 6.0(m, 1H), 3.35(q, 2H), 2.6(s, 3H), 2.0(d, 3H), 1.2(t, 3H) |
| 152 | — | 462.21 | (CD$_3$OD) 8.90(d, 1H), 8.81(d, 1H), 8.49(m, 1H), 8.39(d, 1H), 8.04(d, 1H), 7.85(m, 1H), 7.02(br s, 1H), 6.90(d, 1H), 4.82(m, 1H, underneath water peak), 4.42(q, 2H), 4.29(m, 1H), 3.72(m, 1H), 3.35(s, 3H), 2.65&2.90(s, 3H), 1 |
| 153 | 504.3 | 506.3 | 12.14(s, 1H); 11.11(s, 1H); 9.59(s, 1H); 9.08(d, 2H); 8.38(s, 1H); 8.33(d, 1H); 8.22(s, 1H); 7.95(d, 1H); 7.56(dd, 1H); 4.32(q, 2H); 4.12(br. s, 4H); 3.62(br. s, 4H); 2.46(br. s, 2H); 1.31(dd, 2H); 1.22(t, 3H). |
| 154 | 474.3 | 476.3 | 10.31(s, 1H); 9.09(d, 2H); 8.79(s, 1H); 8.44(s, 1H); 8.42(s, 1H); 8.00(s, 1H); 7.68(t, 2H); 7.7-6.6(br. s, 3H); 4.32(q, 2H); 3.55(m, 4H); 3.12(m, 4H); 2.34(s, 6H); 1.32(t, 3H). |
| 155 | 479.3 | 481.2 | 1.33(t, 3H) 2.36(s, 3H) 4.35(q, 2H) 5.60(s, 2H) 6.84(s, 1H) 6.88(s, 1H) 7.68(t, 1H)7.81(d, 2H) 7.99(s, 1H) 8.26(t, 1H) 8.35(s, 1H)8.78(d, 1H) 8.89(d, 3H) 11.75(br s, 2H) |
| 156 | — | 461.22 | (CD$_3$OD) 8.83(m, 1H), 8.44(d, 1H), 8.25(d, 1H), 8.12(m, 1H), 7.88(d, 1H), 7.54(m, 1H), 6.70(s, 1H), 6.68(s, 1H), 4.68(m, 1H), 4.32(m, 1H), 3.70(m, 1H), 3.38(q, 2H), 3.35(s, 3H), 2.56(s, 3H), 1.60(d, 3H), 1.24(t, 3H) ppm |
| 157 | 486.3 | 488.3 | (CD$_3$OD) 1.37(t, 3H) 1.57(m, 4H) 2.27(m, 1H) 2.82(s, 3H) 3.41(t, 2H) 3.96(d, 2H)4.29(d, 2H) 4.43(q, 2H) 7.27(s, 1H) 7.50(s, 1H) 7.90(t, 1H) 8.17(s, 1H) 8.55(s, 1H) 8.659(t, 1H) 8.95(d, 1H) 9.09(d, 1H) |
| 158 | 474.3 | 476.3 | (CD$_3$OD) 1.08(s, 6H) 1.42(t3H) 2.76(s, 3H) 3.57(m, 1H) 2.82(t, 2H)4.42(m, 4H) 6.98(s, 1H) 7.05(s, 1H) 7.86(t, 1H) 8.09(s, 1H) 8.41(s, 1H)8.51(t, 1H) 8.82(d, 1H) 8.91(d, 1H) |
| 159 | 458 | 460 | (CD$_3$OD) 1.43(t, 3H), 3.48(bs, 24H), 3.99(bs, 4H), 4.48(1, 2H), 4.63(s, 2H), 7.55(t, 1H), 7.71(d, 1H), 8.1(s, 1H), 8.33(d, 1H), 8.9(1H), 9.03(d, 2H), 9.13(s.1H). |
| 160 | 457 | 459 | (CD$_3$OD) 1.35(t, 3H), 3.3-3.5(m, 6H), 3.99(bs, 4H), 4.62(s, 2H), 7.52(t, 1H), 7.7(d, 1H), 8.08(s, 1H), 8.32(d, 1H), 8.88(s, 1H), 9.05(d, 2H)9.1(s, 1H). |
| 161 | 446.28 | 448.2 | 1.2(t, 3H), 3.2(m, 2H), 3.3(br s, 4H), 3.9(br s, 4H), 4.7(s, 2H), 7.7(s, 1H), 7.8(br s, 1H), 7.95(m, 1H), 8.1(s, 1H), 8.25(s, 1H), 8.7(m, 1H), 8.8(m, 1H), 9.2(s, 1H), 10.6(br s, 1H) |
| 162 | 550.3 | 552.3 | 12.32(s, 1H); 11.18(s, 1H); 9.08(d, 2H); 8.62(s, 1H); 8.39(s, 1H); 8.37(s, 1H); 7.98(s, 1H); 7.62(m, 2H); 7.58(dd, 1H); 7.48(m, 3H); 6.4-5.9(br. s, 3H); 4.38(s, 2H); 4.33(q, 2H); 3.42(m, 4H); 3.15(m, 4H); 1.35(t, 3H). |
| 163 | 501.3 | 503.3 | (CD$_3$OD) 9.1(d, 1H), 8.8(d, 1H), 8.5(d, 1H), 8.4(s, 1H), 8.3(s, 1H), 8.2(t, 1H), 7.7(s, 1H), 7.5(s, 1H), 4.8(t, 2H), 4.4(q, 2H), 4.1(d, 2H), 3.9(t, 2H), 3.75(d, 2H), 3.7(t, 2H), 3.4(m, 2H), 3.3(s, 2H), 2.85(s, 3H), 2.0(s, 5H), 1.4(t, 3H) |

TABLE 3-continued

Characterization Data for Selected Compounds of Formula I

| Compound No. I- | M − 1(obs) | M + 1(obs) | ¹H NMR |
|---|---|---|---|
| 164 | 500.4 | 502.3 | (CD₃OD) 8.75(d, 1H), 8.3(d, 1H), 8.2(s, 1H), 8.0-8.05(t, 1H), 7.8(s, 1H), 7.5(t, 1H), 6.8(s, 1H), 6.7(s, 1H), 4.5-4.6(t, 2H), 4.0(brd s, 4H), 3.5-3.6(t, 4H), 3.4(q, 2H), 3.3(t, 2H), 2.6(s, 3H), 1.2-1.3(t, 3H) |
| 165 | 474 | 476 | (CD₃OD) 9.04(d, 1H), 8.71(d, 1H), 8.34(d, 1H), 8.23(dd, 1H), 7.94(d, 1H), 7.84(m, 1H), 7.65(d, 1H), 7.57(m, 1H), 4.56(s, 2H), 3.98(t, 4H), 3.45(t, 4H), 3.37(q, 2H), 1.24(t, 3H) |
| 166 | 475 | 477 | (CD₃OD): 9.07(d, 1H), 8.72(d, 1H), 8.49(d, 1H), 8.28(dd, 1H), 8.04(d, 1H), 7.92(m, 1H), 7.69(d, 1H), 7.63(m, 1H), 4.63(s, 2H), 4.47(q, 2H), 3.99(m, 4H), 3.44(m, 4H), 1.43(t, 3H) |
| 167 | 522.3 | 524.4 | (CD₃OD) 8.94(d, 2H), 8.65(s, 1H), 7.85(s, 1H), 7.44(dd, 1H), 7.27(dd, 1H), 6.84(d, 2H), 6.80(s, 1H), 6.70(s, 1H), 6.64(s, 1H), 3.77(s, 3H), 3.36(q, 2H), 2.39(br s, 3H), 1.96(d, 3H), 1.24(t, 3H) |
| 168 | — | 474.3 | (CD₃OD) 1.45(t, 3H) 1.80(d, 3H) 2.69(m, 2H) 3.50(m, 2H) 3.97(m, 4H) 4.49(q, 2H) 4.72(m, 1H)7.55(t, 1H) 7.71(d, 1H) 1.15(s, 1H) 8.33(d, 1H) 8.91(s, 1H) 9.08(d, 2H) 9.17(s, 1H) |
| 169 | 445.44 | 447.24 | 1.3(t, 3H), 2.9(br s, 6H), 3.6(brs, 2H), 4.3(q, 2H), 4.6(m, 2H), 7.1(m, 1H), 7.6(m, 1H), 7.9(s, 1H), 8.2(m, 1H), 8.25(s, 1H), 8.3(m, 1H), 8.6(d, 1H), 8.7(d, 1H), 9.1(s, 1H), 9.7(br, s, !H) |
| 170 | 444.43 | 446.22 | 1.2(t, 3H), 2.9(br s, 6H), 3.25(m, 2H), 3.6(br s, 2H), 4.6(m, 2H), 7.1(m, 1H), 7.4(br s, 1H), 7.6(m, 1H), 7.9(s, 1H), 8.1(br s, 1H), 8.2(s, 1H), 8.3(m, 1H), 8.6(d, 1H), 8.7(d, 1H), 9.1(s, 1H), 9.8(br s, 1H), 10.5(br s, 1H) |
| 171 | 460.2 | 462.2 | (CD₃OD) 8.95(d, 1H), 8.86(d, 1H), 8.57(dt, 1H), 8.46(d, 1H), 8.17(d, 1H), 7.93(t, 1H), 7.62(br s 1H), 7.33(d, 1H), 5.14(m, 1H), 4.42(q, 2H), 4.26(m, 1H), 3.75(dd, 1H), 3.36(s, 3H), 2.81(s, 3H), 1.42(d, 3H), 1.30(t, 3H) ppm |
| 172 | 485 | 487 | (CD₃OD) 1.45-1.12(m, 3H), 1.9(m, 1H), 2.1(m, 2H), 2.32(m, 1H), 3.5-3.3(m, 5H), 3.7(m, 4H), 3.99(bs, 1H), 4.4(q, 2H), 4.57(bd, 1H), 7.58(d, 1H), 7.8(t, 1H), 8.03(s, 1H0, 8.32(d, 1H), 8.42(m, 2H), 8.75(d, 1H), 8.88(s, 1H) 9.1(s, 1H). |
| 173 | 484 | 486 | (CD₃OD) 1.15(t, 3H), 1.4(t, 3H), 3.02(s, 2H), 3.6(m, 2H), 3.68(m, 2H), 3.95(s, 2H), 4.4(m, 2H), 4.61(s, 2H), 7.8(m, 2H), 8.08(s, 1H), 8.48(m, 3H), 8.78(d, 1H), 8.9(d, 1H), 9.17(s, 1H). |
| 174 | 503.2 | 505.2 | (CDCl₃) 8.94(d, 1H), 8.87(d, 1H), 8.15(d, 1H), 8.11(d, 2H), 7.95(ddd, 1H), 7.90(s, 1H), 7.70(d, 1H), 7.42(dd, 1H), 4.76(s, 2H), 4.46(q, 2H), 3.82(t, 4H), 3.64(t, 4H), 3.40(s, 6H), 1.45(t, 3H) |
| 175 | 593.4 | 595.3 | 10.85(s, 1H); 8.84(s, 1H); 8.72(s, 1H); 8.58(d, 1H); 8.52(s, 1H); 8.30(d, 1H); 8.08(s, 1H); 7.92(d, aH); 7.44(d, 2H); 7.34(dd, 2H); 7.24(t, 1H); 6.05-4.9(br. s); 5.21(dq, 1H); 4.78(d, 2H); 4.31(q, 2H); 3.58(d, 2H); 3.52( |
| 176 | 543.5 | 545.3 | 11.76(s, 1H); 9.59(s, 1H); 8.89(d, 1H); 8.78(s, 1H); 8.65(s, 1H); 8.40(s, 1H); 8.05(d, 1H); 7.9-6.2(br. s, 2H); 4.87(d, 2H); 4.32(q, 2H); 3.96(dd, 2H); 3.68(dd, 2H); 3.58(m, 4H); 3.20(m, 2H); 2.94(m, 3H); 1.98(m, 2H); 1.88 |
| 177 | 542.5 | 544.3 | 11.12(s, 1H); 10.84(s, 1H); 9.08(s, 1H); 8.87(d, 1H); 8.66(s, 1H); 8.41(s, 1H); 8.01(s, 1H); 7.96(d, 1H); 7.58(s, |

TABLE 3-continued

Characterization Data for Selected Compounds of Formula I

| Compound No. I- | M − 1(obs) | M + 1(obs) | ¹H NMR |
|---|---|---|---|
| 178 | 470.4 | 472.3 | 1H); 6.3-4.6(br. s, 6H); 4.82(d, 2H); 3.96(dd, 2H); 3.58(m, 6H); 3.26(m, 2H); 3.15(m, 2H); 2.84(d, 3H); 1.96( 9.05(d, 2H); 8.54(s, 1H); 7.89(s, 1H); 8.01(s, 1H); 7.78(d, 1H); 7.55(t, 1H); 7.05(d, 1H); 5.5-4.2(br. s, 1H); 4.33(q, 2H); 3.50(dd, 2H); 3.36(dd, 2H); 3.12(s, 3H); 2.85(s, 3H); 1.33(t, 3H). |
| 179 | 415.4 | 417.3 | (CD$_3$OD) 9.54(d, 1H), 9.21(m, 1H), 9.15(s, 1H), 8.97(d, 1H), 8.92(d, 1H), 8.83(d, 1H), 8.28(dd, 1H), 8.20(d, 1H), 7.69(m, 1H), 4.62(s, 2H), 4.48(q, 2H), 3.00(s, 6H), 1.44(t, 3H) ppm |
| 180 | 414.4 | 416.3 | (CD$_3$OD) 9.54(d, 1H), 9.22(m, 1H), 9.05(s, 1H), 8.97(d, 1H), 8.93(d, 1H), 8.79(d, 1H), 8.28(dd, 1H), 8.17(d, 1H), 7.62(m, 1H), 4.59(s, 2H), 3.39(q, 2H), 2.99(s, 6H), 1.25(t, 3H) ppm |
| 181 | 513 | 515 | (CD$_3$OD): 9.14(d, 1H), 9.06(d, 1H), 8.85(t, 1H), 8.67(t, 1H), 8.46(d, 1H), 8.37(d, 1H) 8.11(m, 1H), 7.97(d, 1H), 7.55(m, 1H), 4.07(brs, 2H), 3.88(t, 4H), 3.71(brs, 2H), 3.48(t, 4H), 3.36(q, 2H), 1.24(t, 3H) |
| 182 | 477.4 | 479.37 | 0.9(d, 6H), 1.3(t, 3H), 2.1(m, 1H), 2.9(s, 6H), 3.75(d, 2H), 4.3(q, 2H), 4.6(s, 2H), 6.6(dt, 1H), 6.7(d, 1H), 7.7(s, 1H), 7.8(d, 1H), 7.95(s, 1H), 8.010.2(br s, 1H)(s, 1H), |
| 183 | 476.42 | 478.41 | 0.9(d, 6H), 1.1(t, 3H), 2.1(m, 1H), 2.9(s, 6H), 3.2(m, 2H), 3.8(d, 2H), 4.6(s, 2H), 6.6(dt, 1H), 6.7(d, 1H), 7.3(br s, 1H), 7.7(s, 1H), 7.8(d, 1H), 7.95(s, 1H), 8.0(s, 1H), 10.2(br s, 1H) |
| 184 | 514 | 516 | — |
| 185 | 470.4 | 472.2 | (CD$_3$OD) 1.25(t, 3H) 1.78(d, 3H) 3.30(m, 2H) 3.35(q, 2H) 3.50(m, 2H) 3.93(m, 4H)4.73(q, 1H) 7.72(t, 1H) 7.45(d, 1H) 8.01(s, 1H) 8.27(t, 1H) 8.35(m, 2H) 8.52(d, 1H) 8.91(d, 1H) 9.18(s, 1H) |
| 186 | 498.4 | 500.3 | (CD$_3$OD) 1.16(m, 3H) 1.26(m, 6H) 1.80(m, 3H) 2.82(t, 2H) 3.20(d, 1H) 3.35(q, 2H)3.72(d, 1H) 3.91(m, 1H) 4.04(m, 1H) 4.68(q, 2H) 7.65(t, 1H) 7.71(d, 1H) 8.01(s, 1H)8.22(t, 1H) 8.35(m, 2H) 8.49(d, 1H) 8.89(d, 1H) 9.18(s, 1H) |
| 187 | 499.5 | 501.3 | (CD$_3$OD) 1.16(m, 3H) 1.29(d, 3H) 1.41(t, 3H) 1.79(d, 3H) 2.82(t, 2H) 3.20(d, 1H) 3.74(d, 1H) 3.92(m, 1H) 4.04(m, 1H) 4.43(q, 2H) 4.69(q, 1H) 7.70(d, 1H)7.87(t, 1H) 8.11(s, 1H) 8.35(d, 1H) 8.46(m, 2H) 8.75(d, 1H) 8.92(d, 1H) 9.34(s, 1H) |
| 188 | 486 | 488 | (CD$_3$OD): 8.91(m, 1H), 8.65(m, 1H), 8.47(m, 1H), 8.31(m, 2H), 8.29(m, 1H), 7.96(m, 1H) 7.73(m, 1H), 7.19(m, 1H), 4.08(m, 2H), 3.90(m, 2H), 3.72(m, 4H), 3.66(m, 4H), 3.37(m, 2H), 1.24(t, 3H) |
| 189 | 487 | 489 | (CD$_3$OD): 8.89(d, 1H), 8.69(d, 1H), 8.61(d, 1H), 8.41(t, 1H), 8.32(d, 1H), 8.20(dd, 1H) 7.95(d, 1H), 7.78(t, 1H), 7.10(d, 1H), 4.42(q, 2H), 4.09(m, 2H), 3.86(m, 2H), 3.70(m, 4H), 3.33(m, 4H), 1.24(t, 3H) |
| 190 | 388.38 | 390.19 | 1.2(t, 3H), 3.3(m, 2H), 3.5(s, 3H), 6.6(dd, 1H), 6.7(d, 1H), 7.6(t, 1H), 7.8(d, 1H), 7.95(br s, 1H), 8.0(s, 1H), 8.6(s, 1H), 9.05(d, 2H) |
| 191 | 359.3 | 361.2 | — |
| 192 | 446.4 | 448.3 | — |
| 193 | 474.2 | 476.4 | (CD$_3$OD) 9.14(s, 1H), 9.08(d, 2H), 8.91(s, 1H), 8.39(d, 1H), 8.14(s, 1H), 7.78(s, 1H), 7.55(dd, 1H), 4.72(s, 2H), 4.48(q, |

TABLE 3-continued

Characterization Data for Selected Compounds of Formula I

| Compound No. I- | M − 1(obs) | M + 1(obs) | ¹H NMR |
|---|---|---|---|
| | | | 2H), 3.81(t, 2H), 3.56(t, 2 H), 3.46(q, 2H), 3.41(s, 3H), 1.44(t, 3H), 1.43(t, 3H) |
| 194 | 486.1 | 488.1 | (CDCl₃) 12.31(br s, 1H), 8.95(s, 1H), 8.93(d, 1H), 8.58(s, 1H), 8.05(s, 1H), 8.01(d, 1H), 7.50(d, 1H), 7.24(dd, 1H), 4.46(q, 2H), 3.78(m, 2H), 3.72(s, 2H), 2.78(d, 2H), 1.91(dd, 2H), 1.41(t, 3H), 1.17(d, 6H) |
| 195 | — | — | 11.5(br s, 1H), 9.19(br s, 1H), 8.97(s, 1H), 8.88(d, 1H), 8.45(m, 1H), 8.40(s, 1H), 7.98(d, 1H), 7.77(d, 1H), 7.60(d, 1H), 4.57(s, 2H), 4.47(br d, 2H), 4.32(q, 2H), 3.90(br m, 4H), 3.32(br s, 4H), 2.80(d, 6H), 1.34 |
| 197 | 460.2 | 462.2 | (CD₃OD&CDCl₃): 8.98(d, 2H), 8.85(d, 1H), 8.60(d, 1H), 8.16(dd, 1H), 7.86(d, 1H), 7.67(d, 1H), 7.40(dd, 1H), 4.37(q, 2H), 3.81(s, 2H), 3.60(t, 2H), 3.37(s, 3H), 2.74(t, 2H), 2.38(s, 3H), 1.41(t, 3H) |
| 198 | 459.3 | 461.2 | (CD₃OD): 8.95(d, 2H), 8.83(s, 1H), 8.54(s, 1H), 8.15(d, 1H), 7.82(s, 1H), 7.65(d, 1H), 7.39(dd, 1H), 3.79(s, 2H), 3.59(t, 2H), 3.36(q, 2H), 3.35(s, 3H), 2.72(t, 2H), 2.36(s, 3H), 1.24(t, 3H) |
| 199 | 488 | 490 | — |
| 200 | 487 | 489 | — |
| 201 | 488 | 490 | — |
| 202 | 487 | 489 | — |
| 203 | 489 | 491 | 9.06(m, 4H), 8.50(d, 1H), 7.98(d, 1H), 7.54(t, 1H), 4.79(t, 2H), 4.31(q, 2H), 4.01(m, 2H), 3.79(m, 2H), 3.67(m, 2H), 3.56(m, 2H), 3.25(m, 2H) 1.33(t, 3H) |
| 204 | 488 | 490 | (CD₃OD): 9.02(m, 4H), 8.75(s, 1H), 7.97(d, 1H), 7.52(m, 1H), 4.88(m, 2H), 3.75-3.73(m, 10H), 3.35(m, 2H), 1.25(t, 3H) |
| 205 | 400.1 | 402.1 | 1.31(t, 3H) 2.70(s, 3H) 4.32(q, 2H) 7.55(t, 1H) 8.00(s, 1H) 8.09(d, 1H)8.14(t, 1H) 8.39(s, 1H) 8.44(d, 1H) 8.70(d, 1H) 8.81(d, 1H) 9.19(s, 1H) |
| 206 | 458.1 | 460 | (CD₃OD) 9.41(d, 2H), 8.92(m, 1H), 8.80(d, 1H), 8.48(m, 2H), 8.10(br s, 1H), 7.84(m, 1H), 4.76(s, 2H with water peak), 4.42(q, 2H), 4.11(br m, 2H), 3.95(nr m, 2H), 3.71(br m, 2H), 3.45(br m, 2H), 1.42(t, 3H) ppm. |
| 207 | 457.2 | 459.1 | (CD₃OD) 9.33(s, 2H), 8.89(d, 1H), 8.53(d, 1H), 8.44(d, 1H), 8.20(m, 1H), 8.04(d, 1H), 7.63(m, 1H), 4.76(s, 2H, with water peak), 4.12(br m, 2H), 3.94(br m, 2H), 3.71(br m, 2H), 3.44(br m, 2H), 3.39(q, 2H), 1.25(t, 3H) ppm |
| 208 | 391 | 393 | — |
| 209 | 441.1 | 443 | (CD₃OD) 1.43(t, 3H) 4.50(s, 2H) 4.89(s, 2H) 7.55(t, 1H) 8.10(d, 1H)8.20(s, 1H) 8.87(d, 1H) 9.01(s, 1H) 9.10(d, 2H) 9.30(s, 1H) |
| 210 | 472.4 | 474.2 | (CD₃OD) 9.25(s, 1H), 9.02(d, 2H), 8.87(d, 1H), 8.65(d, 1H), 8.18(s, 1H), 8.08(d, 1H), 7.54(dd, 1H), 4.88(s, 2H), 4.49(q, 2H), 4.27(br s, 1H), 3.68(m, 4H), 3.40(s, 3H), 2.32(m, 2H), 1.45(t, 3H) |
| 211 | 471.2 | 473.1 | (CD₃OD) 9.16(s, 1H), 8.98(d, 2H), 8.76(d, 1H), 8.48(d, 1H), 8.05(s, 1H), 7.91(d, 1H), 7.50(dd, 1H), 4.81(s, 2H), 4.27(br s, 1H), 3.69(m, 4H), 3.40(s, 3H), 3.38(q, 2H), 2.32(m, 2H), 1.26(t, 3H) |
| 212 | 485.2 | 487.3 | (CD₃OD) 9.16(s, 1H), 9.03(d, 2H), 8.87(s, 1H), 8.50(d, 1H), 8.14(s, 1H), 7.92(d, 1H), 7.54(dd, 1H), 4.75(s, 2H), 4.49(q, |

TABLE 3-continued

Characterization Data for Selected Compounds of Formula I

| Compound No. I- | M − 1(obs) | M + 1(obs) | ¹H NMR |
|---|---|---|---|
| | | | 2H), 4.06(s, 2H), 3.74(br s, 4H), 3.06(s, 3H), 1.45(t, 3H) |
| 213 | 484.2 | 486.2 | (CD₃OD) 9.16(s, 1H), 9.01(d, 2H), 8.78(s, 1H), 8.52(d, 1H), 8.07(s, 1H), 7.96(d, 1H), 7.52(dd, 1H), 4.77(s, 2H), 4.07(s, 2H), 3.75(br s, 4H), 3.38(q, 2H), 3.06(s, 3H), 1.26(t, 3H) |
| 214 | | 350.1 | 12.28(br. s, 1H); 11.77(br. s, 1H); 9.73(s, 1H); 9.08(d, 2H); 8.49(d, 1H); 8.37(m, 1H); 8.08(d, 1H); 7.94(m, 1H); 7.59(t, 1H); 4.32(q, 2H); 2.30(s, 3H); 1.32(t, 3H). |
| 215 | 502.4 | 504.1 | (CD₃OD) 9.17(s, 1H), 9.02(d, 2H), 8.85(s, 1H), 8.48(d, 1H), 8.15(s, 1H), 7.90(d, 1H), 7.53(dd, 1H), 4.81(d, 1H), 4.77(d, 1H), 4.48(q, 2H), 4.18(br s, 2H), 3.75(m, 4H), 3.47(s, 6H), 1.45(t, 3H) |
| 216 | 347.2 | 349.1 | 12.28(br. s, 1H); 10.22(br. s, 1H); 9.53(s, 1H); 9.08(d, 2H); 8.41(d, 1H); 8.29(m, 1H); 7.98(d, 1H); 7.83(m, 1H); 7.57(t, 1H); 7.22(m, 1H); 3.26(dq, 2H); 2.31(s, 3H); 1.15(t, 3H). |
| 217 | 501.4 | 503.1 | (CD₃OD) 9.15(s, 1H), 9.03(d, 2H), 8.85(s, 1H), 8.43(d, 1H), 8.10(s, 1H), 7.83(d, 1H), 7.53(dd, 1H), 4.78(d, 1H), 4.74(d, 1H), 4.18(br s, 2H), 3.74(m, 4H), 3.47(s, 6H), 3.38(q, 2H), 1.26(t, 3H) |
| 218 | 456 | 458 | (CD₃OD) 1.24(t, 3H), 3.38(m, 2H), 3.57(bs, 4H), 3.99(bs, 4H), 4.63(s, 2H), 7.68(m, 1H), 7.73(m, 1H), 8.02(s, 1H), 8.24(t, 1H), 8.48(m, 1H), 8.49(d, 1H), 8.9(d, 1H), 9.13(s, 1H). |
| 219 | — | — | 12.25(s, 1H); 11.75(s, 1H); 9.61(d, 1H); 9.07(d, 2H); 8.45(s, 1H); 8.11(s, 1H); 8.02(d, 1H); 7.59(t, 1H); 4.31(q, 2H); 2.38(s, 3H); 2.29(s, 3H); 1.32(t, 3H). |
| 220 | 502.3 | 504.2 | (CD₃OD) 9.10(d, 1H), 9.05(d, 2H), 8.91(d, 1H), 8.32(dd, 1H), 8.11(d, 1H), 7.69(d, 1H), 7.55(dd, 1H), 4.73(d, 1H), 4.69(d, 1H), 4.49(q, 2H), 4.17(br s, 2H), 3.70(m, 4H), 3.46(s, 6H), 1.44(t, 3H) |
| 221 | 501.3 | 503.2 | (CD₃OD) 9.09(s, 1H), 9.05(d, 2H), 8.86(s, 1H), 8.29(d, 1H), 8.09(s, 1H), 7.67(d, 1H), 7.54(dd, 1H), 4.72(d, 1H), 4.67(d, 1H), 4.17(br s, 2H), 3.71(m, 4H), 3.47(s, 6H), 3.39(q, 2H), 1.26(t, 3H) |
| 222 | — | 559 | (CDCl₃) 12.29(br s, 1H), 8.94(s, 1H), 8.94(d, 2H), 8.60(s, 1H), 8.04(s, 1H), 8.02(d, 1H), 7.50(d, 1H), 7.25(dd, 1H), 4.46(q, 2H), 3.75(s, 2H), 3.50(m, 4H), 2.51(m, 4H), 1.47(s, 9H), 1.41(t, 3H) |
| 223 | 513.2 | 515.14 | 1.1(d, 6H), 1.3(t, 3H), 3.5(m, 4H), 3.7(br s, 2H), 4.3(q, 2H), 4.5(br s, 2H), 4.65(m, 1H), 7.5(t, 1H), 7.7(d, 1H), 8.0(d, 1H), 8.3(dd, 1H), 8.5(d, 1H), 9.0(d, 2H), 9.05(d, 1H) |
| 224 | 457.207 | 459.207 | (CD₃OD) 9.54(s, 1H), 9.28(s, 1H), 9.22(d, 1H), 8.97(d, 1H), 8.93(d, 1H), 8.85(br s, 1H), 8.27(t, 1H), 8.20(br s, 1H), 7.71(d, 1H), 4.63(s, 2H), 4.48(q, 2H), 4.05(br s, 4H), 3.44(br m, 4H), 1.44(t, 3H) ppm |
| 225 | 472.2 | 474.49 | (CD₃OD) 9.0(d, 1H), 8.95(m, 1H), 8.6(s, 1H), 8.5(s, 1H), 8.4(s, 1H), 8.3(s, 1H), 7.9(s, 1H), 7.55(m, 1H), 4.5(s, 2H), 3.9(s, 2H), 3.4(q, 2H), 3.0(s, 6H), 1.3(t, 3H) |
| 226 | 562.3 | 564.2 | (CD₃OD) 9.0(d, 1H), 8.9(m, 1H), 8.6(s, 1H), 8.5(s, 1H), 8.3(s, 1H), 8.25(s, 1H), 7.9(s, 1H), 7.55(m, 1H), 7.3-7.4(m, 5H), 5.2(s, 2H), 4.5(s, 2H), 4.0(s, 2H), 3.4(q, 2H), 3.0(s, 6H), 1.3(t, 3H) |

TABLE 3-continued

Characterization Data for Selected Compounds of Formula I

| Compound No. I- | M − 1(obs) | M + 1(obs) | ¹H NMR |
|---|---|---|---|
| 227 | 389 | 391 | — |
| 228 | 457.3 | 459.1 | — |
| 229 | 456.3 | 458.1 | — |
| 230 | 433.3 | 435.1 | — |
| 231 | 487 | 489 | (CD₃OD) 9.30(s, 2H), 9.04(d, 2H), 8.89(d, 1H), 8.11(d, 1H), 7.54(t, 1H), 4.46(q, 2H), 4.02(m, 2H), 3.59(m, 2H), 2.89(m, 2H), 1.44(t, 2H), 1.13(t, 3H) ppm. |
| 232 | 456.3 | 458.3 | (CD₃OD) 9.22(s, 1H), 9.05(d, 2H), 8.92(s, 1H), 8.78(d, 1H), 8.17(s, 1H), 8.08(d, 1H), 7.54(dd, 1H), 4.42(s, 2H), 3.,52(m, 4H), 3.39(q, 4H), 3.28(m, 4H), 1.26(t, 3H) |
| 233 | — | 459.1 | (CD₃OD) 9.22(s, 1H), 9.06(d, 2H), 8.96(s, 1H), 8.77(d, 1H), 8.22(s, 1H), 8.07(d, 1H), 7.56(dd, 1H), 4.49(q, 2H), 4.42(s, 2H), 3.,52(m, 4H), 3.29(m, 4H), 1.45(t, 3H) |
| 234 | — | 537 | (CD₃OD) 9.22(s, 1H), 9.04(d, 2H), 8.90(s, 1H), 8.54(d, 1H), 8.16(s, 1H), 7.99(d, 1H), 7.54(dd, 1H), 4.78(s, 2H), 4.49(q, 2H), 3.69&3.63(m, 8H), 3.00(s, 3H), 1.45(t, 3H) |
| 235 | 534.2 | 536.1 | (CD₃OD) 9.20(s, 1H), 9.02(d, 2H), 8.82(s, 1H), 8.52(d, 1H), 8.09(s, 1H), 7.98(d, 1H), 7.52(dd, 1H), 4.78(s, 2H), 3.69&3.62(m, 8H), 3.39(q, 2H), 3.00(s, 3H), 1.25(t, 3H) |
| 236 | 496.4 | 498.3 | (CD₃OD) 9.28(s, 1H), 9.06(br s, 2H), 8.96(s, 1H), 8.85(br s, 1H), 8.24(s, 1H), 8.15(br s, 1H), 7.56(br s, 1H), 4.49(q, 2H), 4.42(s, 2H), 3.73(br s, 4H), 3.35(br s, 4H), 3.01(br s, 1H), 1.45(t, 3H), 1.20(br s, 2H), 1.00(br s 2H) |
| 237 | 496.4 | 498.3 | (CDCl₃) 11.82(br s, 1H), 8.88(s, 1H), 8.71(br s, 2H), 8.48(s, 1H), 7.89(d, 1H), 7.79(s, 1H), 7.42(d, 1H), 7.05(br s, 1H), 3.71(s, 2H), 3.46(q, 2H), 2.70&2.55(m, 8H), 1.28(t, 3H), 0.45-0.41(m, 4H) |
| 238 | 447.2 | 449 | 12.35(s, 1H); 9.07(d, 2H); 8.82(s, 1H); 8.41(d, 1H); 8.13(s, 1H); 7.95(d, 1H); 7.57(t, 1H); 6.7-5.2(br. s, 4H); 4.38(s, 2H); 4.32(q, 2H); 3.92(br. d, 4H); 3.32(br. d, 4H); 1.33(t, 3H). |
| 239 | 490.1 | 492.2 | (CD₃OD) 9.21(s, 1H), 9.05(d, 2H), 8.92(s, 1H), 8.54(d, 1H), 8.17(s, 1H), 7.97(d, 1H), 7.55(dd, 1H), 4.78(s, 2H), 4.49(q, 2H), 4.01(br dd, 2H), 3.74(br d, 2H), 3.43(br dd, 2H), 3.27(br d, 2H), 1.45(t, 3H) |
| 240 | 471.3 | 473 | (CD₃OD) 9.28(s, 1H), 9.05(br s, 2H), 8.96(s, 1H), 8.89(s, 1H), 8.25(s, 1H), 8.17(s, 1H), 7.55(br s, 1H), 4.49(q, 2H), 4.39(s, 2H), 3.64-3.13(m, 8H), 3.00(s, 3H), 1.45(t, 3H) |
| 241 | — | 531.01 | 1.3(t, 3H), 1.55(d, 3H), 3.3(br s, 4H), 3.9(br s, 4H), 4.0(q, 1H), 4.35(q, 2H), 4.6(s, 2H), 7.6(dd, 1H), 7.8(d, 1H), 8.0(s, 1H), 8.4(d, 1H), 8.42(s, 1H), 8.7(s, 1H), 8.8(d, 1H), 9.15(s, 1H), 11 . . . 2(br s, 1H) |
| 242 | 486.2 | 488.1 | (CD₃OD) 9.33(s, 2H), 8.92(d, 1H), 8.79(d, 1H), 8.47(m, 2H), 8.09(d, 1H), 7.84(m, 1H), 4.42(q, 2H), 4.05(m, 2H), 3.67(m, 2H), 3.39(m, 2H, underneath solvent peak), 3.00(m, 2H), 1.42(t, 3H), 1.28(d, 6H) ppm |
| 243 | 488.2 | 490.05 | 1.3(t, 3H), 3.2(m, 2H), 3.5(m, 2H), 3.7(m, 2H), 3.9(m, 2H), 4.0(m, 2H), 4.3(q, 2H), 4.8(m, 2H), 7.6(7, 1H), 8.1(d, 1H), 8.2(br s, 1H), 8.6(d, 1H), 8.65(d, 1H), 8.8(d, 1H), 9.05(d, 2H), 11.6(br s, 1H), 12.7(br s, 1H) |

TABLE 3-continued

Characterization Data for Selected Compounds of Formula I

| Compound No. I- | M − 1(obs) | M + 1(obs) | $^1$H NMR |
|---|---|---|---|
| 244 | 457.21 | 459.09 | 1.35(t, 3H), 2.8(br s, 3H), 3.2(m, 2H), 3.4(m, 2H), 3.55(m, 2H), 4.3(m, 2H), 4.35(q, 2H), 7.6(t, 1H), 8.1(d, 1H), 8.3(br s, 1H), 8.55(d, 1H), 8.6(d, 1H), 8.7(d, 1H), 9.05(d, 2H), 11.2(br s, 1H), 12.4(br s, 1H) |
| 245 | 529.2 | 531.1 | (CD$_3$OD) 9.08(d, 1H), 9.01(d, 2H), 8.82(d, 1H), 8.30(d, 1H), 8.04(d, 1H), 7.68(d, 1H), 7.51(dd, 1H), 4.63(s, 2H), 4.47(q, 2H), 4.22(s, 2H), 3.91(br s, 4H), 3.49(br s, 4H), 3.43(s, 3H), 1.44(t, 3H) |
| 246 | 555.3 | 557.1 | (CD$_3$OD) 9.23(s, 1H), 9.04(d, 2H), 8.90(s, 1H), 8.56(d, 1H), 8.17(s, 1H), 8.00(d, 1H), 7.55(dd, 1H), 4.77(s, 2H), 4.49(q, 2H), 4.12-3.84(m, 6H), 3.57(br s, 4H), 3.48(br s, 1H), 2.18(m, 2H), 1.97(m, 2H), 1.45(t, 3H) |
| 247 | 485.1 | 487 | (CD$_3$OD) 9.34(s, 2H), 8.93(d, 1H), 8.80(d, 1H), 8.48(m, 2H), 8.10(d, 1H), 7.85(t, 1H), 4.88(s, 2H), 4.44(q, 2H), 4.21(s, 2H), 3.86(m, 2H), 3.79(m, 2H), 3.09(s, 3H), 1.42(t, 3H) ppm. |
| 248 | 458.15 | 460.02 | 1.23(t, 3H) 3.17(m, 4H) 3.65(m, 4H) 4.34(q, 2H) 4.77(s, 2H) 7.57(t, 1H) 8.11(s, 1H) 8.61(s, 1H) 9.06(d, 2H) 9.39(s, 2H) 9.87(br s, 2H) |
| 249 | 472.3 | 474 | (CD$_3$OD) 9.17(s, 1H), 9.04(d, 2H), 8.92(s, 1H), 8.45(d, 1H), 8.15(s, 1H), 7.87(d, 1H), 7.55(dd, 1H), 4.68(s, 2H), 4.69(q, 2H), 4.11(dd, 1H), 4.02-3.95(m, 2H), 3.57(m, 2H), 3.03(dd, 1H), 1.44(t, 3H), 1.26(d, 3H) |
| 250 | 499.2 | 501.3 | (CD$_3$OD) 9.25(s, 1H), 9.06(d, 2H), 8.97(s, 1H), 8.84(d, 1H), 8.23(s, 1H), 8.12(d, 1H), 7.56(dd, 1H), 4.49(q, 2H), 4.37(s, 2H), 3.65-3.12(m, 9H), 1.46-1.43(m, 9H) |
| 251 | 514.9 | 517 | (CD$_3$OD) 9.27(s, 1H), 9.05(d, 2H), 8.95(s, 1H), 8.86(d, 1H), 8.25(s, 1H), 8.16(d, 1H), 7.56(dd, 1H), 4.49(q, 2H), 4.46(s, 2H), 3.81-3.50(m, 12 H), 3.44(s, 3H), 1.45(t, 3H) |
| 252 | 527.2 | 529 | (CD$_3$OD) 9.06(s, 1H), 8.97(d, 2H), 8.76(s, 1H), 8.28(d, 1H), 8.00(s, 1H), 7.69(d, 1H), 7.49(dd, 1H), 4.65(s, 2H), 4.45(q, 2H), 3.99(br s, 4H), 3.49(br s, 4H), 2.99(hept, 1H), 1.44(t, 3H), 1.14(d, 6H) |
| 253 | 502 | 504 | (CD$_3$OD) 9.08(d, 2H), 8.73(s, 1H), 8.51(s, 1H), 8.38(dd, 1H), 8.07(d, 1H), 7.92(m, 1H), 7.77(d, 1H), 7.64(m, 1H), 4.67(s, 2H), 4.48(q, 2H), 4.01(s, 2H), 3.65(m, 4H), 3.06(m, 2H), 1.43(t, 2H), 1.13(t, 3H) ppm. |
| 254 | 454.17 | 456.02 | 14.52(s, 1H); 9.22(s, 2H); 9.05(d, 2H); 8.56(d, 1H); 8.04(d, 1H); 7.74(s, 1H); 7.62(s, 1H); 7.55(t, 1H); 6.8-5.6(br. s); 5.79(s, 2H); 4.33(q, 2H); 2.62(s, 3H); 1.33(t, 3H). |
| 255 | 530.17 | 532.03 | 1.1(d, 6H), 1.35(t, 3H), 2.3(s, 6H), 3.5(m, 2H), 3.6(m, 2H), 3.9(s, 2H), 4.3(q, 2H), 4.6(s, 2H), 4.65(m, 1H), 7.7(d, 1H), 7.9(s, 1H), 8.0(dt, 1H), 8.3(s, 1H), 8.4(dd, 1H), 8.8(d, 1H), 8.85(m, 1H), 9.1(s, 1H) |
| 256 | 486.23 | 488.05 | 1.3(d, 6H), 1.35(t, 3H), 3.1(m, 2H), 3.5(m, 1H), 3.6(m, 4H), 4.3(q, 2H), 4.8(m, 2H), 7.6(t, 1H), 7.9(s, 1H), 8.5(s, 1H), 8.9(s, 2H), 9.05(d, 1H), 10.5(br s, 1H) |
| 257 | 499.2 | 501.1 | (CD$_3$OD) 9.34(s, 2H), 8.93(m, 1H), 8.81(d, 1H), 8.49(m, 2H), 8.11(d, 1H), 7.85(t, 1H), 4.87(s, 2H), 4.42(q, 2H), |

TABLE 3-continued

Characterization Data for Selected Compounds of Formula I

| Compound No. I- | M − 1(obs) | M + 1(obs) | ¹H NMR |
|---|---|---|---|
| 258 | 571.3 | 573.1 | 4.11(br s, 2H), 3.87(br m, 4H), 3.71(m, 3H), 1.48(d, 6H), 1.42(t, 3H) ppm. (CDCl₃) 12.75(br s, 1H), 12.29(s, 1H), 8.94(d, 2H), 8.92(s, 1H), 8.60(s, 1H), 8.05(s, 1H), 8.04(d, 1H), 7.59(d, 1H), 7.25(dd, 1H), 4.46(q, 2H), 4.23(br s, 1H), 3.86(d, 1H), 3.80(d, 1H), 3.65(d, 1H), 3.19(ddd, 1H), 2.86(d, 1H), 2.66(d, 1H) |
| 259 | — | 473 | (CD₃OD) 9.24(s, 1H), 9.04(d, 2H), 8.94(s, 1H), 8.81(d, 1H), 8.22(s, 1H), 8.11(d, 1H), 7.55(dd, 1H), 4.49(q, 2H), 4.42(s, 2H), 3.77-2.89(m, 7H), 1.45(t, 3H), 1.41(d, 3H) |
| 260 | 485.3 | 487.3 | (CD₃OD) 9.24(s, 1H), 9.06(d, 2H), 8.96(s, 1H), 8.83(d, 1H), 8.23(s, 1H), 8.11(d, 1H), 7.56(dd, 1H), 4.49(q, 2H), 4.39(s, 2H), 3.76(m, 2H), 3.40(d, 2H), 2.80(d, 2H), 1.45(t, 3H), 1.40(d, 6H) |
| 261 | 485.2 | 487 | (CD₃OD) 9.23(s, 1H), 9.06(d, 2H), 8.97(s, 1H), 8.82(d, 1H), 8.24(s, 1H), 8.13(d, 1H), 7.56(dd, 1H), 4.74(d, 2H), 4.49(q, 2H), 4.25(d, 1H), 3.80-2.92(m, 6H), 1.45(t, 3H), 1.36(d, 6H) |
| 262 | 513.2 | 515 | (CD₃OD) 9.10(s, 1H), 9.02(d, 2H), 8.85(s, 1H), 8.31(d, 1H), 8.06(s, 1H), 7.68(d, 1H), 7.52(dd, 1H), 4.62(s, 2H), 4.46(q, 2H), 3.92-3.16(m, 8 H), 2.48(q, 2H), 1.86(m, 2H), 1.44(t, 3H), 1.14(t, 3 H) |
| 263 | — | 557.3 | (CD₃OD) 9.11(s, 1H), 9.03(d, 2H), 8.85(s, 1H), 8.32(d, 1H), 8.07(s, 1H), 7.69(d, 1H), 7.52(dd, 1H), 4.63(s, 2H), 4.47(q, 2H), 3.99-3.79(m, 8 H), 3.50-3.45(m, 5H), 2.15(m, 2H), 1.44(t, 3H) |
| 264 | — | 501.1 | (CD₃OD) 9.10(s, 1H), 9.03(d, 2H), 8.85(s, 1H), 8.62(d, 1H), 8.08(s, 1H), 7.94(d, 1H), 7.52(dd, 1H), 4.46(q, 2H), 4.12(s, 2H), 3.46-3.01(m, 10H), 1.80(m, 2H), 1.43(t, 3H), 1.04(t, 3H) |
| 265 | — | 531.1 | (CD₃OD) 9.21(s, 1H), 8.96(d, 2H), 8.82(s, 1H), 8.59(d, 1H), 8.12(s, 1H), 8.06(d, 1H), 7.48(dd, 1H), 4.75(s, 2H), 4.42(q, 2H), 4.12(q, 2H), 3.83(br s, 4H), 3.47(br s, 4H), 1.38(t, 3H), 1.23(t, 3H) |
| 266 | 543.2 | 545 | (CD₃OD) 9.33(s, 1H), 8.99(d, 2H), 8.83(s, 1H), 8.79(br s, 1H), 8.18(s, 1H), 7.54(br s, 1H), 4.93(m, 1H), 4.89(s, 2H), 4.49(q, 2H), 3.90(br s, 4H), 3.57(br s, 4H), 1.45(t, 3H), 1.29(d, 6H) |
| 267 | 516 | 518 | — |
| 268 | 557.3 | 559.2 | (CD₃OD) 9.08(s, 1H), 8.969(d, 2H), 8.78(s, 1H), 8.29(d, 1H), 8.01(s, 1H), 7.67(d, 1H), 7.49(dd, 1H), 4.62(s, 2H), 4.45(q, 2H), 3.93(d, 2H), 3.85(br s, 4H), 3.46(br s, 4H), 1.96(m, 1H), 1.43(t, 3H), 0.98(d, 6H) |
| 269 | 553.3 | 555.1 | (CD₃OD) 9.15(s, 1H), 9.05(d, 2H), 8.91(s, 1H), 8.39(d, 1H), 8.14(s, 1H), 7.79(d, 1H), 7.55(dd, 1H), 4.71(q, 2H), 4.68(s, 2H), 4.49(q, 2H), 3.88(br s, 4H), 3.49(br s, 4H), 1.82(t, 3H), 1.44(t, 3H) |
| 270 | 557.3 | 559.2 | (CD₃OD) 9.11(s, 1H), 9.03(d, 2H), 8.84(s, 1H), 8.31(d, 1H), 8.05(s, 1H), 7.68(d, 1H), 7.52(dd, 1H), 4.63(s, 2H), 4.46(q, 2H), 3.96(br s, 4H), 3.52(br s, 2H), 3.44(br s, 2H), 2.71(t, 2H), 2.65(t, 2H), 1.43(t, 3H) |
| 271 | 573.2 | 575.2 | (CD₃OD) 9.12(s, 1H), 9.05(d, 2H), 8.86(s, 1H), 8.32(d, 1H), 8.07(s, 1H), 7.68(d, 1H), 7.53(dd, 1H), 4.63(s, 2H), 4.46(q, 2H), 4.37(s, 2H), 4.21(s, 2H), 3.98(br s, 4H), 3.52(br s, 2H), 3.47(br s, 2H), 1.44(t, 3H) |

TABLE 3-continued

Characterization Data for Selected Compounds of Formula I

| Compound No. I- | M − 1(obs) | M + 1(obs) | $^1$H NMR |
|---|---|---|---|
| 272 | 500.23 | 502.05 | 1.21(m, 9H) 3.17(s, 1H) 3.61(m, 8H) 4.32(q, 2H) 4.65(s, 2H)7.56(t, 1H) 8.10(s, 1H) 8.58(s, 1H) 9.07(d, 2H) 9.30(s, 2H) |
| 273 | 476 | 478 | 9.29(s, 2H), 8.66(s, 1H), 8.02(s, 1H), 7.95(m, 2H), 7.59(m, 1H), 4.76(s, 2H), 4.30(m, 2H), 3.94-3.68(m, 4H), 3.50-3.17(m, 4H), 1.30(t, 3H) |
| 274 | 417.1 | 419 | 9.1(s, 2H), 9.0(s, 2H), 8.4(s, 1H), 7.8(s, 1H), 7.5(t, 1H), 4.1-4.2(q, 2H), 3.7(s, 2H), 2.3(s, 6H), 1.3(t, 3H). |
| 275 | 466 | 468 | — |
| 276 | 445.1 | 447 | 1.33(t, 3H) 2.06(m, 1H) 2.26(m, 1H) 3.88(m, 4H) 4.33(q, 2H)5.85(m, 1H) 6.97(d, 1H) 7.55(t, 1H) 7.91(s, 1H) 8.08(d, 1H) 8.52(m, 2H)9.05(d, 2H) 12.44(br s, 1H) |
| 277 | 475.1 | 477 | 1.3(t, 3H), 2.3(s, 6H), 3.35(m, 4H), 3.9(m, 4H), 4.3(q, 2H), 4.6(s, 2H), 7.7(d, 1H), 7.9(s, 1H), 8.0(dt, 1H), 8.3(s, 1H), 8.35(dd, 1H), 8.75(d, 1H), 8.8(br s, 1H), 9.1(d, 1H), 10.4(br s, 1H) |
| 278 | 502.1 | 504 | 1.3(t, 3H), 3.2(s, 3H), 3.4(br s, 4H), 3.7(br s, 4H), 3.8(br s, 2H), 4.3(q, 2H), 4.8(br s, 2H), 7.55(t, 1H), 8.0(d, 1H), 8.5(d, 1H), 9.0(s, 2H), 9.05(d, 2H), 11.8(br s, 1H), 12.6(br s, 1H) |
| 279 | 525.2 | 527 | — |
| 280 | 567.2 | 569 | (CD$_3$OD) 9.11(s, 1H), 9.03(d, 2H), 8.83(s, 1H), 8.33(d, 1H), 8.06(s, 1H), 7.68(d, 1H), 7.52(dd, 1H), 4.63(s, 2H), 4.46(q, 2H), 3.94(m, 4H), 3.59(q, 2H), 3.47(m, 4H), 1.44(t, 3H) |
| 281 | 458.15 | 459.98 | 9.11(br. s, 2H); 9.09(s, 1H); 8.82(d, 1H); 8.78(br. s, 1H); 8.64(d, 1H); 8.28(s, 1H); 8.10(dd, 1H); 7.88(s, 1H); 7.52(dd, 1H); 5.38(m, 1H); 5.5-4.2(br. s, 4H); 4.32(q, 2H); 3.45(m, 1H); 3.37(m, 1H); 3.12(m, 2H); 2.05(M, 1 |
| 282 | 514.2 | 516 | 10.05(m, 1H); 9.24(m, 1H); 9.15(d, 2H); 8.82(d, 1H); 8.67(d, 1H); 8.31(s, 1H); 8.12(m, 1H); 7.90(s, 1H); 7.53(m, 1H); 5.52(m, 1H); 4.32(q, 2H); 3.78(m, 1H); 3.55-2.88(m, 4H); 2.12(m, 1H); 2.02(m, 1H); 1.88(m, 1H); 1.33(t |
| 283 | 519.15 | 521.02 | 1.3(t, 3H), 2.35(s, 12H), 2.8(s, 3H), 3.0-3.7(br s, 10H), 4.3(q, 2H), 4.7(br s, 2H), 7.6(m, 1H), 7.9(s, 1H), 7.95(m, 2H), 8.65(m, 1H), 9.0(s, 2H) |
| 290 | 487.1 | 489 | — |
| 291 | — | 490 | — |
| 292 | 482.1 | 484 | — |
| 293 | 483 | 484.9 | — |
| 294 | 460.11 | 461.96 | 1.15(t, 3H), 2.3(s, 9H), 3.25(m, 2H), 3.5(m, 4H), 3.8(m, 4H), 7.5(br s, 1H), 7.6(m, 1H), 7.95(m, 1H), 8.0(s, 1H), 8.1(m, 1H), 8.2(m, 1H), 8.4(d, 1H), 8.6(s, 1H), 8.7(d, 1H), 10.3(br s, 1H) |
| 295 | — | — | (CD$_3$OD) 9.13(d, 1H), 9.05(d, 2H), 8.92(d, 1H), 8.37(m, 1H), 8.13(d, 1H), 7.75(dt, 1H), 7.55(t, 1H), 4.70(s, 2H), 4.49(q, 2H), 3.62(m, 4H), 2.47(m, 4H), 1.44(t, 3H) ppm |

TABLE 3a

Characterization Data for Selected Compounds of Formula I

| Compound No. I- | M − 1(obs) | M + 1(obs) | NMR (500 MHz) |
|---|---|---|---|
| 296 | 404.10 | 405.90 | DMSO-$d_6$: 1.15(t, 3H), 3.05(s, 3H), 3.25(m, 2H), 7.2(d, 1H), 7.65(m, 1H), 7.85(s, 1H), 8.05(m, 3H), 8.15(br s, 1H), 8.3(m, 1H), 8.7(d, 1H), 9.2(br s, 1H), 11.4(br s, 1H) ppm |
| 297 | 503.20 | 505.20 | $CD_3OD$: 9.27(s, 2H), 8.72(d, 1H), 8.49(m, 1H), 8.08(m, 1H), 7.92(m, 1H), 7.64(m, 1H), 4.87(s, 2H), 4.45(q, 2H), 4.19(m, 2H), 3.84(m, 2H), 3.77(m, 2H), 3.08(s, 3H), 1.43(t, 3H) ppm |
| 298 | 461.09 | 462.92 | DMSO-$d_6$: 1.3(t, 3H), 2.3(s, 6H), 3.5(m, 4H), 3.8(m, 4H), 4.3(q, 2H), 7.6(m, 1H), 7.9(m, 1H), 8.0(m, 1H), 8.05(s, 1H), 8.25(m, 1H), 8.35(s, 1H), 8.6(s, 1H), 8.7(m, 1H) ppm |
| 299 | 447.12 | 448.98 | DMSO-$d_6$: 10.75(s, 1H); 8.72(d, 1H); 8.67(s, 2H);, 8.04(d, 1H); 8.03(dd, 1H); 7.87(d, 1H); 7.73(m, 1H); 7.68,(m, 2H); 3.28(dq, 2H); 3.19(d, 2H); 2.36(s, 6H); 1.91(m, 1H);, 1.15(t, 3H); 0.92(d, 6H) ppm |
| 300 | 419.10 | 421.10 | $CD_3OD$: 8.70(s, 1H), 8.28(s, 1H), 7.88(s, 1H), 7.85(d, 1H), 7.83(s, 1H), 7.57(dd, 1H), 7.28(s, 1H), 6.20(s, 2H), 3.37(q, 2H), 1.24(t, 3H) ppm |
| 301 | 407.10 | 409.10 | $CD_3OD$: 8.69(s, 1H), 8.23(s, 1H), 7.86(dd, 1H), 7.77(s, 1H), 7.56(s, 1H), 7.27(br s, 2H), 3.37(q, 2H), 1.24(t, 3H) ppm |
| 302 | 462.10 | 464.10 | $CD_3OD$: 8.90(s, 2H), 8.70(s, 1H), 8.34(s, 1H), 7.91(s, 1H), 7.86(dd, 1H), 7.59(m, 1H), 5.67(dd, 1H), 4.10-3.91(m 4H), 3.37(q, 2H), 2.39-2.21(m, 2H), 1.28(m, 1H), 1.25(t, 3H) ppm |
| 303 | 433.12 | 434.99 | DMSO-$d_6$: 10.66(s, 1H); 8.70(d, 1H); 8.64(s, 1h);, 8.05(d, 1H); 8.01(dd, 1H); 7.84(d, 1H); 7.71(m, 1H); 7.64,(m, 1H); 7.41(m, 1H); 4.13(ddq, 1H); 4.2-3.4(very br. s, many H);, 3.26(dq, 2H); 2.33(s, 6H); 1.20(d, 6H); 1.15(t, 3H) ppm |
| 304 | 488.00 | 490.00 | $CD_3OD$: 1.42(t, 3H), 2.48(m, 2H), 3.5(t.2H), 3.68(m, 2H), 3.73(m, 2H), 3.86(m, 2H), 4.44(q, 2H), 4.71(s, 2H), 7.62(m, 1H), 7.8(d, 1H), 7.92(m, 1H), 8.08(s, 1H), 8.38(d, 1H), 8.5(s, 1H), 8.71(m, 1H), 9.09(s, 1H) ppm |
| 305 | 446.20 | 448.00 | DMSO-$d_6$: 1.0(d, 6H), 1.15(t, 3H), 1.95(m, 1H), 2.35(s, 6H), 3.25(m, 4H), 7.2(d, 1H), 7.55(br s, 1H), 7.65(m, 1H), 7.9(s, 1H, 8.0(m, 2H), 8.2(m, 1H), 8.3(m, 1H), 8.7(d, 1H), 10.4(br s, 1H) ppm |
| 306 | 432.10 | 434.00 | DMSO-$d_6$: 1.1(t, 3H), 1.3(d, 6H), 2.35(s, 6H), 3.25(m, 2H), 4.0(m, 1H), 7.15(d, 1H), 7.55(br s, 1H), 7.6(m, 1H), 7.85(d, 1H), 8.0(m, 2H), 8.2(s, 1H), 8.3(d, 1H), 8.7(m, 2H), 10.5(br s, 1H) ppm |
| 307 | 389.10 | 391.10 | (salt in d4-methanol) 9.07(s, 1H), 9.03(d, 2H), 8.86(d, 1H), 8.84(s, 1H), 8.09(s, 1H), 8.07(d, 1H), 7.50(dd, 1H), 5.04(s, 2H), 4.43(q, 2H), 1.42(t, 3H) ppm |
| 308 | 546.20 | 548.10 | (salt in d4-methanol) 8.99(s, 1H), 8.67(s, 1H), 8.30(s, 1H), 8.21(d, 1H), 7.97(s, 1H), 7.82(dd, 1H), 7.73(d, 1H), 7.55(m, 1H), 4.66(s, 2H), 4.45(q, 2H), 4.19(q, 2H), 3.87(br s, 4H), 3.59(br s, 4H), 2.75(s, 6H), 1.43(t, 3H), 1.29(t, 3H) ppm |
| 309 | 532.20 | 534.10 | (salt in d4-methanol) 9.02(s, 1H), 8.69(s, 1H), 8.39(s, 1H), 8.23(d, 1H), 8.02(s, 1H), 7.86(dd, 1H), 7.71(d, 1H), 7.58(m, 1H), 4.64(s, 2H), 4.46(q, 2H), 3.85(br s, 4H), 3.75(s, 3H), 3.47(br s, 4H), 2.73(s, 6H), 1.43(t, 3H) ppm |
| 310 | 570.10 | 572.10 | (salt in d4-methanol) 9.01(s, 1H), 8.66(s, 1H), 8.32(s, 1H), 8.21(d, 1H), 7.96(s, 1H), 7.83(dd, 1H), 7.69(d, 1H), 7.56(m, 1H), 4.71(t, 2H), 4.63(s, 2H), 4.44(q, 2H), 3.87(br s, |

TABLE 3a-continued

Characterization Data for Selected Compounds of Formula I

| Compound No. I- | M − 1(obs) | M + 1(obs) | NMR (500 MHz) |
|---|---|---|---|
| | | | 4H), 3.75(s, 3H) 3.49(br s, 4H), 2.73(s, 6H), 1.82(t, 3H), 1.42(t, 3H) ppm |
| 311 | 530.00 | 532.00 | (salt in d4-methanol) 9.06(s, 1H), 8.71(s, 1H), 8.43(s, 1H), 8.28(d, 1H), 8.05(s, 1H), 7.89(dd, 1H), 7.74(d, 1H), 7.61(m, 1H), 4.66(s, 2H), 4.47(q, 2H), 3.94(br s, 4H), 3.52(br s, 2H), 3.46(br s, 2H), 2.70(s, 6H), 2.49(q, 2H), 1.44(t, 3H), 1.14(t, 3H) ppm |
| 312 | 559.10 | 561.00 | (salt in d4-methanol) 9.20(s, 1H), 9.02(d, 2H), 8.84(s, 1H), 8.53(d, 1H), 8.16(s, 1H), 8.01(d, 1H), 7.53(dd, 1H), 4.78(s, 2H), 4.49(q, 2H), 4.27(t, 2H), 3.91(br s, 4H), 3.64(t, 2H), 3.53(br s, 4H), 3.38(s, 3H), 1.45(t, 3H) ppm |
| 313 | 405.22 | 406.95 | DMSO-$d_6$: 1.3(t, 3H), 2.35(s, 6H), 3.0(s, 3H), 4.3(q, 2H), 7.2(d, 1H), 7.6(m, 1H), 7.85(s, 1H), 7.9(br s, 1H), 8.0(dd, 1H), 8.2(s, 1H), 8.3(d, 1H), 8.65(d, 1H), 8.85(br s, 1H) ppm |
| 314 | 501.14 | 502.98 | $CD_3OD$: 1.74(t, 3H) 2.38(s, 3H) 2.17(s, 2H) 3.37(m, 4H) 3.46(t, 2H) 4.77(s, 2H) 7.48(m, 2H) 7.78(m, 2H) 8.05(d, 2H) 8.66(s, 1H) 8.81(s, 1H) ppm |
| 315 | 502.20 | 504.00 | $CD_3OD$: 1.41(t, 3H) 3.05(s, 3H) 3.72(m2H) 3.88(m, 2H) 4.09(s, 2H) 4.48(m, 2H) 5.00(s, 2H) 7.61(m, 1H) 7.71(d, 1H) 7.90(t, 1H) 8.02(s 1H) 8.35(d, 1H) 8.45(s, 1H) 8.72(m, 1H) 8.95(s, 1H) ppm |
| 316 | 388.16 | 390.16 | $CD_3OD$: 9.03(d, 2H), 8.75(s, 1H), 8.36(d, 1H), 8.26(s, 1H), 8.03(s, 1H), 7.53(t, 1H), 7.24(d, 1H), 4.48(q, 2H), 3.14(s, 3H), 1.44(t, 3H) ppm |
| 317 | 496.10 | 498.00 | DMSO-$d_6$: 10.60(br. s, 1H); 8.70(m, 4H); 8.22(m, 1H); 8.11(m, 1H); 8.02(m, 3H); 7.82(s, 1H); 7.80(m, 1H); 7.63(m, 4H); 5.28(m, 1H); 3.24(dq, 2H); 2.32(s, 6H); 1.58(d, 3H); 1.15(t, 3H) ppm |
| 318 | 497.20 | 499.00 | DMSO-$d_6$: 8.73(d, 1H); 8.64(m, 3H); 8.19(m, 1H); 8.09(m, 1H); 7.94(dd, 1H): 7.87(m, 2H); 7.78(d, 1H); 7.70(m, 1H); 7.58(m, 1H); 5.30(m, 1H); 4.28(q, 2H); 2.32(s, 6H); 1.58(d, 3H); 1.30(t, 3H) ppm |
| 319 | 504.10 | 506.00 | DMSO-$d_6$: 10.48(br. s, 1H); 9.64(s, 1H); 8.72(s, 2H); 8.69(d, 1H); 7.99(m, 2H); 7.81(s, 1H); 7.62(m, 1H); 7.58(m, 1H); 7.55(m, 1H); 4.02(m, 2H); 3.73(m, 3H); 3.59(m, 2H); 3.38(m, 2H); 3.25(dq, 2H); 3.18(m, 2H); 2.54(m, 2H); 2.32(s, 6H); 1.14(t, 3H) ppm |
| 320 | 505.10 | 507.00 | DMSO-$d_6$: 9.63(m, 1H); 8.72(s, 2H); 8.66(d, 1H); 7.96(dd, 1H); 7.87(m, 1H); 7.82(d, 1H); 7.59(m, 1H); 7.52(m, 1H); 4.29(q, 2H); 4.00(m, 2H); 3.72(m, 3H); 3.55(m, 2H); 3.38(m, 2H); 3.18(m, 2H); 2.51(m, 2H); 2.33(s, 6H); 1.29(t, 3H) ppm |
| 321 | 560.00 | 562.00 | DMSO$d_6$: 1.2(t, 3H), 1.29(t, 3H), 2.1(bs, 2H), 2.3(s, 3H), 3.41(bs, 2H), 3.48(m, 2H), 3.7(bs, 2H), 4.08(q, 2H), 4.27(q, 2H), 4.6(s, 2H), 7.59(m, 1H), 7.62(d, 1H), 7.95(m, 2H), 8.28(d, 1H), 8.63(bs, 1H), 9.04(s, 1H), 10.08(bs, 1H), 11.51(bs, 1H) ppm |
| 322 | 482.00 | 484.00 | DMSO$d_6$: 1.3(t, 3H), 4.2(q, 2H), 4.8(s, 2H), 7.2(d, 1H), 7.54(m, 1H), 7.6(m, 2H), 7.8-8.05(m, 4H), 8.28(s, 2H), 8.7(s, 1H), 8.8(bm, 1H), 11.5(bs, 1H) ppm |
| 323 | 506.00 | 508.00 | $CD_3OD$: 8.99(s, 2H), 8.71(m, 1H), 8.40(d, 1H), 7.99(d,, 1H), 7.9(m, 1H), 7.62(m, 1H), 4.88(m, 2H), 4.46(q, 2H), 4.11(m, 2H), 3.86(m, 2H), 3.74(m, 2H), 3.68(m, 2H), 3.35(m, 2H), 1.43(t, 3H) ppm |
| 324 | 405.10 | 407.00 | (DMSO-d6): 8.8(s, 1H), 8.7(d, 1H), 8.6(s, 1H), 8.3(s, 1H), 8.25(s, 1H), 8.1(s, 1H), 8.0-8.1(s, 1H), 7.7(m, 2H), 4.05(s, 3H), 3.8(m, |

TABLE 3a-continued

Characterization Data for Selected Compounds of Formula I

| Compound No. I- | M − 1(obs) | M + 1(obs) | NMR (500 MHz) |
|---|---|---|---|
| | | | 1H), 3.2-3.3(q, 2H), 2.4(s, 6H), 1.1-1.2(t, 3H) ppm |
| 325 | 406.10 | 407.90 | DMSO-d6): 8.8(s, 1H), 8.7(d, 1H), 8.6(s, 1H), 8.25(s, 1H), 8.1(s, 1H),, 8.05(s, 1H), 8.0(t, 1H), 7.6(m, 1H), 4.3(q, 2H), 4.05(s, 3H),, 2.4(s, 6H), 1.35(t, 3H) |
| 326 | 415.10 | 417.00 | CD$_3$OD: 9.05(d, 2H), 8.77(d, 1H), 8.33(dd, 1H), 8.18(d, 1H), 7.98(s, 1H), 7.53(t, 1H), 7.20(d, 1H), 4.00(m, 1H), 3.38(q, 2H), 2.72(s, 6H, 2 MsOH), 1.39(d, 6H), 1.17(t, 3H) ppm |
| 327 | 505.00 | 507.00 | CD$_3$OD: 8.98(s, 2H), 8.72(dd, 1H), 8.35(d, 1H), 7.94(d,, 1H), 7.87(m, 1H), 7.59(m, 1H), 4.87(m, 2H), 4.10(m, 2H), 3.85(m, 2H), 3.74(m, 2H), 3.67(m, 2H), 3.37(m,, 4H), 1.24(t, 3H) ppm |
| 328 | 418.14 | 419.94 | DMSO-d6: 1.15(t, 3H), 2.3(s, 6H), 3.15(s, 6H), 3.25(m, 2H), 7.55 br s, 1H), 7.65(m, 1H), 7.6(s, 1H), 8.0(dd, 1H), 8.05(s, 1H), 8.15(s, 1H), 8.2(s, 1H), 8.45(s, 1H), 8.7(d, 1H), 10.6(br s, 1H) ppm |
| 329 | 473.10 | 475.00 | CD$_3$OD: 9.04(s, 1H), 8.58(d, 1H), 8.51(d, 1H), 8.32(s, 1H), 7.93(d, 1H), 7.88(s, 1H), 7.77(dd, 1H), 7.49(m, 1H), 4.32(s, 2H), 3.49(m, 4H), 3.33(q, 2H), 3.32(m, 4H), 1.23(t, 3H) ppm |
| 330 | 545.10 | 547.00 | CD$_3$OD: 9.07-7.58(m, 8H), 4.61&4.60(s, 2H), 4.19&4.09(q, 2H), 3.83(br s, 4H), 3.44(br s, 4H), 3.37(q, 2H), 1.33&1.24(t, 3H), 1.29(t, 3H) ppm |
| 331 | 528.00 | 530.10 | CD$_3$OD: 9.11(s, 1H), 9.03(d, 2H), 8.85(s, 1H), 8.31(d, 1H), 8.05(s, 1H), 7.66(dd, 1H), 7.52(dd, 1H), 4.62(s, 2H), 4.46(q, 2H), 3.74(br s, 4H), 3.43(br s, 4H), 3.21(q, 2H), 1.43(t, 3H), 1.13(t, 3H) ppm |
| 332 | 545.00 | 547.10 | CD$_3$OD: 9.04(s, 1H), 8.68(d, 1H), 8.41(s, 1H), 8.24(d, 1H), 7.99(s, 1H), 7.86(dd, 1H), 7.66(d, 1H), 7.57(m, 1H), 4.62(s, 2H), 4.44(q, 2H), 3.76(br s, 4H), 3.44(br s, 4H), 3.22(q, 2H), 1.43(t, 3H), 1.13(t, 3H) ppm |
| 333 | 473.16 | 474.98 | DMSO-d$_6$: 1.15(t, 3H), 2.35(s, 6H), 2.9(s, 3H), 3.25(m, 6H), 3.6(m, 2H), 4.2(m, 2H), 7.45(br s, 1H), 7.6(m, 1H), 7.95(dd, 1H), 8.0(s, 1H), 8.05(m, 2H), 8.45(d, 1H), 8.55(s, 1H), 8.7(d, 1H), 9.7(br s, 1H), 10.25(br s, 1H) ppm |
| 334 | 405.00 | 407.00 | CD$_3$OD: 8.72(m, 1H), 8.43(d, 1H), 8.0(d, 1H), 7.91(dd, 1H), 7.88(m, 1H), 7.60(m, 1H), 6.99(d, 1H), 6.96(dd, 1H), 3.72(s, 3H), 3.36(m, 2H)), 1.24(t, 3H) ppm |
| 335 | 444.10 | 446.10 | CD$_3$OD: 8.7(d, 1H), 8.4(s, 1H), 8.3(s, 1H), 8.1(s, 1H), 7.8-7.9(m, 2H), 7.6(m, 1H), 3.5(t, 4H), 3.35(q, 2H), 2.7(s, 12H), 2.2(t, 4H), 1.3(t, 3H) ppm |
| 336 | 405.10 | 406.95 | DMSO-d6: 1.15(t, 3H), 2.3(s, 6H), 3.2(m, 2H), 3.9(s, 3H), 6.9(d, 1H), 7.4(br s, 1H), 7.6(m, 1H), 7.8(s, 1H), 7.9(br s, 1H), 7.95(m, 1H), 8.05(dd, 1H), 8.5(d, 1H), 8.65(d, 1H), 10.1(br s, 1H) ppm |
| 337 | 536.10 | 537.90 | DMSO-d6: 1.15(t, 3H), 2.35(s, 6H), 2.65(m, 2H), 2.85(s, 3H), 3.15(m, 2H), 3.25(m, 2H), 3.45(m, 2H), 3.85(m, 2H), 7.55(br s, 1H), 7.65(m, 1H), 7.9(d, 2H), 7.95(m, 1H), 8.0(s, 1H), 8.05(d, 2H), 8.15(br s, 1H), 8.7(d, 1H), 9.35(br s, 1H), 10.6(br s, 1H) ppm |
| 338 | 376.14 | 378.14 | CDCl$_3$: 13.6(br s, 1H), 13.1(m, 1H), 12.8(s, 1H), 9.00(d, 2H), 8.72(s, 1H), 8.54(d, 1H), 8.08(dt, 1H), 7.78(d, 1H), 7.36(t, 1H), 7.08(dd, 1H), 6.00(br s, 1H), 3.43(m, 2H), 2.98(s, 3H), MsOH), 1.26(t, 3H) ppm. |
| 339 | 415.10 | 417.10 | CD$_3$OD: 9.08(s, 1H), 9.01(d, 2H), 8.80(s, 1H), 8.28(d, 1H), 8.01(s, 1H), 7.64(d, 1H), |

TABLE 3a-continued

Characterization Data for Selected Compounds of Formula I

| Compound No. I- | M − 1(obs) | M + 1(obs) | NMR (500 MHz) |
|---|---|---|---|
| | | | 7.50(dd, 1H), 4.58(s, 2H), 3.37(q, 2H), 3.01(s, 6H), 1.25(t, 3H) ppm |
| 340 | 432.10 | 434.10 | CD₃OD: 9.00(s, 1H), 8.65(s, 1H), 8.30(s, 1H), 8.23(d, 1H), 7.93(s, 1 H), 7.81(dd, 1 H), 7.69(d, 1H), 7.53(m, 1H), 4.61(s, 2H), 3.33(q, 2H), 3.03(s, 6H), 2.76(s, 6H), 1.24(t, 3H) ppm |
| 341 | 408.10 | 410.10 | CD₃OD: 9.08(s, 1H), 8.77(d, 2H), 8.67(s, 1H), 8.36(s, 1H), 7.94-7.81(m, 3H), 7.68(d, 1H), 7.65(s, 1H), 7.31(dd, 1H), 3.26(q, 2 H), 1.20(t, 3 H) ppm |
| 342 | 579.00 | 581.00 | CD₃OD: 1.24(t, 3H), 2.7(s, 6H), 3.48(m, 6H), 3.59(bs, 4H), 3.88(s, 3H), 4.68(s, 2H), 6.9-7.1(m, 4H), 7.61(m, 1H), 7.7(d, 1H), 7.89(m, 1H), 8.02(s, 1H), 8.29(d, 1H), 8.46(s, 1H), 8.72(d, 1H), 9.09(s, 1H) ppm |
| 343 | 376.00 | 378.00 | DMSO-d6: 1.14(t, 3H), 2.32(s, 3H), 3.25(m, 2H), 7.61(m, 2H), 8.0(m, 1H), 8.39(s, 1H), 8.62(s, 1H), 8.63(s, 1H), 8.69(s, 1H), 8.78(s, 1H), 9.4(s, 1H) ppm |
| 344 | 468.00 | 470.00 | CD₃OD: 1.24(t, 3H), 2.7(s, 6H), 3.35(m, 2H), 7.39(d, 1H), 7.6(m, 1H), 7.88(m, 1H), 7.94(s, 1H), 8.09(m, 1H), 8.31(m, 1H), 8.4(s, 1H), 8.49(d, 1H), 8.51(s, 1H), 8.7(s, 2H), 8.99(s, 1H) ppm |
| 345 | 389.10 | 391.00 | CD₃OD: 9.1(s, 1H), 8.85(d, 1H), 8.8(d, 1H), 8.5(s, 1H), 8.0-8.1(m, 2H), 7.9(t, 1H), 7.6(m, 1H), 3.4(q, 2H), 2.9(s, 3H), 2.7(s, 6H), 1.2(t, 3H) ppm |
| 346 | 361.10 | 363.00 | CD₃OD: 9.2(s, 1H), 8.9(d, 1H), 8.7(d, 1H), 8.5(s, 1H), 8.25(s, 1H), 8.1(d, 1H), 7.9(t, 1H), 7.6(m, 1H), 2.9(s, 3H), 2.7(s, 6H) ppm |
| 347 | 512.10 | 513.90 | DMSO-d6: 10.68(br. s, 1H); 8.68(m, 2H); 8.67(s, 2H); 8.05(s, 1H); 8.01(dd, 1H); 7.85(s, 1H); 7.69(m, 1H); 7.64(m, 1H); 7.48(m, 1H); 7.11(m, 1H); 3.47(m, 2H); 3.26(dq, 2H); 3.17(m, 2H); 2.93(s, 3H); 2.34(s, 6H); 1.14(t, 3H) ppm |
| 348 | 501.00 | 503.00 | CD₃OD: 8.98(d, 1H), 8.73(m, 1H), 8.43(s, 1H), 8.33(m, 1H), 8.01(s, 1H), 7.91(d, 1H), 7.88(m, 1H), 7.60(m, 1H), 3.37(q, 2H), 3.78-3.30(m, 8H), 3.03(s, 3H), 1.24(t, 3H) ppm |
| 349 | 581.25 | 583.25 | CD₃OD: 8.94(s, 2H), 8.73(m, 1H), 8.38(m, 1H), 7.95(d, 1H), 7.88(m, 1H), 7.62(m, 1H), 7.58(m, 2H), 5.53(m, 3H), 4.60(m, 2H), 4.45(s, 2H), 4.20(m, 2H), 3.90(m, 1H), 3.61(m, 1H), 3.43(m, 1H), 3.36(q, 2H), 3.26-3.35(m, 2H, underneath solvent peak), 1.24(t, 3H) ppm |
| 350 | 405.00 | 407.00 | CD₃OD: 1.23(t, 3H), 2.7(s, 6H), 3.38(m, 2H), 4.22(s, 3H), 7.61(m, 1H), 7.8(d, 1H), 7.88(m, 1H), 7.95(s, 1H), 8.34(s, 1H), 8.72(d, 1H), 8.81(m, 2H) ppm |
| 351 | 573.20 | 575.00 | CD₃OD: 9.06(d, 1H), 8.74(d, 1H), 8.45(s, 1H), 8.27(dd, 1H), 8.02(s, 1H), 7.88(m, 1H), 7.67(d, 1H), 7.61(m, 1H), 4.34(br d, 2H), 4.15(app q, 2H), 3.64(m, 1H), 3.37(q, 2H), 3.22(q, 1H), 2.94(s, 3H), 2.86-2.99(br m, 3H), 2.71(s, 6H, MsOH), 2.20(m, 2H), 1.79(m, 2H), 1.25(m, 6H) ppm |
| 352 | 512.10 | 514.20 | CD₃OD: 9.02(s, 1H), 8.87(d, 2H), 8.63(s, 1H), 8.30(d, 1H), 7.84(s, 1H), 7.74(d, 1H), 7.41(dd, 1H), 4.57-3.11(m, 13 H), 1.24(t, 3H) ppm |
| 353 | 468.00 | 470.00 | CD₃OD: 8.70(m, 1H), 8.56(d, 1H), 8.32(s, 1H), 8.07(dd, 1H), 7.85(m, 2H), 7.57(m, 1H), 7.19(d, 1H), 3.37(q, 2H), 3.32(s, 3H), 1.24(t, 3H) ppm |
| 354 | 529.10 | 531.10 | CD₃OD: 9.67(s, 1H), 8.73(s, 1H), 8.41(s, 1H), 8.34(d, 1H), 8.01(s, 1H), 7.87(dd, 1H), 7.76(m, 1H), 4.59(d, 1H), 4.55(d, 1H), 4.52(dd, 1H), 4.31(m, 1H), 4.11(dd, |

TABLE 3a-continued

Characterization Data for Selected Compounds of Formula I

| Compound No. I- | M − 1(obs) | M + 1(obs) | NMR (500 MHz) |
|---|---|---|---|
| | | | 1H), 4.01(dd, 1H), 3.66(d, 1H), 3.55(d, 1H), 3.49(d, 1H), 3.37(q, 2H), 3.15(dd, 1H), 3.10(d, 1H), 2.73(s, 6H), 1.24(t, 3H) ppm |
| 355 | 418.10 | 420.10 | CD$_3$OD: 9.02(d, 2H), 8.71(s, 1H), 8.04(d, 1H), 7.92(s, 1H), 7.58(d, 1H), 7.50(dd, 1H), 4.02(s, 3H), 3.98(s, 3H), 3.37(q, 2H), 1.25(t, 3H) ppm |
| 356 | 435.10 | 437.10 | CD$_3$OD: 8.69(d, 1H), 8.29(s, 1H), 7.99(d, 1H), 7.86(d, 1H), 7.84(d, 1H), 7.56(m, 1H), 7.52(d, 1H), 4.02(s, 3H), 3.95(s, 3H), 3.37(q, 2H), 1.24(t, 3H) ppm |
| 357 | 462.10 | 464.18 | CD$_3$OD: 9.18(s, 1H), 8.88(s, 1H), 8.71(m, 1H), 8.67(m, 1H), 8.37(s, 1H), 8.03(s, 1H), 7.85(m, 1H), 7.56(m, 1H), 4.33(q, 2H), 3.35(q, 2H, overlap w/solvent peak), 2.77(s, 6H), 1.39(t, 3H), 1.23(t, 3H) ppm |
| 358 | 419.17 | 420.96 | DMSO-d6: 1.15(t, 3H), 2.3(s, 6H), 3.25(m, 2H), 3.4(s, 3H), 4.65(s, 2H), 7.55(br s, 1H), 7.65(m, 1H), 8.0(m, 1H), 8.05(d, 1H), 8.1(s, 1H), 8.4(s, 1H), 8.7(d, 1H), 9.0(s, 1H), 10.4(br s, 1H) ppm |
| 359 | 402.10 | 404.10 | CD$_3$OD: 9.02(d, 2H), 8.51(d, 1H), 8.23(s, 1H), 7.78(d, 1H), 7.50(dd, 1H), 7.34(s, 1H), 4.17(s, 3H), 3.38(q, 2H), 2.71(s, 6H), 2.48(s, 3H), 1.25(t, 3H) ppm |
| 360 | 419.10 | 421.10 | CD$_3$OD: 8.74(d, 1H), 8.30(s, 1H), 8.12(s, 1H), 7.84(dd, 1H), 7.77(s, 1H), 7.58(m, 1H), 7.52(s, 1H), 4.25(s, 3H), 3.36(q, 2H), 2.72(s, 6H), 2.54(s, 3H), 1.24(t, 3H) ppm |
| 361 | 376.10 | 378.10 | CD$_3$OD: 9.13(s, 1H), 8.97(s, 2H), 8.51(s, 1H), 8.08(s, 1H), 7.75(s, 1H), 7.68(dd, 1H), 7.41(m, 1H), 3.29(q, 2H), 2.79(s, 3H), 1.21(t, 3H) ppm |
| 362 | 389.20 | 391.00 | CD$_3$OD: 9.1(s, 1H), 8.85(s, 1H), 8.8(s, 1H), 8.75(d, 1H), 8.5(s, 1H),, 8.1(s, 1H), 7.9(d of d, 1H), 7.6(m, 1H), 3.3-3.4(q, 2H), 2.7(s, 3H), 1.2(t, 3H), 2.75(s, 9H) ppm |
| 363 | 455.18 | 456.97 | DMSO-d6: 12.34(s, 1H); 9.07(d, 2H); 8.92(s, 1H);, 8.52(s, 1H); 8.18(d, 1H); 7.97(s, 1H); 7.58(s, 1H); 7.55(t, 1H);, 7.41(d, 1H); 4.56(s, 2H); 3.40(dd, 2H); 3.28(dq, 2H); 2.33,(dd, 2H); 1.99(dddd, 2H); 1.17(t, 3H) ppm |
| 364 | 455.12 | 456.97 | CD$_3$OD: 0.87(m, 2H) 0.92(m, 2H) 1.26(t, 3H) 1.76(m, 1H) 3.40(q, 2H), 4.93(s, 2H) 7.53(t, 1H) 8.13(d, 1H) 8.17(s, 1H) 8.90(s, 1H) 8.95(d, 1H), 9.05(d, 2H) 9.17(s, 1H) ppm |
| 365 | 388.10 | 390.00 | CD$_3$OD: 9.05(s, 2H), 8.95(s, 1H), 8.85(s, 1H), 8.7(s, 1H), 8.6(s, 1H), 8.2(s, 1H), 7.5(m, 1H), 4.2(s, 3H), 3.4(q, 2H), 3.3(s, 9H), 1.2(t, 3H) ppm |
| 366 | 458.00 | 460.00 | CD$_3$OD: 0.91(bs, 3H), 1.24(t, 3H), 2.7(s, 3H), 2.98(bs, 1H), 3.02(s, 3H), 3.38(q, 2H), 4.63(s, 2H), 7.5(m, 1H), 7.68(d, 1H), 7.8(m, 1H), 7.87(s, 1H), 8.08(bs, 1H), 8.22(d, 1H), 8.69(d, 1H), 9.02(s, 1H) ppm |
| 367 | 401.20 | 403.00 | DMSO-d6: 1.15(t, 3H), 1.4(t, 3H), 2.3(s, 6H), 3.25(m, 2H), 4.25(q, 2H), 7.5(m, 1H), 7.65(m, 1H), 7.75(d, 1H), 7.9(dd, 1H), 8.0(s, 1H), 8.4(d, 1H), 8.5(m, 2H), 8.8(d, 1H), 9.1,(s, 1H), 10.7(br s, 1H) ppm |
| 368 | 415.17 | 417.17 | CD$_3$OD: 9.04(d, 2H), 8.74(d, 1H), 7.95(m, 2H), 7.90(d, 1H), 7.52(t, 1H), 4.41(t, 2H), 3.75(t, 2H), 3.39(q, 2H), 1.25(t, 3H) ppm. |
| 369 | 465.10 | 466.90 | CD$_3$OD: 1.14(t, 3H) 2.77(s, 6H) 3.31(s, 3H) 3.39(q, 2H) 4.78(s, 2H), 7.49(t, 1H) 8.12(s, 1H) 8.24(d, 1H) 8.86(s, 1H) 8.96(d, 1H) 9.1(d, 2H) 9.30(s, 1H) ppm |

TABLE 3a-continued

Characterization Data for Selected Compounds of Formula I

| Compound No. I- | M − 1(obs) | M + 1(obs) | NMR (500 MHz) |
|---|---|---|---|
| 370 | 482.00 | 484.00 | DMSO-d6: 9.13(s, 1H), 8.67(s, 1H), 8.43(d, 1H), 8.12(s, 1H), 7.99(d, 2H), 7.57(m, 2H), 7.40(m, 1H), 4.05(q, 2H), 2.86(s, 6H), 1.13(t, 3H) ppm |
| 371 | 414.10 | 416.10 | CD$_3$OD: 8.65(d, 1H), 8.54(s, 1H), 8.49(s, 1H), 8.31(s, 1H), 7.85(s, 1H), 7.79(dd, 1H), 7.59(d, 1H), 7.52(m, 1H), 6.72(d, 1H), 3.35(q, 2H), 1.24(t, 3H) ppm |
| 372 | 402.10 | 404.10 | CD$_3$OD: 8.99(d, 2H), 8.63(s, 1H), 7.90(s, 1H), 7.86(s, 1H), 7.49(d, 1H), 7.47(dd, 1H), 6.20(s, 2H), 3.38(q, 2H), 1.24(t, 3H) ppm |
| 373 | 391.10 | 393.11 | CD$_3$OD: 9.09(d, 1H), 8.89(dd, 1H), 8.84(d, 1H), 8.70(d, 1H), 8.55(d, 1H), 8.42(d, 1H), 8.23(dt, 1H), 8.03(d, 1H), 7.65(m, 1H), 3.37(q, 2H), 2.72(s, MsOH, 6H), 1.24(t, 3H) ppm |
| 374 | 360.00 | 362.00 | CD$_3$OD: 8.85(m, 1H), 8.38(d, 1H), 8.17(m, 3H), 8.04(s, 1H), 7.8(d, 1H), 7.60(m, 1H), 4.0(s, 3H), 3.36(q, 2H), 2.72(s, MsOH, 6H), 1.24(t, 3H) ppm |
| 375 | 471.18 | 473.00 | DMSO-d6; 1.14(t, 3H) 3.24(t, 2H) 3.45(t, 2H) 3.89(q, 2H) 4.15(s, 2H) 4.73(s, 2H) 7.40(m, 2H) 7.50(t, 1H) 7.91(s, 1H) 8.15(d, 1H) 8.45(s, 1H) 8.90(s, 1H) 9.02(d, 2H) 9.97(s, 1H) 12.04(s, 1H) ppm |
| 376 | 470.20 | 472.00 | DMSO-d6: 12.3(s, 1H); 10.2(br.s, 1H); 9.05(d, 2H); 8.96(d, 1H); 8.52(s, 1H); 8.21(dd, 1H); 7.97(s, 1H); 7.55(t, 1H); 7.47(d, 1H); 4.47(s, 2H); 3.32(s, 3H); 3.29(dq, 2H); 2.51(s, 4H); 1.18(t, 3H) ppm |
| 377 | 474.00 | 476.00 | CD$_3$OD: 1.23(t, 3H), 2.7(s, 6H), 3.5 to 3.35(bm, 6H), 4.15 to 3.7(bd, 4H), 4.59(s, 2H), 7.61(m, 1H), 7.89(m, 1H), 8.08(s, 1H), 8.47(s, 1H), 8.52(s, 1H), 8.73(d, 1H), 8.81(s, 1H), 9.09(s, 1H) ppm |
| 378 | 455.10 | 457.00 | CD$_3$OD: 9.1(s, 1H), 8.9(d, 1H), 8.8(d, 1H), 8.75(s, 1H), 8.6(d, 1H), 8.5(s, 1H), 8.25(t, 1H), 8.1(s, 1H), 7.7(m, 1H), 5.1(q, 2H), 3.35-3.4(q, 2H), 1.3(t, 3H), 2.7(s, 9H)ppm |
| 379 | 481.20 | 483.00 | CD$_3$OD: 8.9(s, 1H), 8.8(d, 1H), 8.75(d, 1H), 8.6(s, 1H), 8.45(s, 1H), 8.1(s, 1H), 7.9(m, 1H), 7.6(m, 1H), 7.55(d, 2H), 7.4-7.45(t, 2H), 7.35(d, 1H), 5.5(s, 2H), 3.35-3.4(q, 2H), 1.25-1.3(t, 3H), 2.7(s, 9H)ppm |
| 380 | 361.00 | 363.00 | CD$_3$OD: 9.00(d, 2H), 8.67(d, 1H), 8.09(s, 1H), 7.92(d, 1H), 7.83(d, 1H), 7.48(t, 3H), 3.97(s, 3H), 3.87(q, 2H), 1.25(t, 3H)ppm |
| 381 | 391.00 | 393.00 | CD$_3$OD: 8.86(d, 1H), 8.34(d, 1H), 8.12(t, 1H), 8.09(d, 1H), 7.72(d, 1H), 7.57(m, 3H), 3.37(q, 2H),, 2.75(s, 3H), 2.49(s, 3H), 1.24(t, 3H) ppm |
| 382 | 388.20 | 390.00 | DMSO-d6: 1.15(t, 3H), 2.35(s, 6H), 3.3(m, 2H), 4.8(s, 2H), 7.6(t, 3H), 7.65(br s, 1H), 8.1(d, 1H), 8.65(m, 2H), 8.75(s, 1H), 9.1(d, 2H), 9.2(s, 1H), 10.6(br s, 1H), 12.6(br s, 1H) ppm |
| 383 | 391.10 | 393.00 | CD$_3$OD: 8.75(s, 1H), 8.65(s, 1H), 8.4(s, 1H), 8.3(s, 1H), 8.25(s, 1H), 8.0(s, 1H), 7.8(t, 1H), 7.5(m, 1H), 2.7(s, 6H), 1.2(t, 3H) ppm |
| 384 | 418.10 | 420.10 | CD$_3$OD: 8.48(s, 1H), 7.80(s, 1H), 7.60(dd, 1H), 7.37(s, 1H), 7.36(m, 1H), 6.86(d, 1H), 6.78(s, 1H), 6.77(d, 1H), 5.99(s, 2H), 3.72(q, 2H), 2.81(s, 3H), 1.23(t, 3H) ppm |
| 385 | 464.10 | 466.30 | CD$_3$OD: 8.50(s, 1H), 7.95(s, 1H), 7.64(dd, 1H), 7.52(s, 1H), 7.40(m, 1H), 6.67(s, 2H), 3.85(s, 6H), 3.80(s, 3H), 3.31(q, 2H), 2.81(s, 3H), 1.23(t, 3H) ppm |
| 386 | 428.10 | 430.20 | CD$_3$OD: 8.58(d, 1H), 8.35(d, 1H), 8.14(s, 1H), 8.09(s, 1H), 7.72(dd, 1H), 7.65(s, 1H), 7.45(m, 1H), 7.39(d, 1H), 6.49(d, 1H), 3.86(s, 3H), 3.34(q, 2H), 1.23(t, 3H) ppm |

TABLE 3a-continued

Characterization Data for Selected Compounds of Formula I

| Compound No. I- | M − 1(obs) | M + 1(obs) | NMR (500 MHz) |
|---|---|---|---|
| 387 | 413.00 | 415.00 | CD₃OD: 1.23(t, 3, H), 2.05(m, 2H), 2.7(s, 6H), 3.02(t, 3H), 3.38(m, 2H), 3.58(t, 2H),, 7.52(t, 1H), 7.96(s, 1H), 8.09(s, 1H), 8.17(s, 1H),, 8.76(s, 1H), 9.05(d, 2H) ppm |
| 388 | 416.20 | 418.00 | CD₃OD: 9.1(S, 2H), 9.0(s, 1H), 8.9(s, 1H), 8.6(d, 1H), 8.5(t, 1H), 8.2(s, 1H), 7.6(t, 1H), 5.1(m, 1H), 3.4(q, 2H), 2.7(s, 6H), 1.5(d, 6H), 1.3(t, 3H) ppm |
| 389 | 431.13 | 432.98 | DMSO-d6: 1.15(t, 3H), 1.45(d, 3H), 2.3(s, 6H), 3.25(m, 2H), 3.95(s, 3H), 4.95(q, 1H), 7.55(dd, 1H), 7.6(br s, 1H), 7.8(d, 1H), 7.95(d, 1H), 8.3(m, 1H), 8.35(br s, 1H), 8.45(dd, 1H), 8.9(dd, 1H), 10.5(br s, 1H) ppm |
| 390 | 433.00 | 435.00 | CD₃OD: 8.75(d, 2H), 8.55(d, 1H), 8.04(m, 2H), 7.76(m, 2H), 7.46(m, 1H), 7.43(m, 1H), 4.23(m, 1H), 3.35(m, 2H), 2.96(m, 2H), 1.20(m, 6H) ppm |
| 391 | 433.00 | 435.00 | CD₃OD: 9.0(s, 1H), 8.94(m, 1H),, 8.75(m, 1H), 8.50(s, 1H), 8.27(dd, 1H), 8.12(s, 1H),, 7.90(m, 1H), 7.62(m, 1H), 3.38(q, 2H), 2.73(s, 6H, MsOH), 1.75(s, 6H), 1.24(t, 3H) ppm |
| 392 | 378.00 | 380.00 | CD₃OD: 8.69(d, 1H), 8.30(s, 1H), 8.05(s, 1H), 7.85(m, 2H), 7.80(s, 1H), 7.56(m, 1H), 3.97(s, 3H), 3.36(q, 2H), 1.24(t, 3H) ppm |
| 393 | 397.10 | 399.20 | CD₃OD: 8.93(br s, 3H), 8.74(s, 1H), 8.61(s, 1H), 7.93(s, 1H), 7.77(s, 1H), 7.43(br s, 1H), 6.94(s, 1H), 3.34(q, 2H), 2.80(s, 6H), 1.23(t, 3H) ppm |
| 394 | 474.20 | 476.00 | DMSO-d6: 1.12(t, 3H) 3.22(q, 2H) 3.61(t, 2H) 4.32(t, 2H)4.65(s, 2H) 7.41(d, 1H) 7.51(m, 1H) 7.79(s, 1H) 7.88(m, 2H) 8.10(d, 1H) 8.61(s, 1H) 8.87(s, 1H) 9.82(br s, 1H) ppm |
| 395 | 388.10 | 390.00 | DMSO-d6: 1.2(t, 3H), 2.35(s, 6H), 3.25(m, 2H), 4.0(s, 3H), 7.6(dd, 1H), 7.65(m, 1H), 7.85(d, 1H), 8.0(d, 1H), 8.35(br s, 1H), 8.45(d, 1H), 9.15(s, 2H), 9.25(s, 1H), 10.7(br s, 1H) ppm |
| 396 | 463.10 | 465.00 | DMSO-d6: 1.2(t, 3H), 2.35(s, 6H), 3.25(m, 2H), 5.3(s, 2H), 7.35(m, 3H), 7.5(dd, 2H), 7.6(dd, 1H), 7.65(br t, 1H), 7.75(dd, 1H), 7.92(d, 1H), 7.95(d, 1H), 8.1(br d, 1H), 8.45(d, 1H), 8.5(dd, 1H), 8.75(dd, 1H), 9.0(d, 1H), 10.7(br s, 1H) ppm |
| 397 | 406.10 | 408.00 | DMSO-d6: 8.6(d, 1H), 8.0(m, 1H), 7.9(s, 2H), 7.6(m, 1H), 6.7(s, 1H), 6.4(s, 1H), 3.2(q, 2H), 2.6(s, 3H), 1.2(t, 3H) ppm |
| 398 | 364.00 | 366.00 | CD₃OD: 8.70(d, 1H), 8.39(s, 1H), 8.30(s, 2H), 7.91(d, 1H), 7.87(dd, 1H), 7.59(m, 3H), 3.34(q, 2H), 1.24(t, 3H) ppm |
| 399 | 373.20 | 375.00 | DMSO-d6: 7.7(d, 1H), 7.9(dd, 1H), 7.95(d, 1H), 8.35(dd, 1H), 8.5(s, 1H), 8.55(d, 1H), 8.8(dd, 1H), 9.1(d, 1H), 10.7(br s, 1H) ppm |
| 400 | 490.20 | 492.00 | DMSO-d6: 1.12(t, 3H) 1.20(d, 6H) 3.20(t, 1H) 3.43(d, 2H) 4.89(m, 1H) 7.29(d, 1H) 7.42(t, 1H) 7.57(m, 2H) 7.71(m, 2H) 8.01(d, 1H) 8.52(s, 1H) 8.77(s, 1H) ppm |
| 401 | 431.20 | 433.00 | CD₃OD: 1.25(t, 3H) 1.35(d, 3H) 2.72(s, 6H) 3.37(q, 2H) 3.63(dod, 1H) 3.80(dod, 1H) 4.01(m, 1H) 7.23(d, 1H) 7.48(t, 1H) 7.89(s, 1H) 8.15(s, 1H) 8.33(d, 1H) 8.63(s, 1H) 9.05(d, 2H) ppm |
| 402 | 431.20 | 433.00 | CD₃OD: 1.25(t, 3H) 1.35(d, 3H) 2.72(s, 6H) 3.37(q, 2H) 3.63(dod, 1H) 3.80(dod, 1H) 4.01(m, 1H) 7.23(d, 1H) 7.48(t, 1H) 7.89(s, 1H) 8.15(s, 1H) 8.33(d, 1H) 8.63(s, 1H) 9.05(d, 2H) ppm |
| 403 | 445.10 | 447.20 | CD₃OD: 8.92(s, 2H); 8.48(s, 1H); 8.27(d, 1H); 8.17(s, 1H); 7.80,(s, 1H); 7.45(t, 1H); |

TABLE 3a-continued

Characterization Data for Selected Compounds of Formula I

| Compound No. I- | M − 1(obs) | M + 1(obs) | NMR (500 MHz) |
|---|---|---|---|
| | | | 7.28(d, 1H); 3.88(q, 2H); 3.66(t, 1H); 3.38(q, 2H), 2.8(s, 6H); 1.8(m, 1H); 1.7(m, 1H); 1.28(t, 3H); 1.1(t, 3H) ppm |
| 404 | 445.10 | 447.10 | CD$_3$OD: 8.92(s, 2H); 8.48(s, 1H); 8.27(d, 1H); 8.17(s, 1H), 7.8(s, 1H); 7.45(t, 1H); 7.28(d, 1H); 3.88(q, 2H); 3.66(t, 1H); 3.38(q, 2H), 2.8(s, 6H); 1.8(m, 1H); 1.7(m, 1H); 1.28(t, 3H); 1.1(t, 3H) ppm |
| 405 | 432.10 | 434.00 | CD$_3$OD: 8.7(d, 1H), 8.4(s, 1H), 8.3(s, 1H), 8.0(s, 2H), 7.9(m, 1H), 7.85(m, 1H), 7.6(m, 1H), 3.8(m, 1H), 3.3(q, 2H), 1.3(d, 6H), 1.2(t, 3H) ppm |
| 406 | 392.00 | 394.10 | CD$_3$OD: 9.03(s, 1H), 8.97(d, 2H), 8.83(s, 1H), 8.70(s, 1H), 8.61(s, 1H), 7.99(s, 1H), 7.48(dd, 1H), 3.36(q, 2H), 2.78(s, 3H), 1.25(t, 3H) |
| 407 | 455.10 | 457.10 | CD$_3$OD: 9.27(s, 1H); 9.03(d, 2H); 9.08(d, 2H), 8.84(s, 1H); 8.17(s, 1H); 7.54(d, 1H); 3.58(t, 2H); 3.38(q, 2H); 2.77(s, 6H); 2.5(m, 2H); 2.18(m, 2H), 1.23(t, 3H) ppm |
| 408 | 364.00 | 366.00 | CD$_3$OD: 8.71(m, 1H), 8.60(d, 1H), 8.10(d, 1H), 7.96(d, 1H), 7.88(m, 1H), 7.59(m, 1H), 6.92(d, 1H), 3.33(q, 2H), 1.23(t, 3H) ppm |
| 409 | 406.20 | 408.00 | CD$_3$OD: 8.7(d, 1H), 8.4(s, 1H), 8.3(s, 1H), 8.0(s, 1H), 7.9(t, 1H), 7.6(m, 1H), 3.8(s, 3H), 3.3-3.4(q, 2H), 2.7(s, 6H), 1.2(t, 3H) ppm |
| 410 | 431.23 | 433.05 | DMSO-d6: 1.15(t, 3H), 2.3(s, 6H), 3.25(m, 2H), 3.4(s, 3H), 3.95(s, 3H), 4.6(s, 2H), 7.6(dd, 1H), 7.65(m, 2H), 7.8(d, 1H), 7.95(dd, 1H), 8.2(d, 1H), 8.3(br s, 1H), 8.45(dd, 1H), 8.9(d, 1H), 10.6(br s, 1H) ppm |
| 411 | 409.00 | 411.10 | CD$_3$OD: 8.83(s, 1H), 8.68(d, 1H), 8.66(s, 1H), 8.32(s, 1H), 8.26(s, 1H), 7.90(s, 1H), 7.83(dd, 1H), 7.55(m, 1H), 3.36(q, 2H), 2.76(s, 3H), 1.24(t, 3H) ppm |
| 412 | 413.10 | 415.10 | CD$_3$OD: 8.92(d, 2H), 8.44(s, 1H), 7.98(s, 1H), 7.87(s, 1H), 7.75(s, 1H), 7.44(dd, 1H), 4.48(m, 1H), 3.54(dd, 1H), 3.31(q, 2H), 2.93(dd, 1H), 2.77(s, 6H), 1.46(d, 3H), 1.24(t, 3H) ppm |
| 413 | 430.20 | 432.10 | CD$_3$OD: 8.67(d, 1H), 8.19(s, 1H), 7.97(s, 1H), 7.86(s, 1H), 7.83(dd, 1H), 7.81(s, 1H), 7.55(dd, 1H), 4.46(m, 1H), 3.54(dd, 1H), 3.35(q, 2H), 2.93(dd, 1H), 2.74(s, 6H), 1.45(d, 3H), 1.24(t, 3H) ppm |
| 414 | 409.10 | 411.10 | CD$_3$OD: 9.71(s, 1H), 9.37(d, 1H), 9.26(d, 2H), 8.99(br s, 2H), 8.89(s, 1H), 8.20(br s 2H), 7.48(dd, 1H), 3.34(q, 2H), 2.77(s, 6H), 1.24(t, 3H) ppm |
| 415 | 364.10 | 366.10 | CD$_3$OD: 8.36(s, 1H), 7.70-7.28(m, 6H), 6.58(s, 1H), 3.30(q, 2H), 2.82(s, 3H), 1.23(t, 3H) ppm |
| 416 | 380.10 | 382.10 | CD$_3$OD: 8.19(s, 1H), 7.51(s, 1H), 7.36-7.03(m, 6H), 3.22(q, 2H), 2.82(s, 3H), 1.20(t, 3H) ppm |
| 417 | 378.00 | 380.00 | CD$_3$OD: 9.06(s, 1H), 8.75(m, 1H), 8.30(d, 1H), 7.92(d, 1H), 7.88(m, 1H), 7.80(d, 1H), 7.62(m,, 1H), 3.95(s, 3H), 3.36(q, 2H), 1.24(t, 3H) ppm |
| 418 | 416.20 | 418.10 | DMSO-d6: 10.91(s, 1H); 9.07(d, 2H); 9.70(s, 2H); 8.51(d, 1H); 7.91(d, 1H); 7.81(m, 1H); 7.58(t, 1H); 7.48(s, 1H); 6.3-4.9(br, s, 3H); 4.14(dq, 1H); 3.27(dt, 2H); 2.36(s, 6H); 1.21(d, 6H); 1.15(t, 3H) ppm |
| 419 | 429.00 | 431.00 | CD$_3$OD: 1.23(t, 3, H), 2.05(m, 4H), 2.7(s, 6H),, 3.1 to 3.4(m, 6H), 7.6(m.1H), 7.9(m, 1H), 8.08(s, 1H), 8.47(s, 1H),, 8.68(s, 1H), 8.72(s, 1H), 8.92(s, 1H) ppm |
| 420 | 419.10 | 421.10 | CD$_3$OD: 8.75(s, 1H); 8.65(s, 1H); 8.52(s, 1H); 8.12(s, 1H); 8.08(s, 1H); 7.78(m, |

TABLE 3a-continued

Characterization Data for Selected Compounds of Formula I

| Compound No. I- | M − 1(obs) | M + 1(obs) | NMR (500 MHz) |
|---|---|---|---|
| | | | 2H); 7.42(m, 1H); 5.0(m, 1H); 3.37(m, 2H); 1.57(d, 2H); 1.22(t, 3H) ppm |
| 421 | 433.10 | 435.10 | CD$_3$OD: 8.75(d, 2H); 8.52(s, 1H); 8.48(s, 1H); 8.05(s, 1H); 7.7(s, 1H), 7.6(m, 1H); 7.4(m, 1H); 3.3(m, 2H); 2.8(s, 3H); 1.7(s, 6H); 1.25(t, 3H) ppm |
| 422 | 429.15 | 431.03 | DMSO-d6: 10.92(s, 1H); 8.69(d, 1H); 8.67(d, 1H); 8.30(d, 1H); 8.10(s, 1H); 8.03(dd, 1H); 7.88(s, 1H); 7.75(m, 1H);; 7.64(m, 1H); 7.35(m, 1H); 3.25(dq, 2H); 2.95(s, 3H); 2.39;(s, 6H); 1.15(t, 3H) ppm |
| 423 | 430.10 | 432.00 | DMSO-d6: 1.15(t, 3H), 2.1(s, 3H), 2.35(s, 6H), 3.3(m, 2H), 5.3(s, 2H), 7.6(t, 1H), 7.7(br s, 1H), 8.1(d, 1H), 8.45(br s, 1H), 8.65(d, 1H), 8.75(d, 1H), 9.05(d, 1H), 9.1(d, 2H), 10.8(br s, 1H), 12.63(br s, 1H) ppm |
| 424 | 421.10 | 422.90 | DMSO-d6: 1.15(t, 3H), 2.35(s, 6H), 3.25(m, 2H), 3.95(s, 3H), 7.65(m, 2H), 7.85(d, 1H), 7.95(d, 1H), 8.25(d, 1H), 8.3(br s, 1H), 8.45(dd, 1H), 8.7(d, 1H), 8.9(d, 1H), 10.9(br s, 1H) ppm |
| 425 | 396.00 | 398.00 | CD$_3$OD: 8.72(m, 1H), 8.24(d, 1H), 7.88(m, 1H), 7.86(d, 1H), 7.69(s, 1H), 7.61(m, 1H), 3.36(q,, 2H), 1.24(t, 3H) ppm |
| 426 | 403.20 | 405.10 | DMSO-d6: 1.16(t, 3H) 1.48(d, 3H) 2.35(s, 3H) 3.27(q, 2H) 4.88(q, 1H) 7.58(t, 1H) 7.74(br s, 1H) 8.05(s, 1H) 8.13(s, 1H) 9.07(d, 2H) 9.17(s, 2H) 10.66(br s, 1H) 12.65(br s, 1H) ppm |
| 427 | 400.10 | 402.10 | CD$_3$OD: 9.08(s, 1H), 9.73(d, 1H), 8.46(s, 1H), 8.34(d, 1H), 8.03(s, 1H), 8.02(d, 1H), 7.90(dd, 1H), 7.60(m, 1H), 3.38(q, 2H), 2.70(s, 3H), 1.25(t, 3H) ppm |
| 428 | 418.10 | 420.10 | CD$_3$OD: 9.03(s, 1H), 9.73(d, 1H), 8.46(s, 1H), 8.45(d, 1H), 8.33(d, 1H), 8.04(s, 1H), 7.88(dd, 1H), 7.60(m, 1H), 3.37(q, 2H), 2.73(s, 3H), 1.24(t, 3H) ppm |
| 429 | 401.20 | 403.20 | CD$_3$OD: 9.08(s, 1H), 9.05(d, 2H), 8.92(s, 1H), 8.45(d, 1H), 8.32(d, 1H), 8.11(s, 1H), 7.54(dd, 1H), 3.39(q, 2H), 1.26(t, 3H) ppm |
| 430 | 430.10 | 432.10 | CD$_3$OD: 9.10(s, 1H), 9.05(d, 2H), 8.92(s, 1H), 8.47(d, 1H), 8.34(d, 1H), 8.11(s, 1H), 7.54(dd, 1H), 4.51(q, 2H), 3.39(q, 2H), 1.47(t, 3H), 1.26(t, 3H) ppm |
| 431 | 415.00 | 417.00 | CD$_3$OD: 1.21(t, 3, H), 2.42(m, 2H), 2.7(s, 6H), 3.42-3.18(m, 6H), 7.61(m.1H), 7.89(m, 1H), 8.06(s, 1H), 8.47(s, 1H), 8.72(m, 2H), 8.92(s, 1H) ppm |
| 432 | 418.20 | 420.10 | CD$_3$OD: 9.29(s, 2H); 8.73(m, 1H); 8.48(d, 1H); 8.05(d, 1H); 7.90(m, 1H); 7.63(m, 1H); 3.36(m, 3H); 1.45(d, 6H); 1.23(t, 3H) ppm |
| 433 | 393.00 | 395.00 | DMSO-d6: 9.22(d, 1H), 8.85(d, 1H), 8.75(m, 2H), 8.20(m, 1H), 8.11(s, 1H), 8.05(d, 1H), 8.02(m, 1H), 3.26(q, 2H), 1.15(t, 3H) ppm |
| 434 | 358.20 | 360.00 | CD$_3$OD: 9.7(s, 1H), 9.0(m, 1H), 8.7(t, 1H), 8.6(t, 1H), 8.55(s, 1H), 8.5(d, 1H), 8.4(d, 1H), 8.3(d, 1H), 8.1(t, 1H), 8.05(s, 1H), 7.5(s, 1H), 3.3(q, 2H), 2.7(s, 7H), 1.2(t, 3H) ppm |
| 435 | 402.20 | 404.20 | CD$_3$OD: 9.1(s, 1H); 9.0(d, 2H); 8.82(s, 2H); 8.8(s, 1H); 8.07(s, 1H); 7.47(d, 1H), 5.18(m, 1H); 3.3(t, 2H); 2.78(s, 6H); 1.6(d, 3H); 1.25(t, 3H) ppm |
| 436 | 416.10 | 418.10 | CD$_3$OD: 9.2(s, 1H); 9.0-9.1(m, 3H); 8.97(s, 1H); 8.9(s, 1H); 8.2(s, 1H); 7.52(t, 1H); 3.38(m, 2H); 2.75(s, 6H); 1.72(s, 6H); 2.25(t, 3H) ppm |
| 437 | 372.20 | 374.00 | CD$_3$OD: 1.26(t, 3H) 2.72(s, 6H) 2.94(s, 3H) 3.39(q, 2H) 7.67(t, 1H) 8.26(t, 1H) 8.32(d, 1H), 8.40(s, 1H) 8.57(d, 2H) 8.79(s, 1H) 8.90(d, 1H) 8.97(d, 1H) ppm |

TABLE 3a-continued

Characterization Data for Selected Compounds of Formula I

| Compound No. I- | M − 1(obs) | M + 1(obs) | NMR (500 MHz) |
|---|---|---|---|
| 438 | 465.10 | 467.10 | CD$_3$OD: 9.2(s, 1H); 8.98(m, 3H); 8.9(s, 1H); 8.77(s, 1H); 8.1(s, 1H); 7.47(s, 1H), 4.67(s, 2H); 3.15(m, 2H); 2.75(s, 6H); 2.0(s, 3H); 1.21(t, 3H) ppm |
| 439 | 428.10 | 430.10 | CD$_3$OD: 9.05(m, 3H); 8.9(s, 1H); 8.48(d, 1H); 8.2(S, 1H); 7.5(t, 1H); 3.34(m, 2H); 3.28(m, 2H); 2.75(s, 6H); 2.62(m, 2H); 2.25(m, 1H); 2.1(m, 1H) ppm |
| 440 | 445.10 | 447.10 | CD$_3$OD: 9.02(s, 1H); 8.99(d, 1H); 8.7(s, 1H); 8.47 9m, 3H); 8.1(s, 1H); 7.75(m, 1H); 7.58(m, 1H); 3.35(m, 2H); 2.75(s, 6H); 2.65(m, 4H); 2.28(m, 1H); 2.12(m, 1H); 1.25(t, 3H) ppm |
| 441 | 388.10 | 390.00 | CD$_3$OD: 1.25(t, 3H) 2.73(s, 6H) 3.38(q, 2H) 4.20(s, 3H) 7.42(d, 1H) 7.57(t, 1H) 8.15(t, 1H)8.21(s, 1H) 8.32(d, 1H) 8.34(d, 1H) 8.58(s, 1H) 8.84(d, 1H) ppm |
| 442 | 405.20 | 407.01 | DMSO-d6: 1.2(t, 3H), 2.3(s, 6H), 3.25(m, 2H), 3.95(s, 3H), 7.6(dd, 1H), 7.65(t, 1H), 7.85(d, 1H), 7.95(d, 1H), 8.1(dt, 1H), 8.3(s, 1H), 8.45(dd, 1H), 8.65(d, 1H), 8.8(t, 1H), 10.75(br s, 1H) ppm |
| 443 | 420.20 | 422.00 | CD$_3$OD: 1.23(t, 3H) 1.59(d, 3H) 2.70(s, 6H) 3.39(q, 2H) 5.02(m, 1H) 7.54(m, 1H) 7.81(m, 1H) 7.81(s, 1H) 8.24(s, 1H) 8.70(d, 1H) 9.10(s, 2H) ppm |
| 444 | 426.10 | 428.10 | CD$_3$OD: 9.72(s, 1H), 9.38(s, 1H), 9.27(m, 1H), 9.23(br s, 1H), 8.74(s, 1H), 8.61(s, 1H), 8.21(s, 1H), 8.19(m, 1H), 7.89(dd, 1H), 7.61(m, 1H), 3.37(q, 2H), 2.74(s, 6H), 1.25(t, 3H) ppm |
| 445 | 414.20 | 416.20 | CD$_3$OD: 9.16(s, 1H), 9.06(d, 2H), 8.93(s, 1H), 8.92(d, 1H), 8.15(s, 1H), 8.05(d, 1H), 7.54(dd, 1H), 3.39(q, 2H), 3.01(d, 2H), 2.71(s, 6H), 2.20(m, 1H), 1.25(t, 3H), 1.07(d, 6H) ppm |
| 446 | 431.20 | 433.10 | CD$_3$OD: 9.13(s, 1H), 8.89(d, 1H), 8.74(s, 1H), 8.50(s, 1H), 8.11(s, 1H), 8.10(d, 1H), 7.90(dd, 1H), 7.61(m, 1H), 3.38(q, 2H), 3.03(d, 2H), 2.73(s, 6H), 2.21(m, 1H), 1.24(t, 3H), 1.07(d, 6H) ppm |
| 447 | 372.10 | 374.20 | CD$_3$OD: 9.16(s, 1H), 9.00(d, 2H), 8.90(d, 1H), 8.83(s, 1H), 8.11(s, 1H), 8.08(d, 1H), 7.50(dd, 1H), 3.37(q, 2H), 2.90(s, 3H), 2.76(s, 6H), 1.25(t, 3H) ppm |
| 448 | 393.14 | 395.14 | CD$_3$OD: 9.04(d, 1H), 8.87(m, 1H), 8.74(dd, 1H), 8.57(dd, 1H), 8.48(d, 1H), 8.08(d, 1H), 7.89(ddd, 1H), 7.61(m, 1H), 3.37(q, 2H), 2.73(s, 6H, 2 MsOH), 1.24(t, 3H) ppm |
| 449 | 416.20 | 418.10 | CD$_3$OD: 9.0(d, 2H), 8.6(s, 1H), 8.4(s, 1H), 8.0(d, 1H), 7.8(s, 1H),, 7.4(t, 1H), 6.8(d, 1H), 5.3(m, 1H), 3.3(q, 2H), 1.4(d, 6H), 1.2(t, 3H) ppm |
| 450 | 419.10 | 421.20 | CD$_3$OD: d 1.24(t, 3H), 1.66(d, 3H), 2.72(s, 6H), 3.38(q, 2H), 5.30(q, 1H), 5.48(s, 1H), 7.57-7.64(m, 1H), 7.85-7.93(m, 1H), 8.11(s, 1H), 8.19(d, 1H), 8.49(s, 1H), 8.69-8.76(m, 1H), 8.88-8.95(m, 1H), 9.04(s, 1H) ppm |
| 451 | 419.10 | 421.20 | CD$_3$OD: d 1.24(t, 3H), 1.66(d, 3H), 2.72(s, 6H), 3.38(q, 2H), 5.30(q, 1H), 5.48(s, 1H), 7.57-7.64(m, 1H), 7.85-7.93(m, 1H), 8.11(s, 1H), 8.19(d, 1H), 8.49(s, 1H), 8.69-8.76(m, 1H), 8.88-8.95(m, 1H), 9.04(s, 1H) ppm |
| 452 | 445.10 | 447.10 | CD$_3$OD: d 1.25(t, 3H), 1.37(t, 3H), 2.73(s, 6H), 3.38(q, 2H), 4.32(q, 2H), 7.53(t, 1H), 8.10-8.13(m, 1H), 8.74-8.76(m, 1H), 8.86-8.88(m, 1H), 8.89-8.91(m, 1H), 9.05(d, 2H), 9.10-9.13(m, 1H) ppm |

TABLE 3a-continued

Characterization Data for Selected Compounds of Formula I

| Compound No. I- | M − 1(obs) | M + 1(obs) | NMR (500 MHz) |
|---|---|---|---|
| 453 | 417.10 | 419.10 | CD$_3$OD: 9.0(s, 1H); 8.7(s, 1H); 8.4(s, 1H); 8.27(d, 1H); 8.15(d, 1H); 7.98(s, 1H), 7.85(m, 1H); 7.55(t, 1H); 3.3(m, 2H); 2.72(s, 3H); 1.25(t, 3H) ppm |
| 454 | 401.10 | 403.20 | CD$_3$OD: 9.0(s, 2H); 8.65(s, 1H); 8.4(m, 1H); 8.22(s, 1H); 7.88(s, 1H); 7.5(t, 1H); 7.38(d, 1H); 3.33(m, 2H); 3.3(s, 6H); 1.25(t, 3H) ppm |
| 455 | 434.34 | 436.36 | DMSO-d6: 1.06(t, 3H) 1.53(s, 6H) 2.37(s, 6H) 3.25(q, 2H) 7.65(m, 1H), 7.67(m, 1H) 8.05(m, 2H) 8.12(s, 1H) 8.71(d, 1H) 9.17(s, 2H) 10.92(br s, 1H) ppm |
| 456 | 458.17 | 460.16 | DMSO-d6: 1.12(d, 6H), 1.15(t, 3H), 2.35(s, 6H), 2.7(m, 1H), 3.25(m, 2H), 5.3(s, 2H), 7.6(t, 1H), 7.7(br s, 1H), 8.05(d, 1H), 8.4(br s, 1H), 8.65(d, 1H), 8.75(d, 1H), 9.05(d, 1H), 9.1(d, 2H), 10.6(br s, 1H), 12.7(br s, 1H) ppm |
| 457 | 419.20 | 421.20 | CD$_3$OD: 9.0(s, 2H); 8.72(d, 1H); 8.35(s, 1H); 7.97(s, 1H); 7.9(m, 1H); 7.6(m, 1H), 3.36(q, 2h); 2.72(s, 9H); 2.0(s, 6H); 1.22(t, 3H) ppm |
| 458 | 415.37 | 417.36 | DMSO-d6: 1.61(s, 6H) 2.38(s, 6H) 3.27(q, 2H) 7.56(q, 1H) 7.66(t, 1H) 8.05(s, 1H) 8.16(m, 2H) 8.45(s, 1H) 8.58(d, 1H), 8.72(m1H) 9.01(d, 1H) 9.20(s, 1H) 10.96(br s, 1H) ppm |
| 459 | 405.40 | 407.30 | DMSO-d6: 12.56(s, 1H); 10.86(s, 1H); 10.72(s, 1H), 9.07(d, 2H); 8.52(d, 1H); 7.78(d, 1H); 7.70(m, 1H); 7.57(t, 1H); 7.22(s, 1H); 4.26(dq, 1H); 3.25(dt, 1H); 2.34(s, 3H); 1.31(d, 6H); 1.15(t, 3H) ppm |
| 460 | 400.20 | 402.10 | CD$_3$OD: 9.15(s, 1H), 9.02(d, 2H), 8.97(d, 1H), 8.87(s, 1H), 8.18(d, 1H), 8.15(s, 1H), 7.52(dd, 1H), 3.48(m, 1H), 3.37(q, 2H), 2.75(s, 6H), 1.53(d, 6H), 1.25(t, 3H) ppm |
| 461 | 400.20 | 402.20 | CD$_3$OD: 9.20(s, 1H), 9.02(d, 2H), 8.97(d, 1H), 8.92(s, 1H), 8.23(s, 1H), 8.14(d, 1H), 7.55(dd, 1H), 3.38(q, 2H), 3.15(t, 2H), 2.71(s, 6H), 1.94(m, 2H), 1.25(t, 3H), 1.10(t, 3H) ppm |
| 462 | 417.20 | 419.20 | CD$_3$OD: 9.10(s, 1H), 8.90(d, 1H), 8.64(d, 1H), 8.39(s, 1H), 8.17(d, 1H), 8.05(s, 1H), 7.82(dd, 1H), 7.54(m, 1H), 3.49(m, 1H), 3.34(q, 2H), 2.77(s, 6H), 1.54(d, 6H), 1.23(t, 3H) ppm |
| 463 | 417.20 | 419.20 | CD$_3$OD: 9.11(s, 1H), 8.86(d, 1H), 8.69(d, 1H), 8.42(s, 1H), 8.10(d, 1H), 8.06(s, 1H), 7.84(dd, 1H), 7.56(m, 1H), 3.35(q, 2H), 3.13(t, 2H), 2.76(s, 6H), 1.93(m, 2H), 1.23(t, 3H), 1.11(t, 3H) ppm |
| 464 | 430.20 | 432.20 | CD$_3$OD: 9.15(s, 1H), 8.99(d, 2H), 8.82(d, 1H), 8.20(d, 1H), 8.16(s, 1H), 7.49(dd, 1H), 5.04(d, 1H), 3.36(q, 2H), 2.75(s, 6H), 2.26(m, 1H), 1.24(t, 3H), 1.14(d, 3H), 0.92(d, 3H) ppm |
| 465 | 447.10 | 449.10 | CD$_3$OD: 9.05(s, 1H), 8.93(d, 1H), 8.75(d, 1H), 8.51(s, 1H), 8.18(d, 1H), 8.12(s, 1H), 7.90(dd, 1H), 7.62(m, 1H), 5.01(d, 1H), 3.38(q, 2H), 2.72(s, 6H), 2.24(m, 1H), 1.24(t, 3H), 1.12(d, 3H), 0.90(d, 3H) ppm |
| 466 | 428.20 | 430.20 | CD$_3$OD: 9.12(s, 1H), 9.01(d, 2H), 8.99(d, 1H), 8.85(s, 1H), 8.30(d, 1H), 8.14(s, 1H), 7.51(dd, 1H), 4.61(d, 1H), 3.36(q, 2H), 2.76(s, 6H), 1.31(m, 1H), 1.24(t, 3H), 0.80-0.70(m, 4H) ppm |
| 467 | 445.20 | 447.10 | CD$_3$OD: 9.06(s, 1H), 8.93(d, 1H), 8.65(s, 1H), 8.40(s, 1H), 8.29(d, 1H), 8.06(s, 1H), 7.82(dd, 1H), 7.55(m, 1H), 4.61(d, 1H), 3.34(q, 2H), 2.77(s, 6H), 1.31(m, 1H), 1.23(t, 3H), 0.80-0.70(m, 4H) ppm |

TABLE 3a-continued

Characterization Data for Selected Compounds of Formula I

| Compound No. I- | M − 1(obs) | M + 1(obs) | NMR (500 MHz) |
|---|---|---|---|
| 468 | 425.20 | 427.20 | CD$_3$OD: 9.04(s, 1H), 9.02(d, 2H), 8.81(s, 1H), 8.47(d, 1H), 8.04(s, 1H), 7.96(d, 1H), 7.50(dd, 1H), 3.37(q, 2H), 2.74(s, 6H), 1.89(s, 6H), 1.25(t, 3H) ppm |
| 469 | 442.10 | 444.10 | CD$_3$OD: 9.05(s, 1H), 8.61(d, 1H), 8.58(s, 1H), 8.23(s, 1H), 8.12(d, 1H), 7.93(s, 1H), 7.82(dd, 1H), 7.54(m, 1H), 3.31(q, 2H), 2.79(s, 6H), 1.96(s, 6H), 1.22(t, 3H) ppm |
| 470 | 431.40 | 433.30 | DMSO-d6: 1.15(t, 3H), 2.3(s, 6H), 3.2(s, 3H), 3.25(m, 2H), 3.75(m, 2H), 4.35(m, 2H), 7.5(dd, 1H), 7.6(m, 1H), 7.7(m, 1H), 7.8(d, 1H), 7.9(s, 1H), 8.3(m, 1H), 8.4(d, 1H), 8.6(m, 1H), 8.65(d, 1H), 9.0(d, 1H), 10.3(br s, 1H), 12.5(br s, 1H) ppm |
| 471 | 489.10 | 491.10 | CD$_3$OD: 1.18-1.27(m, 9H), 1.73(d, 3H), 2.72(s, 6H), 3.38(q, 2H), 6.06(q, 1H), 7.59-7.63(m, 1H), 7.86-7.92(m, 1H), 8.05-8.09(m, 2H), 8.47-8.50(m, 1H), 8.72-8.77(m, 2H), 9.09-9.11(m, 1H) ppm |
| 472 | 324.40 | 326.20 | DMSO-d6: 11.58(s, 1H); 9.72(s, 1H); 8.98(d, 2H); 7.70(d, 1H); 7.49(s, 1H); 7.43(t, 1H); 6.99(d, 1H); 3.28(s, 3H); 3.25(dq, 2H); 2.94(s, 3H); 1.12(t, 3H) ppm |
| 473 | 390.10 | 392.10 | CD$_3$OD: 1.24(t, 3H), 2.72(s, 6H), 3.37(q, 2H), 7.58-7.63(m, 1H), 7.85-7.91(m, 1H), 7.98-8.01(m, 2H), 8.03-8.06(m, 1H), 8.32(s, 1H), 8.39(s, 1H), 8.72-8.75(m, 1H) ppm |
| 474 | 423.10 | 425.20 | CD$_3$OD: 8.83(d, 2H), 8.75(s, 1H), 8.36(s, 1H), 8.22(d, 1H), 7.79(d, 1H), 7.71(s, 1H), 7.38(dd, 1H), 3.32(q, 2H), 2.80(s, 6H), 1.94-1.87(m, 4H), 1.24(t, 3H) ppm |
| 475 | 390.20 | 392.10 | CD$_3$OD: 1.24(t, 3H), 2.73(s, 6H), 3.36(q, 2H), 7.19(d, 1H), 7.57-7.62(m, 1H), 7.84-7.92(m, 2H), 8.20-8.23(m, 1H), 8.30-8.35(m, 2H), 8.71-8.74(m, 1H) ppm |
| 476 | 373.10 | 375.20 | CD$_3$OD: 1.25(t, 3H), 2.73(s, 6H), 3.38(q, 2H), 7.51-7.55(m, 1H), 8.03-8.07(m, 3H), 8.36-8.39(m, 1H), 8.82-8.85(m, 1H), 9.03-9.06(m, 2H) ppm |
| 477 | 440.20 | 442.10 | CD$_3$OD: 8.77(s, 1H), 8.56(s, 1H), 8.27(d, 1H), 8.08(s, 1H), 7.84(d, 1H), 7.77(s, 1H), 7.74(d, 1H), 7.50(m, 1H), 3.30(q, 2H), 2.78(s, 6H), 1.96-1.91(m, 4H), 1.23(t, 3H) ppm |
| 478 | 445.50 | 447.30 | DMSO-d6: 1.15(t, 3H). 1.6(s, 6H), 2.35(s, 6H), 3.25(m, 2H), 3.95(s, 3H), 7.6(dd, 1H), 7.65(m, 1H), 7.8(d, 1H), 7.95(d, 1H), 8.05(m, 1H), 8.3(s, 1H), 8.45(d, 1H), 8.5(br s, 1H), 8.9(d, 1H), 10.7(br s, 1H) ppm |
| 479 | 376.14 | 378.14 | CD$_3$OD: 9.09(s, 1H), 9.05(d, 2H), 8.91(s, 1H), 8.67(t, 1H), 8.63(d, 1H), 8.14(s, 1H), 7.54(t, 1H), 3.39(q, 2H), 2.73(s, 6H), 1.25(t, 3H) ppm |
| 480 | 391.20 | 393.10 | CD$_3$OD: 9.24(s, 1H); 8.87(d, 1H); 8.72(d, 1H); 8.6(d, 1H); 8.45(s, 1H); 8.08(m, 2H); 7.88(m, 1H); 7.6(m, 1H); 3.35(m, 2H); 2.73(s, 6H); 1.34(t, 3H) ppm |
| 481 | 457.20 | 459.20 | CD$_3$OD: 9.04(s, 1H), 8.90(d, 1H), 8.55(s, 1H), 8.44(s, 1H), 8.27(d, 1H), 8.03(s, 1H), 7.89(dd, 1H), 7.64(m, 1H), 4.58(d, 1H), 4.09(s, 3H), 3.35(q, 2H), 2.75(s, 6H), 1.31(m, 1H), 1.22(t, 3H), 0.79-0.70(m, 4H) ppm |
| 482 | 388.20 | 390.20 | CD$_3$OD: 9.26(s, 1H), 8.76(s, 1H), 8.65(s, 1H), 8.62(s, 1H), 8.56(d, 1H), 8.54(s, 1H), 8.31(d, 1H), 8.03(dd, 1H), 4.15(s, 3H), 3.36(q, 2H), 2.71(s, 6H), 1.23(t, 3H) ppm |
| 483 | 454.00 | 456.20 | CD$_3$OD: 9.01(s, 1H), 8.60-7.83(m, 7H), 4.15(s, 3H), 3.34(q, 2H), 2.71(s, 6H), 1.84(s, 6H), 1.22(t, 3H) ppm |
| 484 | 459.20 | 461.20 | CD$_3$OD: 9.04-7.52(m, 8H), 5.01(d, 1H), 4.07(s, 3H), 3.33(q, 2H), 2.76(s, 6H), 2.26(m, 1H), 1.23(t, 3H), 1.14(d, 3H), 0.93(d, 3H) ppm |

TABLE 3a-continued

Characterization Data for Selected Compounds of Formula I

| Compound No. I- | M − 1(obs) | M + 1(obs) | NMR (500 MHz) |
|---|---|---|---|
| 485 | 401.20 | 403.20 | CD₃OD: 9.07(s, 1H), 8.83(d, 1H), 8.54(s, 1H), 8.45(d, 1H), 8.05(d, 1H), 8.00(s, 1H), 7.87(d, 1H), 7.63(m, 1H), 4.08(s, 3H), 3.34(q, 2H), 2.88(s, 3H), 2.73(s, 6H), 1.23(t, 3H) ppm |
| 486 | 405.20 | 407.20 | CD₃OD: 8.57(s, 1H), 8.56(d, 1H), 8.33(d, 1H), 8.31(d, 1H), 8.12(s, 1H), 8.06(s, 1H), 8.05(d, 1H), 7.23(d, 1H), 4.14(s, 3H), 3.35(q, 2H), 2.71(s, 6H), 1.22(t, 3H) ppm |
| 487 | 446.10 | 448.10 | CD₃OD: 9.38(s, 2H), 8.52(dd, 1H), 8.36(s, 1H), 8.16(dd, 1H), 8.13(s, 1H), 7.89(br s, 1H), 4.10(s, 3H), 3.33(q, 2H), 2.71(s, 6H), 1.71(s, 6H), 1.21(t, 3H) ppm |
| 488 | 461.30 | 463.30 | CD₃OD: 9.1(s, 1H), 9.0(d, 1H), 8.8(m, 1H), 8.5(s, 1H), 8.3(s, 1H), 8.2(s, 1H), 8.0(m, 1H), 7.7(m, 1H), 4.3(m, 3H), 4.2(d, 1H), 4.1(m, 2H), 3.4(q, 2H), 2.7(s, 6H), 1.2(t, 3H) ppm |
| 489 | 444.20 | 446.20 | DMSO-d6: 1.14(t, 3H), 1.28(d, 6H), 2.35(s, 6H), 3.21-3.28(m, 2H), 3.96(s, 3H), 7.15(d, 1H), 7.57(dd, 1H), 7.77-7.83(m, 2H), 8.13-8.27(m, 3H), 8.39-8.43(m, 1H) ppm |
| 490 | 402.20 | 404.20 | DMSO-d6: 1.14(t, 3H), 2.35(s, 6H), 3.21-3.28(m, 2H), 3.96(s, 3H), 7.13(d, 1H), 7.57(dd, 1H), 7.76-7.82(m, 2H), 8.15(s, 1H), 8.26-8.33(m, 2H), 8.39-8.42(m, 1H) ppm |
| 491 | 446.10 | 448.10 | CD₃OD: 9.37(s, 1H); 8.69(s, 1H); 8.37(s, 1H); 8.05(s, 1H); 7.8(m, 1H); 7.52(m, 1H), 7.3(s, 1H); 4.56(d, 1H); 3.32(m, 2H); 2.75(s, 6H); 1.3(m, 1H); 1.25(t, 3H); 06-0.8(m, 3H) ppm |
| 492 | 463.40 | 465.30 | CD₃OD: 9.1(s, 1H), 8.9(d, 1H), 8.7(s, 1H), 8.4(s, 1H), 8.3(d, 1H), 8.1(s, 1H), 7.9(t, 1H), 7.6(s, 1H), 3.9(q, 1H), 3.8(d, 1H), 3.6(d, 1H), 3.4(q, 3H), 3.3(q, 2H), 2.7(s, 9H), 1.7(s, 3H), 1.2(t, 3H) ppm |
| 493 | 437.00 | 439.20 | CD₃OD: 8.9(s, 1H); 8.7(m, 2H); 8.6(s, 1H); 8.1(s, 1H); 7.9(t, 1H); 7.6(m, 1H); 5.4(q, 1H); 3.38(q, 2H); 2.7(s, 6H); 1.65(d, 3H); 1.25(t, 3H) ppm |
| 494 | 445.20 | 447.20 | DMSO-d6: 1.14(t, 3H), 1.21(d, 6H), 2.37(s, 6H), 3.21-3.29(m, 2H), 3.97(s, 3H), 4.08-4.17(m, 1H), 7.61(dd, 1H), 7.63-7.68(m, 1H), 7.79-7.85(m, 2H), 8.21(s, 1H), 8.43(d, 1H), 8.67(s, 2) ppm |
| 495 | 373.10 | 375.20 | CD₃OD: 1.25(t, 3H), 2.74(s, 6H), 3.38(q, 2H), 7.20(d, 1H), 7.49-7.52(m, 1H), 7.94(s, 1H), 8.26(s, 1H), 8.37-8.41(m, 1H), 8.71(s, 1H), 9.01-9.04(m, 2H) ppm |
| 496 | 434.40 | 436.30 | CD₃OD: 9.06(d, 2H); 9.0(d, 1H); 8.93(d, 1H); 8.9(dd, 1H); 8.18(s, 1H); 7.54(t, 1H); 3.4(q, 2H); 2.73(s, 6H); 1.79(s, 3H); 1.25(t, 3H)ppm |
| 497 | 446.40 | 448.30 | CD₃OD: 9.03(s, 1H); 9.02(s, 1H); 9.0(d, 1H); 8.88(d, 1H); 8.78(dd, 1H); 8.14(d, 1H), 7.51(t, 1H); 3.38(q, 2H); 2.74(s, 6H); 1.35(m, 1H); 1.25(t, 3H); 0.67(m, 4H)ppm |
| 498 | 420.40 | 422.30 | CD₃OD: 9.03(m, 3H); 8.83(s, 1H); 8.81(dd, 1H); 8.12(s, 1H); 7.51(t, 1H); 5.5(q, 1H); 3.37(q, 2H); 2.76(s, 6H); 1.68(d, 3H); 1.24(t, 3H)ppm |
| 500 | 446.10 | 448.10 | CD₃OD: 9.37(s, 1H); 8.69(s, 1H); 8.37(s, 1H); 8.05(s, 1H); 7.8(m, 1H); 7.52(m, 1H); 7.3(s, 1H); 4.56(d, 1H); 3.32(m, 2H); 2.75(s, 6H); 1.3(m, 1H); 1.25(t, 3H); 06-0.8(m, 3H)ppm |
| 502 | 446.10 | 448.30 | CD₃OD: 9.03(s, 1H); 9.02(s, 1H); 9.0(d, 1H); 8.88(d, 1H); 8.78(dd, 1H); 8.14(d, 1H) 7.51(t, 1H); 3.38(q, 2H); 2.74(s, 6H); 1.35(m, 1H); 1.25(t, 3H); 0.67(m, 4H) ppm. |

Example 27

Gyrase ATPase Assay

The ATP hydrolysis activity of DNA gyrase was measured by coupling the production of ADP through pyruvate kinase/lactate dehydrogenase to the oxidation of NADH. This method has been described previously (Tamura and Gellert, 1990, J. Biol. Chem., 265, 21342).

ATPase assays are carried out at 30° C. in buffered solutions containing 100 mM TRIS pH 7.6, 1.5 mM $MgCl_2$, 150 mM KCl. The coupling system contains (final concentrations) 2.5 mM phosphoenol pyruvate, 200 μM nicotinamide adenine dinucleotide (NADH), 1 mM DTT, 30 ug/ml pyruvate kinase, and 10 ug/ml lactate dehydrogenase. 40 nanomolar enzyme (374 kDa Gyr A2B2 subunit from *Staphylococcus aureus*) and a DMSO solution of the inhibitor to a final concentration of 4% are added and the reaction mixture is allowed to incubate for 10 minutes at 30° C. The reaction is then started by the addition of ATP to a final concentration of 0.9 mM and the rate of NADH disappearance at 340 nanometers is measured over the course of 10 minutes. The $K_i$ values are determined from rate versus concentration profiles.

Compounds of the present invention were found to inhibit gyrase. In certain embodiments, compounds of the present invention inhibit gyrase with a $K_i$ value of less than 50 nM in the above assay.

Example 28

Topo IV ATPase Assay

The conversion of ATP to ADP by Topo4 enzyme is coupled to the conversion of NADH to NAD+ and measured by the change in absorbance at 340 nm. Topo4 is incubated with inhibitor (4% DMSO final) in buffer for 10 minutes at 30° C. Reaction is initiated with ATP and rates are monitored continuously for 20 minutes at 30° C. on a Molecular Devices SpectraMAX plate reader. The inhibition constant, Ki, is determined from plots of rate vs. [Inhibitor] fit to the Morrison Equation for tight binding inhibitors.

*S. aureus* Topo4 Buffer:
100 mM Tris 7.5, 2 mM MgCl2, 200 mM K.Glutamate, 2.5 mM phosphoenol pyruvate, 0.2 mM NADH, 1 mM DTT, 4.25 μg/mL linearized DNA, 50 μg/mL BSA, 30 μg/mL pyruvate kinase, and 10 μg/mL lactate dehyrodgenase (LDH).

*E. coli* Topo4 Buffer:
100 mM Tris 7.5, 6 mM MgCl2, 20 mM KCl, 2.5 mM phosphoenol pyruvate, 0.2 mM NADH, 10 mM DTT, 5.25 μg/mL linearized DNA, 50 μg/mL BSA, 30 μg/mL pyruvate kinase, and 10 μg/mL lactate dehyrodgenase (LDH).

Compounds of the present invention were found to inhibit TopoIV. In certain embodiments, compounds of the present invention inhibit TopoIV with a $K_i$ value of less than 50 nM in the above assay.

Example 29

Susceptibility Testing in Liquid Media

Compounds of this invention were also tested for antimicrobial activity by susceptibility testing in liquid media. Such assays were performed within the guidelines of the latest NCCLS document governing such practices: "M7-A5 Methods for dilution Antimicrobial Susceptibility Tests for Bacteria that Grow Aerobically; Approved Standard—Fifth Edition (2000)". Other publications such as "Antibiotics in Laboratory Medicine" (Edited by V. Lorian, Publishers Williams and Wilkins, 1996) provide essential practical techniques in laboratory antibiotic testing. Essentially, several discrete bacterial colonies of *Staphylococcus aureus, Streptococcus pneumoniae, Enterococcus faecalis, Enterococcus faecium, E. coli, Haemophilus influenzae, Staphylococcus epidermidis,* or *Staphylococcus saprophyticus* (3 to 7) from a freshly streaked plate were transferred to an appropriate rich broth medium such as MHB (Mueller Hinton broth), supplemented where appropriate for the more fastidious organisms. This was grown overnight to high density followed by a 1 or 2-thousand-fold dilution to give an inoculation density of between $5 \times 10^5$ and $5 \times 10^6$ CFU per mL. Alternatively, the freshly picked colonies can be incubated at 37° C. for about 4 to 8 hours until the culture equals or exceeds a turbidity of a 0.5 McFarland standard (approximately $1.5 \times 10^8$ cells per mL) and diluted to give the same CFU per mL as above. In a more convenient method, the inoculum was prepared using a commercially available mechanical device (the BBL PROMPT System) that involves touching five colonies directly with a wand, containing crosshatch grooves at its bottom, followed by suspension of the bacteria in an appropriate volume of saline. Dilution to the appropriate inoculum cell density was made from this cell suspension. The broth used for testing consists of MHB supplemented with 50 mg per L of $Ca^{2+}$ and 25 mg per L of $Mg^{2+}$. In the case of *Staphylococcus aureus*, the relative serum binding was measured in assays containing 50% frozen human serum in cation-adjusted Mueller Hinton broth. Standard dilution panels of control antibiotics were made and stored as in the NCCLS standard M7-A5, the dilution range typically being in the 128 μg per mL to 0.015 μg per mL (by 2-fold serial dilution). The test compounds were dissolved and diluted fresh for experimentation on the same day; the same or similar ranges of concentration as above being used. The test compounds and controls were dispensed into a multiwell plate and test bacteria added such that the final inoculation was approximately $5 \times 10^4$ CFU per well and the final volume was 100 μL. The plates were incubated at 35° C. overnight (16 to 20 hours) and checked by eye for turbidity or quantitated with a multiwell plate reader. The endpoint minimal inhibitory concentration (MIC) is the lowest concentration of drug at which the microorganism tested (*Staphylococcus aureus, Streptococcus pneumoniae, Enterococcus faecalis, Enterococcus faecium, E. coli, Haemophilus influenzae, Staphylococcus epidermidis,* or *Staphylococcus saprophyticus*) does not grow under the test conditions. Such determinations were also compared to the appropriate tables contained in the above two publications to ensure that the range of antibacterial activity is within the acceptable range for this standardized assay.

Compounds of the present invention were found to have antimicrobial activity in the above-described *Staphylococcus aureus, Streptococcus pneumoniae, Enterococcus faecalis, Enterococcus faecium, E. coli, Haemophilus influenzae, Staphylococcus epidermidis,* and *Staphylococcus saprophyticus* MIC assays.

Example 30

Susceptibility Testing to Resistant Bacterial Strains in Liquid Media

Compounds of this invention were also tested for antimicrobial activity against certain resistant bacterial colonies by susceptibility testing in liquid media. Such assays were performed within the guidelines of the latest NCCLS document governing such practices: "M7-A5 Methods for dilution Antimicrobial Susceptibility Tests for Bacteria that Grow Aerobically; Approved Standard—Fifth Edition (2000)". Other publications such as "Antibiotics in Laboratory Medicine" (Edited by V. Lorian, Publishers Williams and Wilkins, 1996) provide essential practical techniques in laboratory antibiotic testing. Essentially, several discrete bacterial colonies of Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, Beta-lactam resistant *Haemophilus influenzae*, Fluoroquinolone resistant *Haemophilus influenzae*, Beta-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, or Rifampin resistant *Mycobacterium tuberculosis* (3 to 7) from a freshly streaked plate were transferred to an appropriate rich broth medium such as MHB (Mueller Hinton broth), supplemented where appropriate for the more fastidious organisms. This was grown overnight to high density followed by a 1 or 2-thousand-fold dilution to give an inoculation density of between $5 \times 10^5$ and $5 \times 10^6$ CFU per mL. Alternatively, the freshly picked colonies can be incubated at 37° C. for about 4 to 8 hours until the culture equals or exceeds a turbidity of a 0.5 McFarland standard (approximately $1.5 \times 10^8$ cells per mL) and diluted to give the same CFU per mL as above. In a more convenient method, the inoculum was prepared using a commercially available mechanical device (the BBL PROMPT System) that involves touching five colonies directly with a wand, containing crosshatch grooves at its bottom, followed by suspension of the bacteria in an appropriate volume of saline. Dilution to the appropriate inoculum cell density was made from this cell suspension. The broth used for testing consists of MHB supplemented with 50 mg per L of $Ca^{2+}$ and 25 mg per L of $Mg^{2+}$. Standard dilution panels of control antibiotics were made and stored as in the NCCLS standard M7-A5, the dilution range typically being in the 128 µg per mL to 0.015 µg per mL (by 2-fold serial dilution). The test compounds were dissolved and diluted fresh for experimentation on the same day; the same or similar ranges of concentration as above being used. The test compounds and controls were dispensed into a multiwell plate and test bacteria added such that the final inoculation was approximately $5 \times 10^4$ CFU per well and the final volume was 100 µL. The plates were incubated at 35° C. overnight (16 to 20 hours) and checked by eye for turbidity or quantitated with a multiwell plate reader. The endpoint minimal inhibitory concentration (MIC) is the lowest concentration of drug at which the microorganism tested does not grow under the test conditions.

Compounds of the present invention were found to have antimicrobial activity in the above-described Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, Beta-lactam resistant *Haemophilus influenzae*, Fluoroquinolone resistant *Haemophilus influenzae*, Beta-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, and Rifampin resistant *Mycobacterium tuberculosis* MIC assays.

While we have described a number of embodiments of the present invention, it is apparent that our basic constructions may be altered to provide other embodiments that utilize the products and processes of this invention.

We claim:

1. A method of controlling, treating or reducing the advancement, severity or effects of a nosocomial or a non-nosocomial bacterial infection in a patient, wherein the bacterial infection is characterized by the presence of one or more of the following: Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound of formula I:

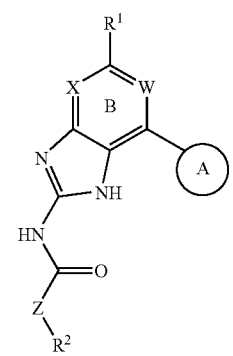

or a pharmaceutically acceptable salt thereof, wherein:
W is selected from CH or CF;
X is selected from CH or CF;
Z is O or NH;

$R^1$ is a 6 membered heteroaryl ring having 1-2 nitrogens, wherein:
  $R^1$ is substituted with 0-3 groups independently selected from —(T)$_y$—Ar, R', oxo, C(O)R', CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R';
y is 0 or 1;
T is a straight or branched $C_{1-4}$ alkylidene chain, wherein one methylene unit of T is optionally replaced by —O—, —NH—, or —S—;
each R' is independently selected from hydrogen, $C_{1-4}$ aliphatic, or a 5-6 membered saturated, unsaturated, or aryl ring having 0-3 heteroatoms independently selected from nitrogen, oxygen, or sulfur, wherein:
  R' is substituted with 0-3 groups independently selected from halogen, oxo, R°, N(R°)$_2$, OR°, CO$_2$R°, NR°C(O)R°, C(O)N(R°)$_2$, SO$_2$R°, SO$_2$N(R°)$_2$, or NR°SO$_2$R°, wherein:
    each R° is independently selected from hydrogen, $C_{1-4}$ aliphatic, or a 5-6 membered saturated, unsaturated, or aryl ring having 0-3 heteroatoms independently selected from nitrogen, oxygen, or sulfur, and wherein:
  two substituents on adjacent positions of $R^1$ may be taken together to form a 5-7 membered saturated, partially unsaturated, or aryl ring having 0-3 heteroatoms independently selected from nitrogen, oxygen, or sulfur;
Ar is a 5-6 membered saturated ring having 1-2 heteroatoms independently selected from oxygen, nitrogen or sulfur, a 5 membered heteroaryl ring having 1-3 heteroatoms independently selected from oxygen, nitrogen or sulfur, a 6-membered heteroaryl ring having 1-3 nitrogens or a phenyl ring, wherein:
  Ar is substituted with 0-3 groups independently selected from R', oxo, CO$_2$R', OR', halogen, SO$_2$R', or C(O)R';
$R^2$ is selected from hydrogen or a $C_{1-3}$ aliphatic group; and
Ring A is a pyrimidine ring wherein:
  Ring A is substituted with 0-3 groups independently selected from R', oxo, CO$_2$R', OR', N(R')$_2$, SR', NO$_2$, halogen, CN, C(O)N(R')$_2$, NR'C(O)R', SO$_2$R', SO$_2$N(R')$_2$, or NR'SO$_2$R'.

2. A method of controlling, treating or reducing the advancement, severity or effects of a nosocomial or a non-nosocomial bacterial infection in a patient, wherein the bacterial infection is characterized by the presence of one or more of the following: Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound of formula VII:

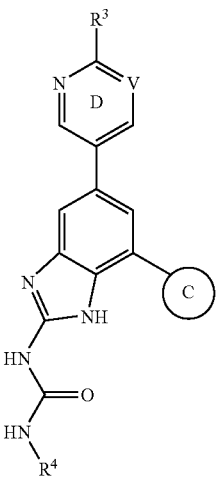

VII or a pharmaceutically acceptable salt thereof, wherein:
  V is selected from nitrogen, CH, or CF;
  $R^3$ is hydrogen or $C_{1-4}$ aliphatic, wherein:
    when $R^3$ is $C_{1-4}$ aliphatic, $R^3$ is substituted with 0-3 groups independently selected from OH, $R^5$, or OR$^5$; wherein:
      $R^5$ is $C_{1-3}$ aliphatic, wherein:
        two $R^5$ aliphatic groups may be optionally taken together with the carbon to which they are bound to form a $C_{3-4}$ cycloalkyl ring;
    provided that if $R^3$ is hydrogen, then V is not CH;
  $R^4$ is a $C_{1-3}$ aliphatic group; and
  Ring C is an unsubstituted 2-pyrimidine ring.

3. The method according to claim 2, comprising the step of administering to said patient a compound of formula VIIA, VIIB, or VIIC:

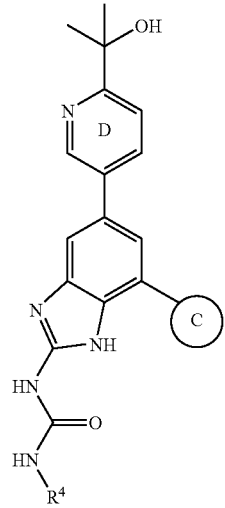

VIIA

-continued

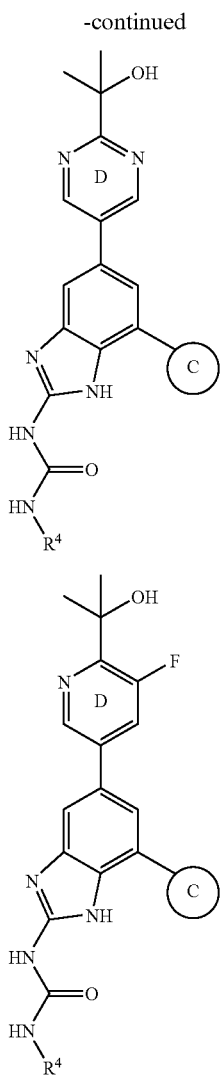

VIIB

VIIC or a pharmaceutically acceptable salt thereof, wherein:
R⁴ is a $C_{1-3}$ aliphatic group; and
Ring C is an unsubstituted 2-pyrimidine ring.

4. The method according to any one of claims 1-3 wherein said patient is a human.

5. The method according to claim 1 or claim 2, wherein said Methicillin resistant Staphylococcci are selected from Methicillin resistant *Staphylococcus aureus*, Methicillin resistant *Staphylococcus epidermidis*, or Methicillin resistant Coagulase negative *staphylcoccus*.

6. The method according to claim 1 or claim 2, wherein said Fluoroquinolone resistant Staphylococci are selected from Fluoroquinolone resistant *Staphylococcus aureus*, Fluoroquinolone resistant *Staphylococcus epidermidis*, or Fluoroquinolone resistant Coagulase negative *staphylcoccus*.

7. The method according to claim 1 or claim 2, wherein said Glycopepetide resistant Staphylococci are selected from Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, or Hetero vancomycin resistant *Staphylococcus aureus*.

8. The method according to claim 1 or claim 2, wherein said Macrolide-Lincosamide-Streptogramin resistant Staphylococci is Macrolide-Lincosamide-Streptogramin resistant *Staphylococcus aureus*.

9. The method according to claim 1 or claim 2, wherein said Linezolid resistant Enterococci are selected from Linezolid resistant *Enterococcus faecalis*, or Linezolid resistant *Enterococcus faecium*.

10. The method according to claim 1 or claim 2, wherein said Glycopepetide resistant Enterococci are selected from Vancomycin resistant *Enterococcus faecium* or Vancomycin resistant *Enterococcus faecalis*.

11. The method according to claim 1 or claim 2, wherein said β-lactam resistant Enterococci are selected from β-lactam resistant *Enterococcus faecalis* or β-lactam resistant *Enterococcus faecium*.

12. The method according to claim 1 or claim 2, wherein said Penicillin resistant Streptococci is Penicillin resistant *Streptococcus pneumoniae*.

13. The method according to claim 1 or claim 2, wherein said Macrolide resistant Streptococci is Macrolide resistant *Streptococcus pneumonia*.

14. The method according to claim 1 or claim 2, wherein said Ketolide resistant Streptococci are selected from Macrolide resistant *Streptococcus pneumoniae* or Ketolide resistant *Streptococcus pyogenes*.

15. The method according to claim 1 or claim 2, wherein said Fluoroquinolone resistant Streptococci is Fluoroquinolone resistant *Streptococcus pneumoniae*.

16. The method according to claim 1 or claim 2, wherein said β-lactam resistant *Haemophilus* is β-lactam resistant *Haemophilus influenzae*.

17. The method according to claim 1 or claim 2, wherein said Fluoroquinolone resistant *Haemophilus* is Fluoroquinolone resistant *Haemophilus influenzae*.

18. The method according to claim 1 or claim 2, wherein said Macrolide resistant *Haemophilus* is Macrolide resistant *Haemophilus influenzae*.

19. The method according to claim 1 or claim 2, wherein said Macrolide resistant *Mycoplasma* is Macrolide resistant *Mycoplasma pneumoniae*.

20. The method according to claim 1 or claim 2, wherein said Isoniazid resistant *Mycobacterium* is Isoniazid resistant *Mycobacterium tuberculosis*.

21. The method according to claim 1 or claim 2, wherein said Rifampin resistant *Mycobacterium* is Rifampin resistant *Mycobacterium tuberculosis*.

22. The method according to claim 1 or claim 2, wherein said β-lactam resistant *Moraxella* is β-lactam resistant *Moraxella catarrhalis*.

23. The method according to claim 1 or claim 2, wherein the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, or Rifampin resistant *Mycobacterium tuberculosis*.

24. The method according to claim 1 or claim 2, wherein the bacterial infection is characterized by the presence of one or more of the following: Methicillin resistant *Staphylococcus aureus*, Methicillin resistant *Staphylococcus epidermidis*, Methicillin resistant Coagulase negative staphylcocci, Fluoroquinolone resistant *Staphylococcus aureus*, Fluoroquinolone resistant *Staphylococcus epidermidis*, Fluoroquinolone resistant Coagulase negative staphylcocci, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus, Hetero vancomycin* intermediate resistant *Staphylococcus aureus, Hetero vancomycin* resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, β-lactam resistant *Haemophilus influenzae*.

25. A method of controlling, treating or reducing the advancement, severity or effects of a nosocomial or a non-nosocomial bacterial infection in a patient, wherein the bacterial infection is characterized by the presence of one or more of the following: Methicillin resistant Staphylococci, Fluoroquinolone resistant Staphylococci, Glycopepetide resistant Staphylococci, Macrolide-Lincosamide-Streptogramin resistant Staphylococci, Linezolid resistant Enterococci, Glycopepetide resistant Enterococci, β-lactam resistant Enterococci, Penicillin resistant Streptococci, Macrolide resistant Streptococci, Ketolide resistant Streptococci, Fluoroquinolone resistant Streptococci, β-lactam resistant *Haemophilus*, Fluoroquinolone resistant *Haemophilus*, Macrolide resistant *Haemophilus*, Macrolide resistant *Mycoplasma*, Isoniazid resistant *Mycobacterium*, Rifampin resistant *Mycobacterium*, or β-lactam resistant *Moraxella*, comprising the step of administering to said patient a compound selected from the group consisting of:

I-32

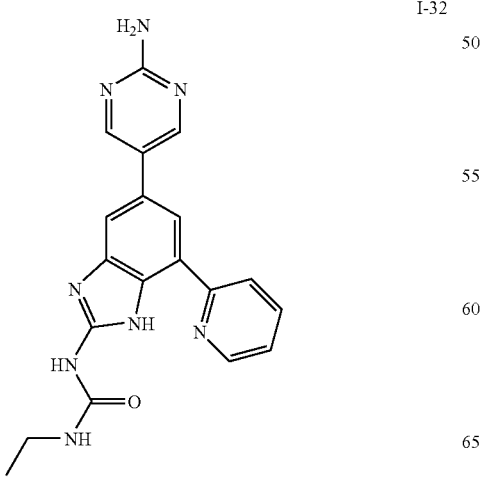

-continued

I-60

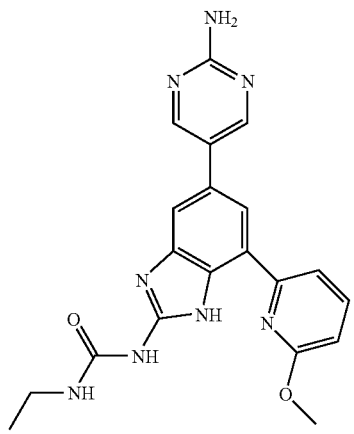

I-76

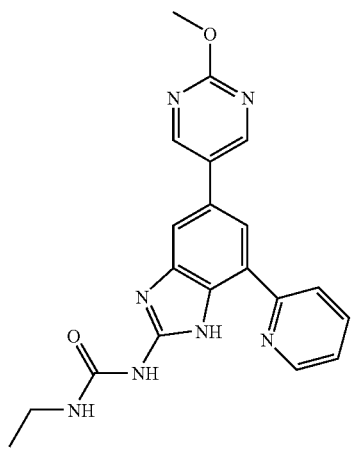

I-88

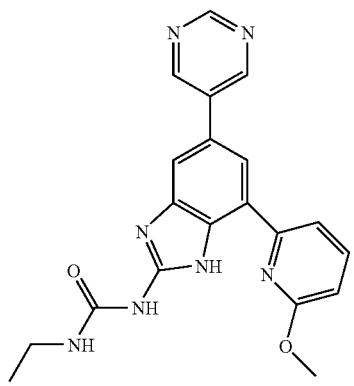

-continued
I-99
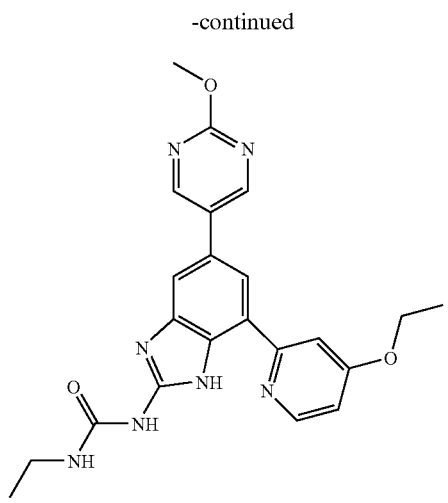
I-100
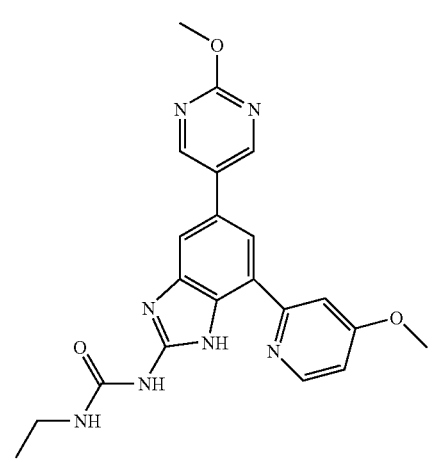
I-105
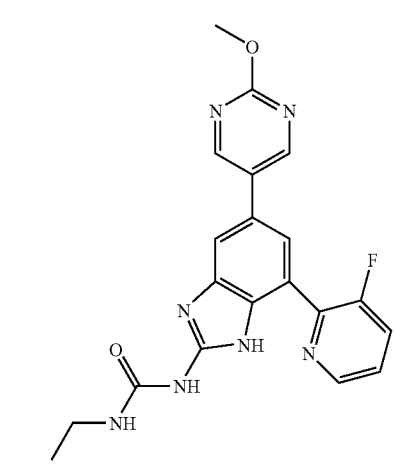
-continued
I-148
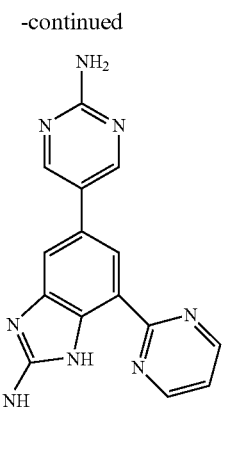
I-150
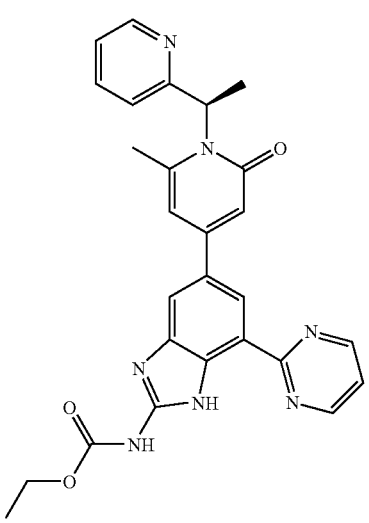
I-151
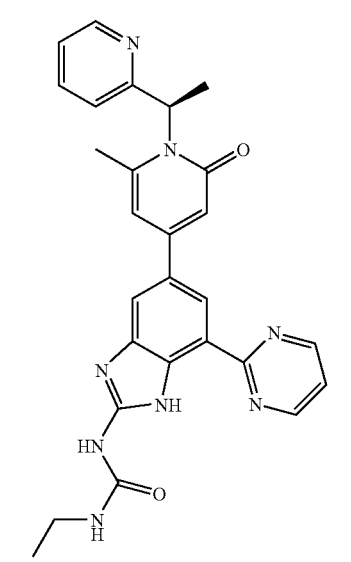

-continued
I-159
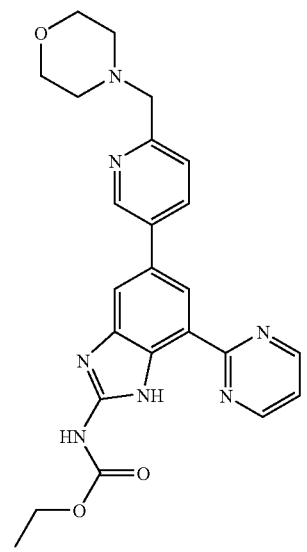
I-160
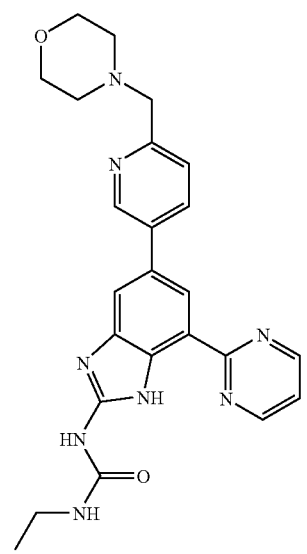
I-168
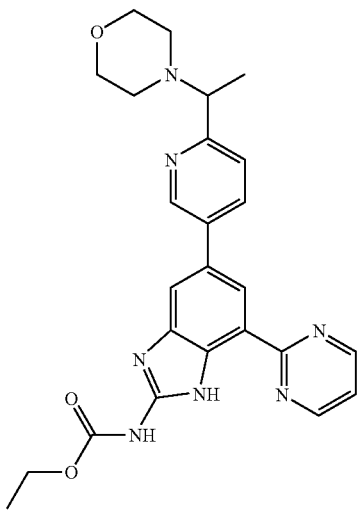
-continued
I-167
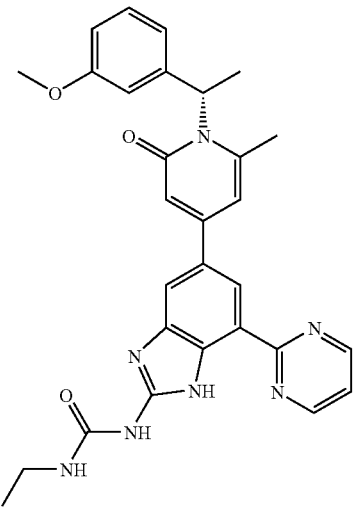
I-190
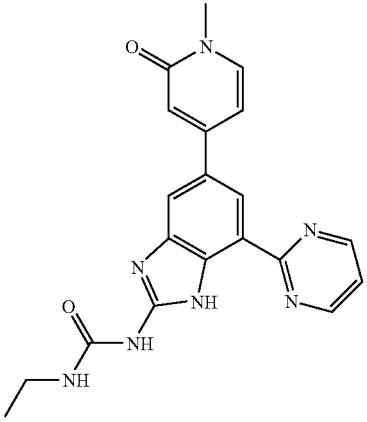
I-191
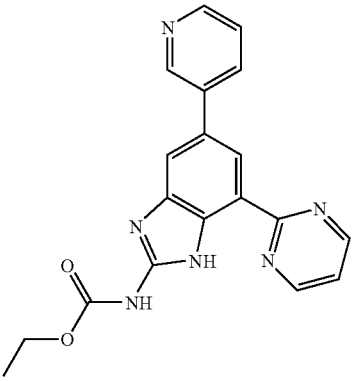

-continued
I-193
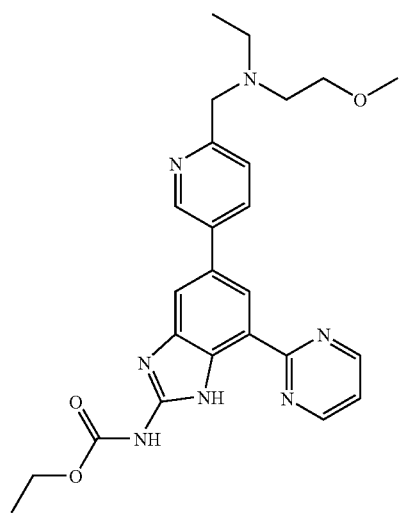
I-194
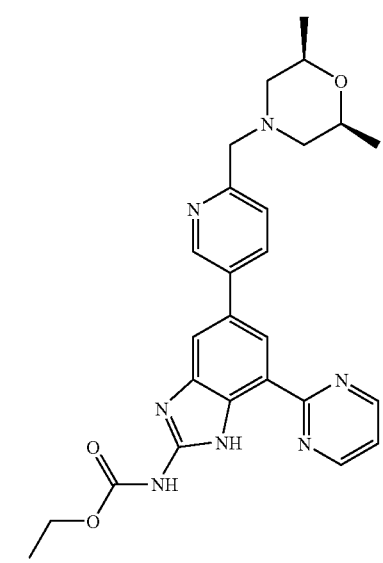
I-197
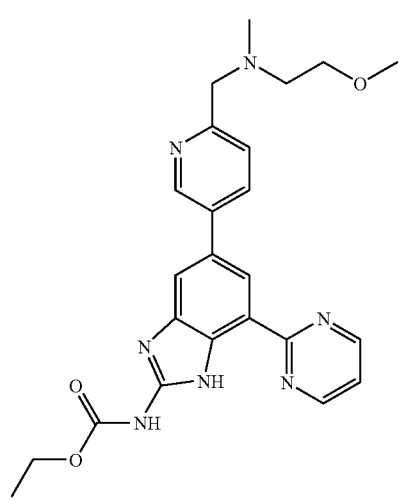
-continued
I-198
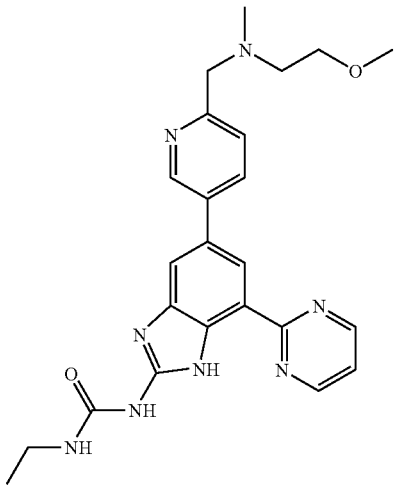
I-199
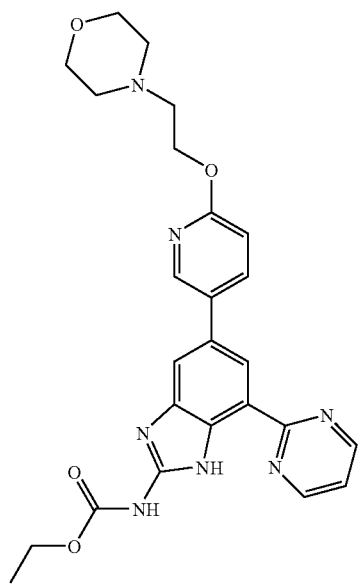
I-200
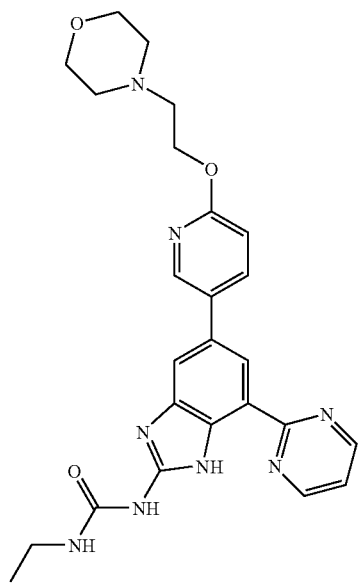

I-201
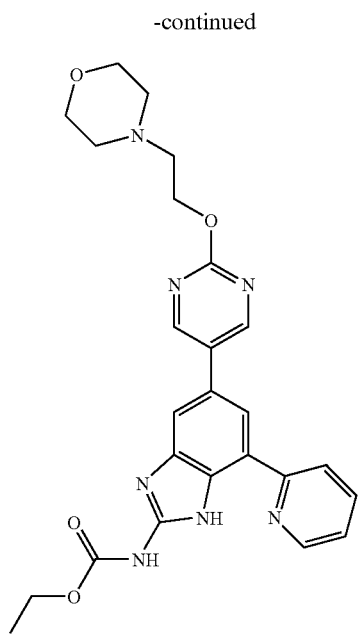
I-203
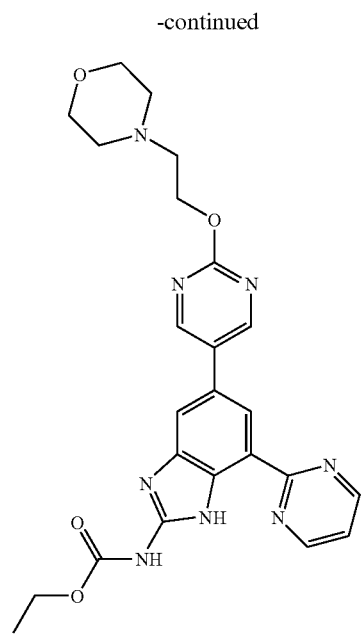
I-202
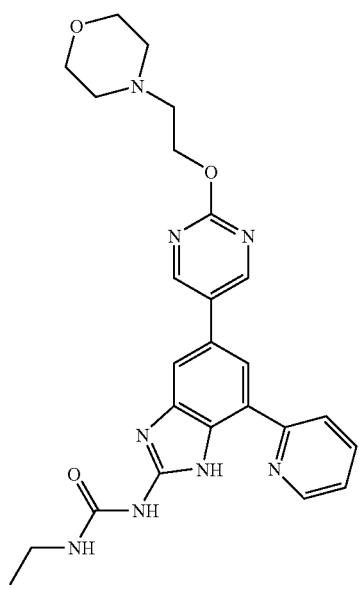
I-204
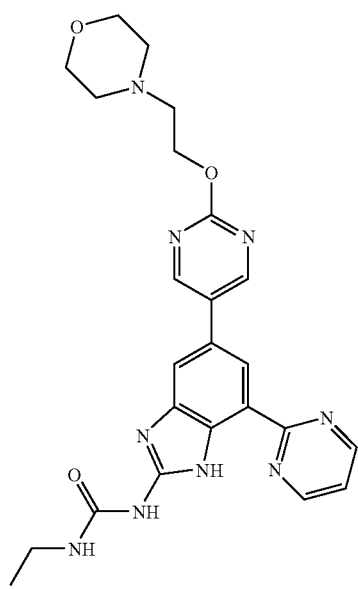

-continued
413
I-206
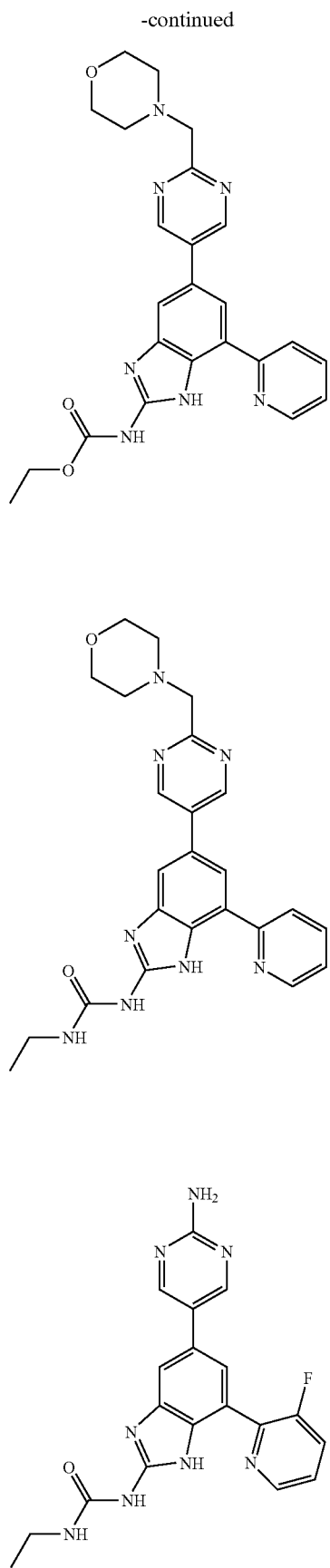
I-207
I-208
414
-continued
I-209
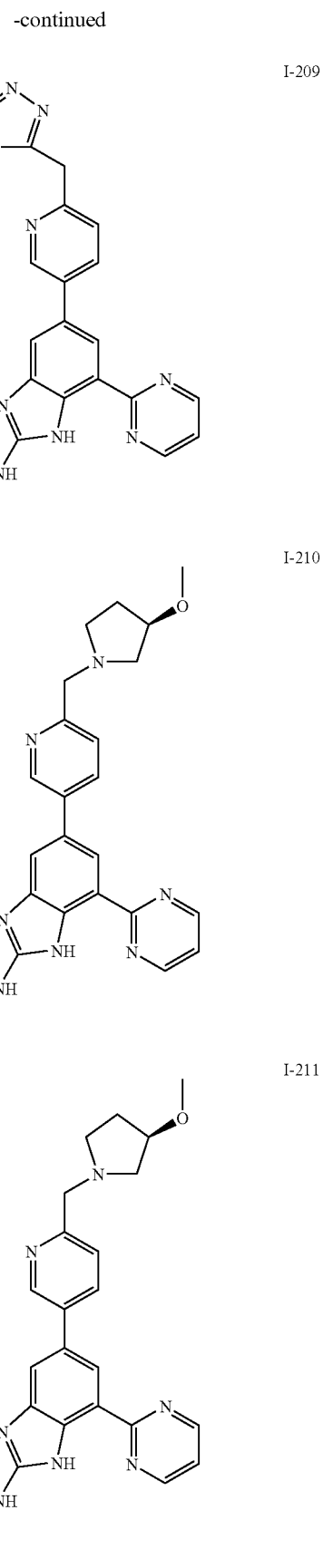
I-210
I-211

-continued
I-212
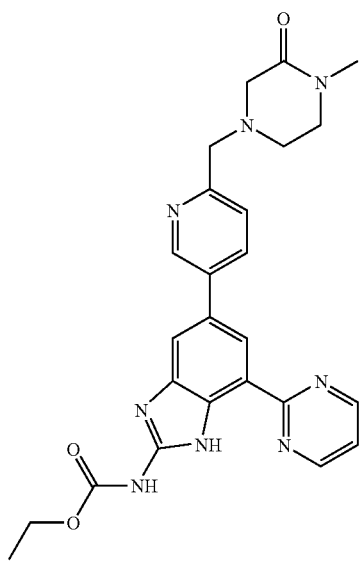
I-215
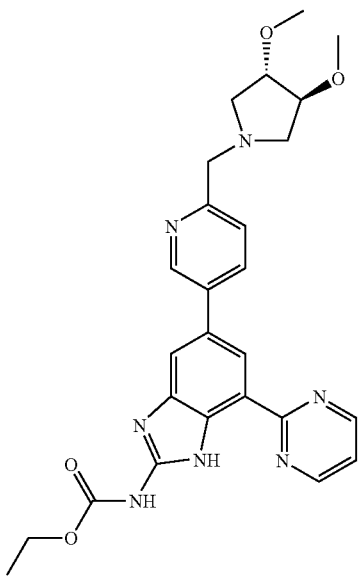
I-213
I-217

-continued
I-220
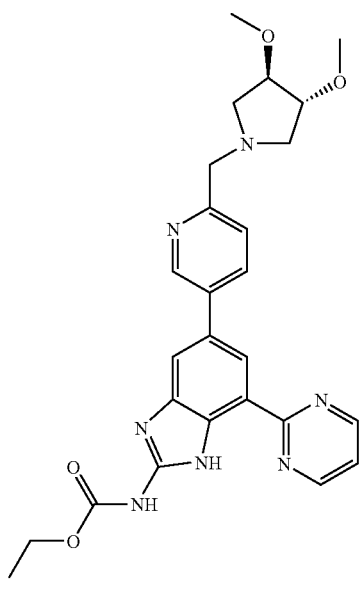
I-221
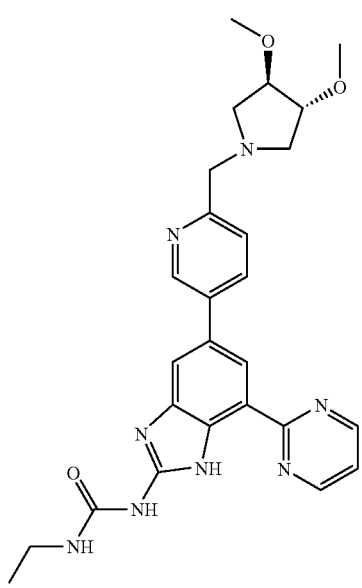
-continued
I-222
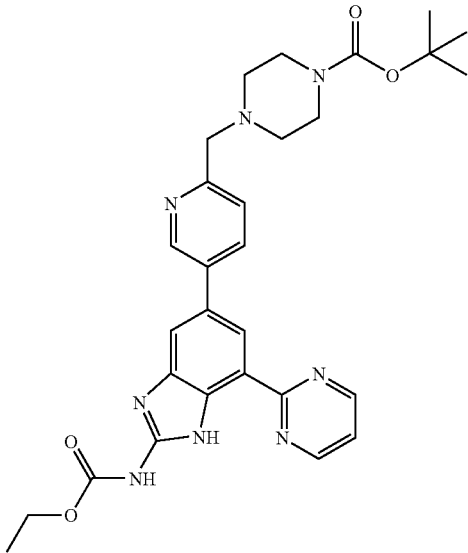
I-223
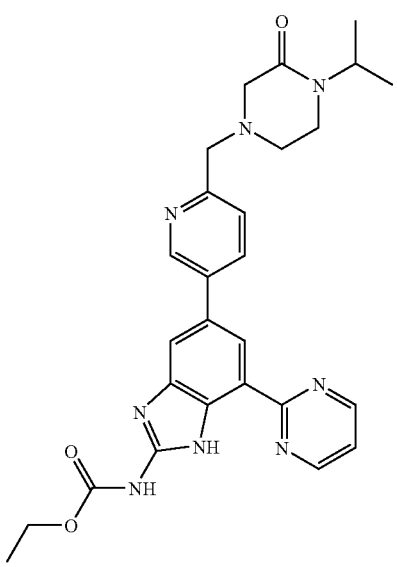
I-228
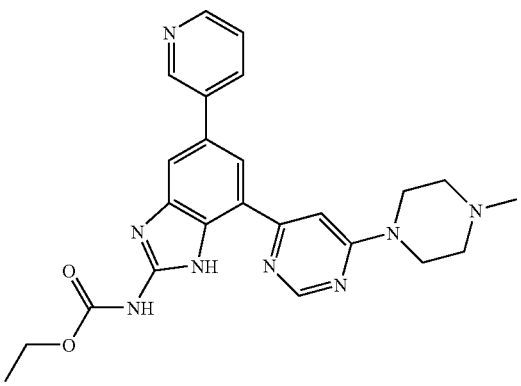

419
-continued
I-229
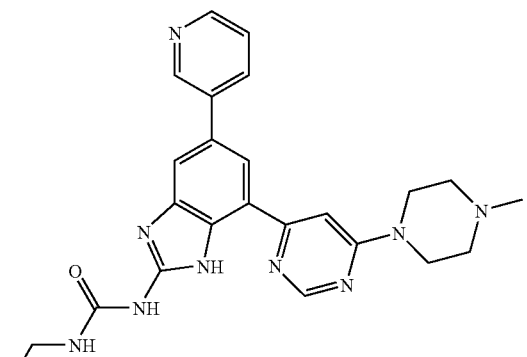
I-227
I-231
420
-continued
I-232
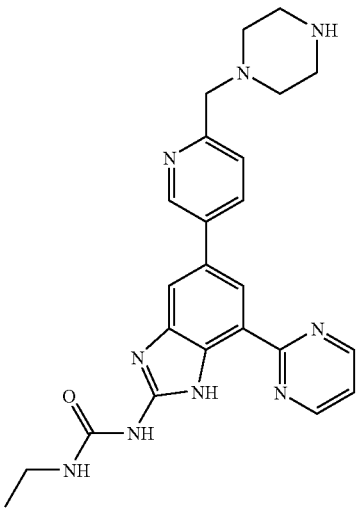
I-233
I-234
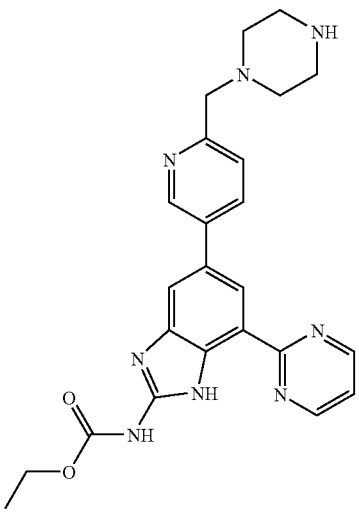

-continued
I-235
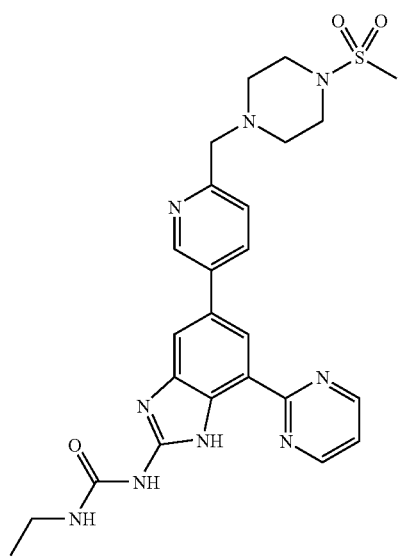
I-236
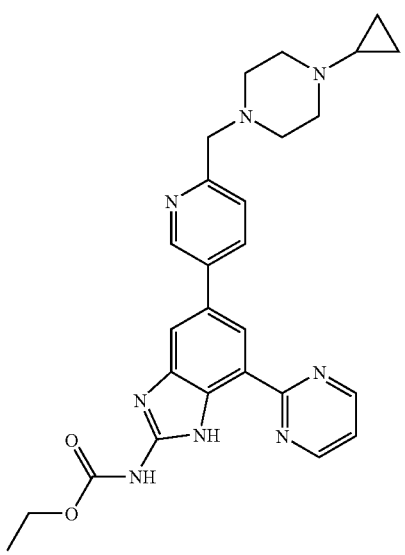
I-237
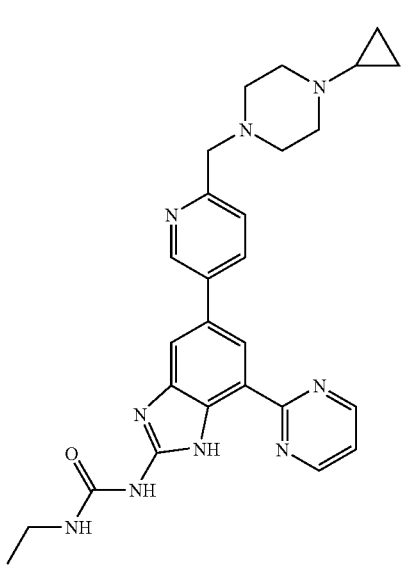
-continued
I-239
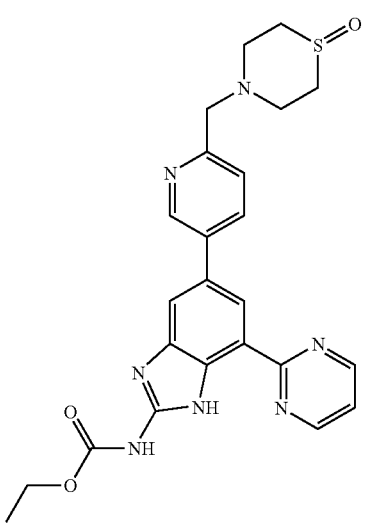
I-240
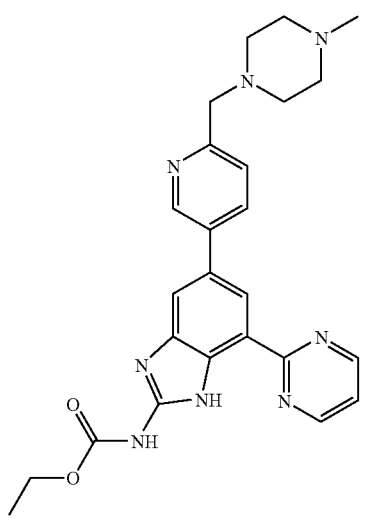
I-242
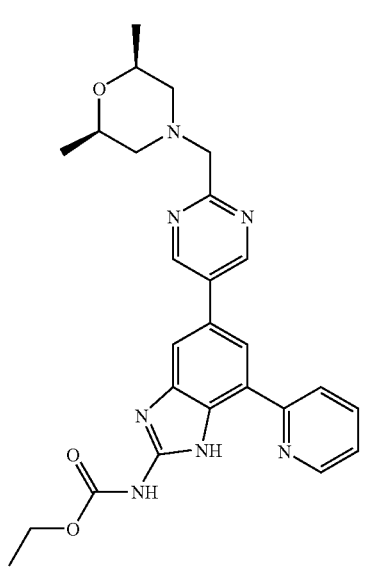

-continued
I-243
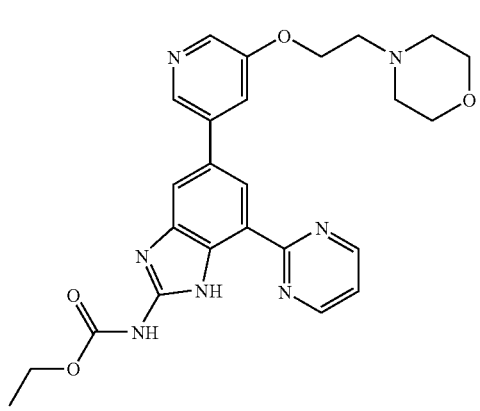
I-244
I-245
-continued
I-246
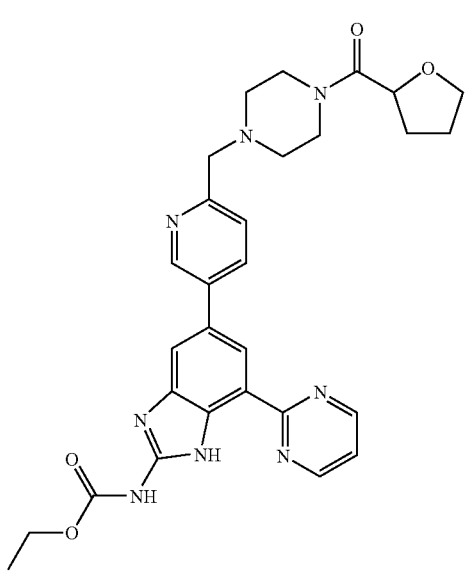
I-247
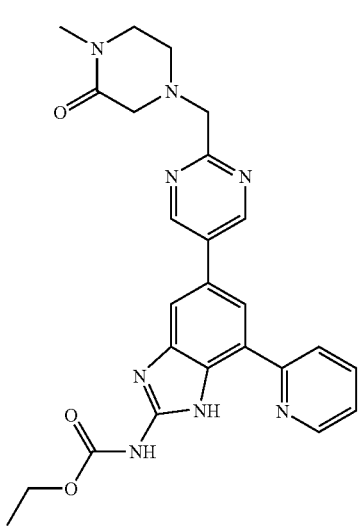
I-248
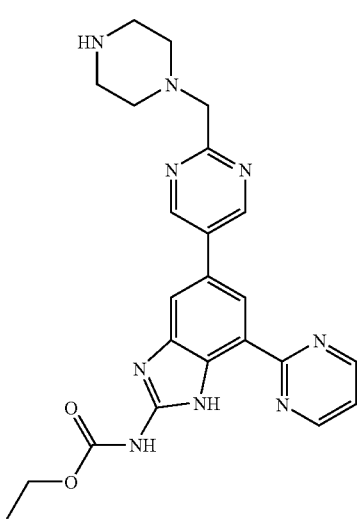

I-249
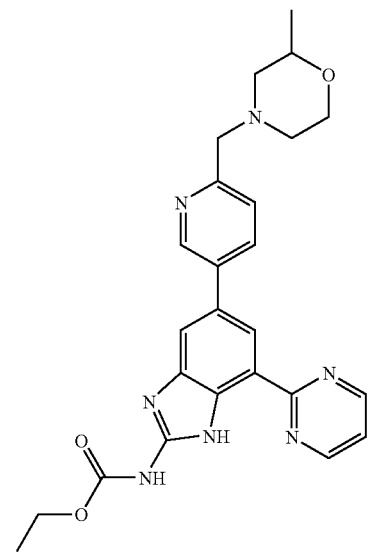
I-250
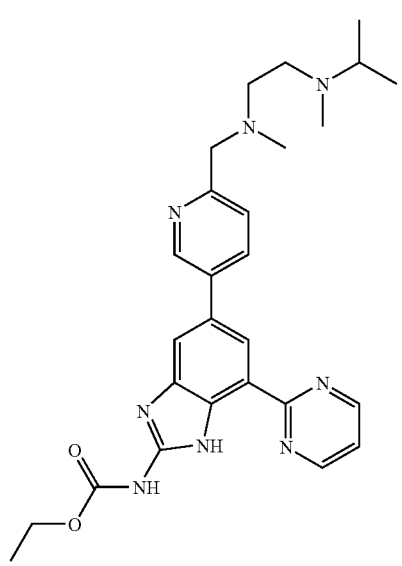
I-251
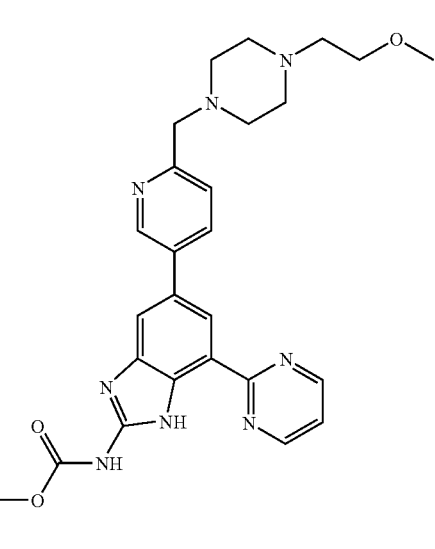
I-252
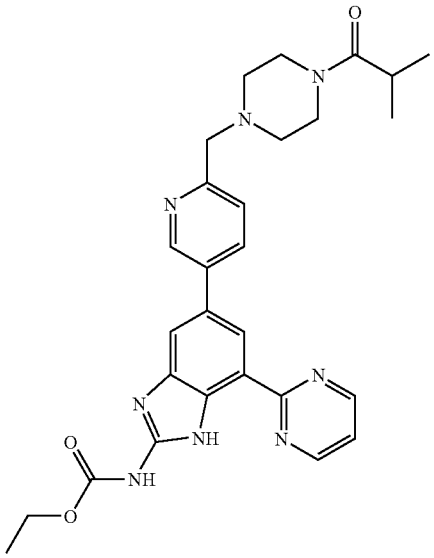
I-254
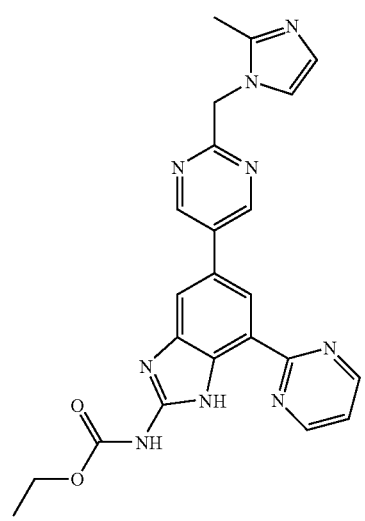
I-256
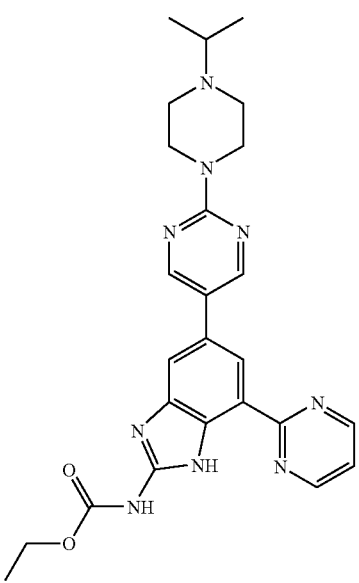

427
-continued
I-257
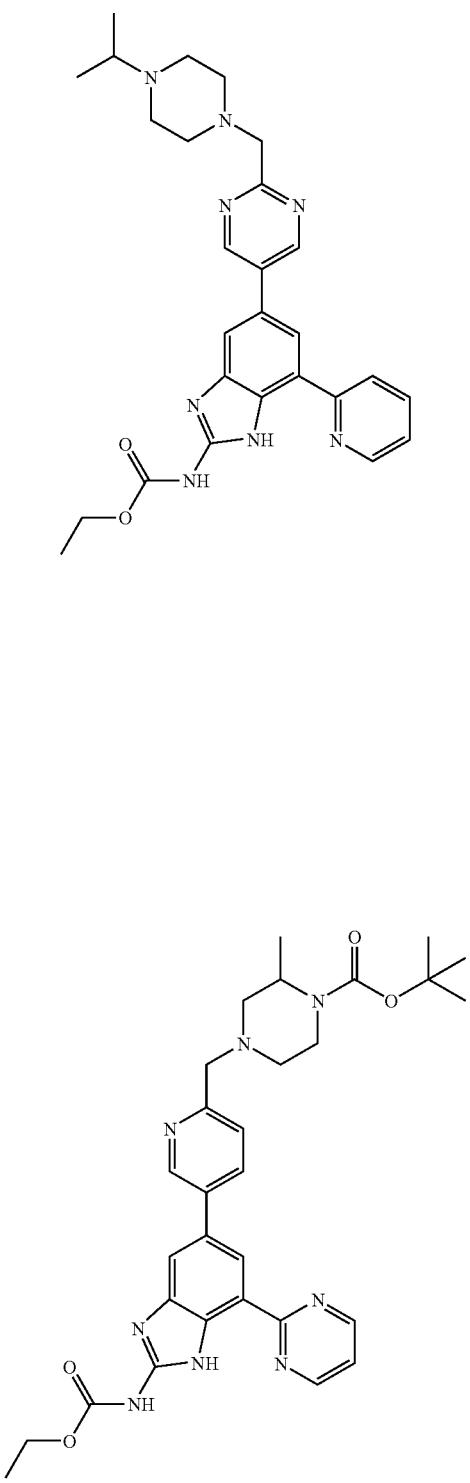
I-258
428
-continued
I-259
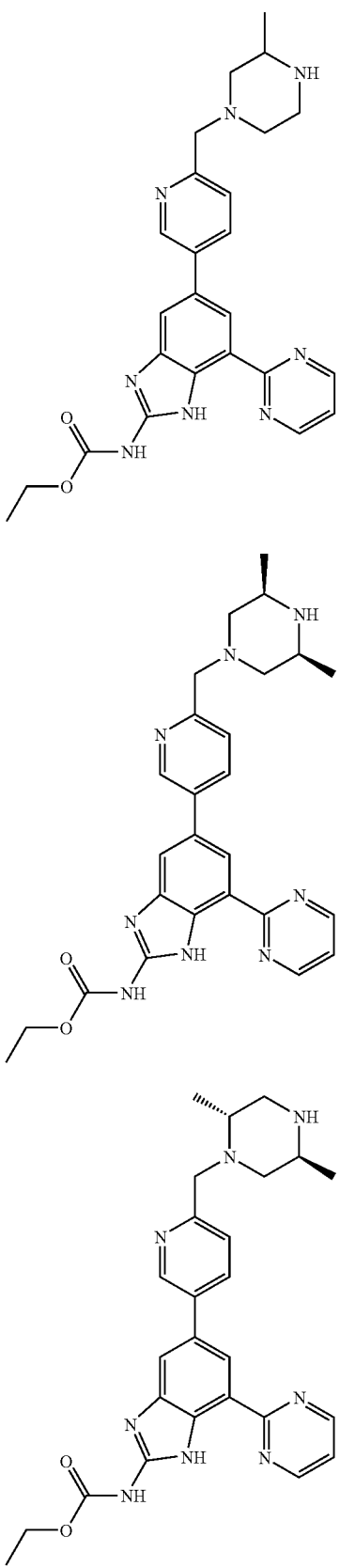
I-260
I-261

429
-continued
I-262
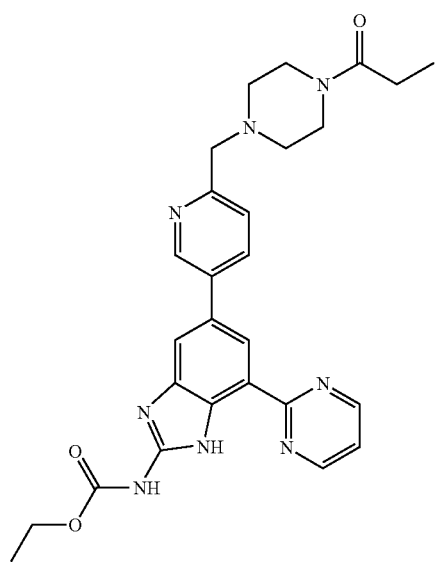
I-263
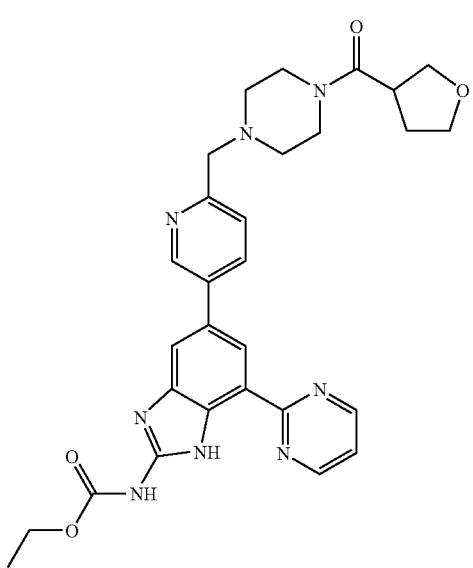
I-264
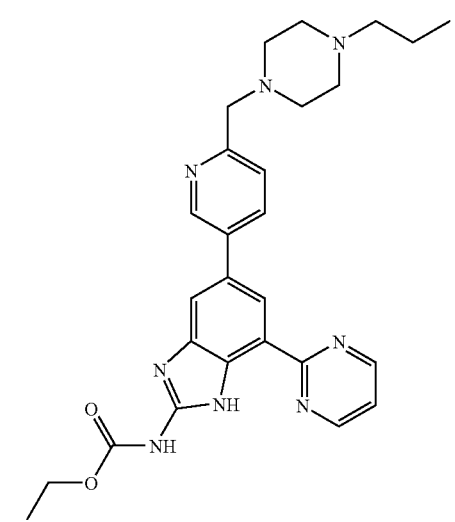
430
-continued
I-265
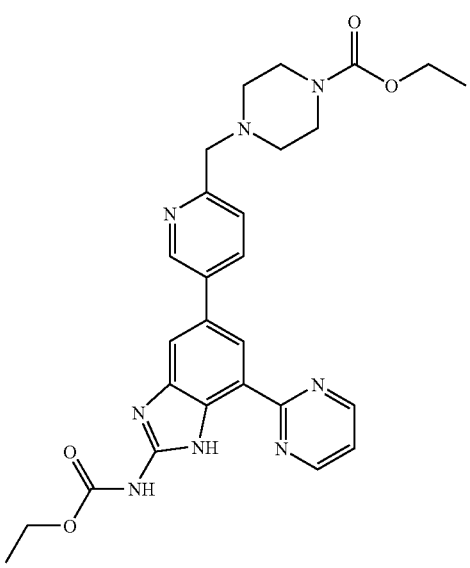
I-266
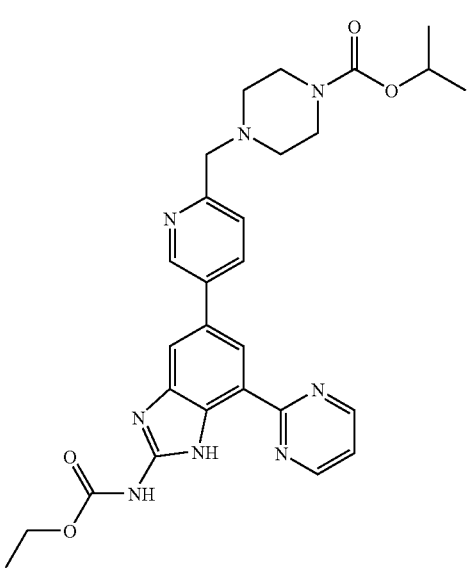

-continued
I-268
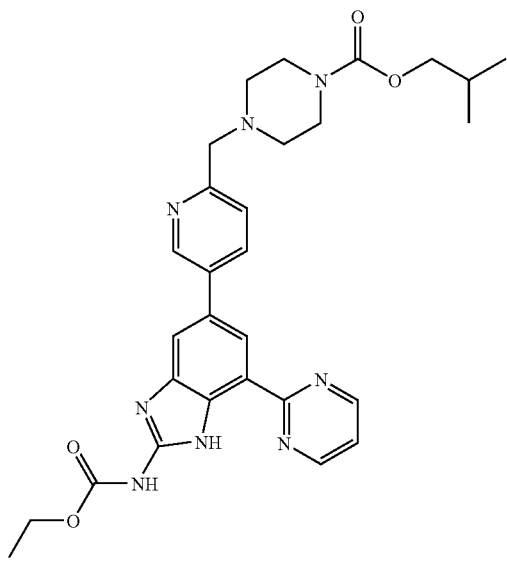
I-269
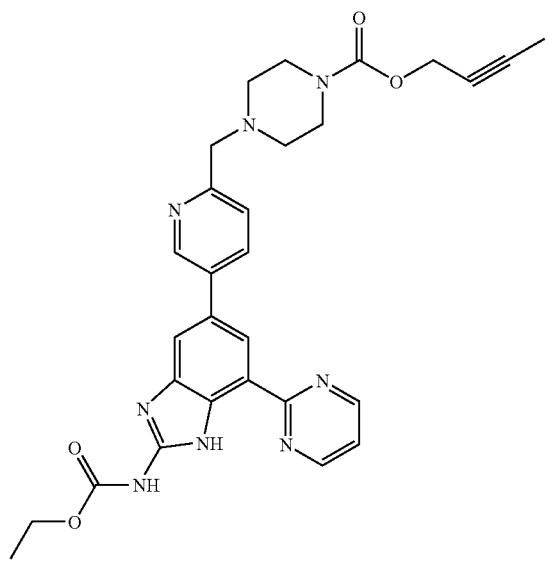
-continued
I-270
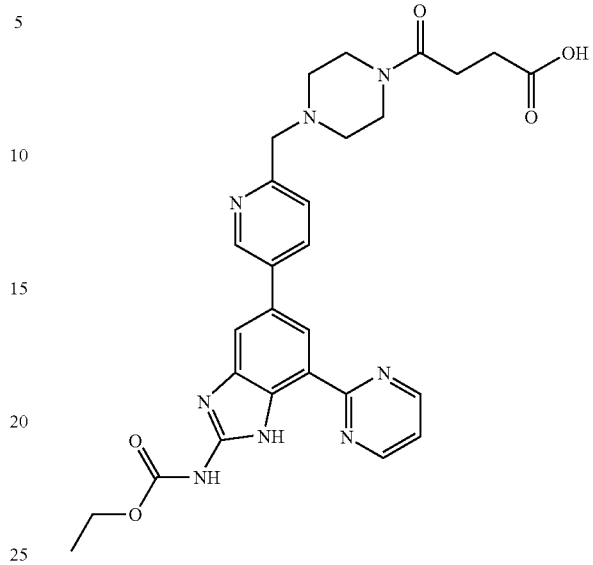
I-271
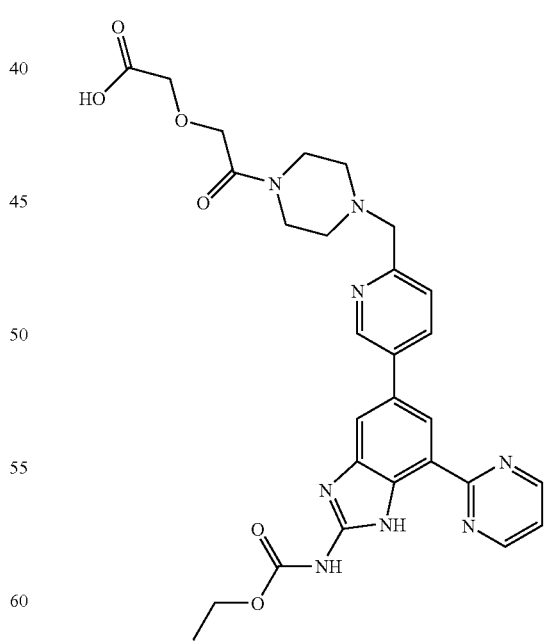

-continued
I-272
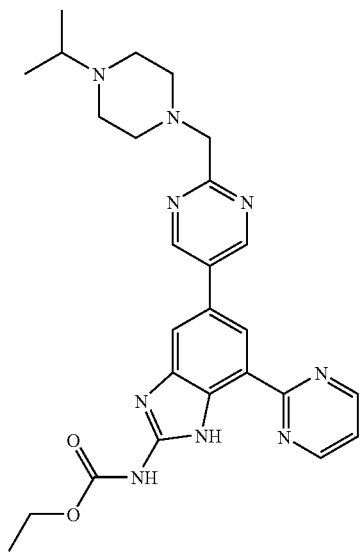
I-273
I-275
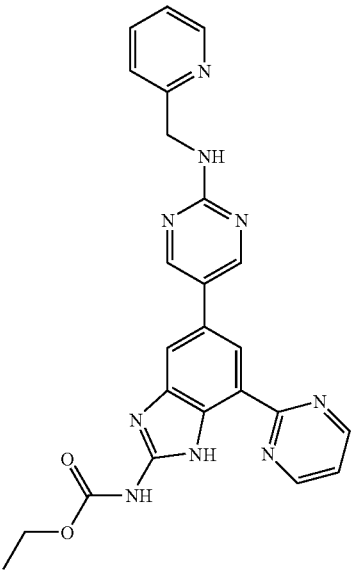
I-278
I-274
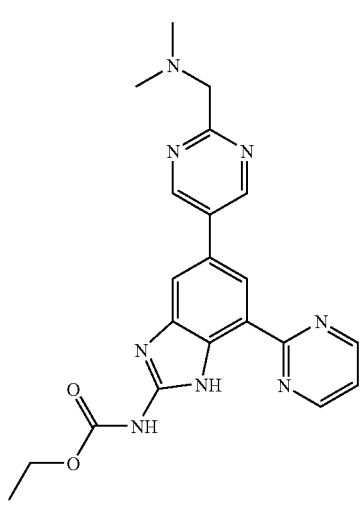
I-276

I-280
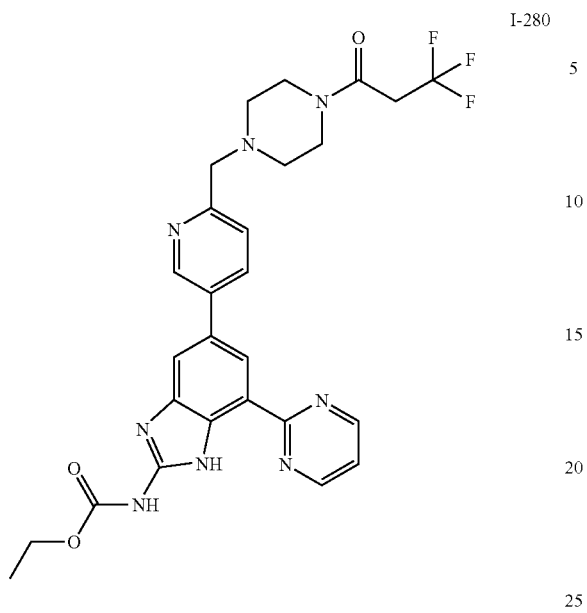
I-282
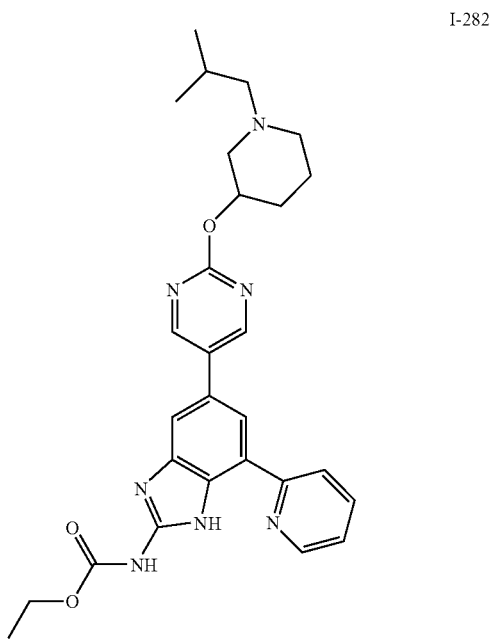
I-281
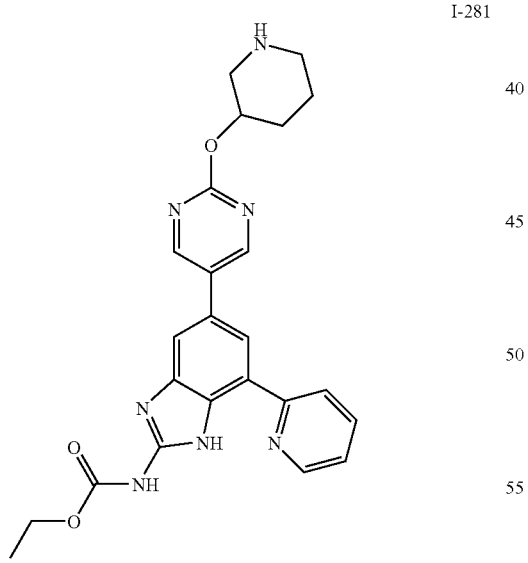
I-283
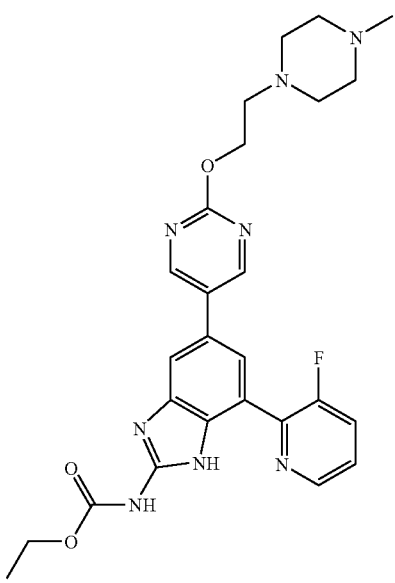

-continued
I-284
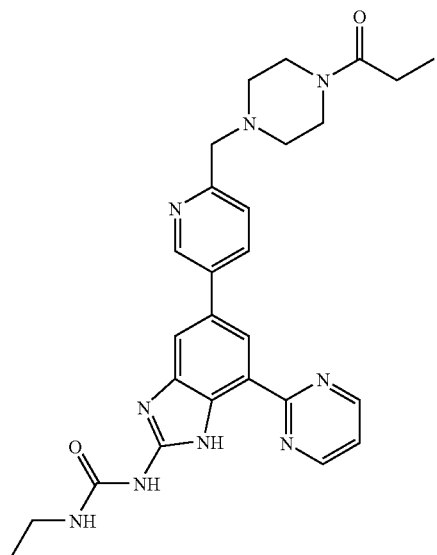
I-287
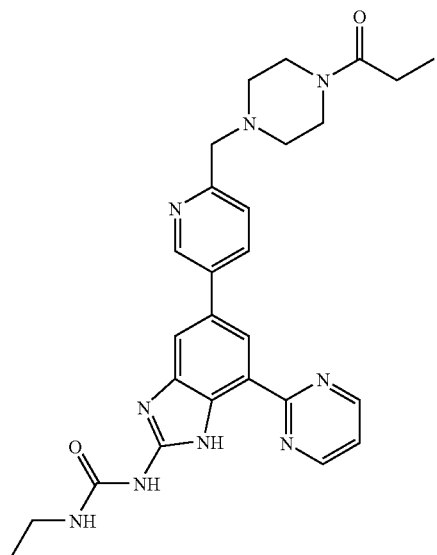
I-290
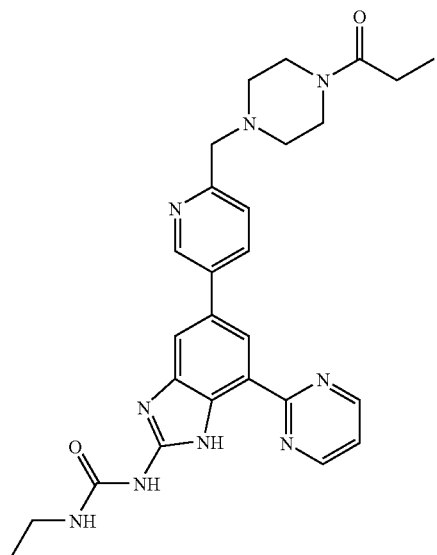
-continued
I-291
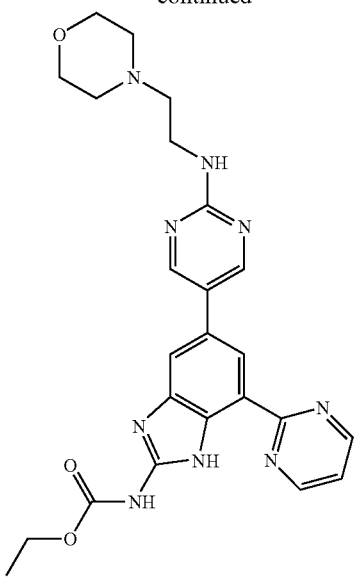
I-292
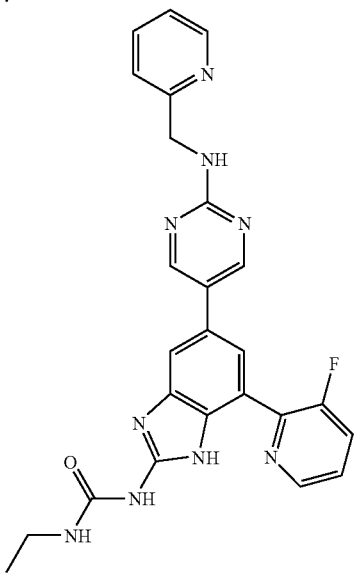
I-293
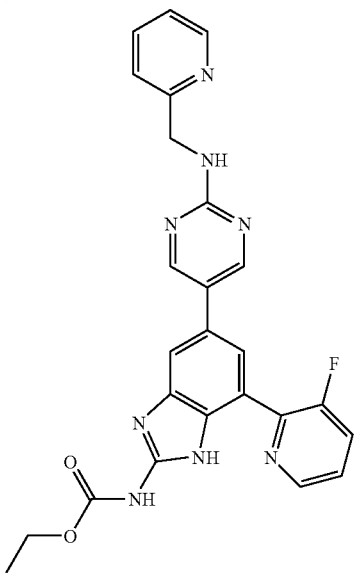

| No. | Structure |
|---|---|
| I-295 | 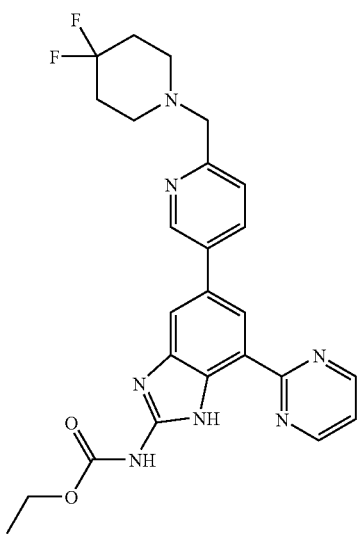 |
| I-299 | 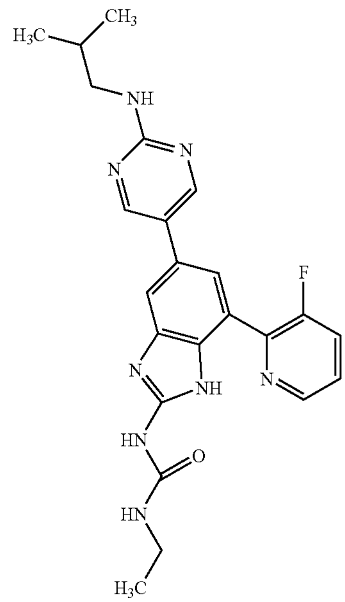 |
| I-297 | |
| I-302 | 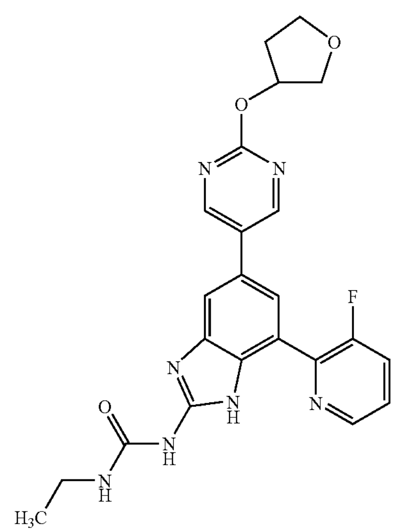 |

-continued
| No. | Structure |
|---|---|
| I-303 | 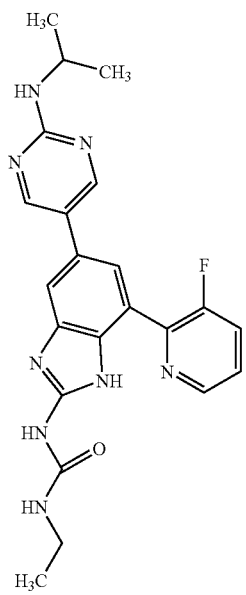 |
| I-307 | 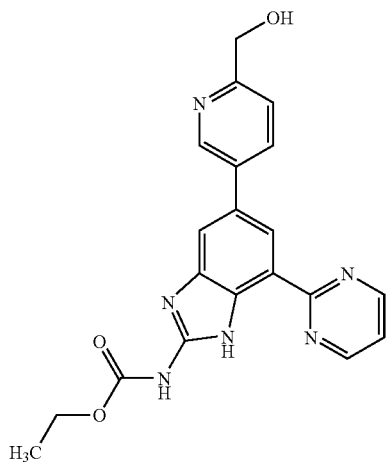 |
| I-312 | 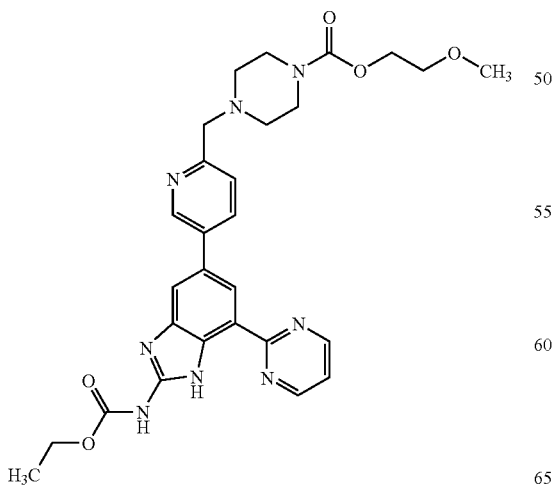 |
-continued
| No. | Structure |
|---|---|
| I-316 | 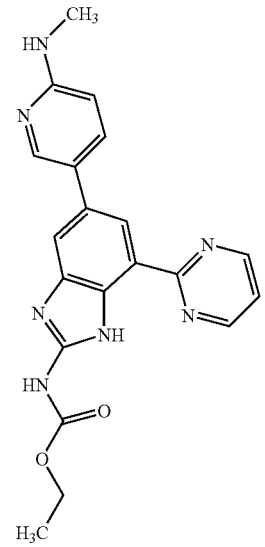 |
| I-317 | 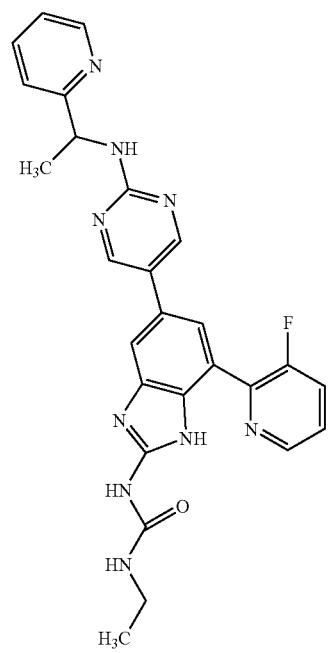 |

| No. | Structure |
|---|---|
| I-318 | 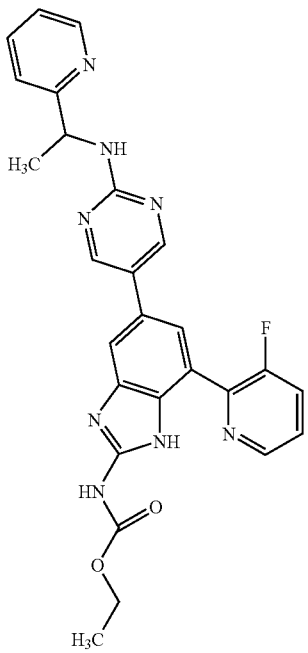 |
| I-319 | 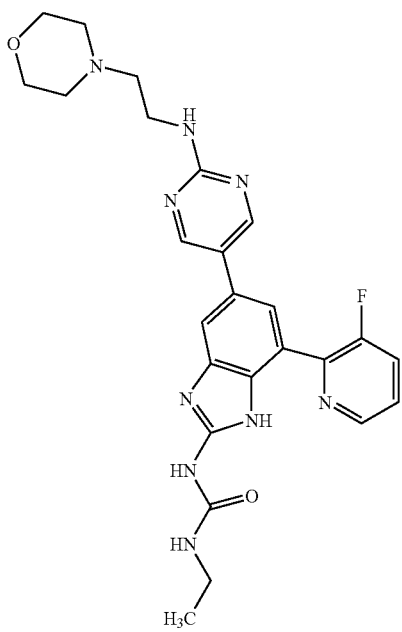 |
| No. | Structure |
|---|---|
| I-320 | 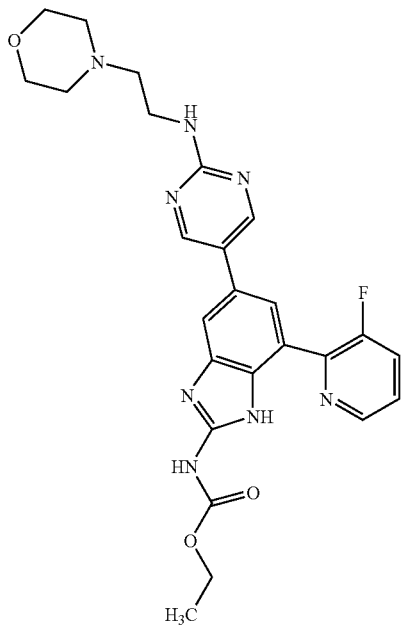 |
| I-323 | 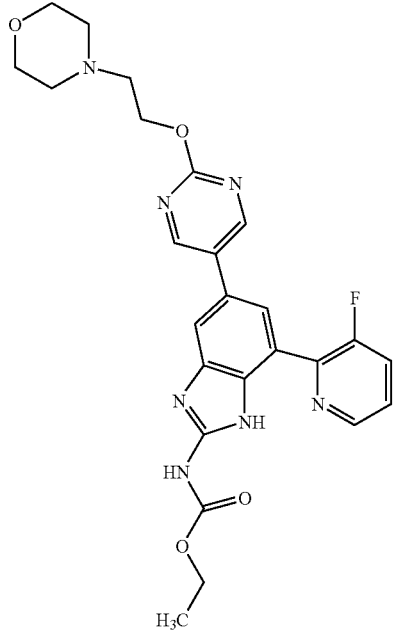 |

| No. | Structure |
|---|---|
| I-326 | 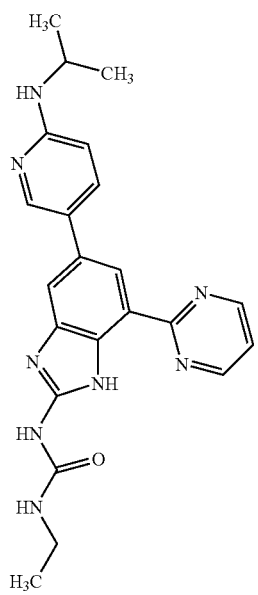 |
| I-327 | 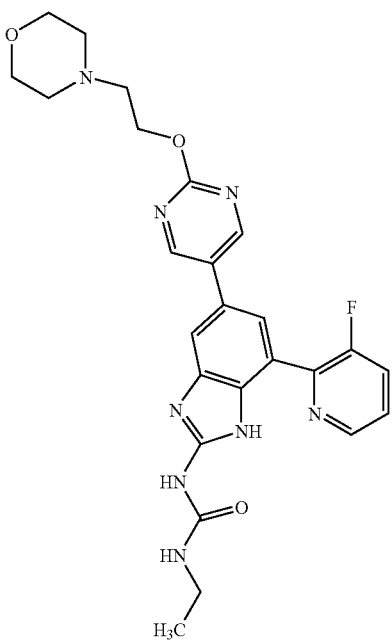 |
| No. | Structure |
|---|---|
| I-331 | 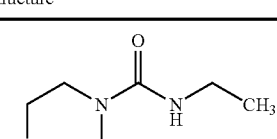 |
| I-338 | 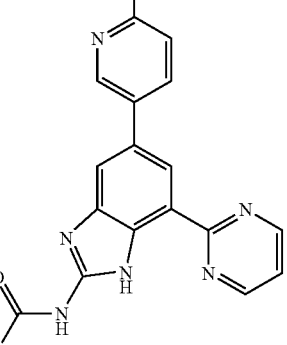 |
| I-339 | 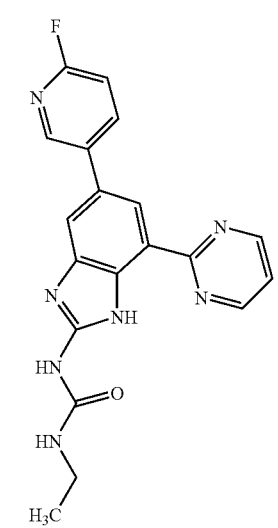 |

-continued
| No. | Structure |
|---|---|
| I-341 | 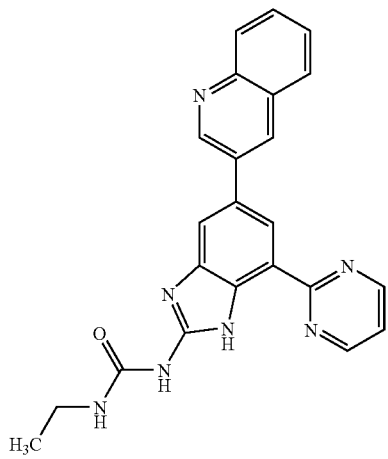 |
| I-347 | 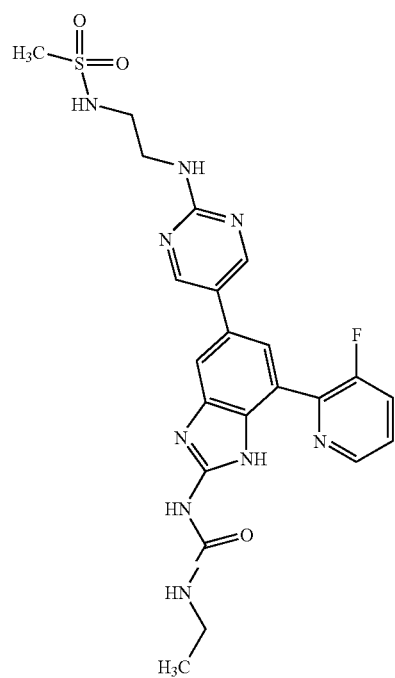 |
-continued
| No. | Structure |
|---|---|
| I-349 | 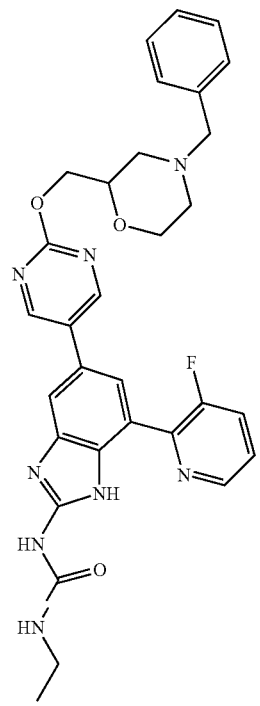 |
| I-352 | 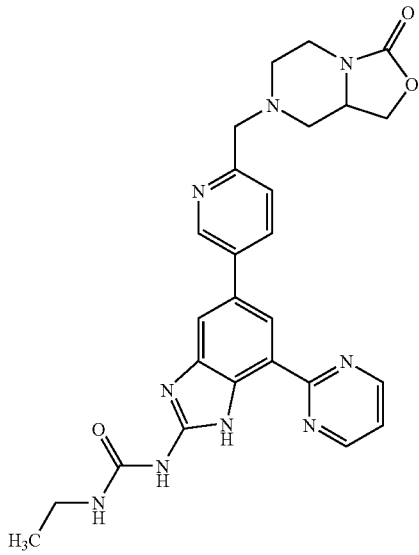 |

| No. | Structure |
|---|---|
| I-355 | 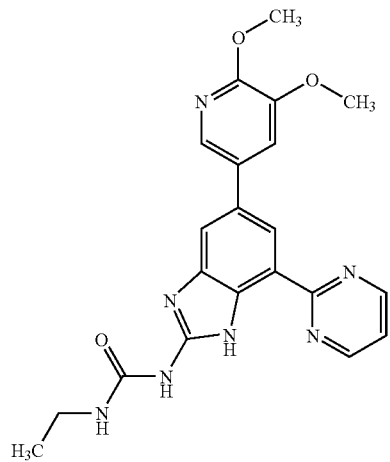 |
| I-359 | 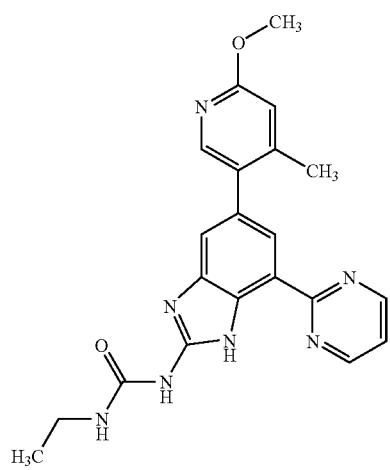 |
| I-361 | 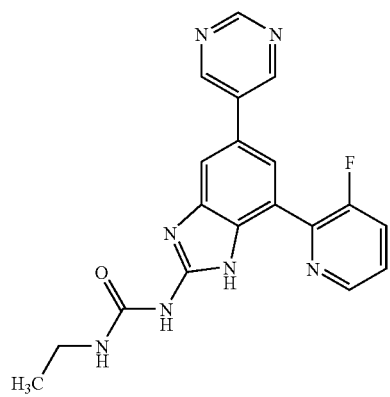 |
| No. | Structure |
|---|---|
| I-363 | 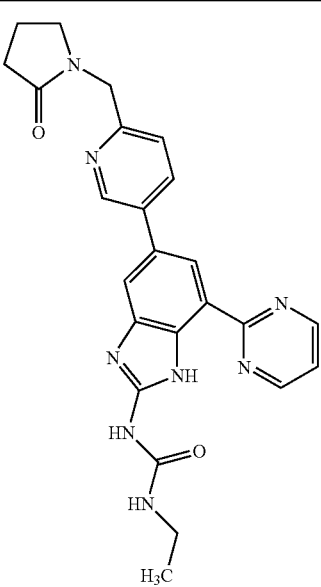 |
| I-364 | 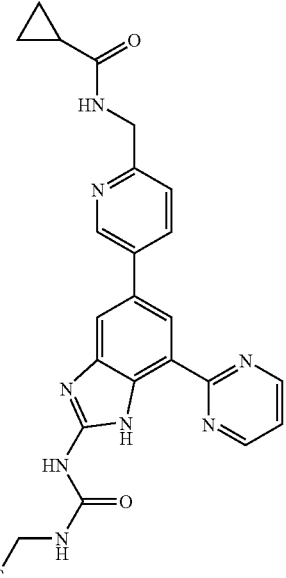 |

451
-continued
| No. | Structure |
|---|---|
| I-365 | 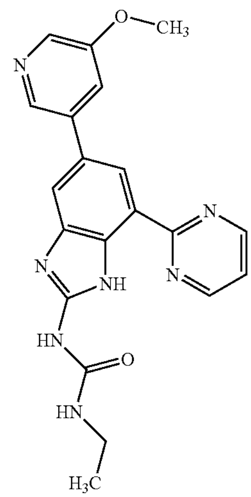 |
| I-368 | 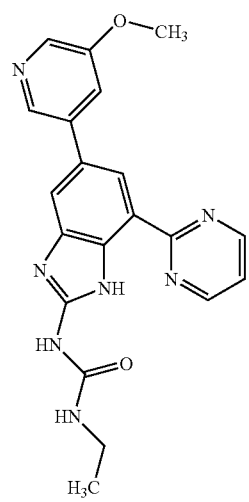 |
452
-continued
| No. | Structure |
|---|---|
| I-369 | 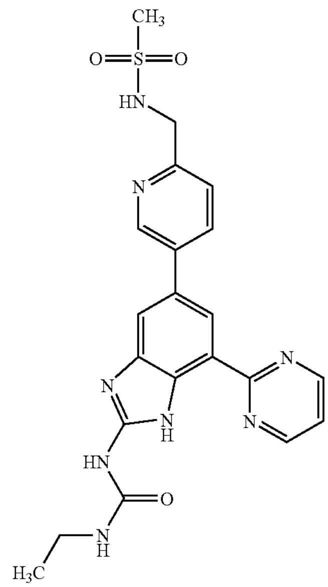 |
| I-372 | 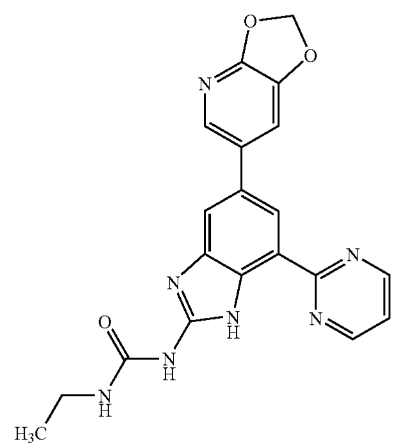 |
| I-375 | 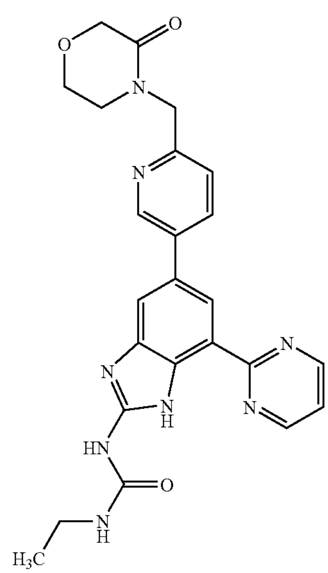 |

-continued
| No. | Structure |
|---|---|
| I-376 | 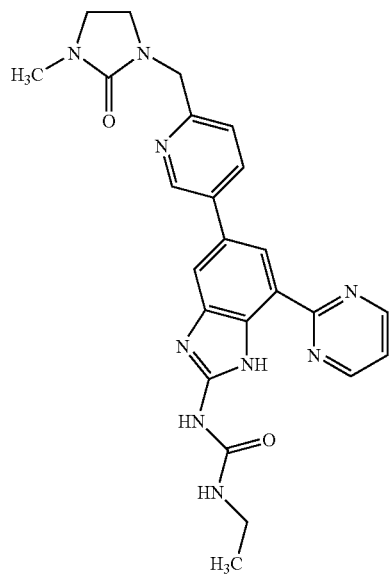 |
| I-382 | 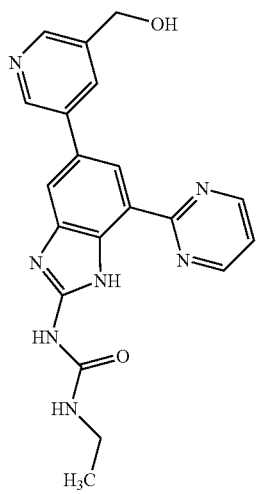 |
| I-387 | 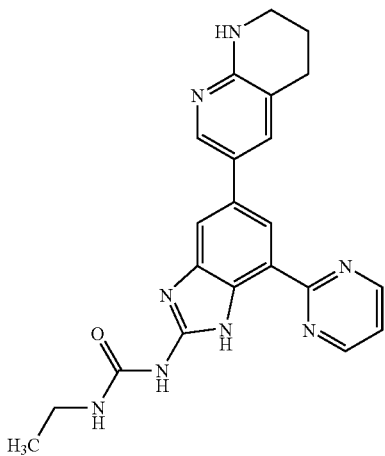 |
-continued
| No. | Structure |
|---|---|
| I-388 | 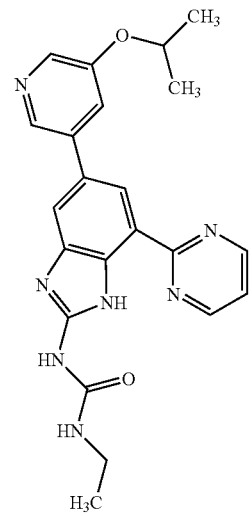 |
| I-393 | 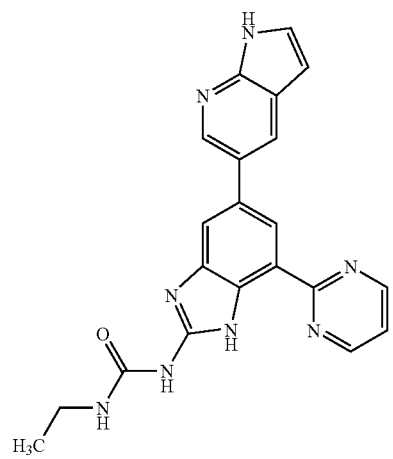 |
| I-395 | 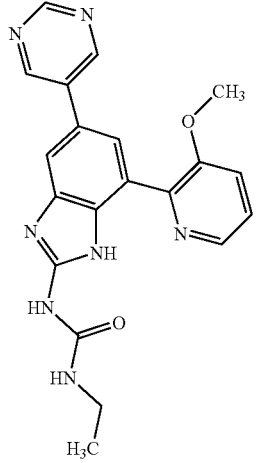 |

-continued
| No. | Structure |
|---|---|
| I-401 | 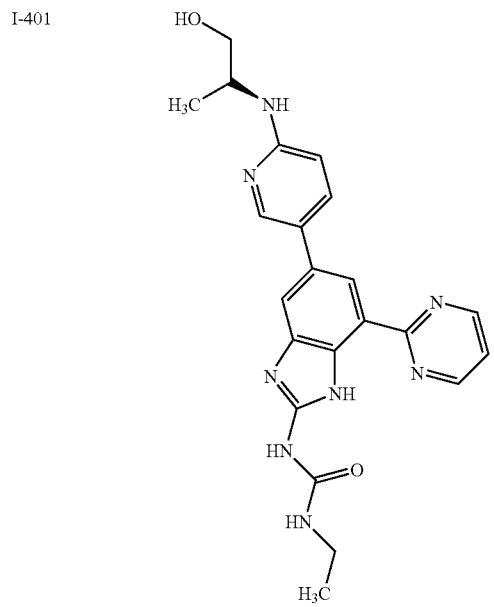 |
| I-402 | 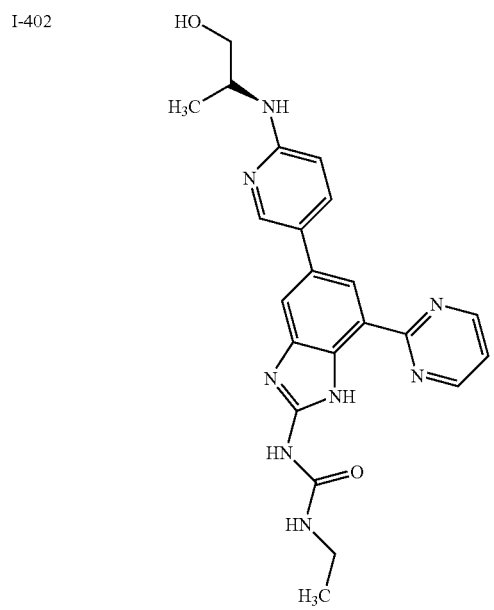 |
-continued
| No. | Structure |
|---|---|
| I-403 | 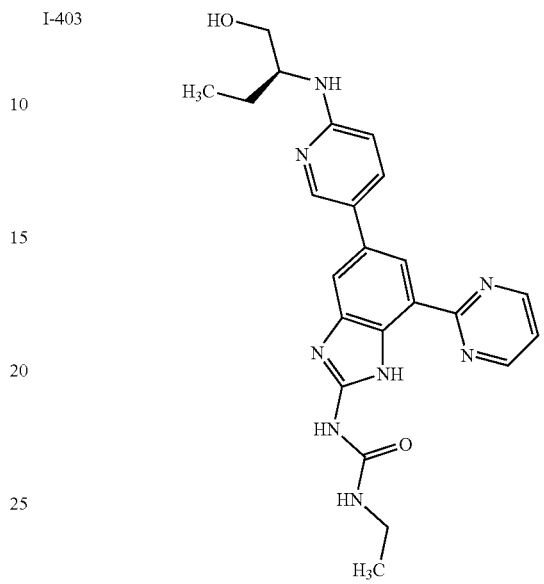 |
| I-404 | 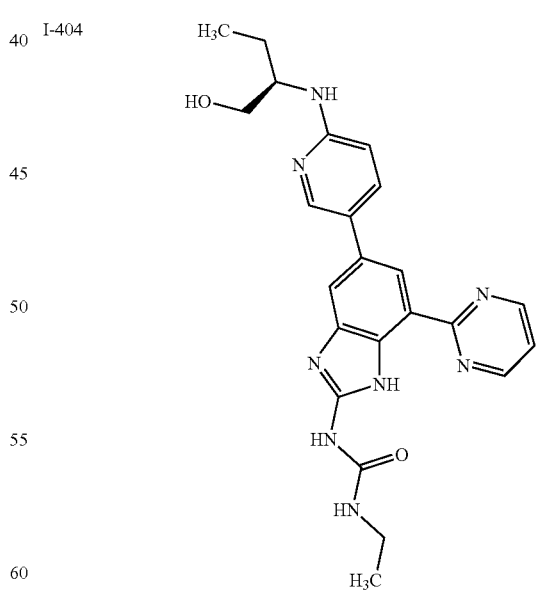 |

| No. | Structure |
|-----|-----------|
| I-406 | 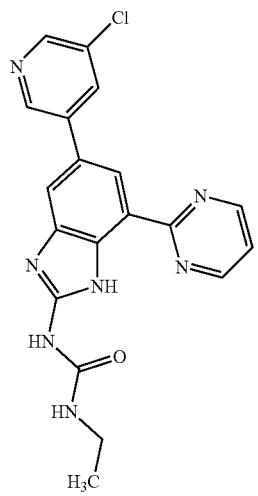 |
| I-407 | 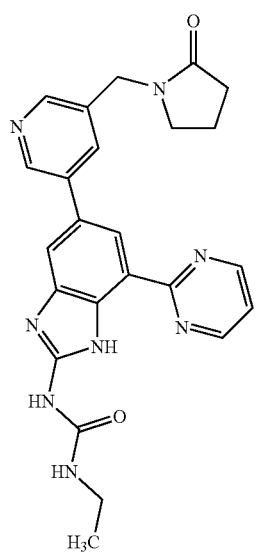 |
| No. | Structure |
|-----|-----------|
| I-412 | 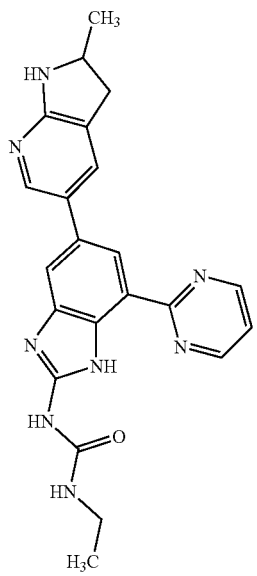 |
| I-414 | 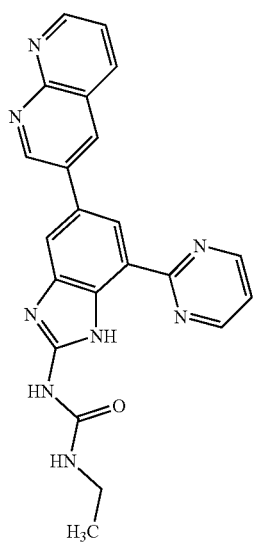 |

-continued
| No. | Structure |
|---|---|
| I-418 | 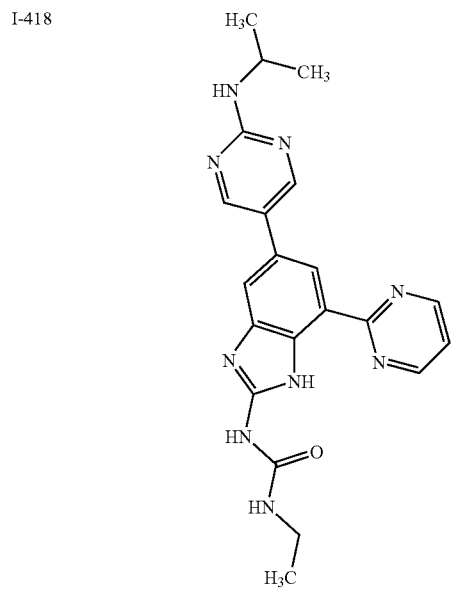 |
| I-423 | 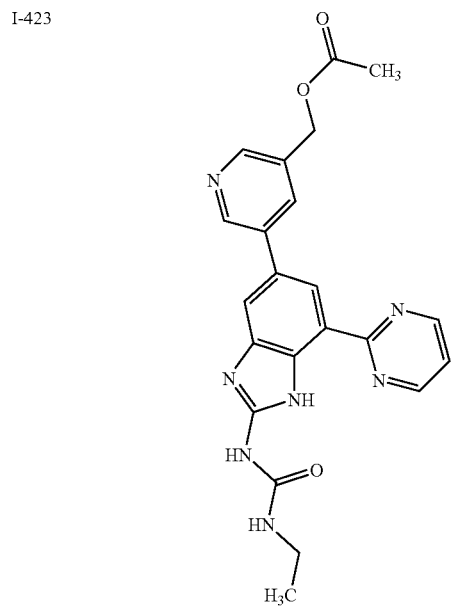 |
-continued
| No. | Structure |
|---|---|
| I-426 | 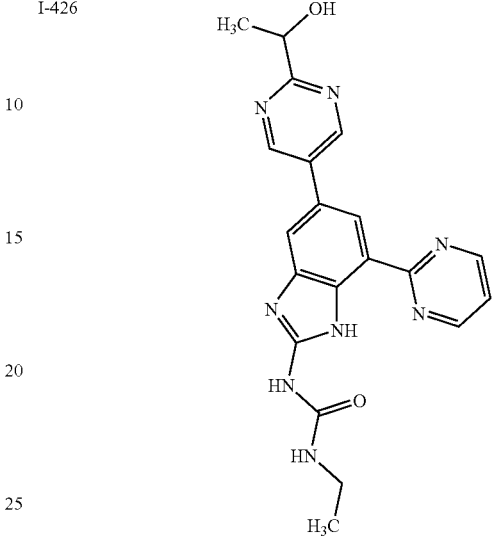 |
| I-429 | 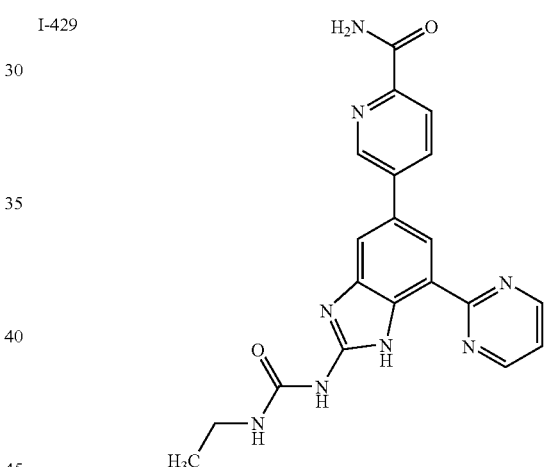 |
| I-430 | 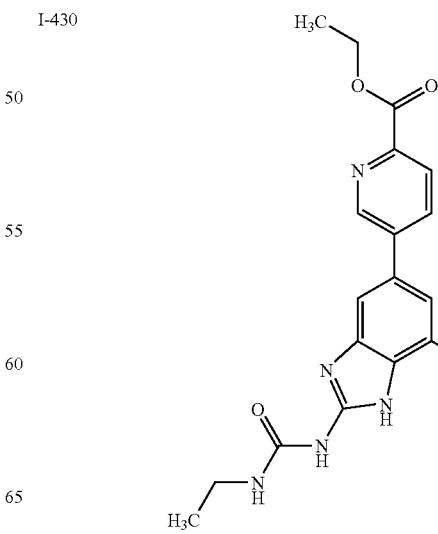 |

| No. | Structure |
|---|---|
| I-432 | 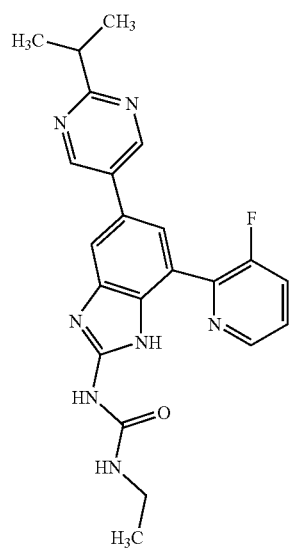 |
| I-434 | 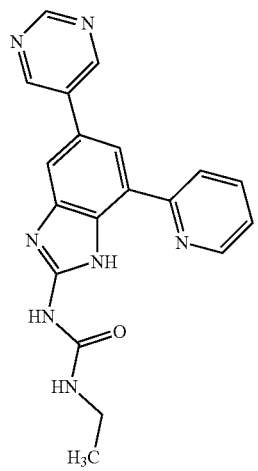 |
| I-435 | 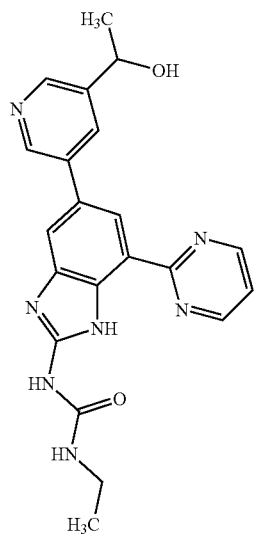 |
| No. | Structure |
|---|---|
| I-436 | 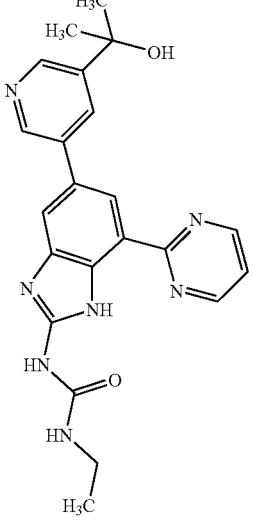 |
| I-438 | |

-continued

| No. | Structure |
|---|---|
| I-439 | 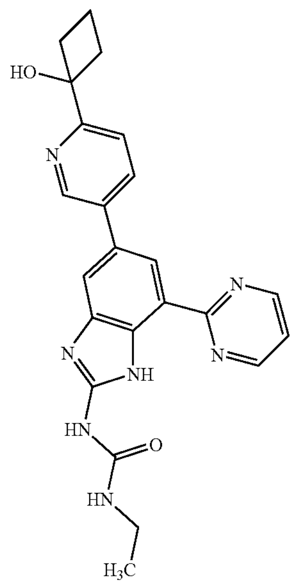 |
| I-443 | 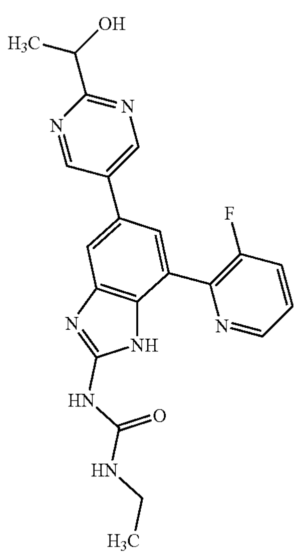 |
| I-445 | |
| I-447 | |

-continued
| No. | Structure |
|-----|-----------|
| I-449 | 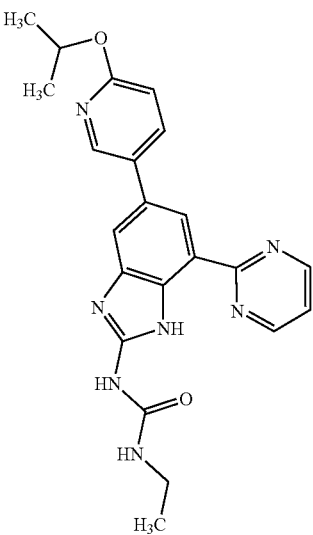 |
| I-452 | 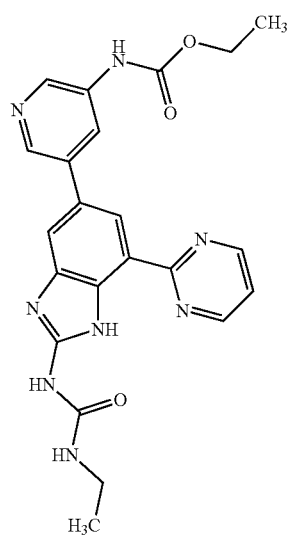 |
-continued
| No. | Structure |
|-----|-----------|
| I-454 | 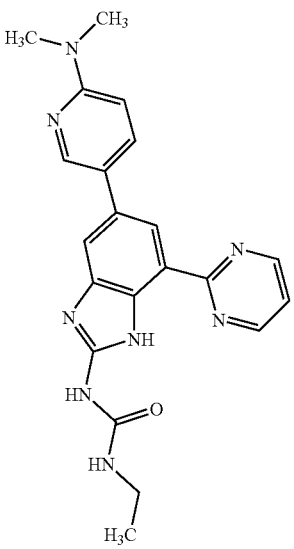 |
| I-455 | 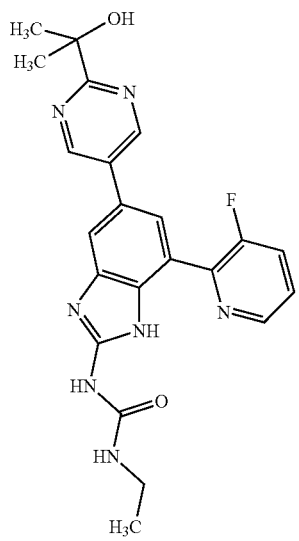 |

| No. | Structure |
|---|---|
| I-456 | 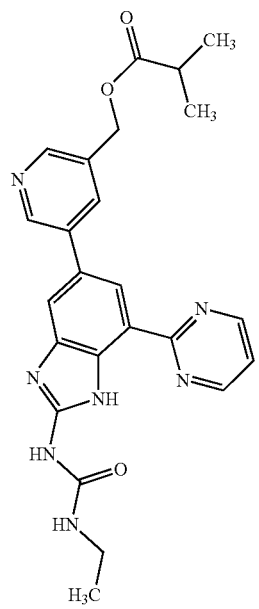 |
| I-457 | 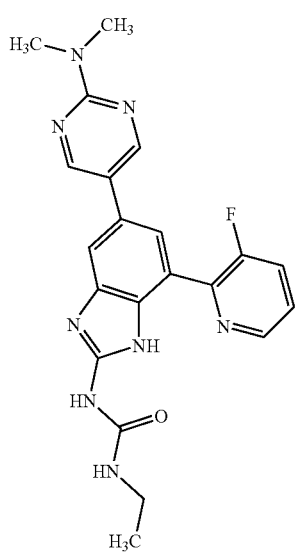 |
| No. | Structure |
|---|---|
| I-460 | 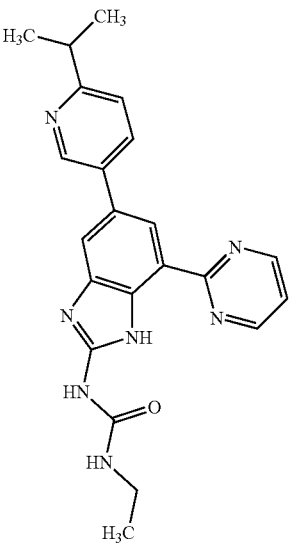 |
| I-461 | 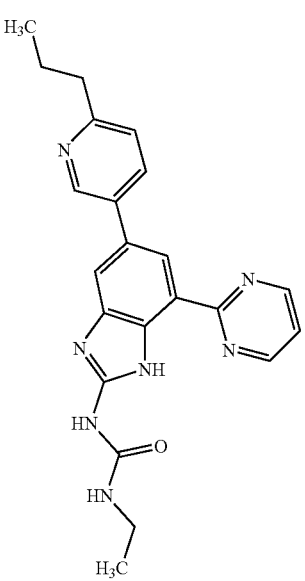 |

-continued
| No. | Structure |
|---|---|
| I-464 | 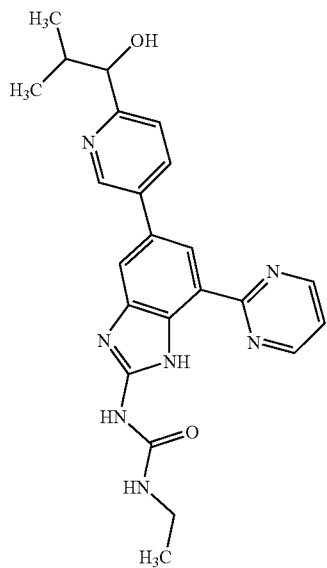 |
| I-466 | 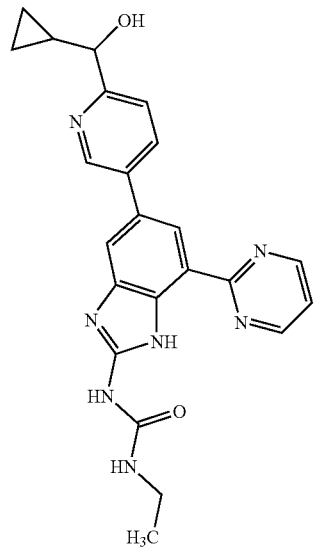 |
-continued
| No. | Structure |
|---|---|
| I-468 | 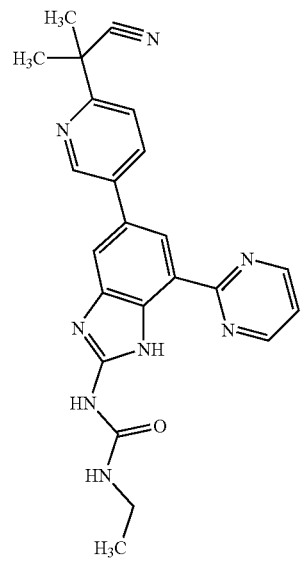 |
| I-474 | 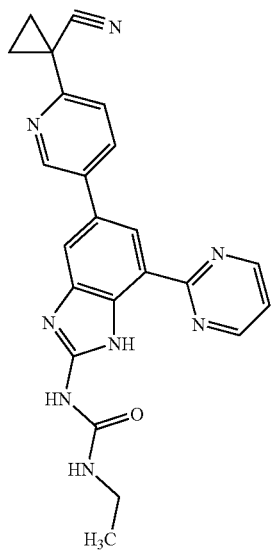 |
| I-476 | 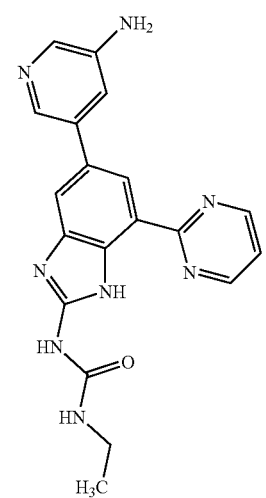 |

-continued
| No. | Structure |
|---|---|
| I-479 | 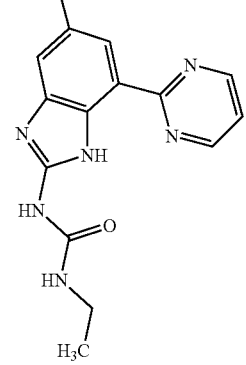 |
| I-487 | 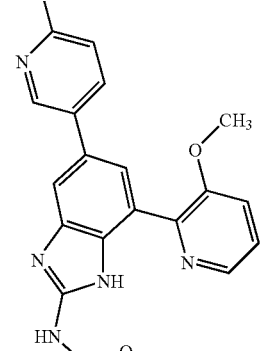 |
| I-491 | 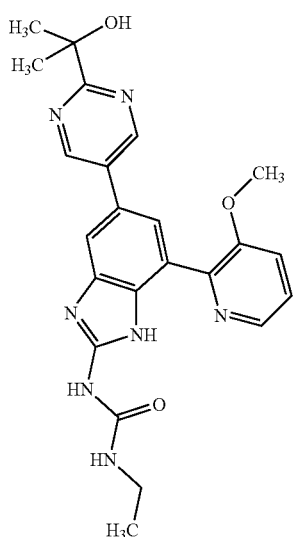 |
-continued
| No. | Structure |
|---|---|
| I-494 | 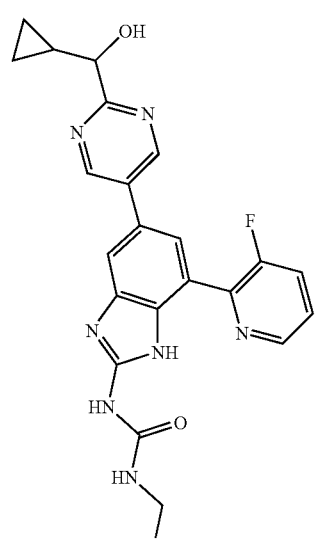 |
| I-495 | 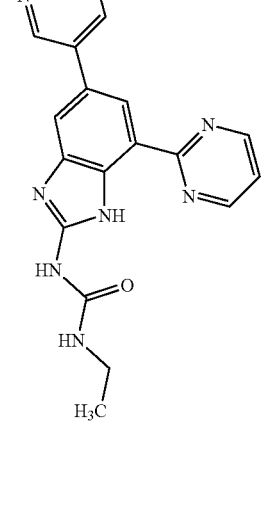 |

-continued
| No. | Structure |
|---|---|
| I-496 | 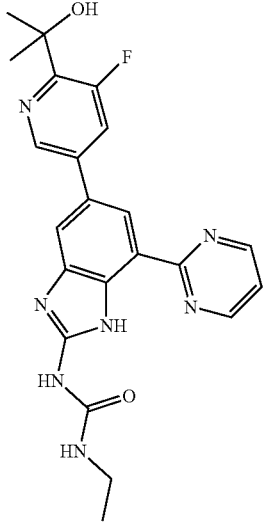 |
| I-497 | 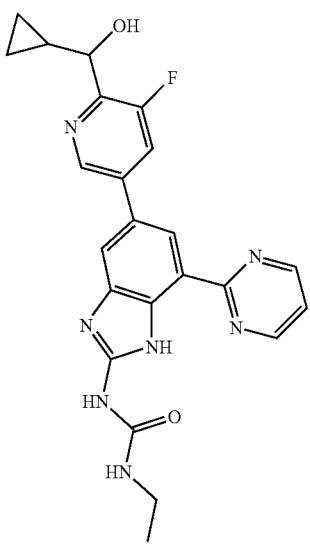 |
| I-498 | 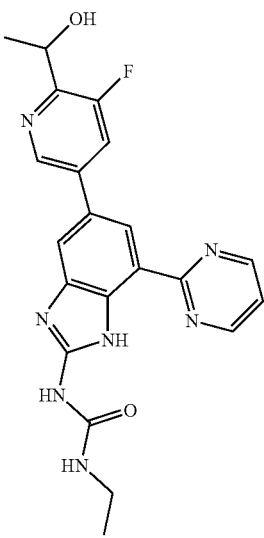 |
-continued
| No. | Structure |
|---|---|
| I-472 | 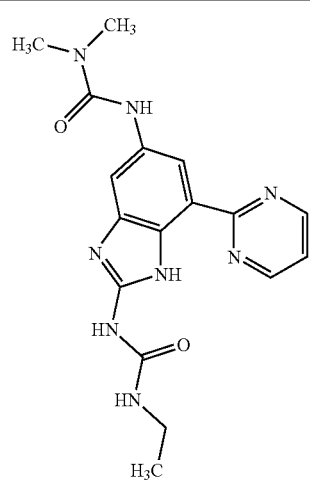 |
| I-500 | 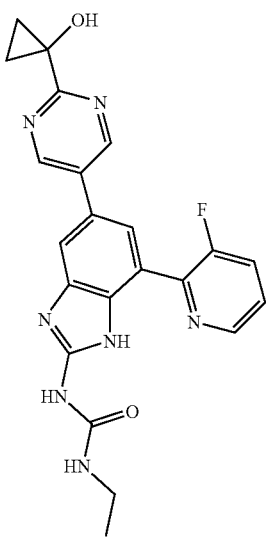 |
| and I-502 | 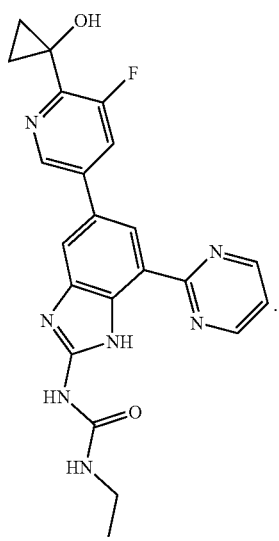 |

26. The method according to claim 25 wherein said patient is a human.

27. The method according to claim 26, wherein the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, or Rifampin resistant *Mycobacterium tuberculosis*.

28. The method according to claim 26, wherein the bacterial infection is characterized by the presence of one or more of the following: Methicillin resistant *Staphylococcus aureus*, Methicillin resistant *Staphylococcus epidermidis*, Methicillin resistant Coagulase negative staphylcocci, Fluoroquinolone resistant *Staphylococcus aureus*, Fluoroquinolone resistant *Staphylococcus epidermidis*, Fluoroquinolone resistant Coagulase negative staphylcocci, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, β-lactam resistant *Haemophilus influenzae*.

* * * * *